United States Patent
Rowbottom

(10) Patent No.: US 11,345,676 B2
(45) Date of Patent: May 31, 2022

(54) APOPTOSIS SIGNAL-REGULATING KINASE 1 (ASK 1) INHIBITOR COMPOUNDS

(71) Applicant: PHARMAKEA, INC., San Diego, CA (US)

(72) Inventor: Martin W. Rowbottom, San Diego, CA (US)

(73) Assignee: PHARMAKEA, INC., San Diego, CA (US)

( * ) Notice: Subject to any disclaimer, the term of this patent is extended or adjusted under 35 U.S.C. 154(b) by 0 days.

(21) Appl. No.: 16/497,695

(22) PCT Filed: Mar. 23, 2018

(86) PCT No.: PCT/US2018/024130
§ 371 (c)(1),
(2) Date: Sep. 25, 2019

(87) PCT Pub. No.: WO2018/183122
PCT Pub. Date: Oct. 4, 2018

(65) Prior Publication Data
US 2020/0048218 A1 Feb. 13, 2020

Related U.S. Application Data

(60) Provisional application No. 62/477,137, filed on Mar. 27, 2017.

(51) Int. Cl.
*C07D 401/04* (2006.01)
*A61P 1/16* (2006.01)
*A61P 11/00* (2006.01)
*C07D 401/14* (2006.01)

(52) U.S. Cl.
CPC .............. *C07D 401/04* (2013.01); *A61P 1/16* (2018.01); *A61P 11/00* (2018.01); *C07D 401/14* (2013.01)

(58) Field of Classification Search
CPC ..... C07D 401/04; C07D 401/14; A61P 11/00; A61P 1/16

USPC ........................................................ 514/269
See application file for complete search history.

(56) References Cited

U.S. PATENT DOCUMENTS

| 2009/0105250 A1 | 4/2009 | Sim et al. | |
| 2015/0342943 A1* | 12/2015 | Bornstein | A61K 31/4439 424/146.1 |
| 2016/0130251 A1 | 5/2016 | Graupe et al. | |

FOREIGN PATENT DOCUMENTS

| WO | WO-2013165606 A1 | 11/2013 |
| WO | WO-2018183122 A1 | 10/2018 |

OTHER PUBLICATIONS

Berge et al. Pharmaceutical Salts. Journal of Pharmaceutical Sciences 66(1): 1 -19 (Jan. 1977).
Bundgaard. Means to Enhance Penetration: Prodrugs as a Means to Improve the Delivery of Peptide Drugs. Advanced Drug Delivery Review 8:1-38 (1992).
Dominguez et al., Discovery of N-phenyl nicotinamides as potent inhibitors of Kdr. Bioorg Med Chem Lett. 17(21):6003-6008 (2007).
Merk et al., Extending the structure-activity relationship of anthranilic acid derivatives as farnesoid X receptor modulators: development of a highly potent partial farnesoid X receptor agonist. Journal of Medicinal Chemistry 57(19):8035-8055 (2014).
PCT/US2018/024130 International Search Report and Written Opinion dated Jul. 30, 2018.
Widder et al. Section III: Prodrugs Kinetics. Method in Enzymology. 112:309-396 (1985).

* cited by examiner

*Primary Examiner* — Kahsay Habte
(74) *Attorney, Agent, or Firm* — Maier & Maier, PLLC

(57) ABSTRACT

Described herein are ASK1 inhibitors, methods of making such compounds, pharmaceutical compositions and medicaments comprising such compounds, and methods of using such compounds in the treatment of conditions, diseases, or disorders associated with ASK1 activity.

17 Claims, No Drawings

APOPTOSIS SIGNAL-REGULATING KINASE 1 (ASK 1) INHIBITOR COMPOUNDS

CROSS-REFERENCE

This application is filed pursuant to 35 U.S.C. § 371 as a United States National Phase Application of International Application No. PCT/US2018/024130 filed on Mar. 23, 2018, which claims benefit of U.S. Provisional Patent Application No. 62/477,137 filed on Mar. 27, 2017, each of which is incorporated herein by reference in its entirety.

FIELD OF THE INVENTION

Described herein are compounds that are apoptosis signal-regulating kinase 1 (ASK1) inhibitors, methods of making such compounds, pharmaceutical compositions and medicaments comprising such compounds, and methods of using such compounds in the treatment of conditions, diseases, or disorders associated with ASK1 activity.

BACKGROUND OF THE INVENTION

ASK1, a serine threonine kinase, activates c-Jun N-terminal kinase (JNK) and p38 mitogen-activated protein kinases in a Raf-independent fashion in response to an array of stresses such as oxidative stress, endoplasmic reticulum stress and calcium influx. ASK1 has been found to be involved in the development of fibrosis, cancer, diabetes, cardiovascular and neurodegenerative diseases.

SUMMARY OF THE INVENTION

In one aspect, described herein are ASK1 inhibitors and uses thereof. In some embodiments, the ASK1 inhibitors described herein have the structure of Formula (I), or a pharmaceutically acceptable salt thereof. In one aspect, described herein is a compound of Formula (I), or a pharmaceutically acceptable salt thereof:

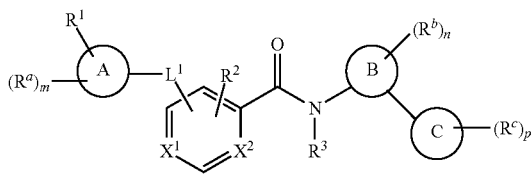

Formula (I)

wherein, ring A is a phenyl, 6-membered heteroaryl, or a 5-membered heteroaryl;

each $R^a$ is independently H, D, halogen, —CN, —OR$^5$, —SR$^5$, —S(═O)R$^4$, —S(═O)$_2$R$^4$, —S(═O)$_2$N(R$^5$)$_2$, —NR$^5$S(═O)$_2$R$^4$, —C(═O)R$^4$, —OC(═O)R$^4$, —CO$_2$R$^5$, —OCO$_2$R$^4$, —N(R$^5$)$_2$, —OC(═O)N(R$^5$)$_2$, —C(═O)N(R$^5$)$_2$, —NR$^5$C(═O)R$^4$, —NR$^5$C(═O)OR$^4$, —NR$^5$C(═O)N(R$^5$)$_2$, substituted or unsubstituted C$_1$-C$_6$alkyl, substituted or unsubstituted C$_1$-C$_6$fluoroalkyl, substituted or unsubstituted C$_1$-C$_6$deuteroalkyl, substituted or unsubstituted C$_1$-C$_6$heteroalkyl, substituted or unsubstituted C$_3$-C$_6$cycloalkyl;

m is 0, 1, 2, or 3;

$R^1$ is H, D, halogen, —CN, —OR$^5$, —SR$^5$, —S(═O)R$^4$, —S(═O)$_2$R$^4$, —N(R$^5$)$_2$, substituted or unsubstituted C$_1$-C$_6$alkyl, substituted or unsubstituted C$_1$-C$_6$fluoroalkyl, substituted or unsubstituted C$_1$-C$_6$deuteroalkyl, substituted or unsubstituted C$_1$-C$_6$heteroalkyl, or substituted or unsubstituted —C$_1$-C$_4$alkylene-N(R$^5$)$_2$;

$L^1$ is linker that is —X$^2$—, L$^2$, -L$^2$-X$^2$—, —X$^2$-L$^3$-, or -L$^2$-X$^2$-L$^3$-.

$X^2$ is —O—, —S—, —S(═O)—, —S(═O)$_2$—, —S(═O)$_2$NR$^6$—, —C(═O)—, —C(═O)O—, —C(═O)NR$^6$—, —OC(═O)NR$^6$—, —NR$^6$C(═O)O—, —NR$^6$C(═O)NR$^6$—, —OC(═O)—, —NR$^6$C(═O)—, —NR$^6$S(═O)$_2$—, or —NR$^6$—;

$R^6$ is H, C$_1$-C$_6$alkyl, C$_1$-C$_6$fluoroalkyl, or C$_1$-C$_6$deuteroalkyl;

$L^2$ is substituted or unsubstituted C$_1$-C$_4$alkylene, substituted or unsubstituted C$_2$-C$_4$alkenylene or substituted or unsubstituted C$_2$-C$_4$alkynylene;

$L^3$ is C$_1$-C$_4$alkylene;

$X^1$ is CR$^2$ or N;

$X^2$ is CR$^2$ or N;

each $R^2$ is independently H, D, halogen, —CN, —OR$^5$, —SR$^5$, —S(═O)R$^4$, —S(═O)$_2$R$^4$, —N(R$^5$)$_2$, substituted or unsubstituted C$_1$-C$_6$alkyl, substituted or unsubstituted C$_1$-C$_6$fluoroalkyl, substituted or unsubstituted C$_1$-C$_6$deuteroalkyl, substituted or unsubstituted C$_1$-C$_6$heteroalkyl, substituted or unsubstituted C$_3$-C$_6$cycloalkyl;

$R^3$ is H, substituted or unsubstituted C$_1$-C$_6$alkyl, substituted or unsubstituted C$_1$-C$_6$fluoroalkyl, or substituted or unsubstituted C$_1$-C$_6$deuteroalkyl;

ring B is a 6-membered heteroaryl, phenyl, or a 5-membered heteroaryl;

each $R^b$ is independently H, D, halogen, —CN, —OR$^5$, —SR$^5$, —S(═O)R$^4$, —S(═O)$_2$R$^4$, —S(═O)$_2$N(R$^5$)$_2$, —NR$^5$S(═O)$_2$R$^4$, —C(═O)R$^4$, —OC(═O)R$^4$, —CO$_2$R$^5$, —OCO$_2$R$^4$, —N(R$^5$)$_2$, —OC(═O)N(R$^5$)$_2$, —NR$^5$C(═O)R$^4$, —NR$^2$C(═O)OR$^4$, —C(═O)N(R$^5$)$_2$, substituted or unsubstituted C$_1$-C$_6$alkyl, substituted or unsubstituted C$_1$-C$_6$fluoroalkyl, substituted or unsubstituted C$_1$-C$_6$deuteroalkyl, substituted or unsubstituted C$_1$-C$_6$heteroalkyl, substituted or unsubstituted C$_3$-C$_6$cycloalkyl;

n is 0, 1, 2, 3, or 4;

ring C is a 5-membered heteroaryl;

each $R^c$ is independently H, D, halogen, —CN, —OR$^5$, —SR$^5$, —S(═O)R$^4$, —S(═O)$_2$R$^4$, —S(═O)$_2$N(R$^5$)$_2$, —NR$^5$S(═O)$_2$R$^4$, —C(═O)R$^4$, —OC(═O)R$^4$, —CO$_2$R$^5$, —OCO$_2$R$^4$, —N(R$^5$)$_2$, —OC(═O)N(R$^5$)$_2$, —NR$^5$C(═O)R$^4$, —NR$^5$C(═O)OR$^4$, —C(═O)N(R$^5$)$_2$, substituted or unsubstituted C$_1$-C$_6$alkyl, substituted or unsubstituted C$_1$-C$_6$fluoroalkyl, substituted or unsubstituted C$_1$-C$_6$deuteroalkyl, substituted or unsubstituted C$_1$-C$_6$heteroalkyl, or substituted or unsubstituted C$_3$-C$_6$cycloalkyl;

p is 0, 1, 2, or 3;

each $R^4$ is independently selected from C$_1$-C$_6$alkyl, C$_1$-C$_6$fluoroalkyl, C$_1$-C$_6$deuteroalkyl, C$_1$-C$_6$heteroalkyl, substituted or unsubstituted C$_3$-C$_{10}$cycloalkyl, substituted or unsubstituted C$_2$-C$_{10}$heterocycloalkyl, substituted or unsubstituted aryl, substituted or unsubstituted benzyl and substituted or unsubstituted heteroaryl;

each $R^5$ is independently selected from H, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted benzyl and substituted or unsubstituted heteroaryl; or two $R^5$ on the same N atom are taken together with the N atom to which they are attached to a substituted or unsubstituted N-containing heterocycle.

In another aspect, described herein is a compound that inhibits apoptosis signal-regulating kinase (ASK1) activity and lysyl oxidase like-2 (LOXL2) activity. In some embodiments, the compound is an aminoalkyl compound. In some embodiments, the compound is an aminomethyl compound. In some embodiments, the compound is an aminoalkyl compound that has the structure of Formula (IV), or a pharmaceutically acceptable salt, or solvate thereof. In some embodiments, the compound is an aminomethyl compound that has the structure of Formula (IV), or a pharmaceutically acceptable salt, or solvate thereof.

In another aspect, described herein is a compound of Formula (IV), or a pharmaceutically acceptable salt thereof:

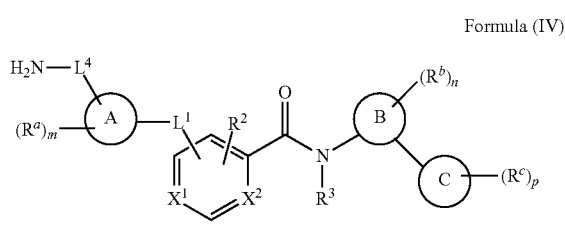

Formula (IV)

wherein,
ring A is a phenyl, 6-membered heteroaryl, or a 5-membered heteroaryl;
each $R^a$ is independently H, D, halogen, —CN, —OR$^5$, —SR$^5$, —S(=O)R$^4$, —S(=O)$_2$R$^4$, —S(=O)$_2$N(R$^5$)$_2$, —NR$^5$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —C(=O)N(R$^5$)$_2$, —NR$^5$C(=O)R$^4$, —NR$^5$C(=O)OR$^4$, —NR$^5$C(=O)N(R$^5$)$_2$, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, substituted or unsubstituted $C_3$-$C_6$cycloalkyl;
m is 0, 1, 2, or 3;
$L^4$ is $C_1$-$C_4$alkylene, $C_1$-$C_4$fluoroalkylene, or $C_1$-$C_4$deuteroalkylene;
$L^1$ is linker that is —X$^2$—, $L^2$, -$L^2$-X$^2$—, —X$^2$-$L^3$-, or -$L^2$-X$^2$-$L^3$-.
$X^2$ is —O—, —S—, —S(=O)—, —S(=O)$_2$—, —S(=O)$_2$NR$^6$—, —C(=O)—, —C(=O)O—, —C(=O)NR$^6$—, —OC(=O)NR$^6$—, —NR$^6$C(=O)O—, —NR$^6$C(=O)NR$^6$—, —OC(=O)—, —NR$^6$C(=O)—, —NR$^6$S(=O)$_2$—, or —NR$^6$—;
$R^6$ is H, $C_1$-$C_6$alkyl, $C_1$-$C_6$fluoroalkyl, or $C_1$-$C_6$deuteroalkyl;
$L^2$ is substituted or unsubstituted $C_1$-$C_4$alkylene, substituted or unsubstituted $C_2$-$C_4$alkenylene or substituted or unsubstituted $C_2$-$C_4$alkynylene;
$L^3$ is $C_1$-$C_4$alkylene;
$X^1$ is CR$^2$ or N;
$X^2$ is CR$^2$ or N;

each $R^2$ is independently H, D, halogen, —CN, —OR$^5$, —SR$^5$, —S(=O)R$^4$, —S(=O)$_2$R$^4$, —N(R$^5$)$_2$, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, substituted or unsubstituted $C_3$-$C_6$cycloalkyl;
$R^3$ is H, substituted or unsubstituted $C_1$-$C_6$alkyl, substituted or unsubstituted $C_1$-$C_6$fluoroalkyl, or substituted or unsubstituted $C_1$-$C_6$deuteroalkyl;
ring B is a 6-membered heteroaryl, phenyl, or a 5-membered heteroaryl;
each $R^b$ is independently H, D, halogen, —CN, —OR$^5$, —SR$^5$, —S(=O)R$^4$, —S(=O)$_2$R$^4$, —S(=O)$_2$N(R$^5$)$_2$, —NR$^5$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —NR$^5$C(=O)R$^4$, —NR$^2$C(=O)OR$^4$, —C(=O)N(R$^5$)$_2$, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, substituted or unsubstituted $C_3$-$C_6$cycloalkyl;
n is 0, 1, 2, 3, or 4;
ring C is a 5-membered heteroaryl;
each $R^c$ is independently H, D, halogen, —CN, —OR$^5$, —SR$^5$, —S(=O)R$^4$, —S(=O)$_2$R$^4$, —S(=O)$_2$N(R$^5$)$_2$, —NR$^5$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —NR$^5$C(=O)R$^4$, —NR$^5$C(=O)OR$^4$, —C(=O)N(R$^5$)$_2$, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, or substituted or unsubstituted $C_3$-$C_6$cycloalkyl;
p is 0, 1, 2, or 3;
each $R^4$ is independently selected from $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted benzyl and substituted or unsubstituted heteroaryl;
each $R^5$ is independently selected from H, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted benzyl and substituted or unsubstituted heteroaryl; or two $R^5$ on the same N atom are taken together with the N atom to which they are attached to a substituted or unsubstituted N-containing heterocycle.

Any combination of the groups described above for the various variables is contemplated herein. Throughout the specification, groups and substituents thereof are chosen by one skilled in the field to provide stable moieties and compounds.

In one aspect, described herein is a pharmaceutical composition comprising a compound described herein, or a pharmaceutically acceptable salt, or solvate thereof, and at least one pharmaceutically acceptable excipient. In some embodiments, the pharmaceutical composition is formulated for administration to a mammal by intravenous administration, subcutaneous administration, oral administration, inhalation, nasal administration, dermal administration, or ophthalmic administration. In some embodiments, the pharmaceutical composition is formulated for administration to a mammal by intravenous administration, subcutaneous administration, or oral administration. In some embodiments, the pharmaceutical composition is formulated for administration to a mammal by oral administration. In some embodiments, the pharmaceutical composition is in the form of a tablet, a pill, a capsule, a liquid, a suspension, a gel, a dispersion, a solution, an emulsion, an ointment, or a lotion. In some embodiments, the pharmaceutical composition is in the form of a tablet, a pill, or a capsule.

In one aspect, described herein is a method of treating a disease or condition in a mammal that would benefit from the inhibition of apoptosis signal-regulating kinase 1 (ASK1) activity comprising administering to the mammal a compound, or pharmaceutically acceptable salt, or solvate thereof, as described herein.

In another aspect, described herein is a method of treating a disease or condition in a mammal that would benefit from the inhibition of apoptosis signal-regulating kinase (ASK1) activity and lysyl oxidase like-2 (LOXL2) activity comprising administering to the mammal a compound, or pharmaceutically acceptable salt, or solvate thereof, as described herein.

In some embodiments, the inhibition of ASK1 inactivates c-Jun N-terminal protein kinase, p38 MAP kinase, or a combination thereof.

In some embodiments, the disease or condition is fibrosis, cancer, an autoimmune disease or condition, an inflammatory disease or condition, a cardiovascular disease or condition, a neurodegenerative disease or condition, or combinations thereof.

In some embodiments, the disease or condition is fibrosis. In some embodiments, the fibrosis comprises lung fibrosis, liver fibrosis, kidney fibrosis, cardiac fibrosis, peritoneal fibrosis or cutaneous fibrosis In one aspect, described herein is a method of treating or preventing any one of the diseases or conditions described herein comprising administering a therapeutically effective amount of a compound described herein, or a pharmaceutically acceptable salt, or solvate thereof, to a mammal in need thereof.

In one aspect, described herein is a method for the treatment or prevention of fibrosis in a mammal comprising administering a therapeutically effective amount of a compound described herein, or a pharmaceutically acceptable salt, or solvate thereof, to the mammal in need thereof. In other embodiments, the fibrosis is amenable to treatment with an ASK1 inhibitor. In some embodiments, the fibrosis is liver fibrosis. In some embodiments, the method further comprises administering a second therapeutic agent to the mammal in addition to the compound described herein, or a pharmaceutically acceptable salt, or solvate thereof.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by inhalation; and/or (e) administered by nasal administration; and/or (f) administered by injection to the mammal; and/or (g) administered topically to the mammal; and/or (h) administered by ophthalmic administration; and/or (i) administered rectally to the mammal; and/or (j) adminstered non-systemically or locally to the mammal.

In any of the aforementioned aspects are further embodiments comprising single administrations of the effective amount of the compound, including further embodiments in which the compound is administered once a day to the mammal or the compound is administered to the mammal multiple times over the span of one day. In some embodiments, the compound is administered on a continuous dosing schedule. In some embodiments, the compound is administered on a continuous daily dosing schedule.

In any of the aforementioned aspects involving the treatment of a disease or condition are further embodiments comprising administering at least one additional agent in addition to the administration of a compound described herein, or a pharmaceutically acceptable salt thereof. In various embodiments, each agent is administered in any order, including simultaneously.

In any of the embodiments disclosed herein, the mammal is a human.

In some embodiments, compounds provided herein are administered to a human.

In some embodiments, compounds provided herein are orally administered.

Articles of manufacture, which include packaging material, a compound described herein, or a pharmaceutically acceptable salt thereof, within the packaging material, and a label that indicates that the compound or composition, or pharmaceutically acceptable salt, pharmaceutically active metabolite, pharmaceutically acceptable prodrug, or pharmaceutically acceptable solvate thereof, is used for inhibiting the activity of ASK1, or for the treatment, prevention or amelioration of one or more symptoms of a disease or condition that would benefit from inhibition or reduction of the ASK1 activity, are provided.

Other objects, features and advantages of the compounds, methods and compositions described herein will become apparent from the following detailed description. It should be understood, however, that the detailed description and the specific examples, while indicating specific embodiments, are given by way of illustration only, since various changes and modifications within the spirit and scope of the instant disclosure will become apparent to those skilled in the art from this detailed description.

DETAILED DESCRIPTION OF THE INVENTION

Mitogen-activated protein kinases (MAPKs) are a highly conserved family of serine/threonine protein kinases involved in a variety of fundamental cellular processes such as proliferation, differentiation, motility, stress response, apoptosis, and survival. MAPK networks are critical for the transmission of extracellular signals into appropriate intracellular responses, such as, but not limited to cell growth, differentiation, inflammation, and apoptosis. Prototypical MAPK activation employs a three-kinase core module consisting of a MAPK kinase kinase (MAPKKK or MAP3K) that phosphorylates and activates a MAPK kinase (MAP2K, MEK, or MKK) that in turn phosphorylates and dramatically increases the activity of one or more MAPKs.

Apoptosis signal-regulating kinase 1 (ASK1) is a member of the MAP3K family that activates the c-Jun N-terminal protein kinase (JNK) and p38 MAPK. ASK1, also known as mitogen-activated protein kinase kinase kinase 5 (MAP3K5), is activated by a variety of stimuli including hyperglycaemia, transforming growth factor beta (TGF-β), oxidative stress, reactive oxygen species (ROS), lipopolysaccharides (LPS), tumor necrosis factor alpha (TNFα), Fas ligand (FasL), endoplasmic reticulum (ER) stress, and increased intracellular calcium concentrations. ROS have been reported to be associated with increase of inflammatory cytokine production, fibrosis, apoptosis, and necrosis in the kidney. Moreover, oxidative stress facilitates the formation of advanced glycation end-products (AGEs) that cause further renal injury and production of ROS. ASK1 induces apoptosis, fibrosis and metabolic dysfunction by activating the p38 and JNK1 pathways.

ASK1 undergoes activation via autophosphorylation at Thr838 in response to these signals and in turn phosphorylates MAP2Ks, such as MKK3/6 and MKK4/7, which then phosphorylate and activates p38 and JNK MAPKs, respectively. ASK2 is a related MAP3K that shares 45% sequence homology with ASK1. Although ASK2 tissue distribution is restricted, in some cell types ASK1 and ASK2 have been reported to interact and function together in a protein complex. In non-stressed conditions, ASK1 is kept in an inactive state through binding to its repressor thioredoxin (Trx) and through association with AKT.

Phosphorylation of ASK1 protein can lead to apoptosis or other cellular responses depending on the cell type. ASK1 activation and signaling have been reported to play a role in a broad range of diseases including fibrosis, neurodegenerative, cardiovascular, inflammatory, autoimmunity, and metabolic disorders. In addition, ASK1 has been implicated in mediating organ damage following ischemia and reperfusion of the heart, brain, liver and kidney.

Fibrosis

Fibrosis is a wound-healing process in which there is excessive deposition of extracellular matrix (ECM). ECM is composed of collagens, noncollagen glycoproteins, matrix bound growth factors, glycosaminoglycans, proteoglycans and matricellular proteins, which provide the scaffolding of both the normal and the fibrotic tissues. However, as fibrosis develops, there are multiple changes in the specific contents of these, with a marked increase in total collagen content; an increase in glycoproteins (e.g. cellular fibronectin, laminin, SPARC, osteonectin, tenascin and von Willebrand factor) and glycosaminoglycans (e.g. perlecan, decorin, aggrecan, lumican and fibromodulin); both an increase in proteoglycans and a shift from heparan sulphate containing proteoglycans to those containing chondroitin and dermatan sulphates; and an increase in the fibril-forming collagens types I, III and V and in some nonfibril-forming collagens (types IV and VI). For example, with all of these changes occurring in the liver, there is a transition from the low-density basement membrane-like matrix in the subendothelial space that is found in the normal liver to the interstitial type which is associated with hepatocyte dysfunction and activation of the hepatic stellate cells (HSCs), which are the primary source of ECM in both the normal and fibrotic liver. During activation, HSCs transition from their normal quiescent state to proliferative, fibrogenic and contractile myofibroblasts.

Non-alcoholic steatotic hepatitis (NASH) is an exemplary type of fibrosis implicating ASK1 activity. Multiple pathways are involved in NASH-associated fibrosis including inflammasome-TLR activation and generation of the inflammatory cytokines, increased levels of hedgehog signalling, changes in lipid and glucose metabolism leading to oxidative stress, hepatocyte injury via apoptosis, cell death inducing inflammatory and pro-fibrogenic pathways in nonparenchymal cells and infiltrating immune cells. These processes lead to HSC activation which is the source of excessive deposition of extracellular matrix (ECM) in the parenchyma.

In some embodiments, disclosed herein are methods of treating fibrosis with a compound disclosed herein.

"Fibrosis," as used herein, refers to the accumulation of extracellular matrix constituents that occurs following trauma, inflammation, tissue repair, immunological reactions, cellular hyperplasia, and neoplasia. Fibrosis may refer to the development of fibrous connective tissue as a reparative response to injury or damage. Fibrosis may also refer to the connective tissue deposition that occurs as part of normal healing or to the excess tissue deposition that occurs as a pathological process.

In some embodiments, disclosed herein is a method of reducing fibrosis in a tissue comprising contacting a fibrotic cell or tissue with a compound disclosed herein, in an amount sufficient to decrease or inhibit the fibrosis. In some embodiments, the fibrosis includes a fibrotic condition.

In some embodiments, the fibrosis comprises liver fibrosis, kidney fibrosis, lung fibrosis, cardiac fibrosis, peritoneal fibrosis, ocular fibrosis or cutaneous fibrosis. In some embodiments, the fibrosis comprises liver fibrosis. In some embodiments, the fibrosis comprises kidney fibrosis. In some embodiments, the fibrosis comprises cardiac fibrosis. In some embodiments, the fibrosis comprises lung fibrosis. In some embodiments, the fibrosis comprises peritoneal fibrosis. In some embodiments, the fibrosis comprises ocular fibrosis. In some embodiments, the fibrosis comprises cutaneous fibrosis.

In some embodiments, reducing fibrosis, or treatment of a fibrotic condition, includes reducing or inhibiting one or more of: formation or deposition of extracellular matrix proteins; the number of pro-fibrotic cell types (e.g., fibroblast or immune cell numbers); cellular collagen or hydroxyproline content within a fibrotic lesion; expression or activity of a fibrogenic protein; or reducing fibrosis associated with an inflammatory response.

In some embodiments, the fibrotic condition is liver fibrosis. Liver fibrosis refers to the scar tissue and nodules that replace liver tissue and disrupt liver function. The scar tissue blocks the portal flow of blood through the organ therefore disturbing normal function. Damage to the hepatic parenchyma due to inflammation leads to activation of the stellate cell, which increases fibrosis through production of myofibroblasts and obstructs blood flow in the circulation. Production of myofibroblasts accelerates the loss of liver function and can lead to death.

Non-alcoholic fatty liver disease (NAFLD) is a common liver disease characterized by fat accumulation in hepatocytes that is not linked to excessive alcohol intake and is correlated with obesity, insulin resistance, and cardiac diseases. NAFLD is categorised into simple steatosis and non-alcoholic steatotic hepatitis (NASH), the latter of which can lead to hepatic fibrosis, hepatic cirrhosis, and liver cancer. High fat diet (HFD) is used to induce hepatic steatosis in mouse models. HFD causes fat accumulation and fatty acid oxidation, which leads to ROS generation and subsequent hepatocyte dysfunction and cell death in the liver. TNFα-deficient mice show reduced hepatic steatosis, indicating that proinflammatory cytokines including TNFα are required for liver injury. TNFα-induced apoptosis of hepatocytes is mediated by ASK1-JNK activation. ASK1-deficient mice have reduced HFD-induced hepatic steatosis, fibrosis, and TGFβ expression, which is responsible for hepatic fibrosis. Olmesartan, an ATI blocker, also improves HFD-induced hepatic steatosis by inhibiting ASK1. Moreover, olmesartan or ASK1 deficiency can attenuate HFD-induced cardiac inflammation and fibrosis, and vascular endothelial dysfunction and remodelling. These findings suggest that ASK1 is involved in obesity-associated cardiovascular complications and hepatic steatosis.

The ASK1 pathway has been shown to be activated in human NASH liver biopsies. In animals with established NASH (F1/2), a small molecule inhibitor of ASK1 significantly reduced hepatic steatosis and fibrosis and significantly improved key metabolic parameters associated with NASH. Treatment with a small molecule inhibitor of ASK1 resulted in a significant reduction in body weight; decreased fasting blood glucose and insulin levels; reduction in plasma AST, ALT and cholesterol levels; a reduction in hepatic steatosis; a reduction in liver hydroxyproline; a reduction in alpha smooth muscle actin and p-P38 expression; a reduction in fibrillar collagen area and reduced synthesis of collagen. ASK1 inhibition also reduced hepatic fibrosis, steatosis and insulin resistance and normalised fatty acid synthesis and lipid metabolism.

In some embodiments, the fibrotic condition is a fibrotic condition of the lung. Lung or pulmonary fibrosis refers to a number of conditions that cause interstitial lung damage, followed by accumulation of extracellular matrix constituents and eventually loss of lung elasticity and function. These conditions lead to symptoms such as persistent coughing, chest pain, difficulty breathing and fatigue. Lung fibrosis may occur as a secondary condition in various diseases.

In some embodiments, the fibrotic condition is a fibrotic condition of the heart. Cardiac fibrosis refers to the damage of the heart areas due to myocardial infarction or Davies' disease. Cardiac fibrosis can affect the valves in the heart as well as the muscles, which become stiff and less compliant. This can increase the risk of heart failure.

In some embodiments, the fibrotic condition is a fibrotic condition of the kidney. Kidney fibrosis refers to an excessive accumulation of extracellular matrix that occurs in virtually every type of chronic kidney disease. The pathogenesis of renal fibrosis is a progressive process that ultimately leads to end-stage renal failure, a devastating disorder that requires dialysis or kidney transplantation. Several cellular pathways, including mesangial and fibroblast activation as well as tubular epithelial-mesenchymal transition, have been identified as the major ways for the generation of the matrix-producing cells in diseased conditions. Among many fibrogenic factors that regulate renal fibrotic process, transforming growth factor-beta (TGF-beta) is one that plays a central role. Although defective matrix degradation may contribute to tissue scarring, the exact action and mechanisms of the matrix-degrading enzymes in the injured kidney have become increasingly complicated.

In some embodiments, the fibrotic condition is a fibrotic condition of the skin.

In some embodiments, the fibrotic condition is a fibrotic condition of the eye.

In some embodiments, the fibrotic condition is a fibrotic condition of the gastrointestinal tract.

In some embodiments, the fibrotic condition is a fibrotic condition of the bone marrow.

In some embodiments, the fibrotic condition is idiopathic. In some embodiments, the fibrotic condition is associated with (e.g., is secondary to) a disease (e.g., an infectious disease, an inflammatory disease, an autoimmune disease, a malignant or cancerous disease, and/or a connective disease); a toxin; an insult (e.g., an environmental hazard (e.g., asbestos, coal dust, polycyclic aromatic hydrocarbons), cigarette smoking, a wound); a medical treatment (e.g., surgical incision, chemotherapy or radiation), or a combination thereof.

In some embodiments, disclosed herein is a method for the treatment or prevention of fibrosis in a mammal comprising administering an ASK1 inhibitor described herein, or a pharmaceutically acceptable salt thereof, to the mammal in need thereof.

In some embodiments, disclosed herein is a method of improving lung function in a mammal comprising administering an ASK1 inhibitor described herein, or a pharmaceutically acceptable salt thereof, to the mammal in need thereof. In some embodiments, the mammal has been diagnosed as having lung fibrosis.

In some embodiments, disclosed herein is a method of treating idopathic pulmonary fibrosis in a mammal comprising administering an ASK1 inhibitor described herein, or a pharmaceutically acceptable salt thereof, to the mammal in need thereof.

In some embodiments, disclosed herein is a method of controlling an abnormal accumulation or activation of cells, fibronectin, collagen or increased fibroblast recruitment in a tissue of a mammal comprising administering an ASK1 inhibitor described herein, or a pharmaceutically acceptable salt thereof, to the mammal in need thereof. In some embodiments, the abnormal accumulation or activation of cells, fibronectin, collagen or increased fibroblast recruitment in the tissue results in fibrosis.

In some embodiments, disclosed herein is a method for the treatment or prevention of scleroderma in a mammal comprising administering an ASK1 inhibitor described herein, or a pharmaceutically acceptable salt thereof, to the mammal in need thereof.

In some embodiments, disclosed herein is a method for reducing undesired or abnormal dermal thickening in a mammal comprising administering to mammal in need thereof an ASK1 inhibitor described herein, or a pharmaceutically acceptable salt thereof. In some embodiments, the dermal thickening is associated with scleroderma.

In some embodiments, described herein is a method of controlling an abnormal accumulation or activation of cells, fibronectin, collagen or increased fibroblast recruitment in tissues of a mammal comprising administering to mammal in need thereof an ASK1 inhibitor described herein, or a pharmaceutically acceptable salt thereof. In some embodiments, the abnormal accumulation or activation of cells, fibronectin, collagen or increased fibroblast recruitment in the dermal tissues results in fibrosis. In some embodiments, described herein is a method of reducing hydroxyproline content in tissues of a mammal with fibrosis comprising administering to mammal in need thereof an ASK1 inhibitor described herein, or a pharmaceutically acceptable salt thereof.

In some embodiments, compounds described herein are used in the treatment of fibrosis associated with arthrofibrosis, Crohn's Disease, Dupuytren's contracture, keloids, myelofibrosis, peyronie's disease, or scleroderma/systemic sclerosis.

In some embodiments, anti-fibrotic strategies include (i) removing the injurious stimuli, (ii) suppressing or modulating inflammation, (iii) protecting the organ at risk of developing fibrosis, and (v) promoting matrix degradation. Some of these strategies have direct effect on fibrosis pathway, while others may have indirect effect. In some embodiments, anti-fibrotic strategies in NASH include (a) removing the injurious stimuli, (b) suppressing or modulating hepatic inflammation, (c) protecting the liver, (d) downregulating stellate cell activation and (e) promoting matrix degradation.

Fibrosis, such as hepatic fibrosis in NASH, is driven by multiple risk factors that may interact with each other via several inter-related mechanistic pathways. It is plausible that the injurious stimuli may be heterogenous, but the resultant response in laying down of collagen and worsening of fibrosis may be a common response. In some embodiments, multiple targets may be required to reverse or halt fibrosis. Removal of cause would be the most efficient way to improve fibrosis. This has been supported by observations seen with other chronic diseases, including hepatitis C and B.

In some embodiments, compounds described herein are dual inhibitors and inhibit the activity of ASK1 and at least one other fibrosis promoting protein. In some embodiments, compounds described herein inhibit the activity of ASK1 and LOXL2.

Lysyl oxidase like-2 (LOXL2) is a member of the lysyl oxidase (LOX) family, which comprises $Cu^{2+}$ and lysine tyrosylquinone (LTQ)-dependent amine oxidases. The family comprises five genes: lox (LOX), loxl1 (lysyl oxidase like-1, LOXL1), loxl2 (LOXL2), loxl3 (lysyl oxidase like-3, LOXL3), and loxl4 (lysyl oxidase like-4, LOXL4). The LOX family is known for catalyzing the oxidative deamination of the ε-amino group of lysines and hydroxylysines in collagen and elastin to promote crosslinking of these molecules. Crosslinking of collagen and elastin is essential for maintaining tensile strength of the extracellular matrix.

LOXL2 has been demonstrated to have intracellular functions aside from its role in remodeling of the extracellular matrix. LOXL2 positively regulates the epithelial-to-mesenchymal transition (EMT) transducer, Snail1, by promoting Snail1 stability and functional activity. LOXL2 contributes positively to the activation of the focal adhesion kinase (FAK) signaling pathway and participates in the organization of focal adhesion complexes. Silencing of LOXL2 gene leads to reacquisition of epithelial cell polarity and decreases the migratory and invasive ability of mammary cell lines. The modulation of cell adhesion and cell polarity has been reported to be mediated by intracellular LOXL2. LOXL2 transcriptionally represses E-cadherin as well as tight junction and cell polarity genes by Snail1-dependent and Snail1-independent mechanisms. LOXL2 has been more recently described to be associated with chromatin and reported to be involved in histone H3 deamination, a function that is dependent on the LOXL2 catalytic domain.

LOXL2 has been shown to be involved in fibrotic processes. Fibrotic processes include an excessive deposition of extracellular matrix components, such as collagen, which alters the physical, biochemical and biomechanical matrix properties leading to defective organ function and organ failure. Tissue fibrosis is also associated with cancer progression by direct promotion of cellular transformation and metastasis. Tumors are typically stiffer than normal tissue and tumor rigidity influences tumor metastasis.

Excessive LOXL2 enzyme activity has been implicated in the increased stiffness of tumors. Elevated LOXL2 is also associated with fibrotic lesions from livers of patients suffering from diseases or conditions such as, but not limited to, Wilson disease, primary biliary cirrhosis, PSC, NAFLD and NASH. Additionally, the administration of a LOXL2-specific monoclonal antibody AB0023 was efficacious in reducing disease in a model of fibrosis. AB0023 was shown to inhibit the production of growth factors and of crosslinked collagenous matrix and TGF-beta signaling.

Cardiovascular diseases. Cardiovascular diseases include, but are not limited to, ischaemia/reperfusion injury, cardiac remodelling, and vascular endothelial dysfunction.

In some embodiments, compounds described herein are used in the treatment of diseases of the retina.

In some embodiments, compounds described herein are used in the treatment of diseases of the spinal cord.

During myocardial infarction, some cardiomyocytes undergo necrosis due to a shortage of oxygen and nutrition, which causes low cardiac output. To compensate for this loss of cardiac function, surviving cardiomyocytes undergo changes in size and location, which is referred to as cardiac hypertrophy. Sustained hypertension and diabetic cardiomyopathy can also induce cardiac hypertrophy. In ventricular hypertrophy, gene reprogramming and accumulation of extracellular matrix proteins are involved in ventricular fibrosis and remodelling. In some embodiments, ASK1 plays a role in the pathogenesis of ventricular remodelling by promoting apoptosis or cardiomyocyte hypertrophy. In some other embodiments, ASK1 is aldosterone-induced cardiac inflammation and fibrosis through induction of monocyte chemoattractant protein (MCP)-1 and transforming growth factor (TGF)-β1 expression, respectively.

In some embodiments, compounds described herein are used in the treatment of neurodegenerative disorders. Neurodegenerative disorders include, but are not limited to, Huntington's disease (HD), spinobulbar muscular atrophy, spinocerebeller ataxia (SCA), Amyotrophic lateral sclerosis (ALS), Alzheimer's disease, Parkinson's disease, Normal-tension glaucoma.

In some embodiments, compounds described herein are used in the treatment of inflammatory diseases. Inflammatory diseases include, but are not limited to, multiple sclerosis, rheumatoid arthritis.

In some embodiments, compounds described herein are used in the treatment of respiratory diseases. ASK1 also plays a role in airway remodelling, an irreversible hypertrophic change that occurs in chronic bronchitis. Leukotriene D4 has been suggested to activate ASK1 and induce AP-1 activation in airway smooth muscle cells, leading to airway remodelling. Respiratory diseases include, but are not limited to, chronic obstructive pulmonary disease (COPD), asthmas and acute lung injury.

In some embodiments, compounds described herein are used in the treatment of diabetes. TNFα is one of the factors that aggravate insulin resistance. In hepatocytes, TNFα induces ROS production in the mitochondria and activates JNK via ASK1, which leads to insulin receptor substrate-1 (IRS-1) serine phosphorylation. Such phosphorylation decreases tyrosine phosphorylation of IRS-1 resulting in insulin resistance and eventually causing type 2 diabetes.

In some embodiments, compounds described herein are used in the treatment of liver linjury. Consumption of large quantities of acetaminophen, a widely used analgesic and antipyretic agent, is known to cause liver injury. In ASK1-deficient mice, acetaminophen-induced, sustained activation of JNK is suppressed and resistance to liver injury increased, indicating that the ASK1-JNK pathway plays a critical role in acetaminophen-induced liver injury. ASK1 has also been reported to be involved in liver injury induced by troglitazone, a first-generation thiazolidinedione insulin sensitizer that has been linked to an unacceptable risk of liver injury in patients.

In some embodiments, compounds described herein are used in the treatment of ageing. ROS is thought to be one of the major causes of ageing. Consistent with this notion, long-lived mouse models, such as Snell dwarf mice, Ames dwarf mice, and Klotho overexpressing mice, are known to be resistant to oxidative stress. Mouse embryonic fibroblasts (MEFs) derived from Ames dwarf mice possess a larger amount of the Trx-bound form of ASK1 and have less p38 activity than those derived from WT mice, suggesting that activity of the ASK1-p38 pathway is attenuated in Ames dwarf mice. Also, in the livers of Klotho overexpressing mice, the activity of the ASK1-p38 pathway and the amount of Trx-bound ASK1 are decreased and increased, respectively, whereas the opposite is observed in liver extracts from Klotho-deficient mice. In some embodiments, ROS-induced ASK1 activity contributes to regulation of ageing-related cellular functions.

Compounds

Compounds described herein, including pharmaceutically acceptable salts, prodrugs, active metabolites and pharmaceutically acceptable solvates thereof, are ASK1 inhibitors.

In one aspect, described herein is a compound of Formula (I), or a pharmaceutically acceptable salt thereof.

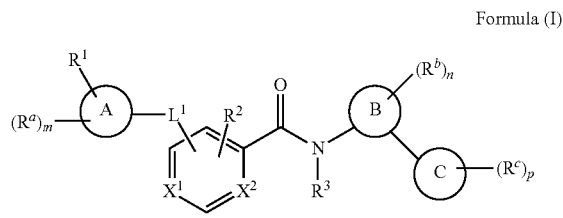

Formula (I)

wherein, ring A is a phenyl, 6-membered heteroaryl, or a 5-membered heteroaryl;

each $R^a$ is independently H, D, halogen, —CN, —OR$^5$, —SR$^5$, —S(=O)R$^4$, —S(=O)$_2$R$^4$, —S(=O)$_2$N(R$^5$)$_2$, —NR$^5$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —C(=O)N(R$^5$)$_2$, —NR$^5$C(=O)R$^4$, —NR$^5$C(=O)OR$^4$, —NR$^5$C(=O)N(R$^5$)$_2$, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, or substituted or unsubstituted $C_3$-$C_6$cycloalkyl;

m is 0, 1, 2, or 3;

$R^1$ is H, D, halogen, —CN, —OR$^5$, —SR$^5$, —S(=O)R$^4$, —S(=O)$_2$R$^4$, —N(R$^5$)$_2$, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, or substituted or unsubstituted —$C_1$-$C_4$alkylene-N(R$^5$)$_2$;

$L^1$ is linker that is —X$^2$—, L$^2$, -L$^2$-X$^2$—, —X$^2$-L$^3$-, or -L$^2$-X$^2$-L$^3$-.

$X^2$ is —O—, —S—, —S(=O)—, —S(=O)$_2$—, —S(=O)$_2$NR$^6$—, —C(=O)—, —C(=O)O—, —C(=O)NR$^6$—, —OC(=O)NR$^6$—, —NR$^6$C(=O)O—, —NR$^6$C(=O)NR$^6$—, —OC(=O)—, —NR$^6$C(=O)—, —NR$^6$S(=O)$_2$—, or —NR$^6$—.

$R^6$ is H, $C_1$-$C_6$alkyl, $C_1$-$C_6$fluoroalkyl, or $C_1$-$C_6$deuteroalkyl;

$L^2$ is substituted or unsubstituted $C_1$-$C_4$alkylene, substituted or unsubstituted $C_2$-$C_4$alkenylene or substituted or unsubstituted $C_2$-$C_4$alkynylene;

$L^3$ is $C_1$-$C_4$alkylene;

$X^1$ is CR$^2$ or N;

$X^2$ is CR$^2$ or N;

each $R^2$ is independently H, D, halogen, —CN, —OR$^5$, —SR$^5$, —S(=O)R$^4$, —S(=O)$_2$R$^4$, —N(R$^5$)$_2$, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, substituted or unsubstituted $C_3$-$C_6$cycloalkyl;

$R^3$ is H, substituted or unsubstituted $C_1$-$C_6$alkyl, substituted or unsubstituted $C_1$-$C_6$fluoroalkyl, or substituted or unsubstituted $C_1$-$C_6$deuteroalkyl;

ring B is a 6-membered heteroaryl, phenyl, or a 5-membered heteroaryl;

each $R^b$ is independently H, D, halogen, —CN, —OR$^5$, —SR$^5$, —S(=O)R$^4$, —S(=O)$_2$R$^4$, —S(=O)$_2$N(R$^5$)$_2$, —NR$^5$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —NR$^5$C(=O)R$^4$, —NR$^2$C(=O)OR$^4$, —C(=O)N(R$^5$)$_2$, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, or substituted or unsubstituted $C_3$-$C_6$cycloalkyl;

n is 0, 1, 2, 3, or 4;

ring C is a 5-membered heteroaryl;

each $R^c$ is independently H, D, halogen, —CN, —OR$^5$, —SR$^5$, —S(=O)R$^4$, —S(=O)$_2$R$^4$, —S(=O)$_2$N(R$^5$)$_2$, —NR$^5$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —NR$^5$C(=O)R$^4$, —NR$^5$C(=O)OR$^4$, —C(=O)N(R$^5$)$_2$, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, or substituted or unsubstituted $C_3$-$C_6$cycloalkyl;

p is 0, 1, 2, or 3;

each $R^4$ is independently selected from $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted benzyl and substituted or unsubstituted heteroaryl;

each $R^5$ is independently selected from H, $C_1$-$C_6$alkyl, $C_1$-$C_6$fluoroalkyl, $C_1$-$C_6$deuteroalkyl, $C_1$-$C_6$heteroalkyl, substituted or unsubstituted $C_3$-$C_{10}$cycloalkyl, substituted or unsubstituted $C_2$-$C_{10}$heterocycloalkyl, substituted or unsubstituted aryl, substituted or unsubstituted benzyl and substituted or unsubstituted heteroaryl; or two $R^5$ on the same N atom are taken together with the N atom to which they are attached to a substituted or unsubstituted N-containing heterocycle.

For any and all of the embodiments, substituents are selected from among a subset of the listed alternatives. For example, in some embodiments m is 0, 1, 2, or 3. In other embodiments, m is 0, 1, or 2. In some embodiments, m is 0 or 1.

In some embodiments, p is 0, 1, 2, or 3. In other embodiments, p is 1, 2, or 3. In some embodiments, p is 1 or 2. In some embodiments, p is 1. In some embodiments, p is 2.

In some embodiments, n is 0, 1, 2, or 3. In other embodiments, n is 0, 1, or 2. In some embodiments, n is 0 or 1. In some embodiments, n is 0.

In some embodiments, ring A is phenyl, a 6-membered heteroaryl containing 1-3 N-atoms, a 5-membered heteroaryl containing 1-4 N atoms, 0-1 O atoms, and 0-1 S atoms, or a 5-membered heteroaryl containing 0-4 N atoms and 1 O or S atom.

In some embodiments, ring A is phenyl, pyridinyl, pyrimidinyl, pyrazinyl, pyridazinyl, or triazinyl.

In some embodiments,

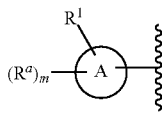

is

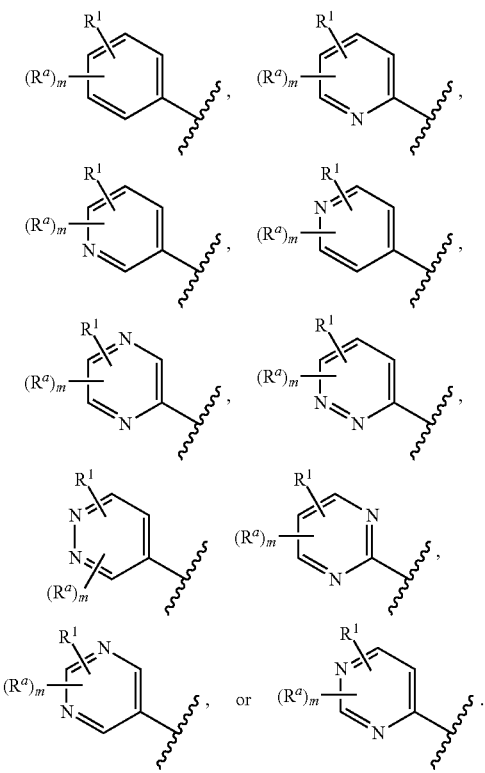

In some embodiments,

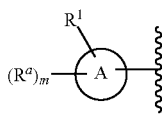

is

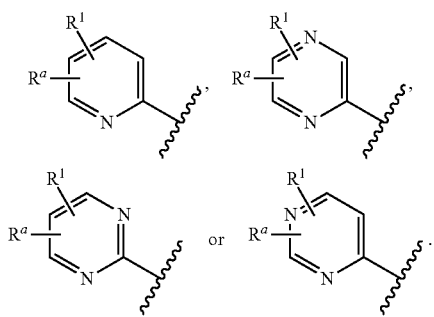

In some embodiments,

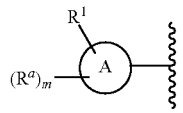

is

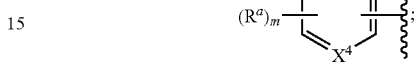

$X^4$ is N or $CR^a$; $X^5$ is N or $CR^a$; $X^6$ is N or $CR^a$.

In some embodiments, ring A is triazolyl, imidazolyl, pyrazolyl, tetrazolyl, furyl, thienyl, isoxazolyl, thiazolyl, oxazolyl, isothiazolyl, pyrrolyl, oxadiazolyl, thiadiazolyl, or furazanyl.

In some embodiments, each $R^a$ is independently selected from the group consisting of H, D, F, Cl, Br, —CN, —OH, —OCH$_3$, —OCF$_3$, —CH$_3$, —CH$_2$F, —CHF$_2$, —CF$_3$, —CD$_3$, —OCD$_3$, cyclopropyl, cyclobutyl, cyclopentyl, and cyclohexyl.

In some embodiments, each $R^a$ is independently selected from the group consisting of H, D, F, Cl, Br, —CN, —OH, —OCH$_3$, —OCF$_3$, —CH$_3$, —CH$_2$F, —CHF$_2$, —CF$_3$, —CD$_3$, and —OCD$_3$.

In some embodiments, $R^1$ is H, D, F, Cl, Br, —CN, —OH, —OCH$_3$, —OCH$_2$CH$_3$, —OCF$_3$, —OCH$_2$CF$_3$, —CH$_3$, —CH$_2$CH$_3$, —CH$_2$F, —CHF$_2$, —CF$_3$, —CH$_2$CH$_2$F, —CH$_2$CHF$_2$, —CH$_2$CF$_3$, —CD$_3$, —OCD$_3$, —CH$_2$NH$_2$, CD$_2$NH$_2$, or CF$_2$NH$_2$. In some embodiments, $R^1$ is H or CF$_2$NH$_2$. In some embodiments, $R^1$ is —CH$_2$NH$_2$.

In some embodiments, each $R^2$ is independently H, D, halogen, —CN, —OR$^5$, —N(R$^5$)$_2$, C$_1$-C$_6$alkyl, C$_1$-C$_6$fluoroalkyl, C$_1$-C$_6$deuteroalkyl, C$_1$-C$_6$heteroalkyl, or C$_3$-C$_6$cycloalkyl.

In some embodiments, each $R^2$ is independently H, D, F, Cl, —CN, —OH, —OCH$_3$, —OCH$_2$CH$_3$, —OCF$_3$, —NH$_2$, —NHCH$_3$, —N(CH$_3$)$_2$, —CH$_3$, —CH$_2$CH$_3$, —CH$_2$F, —CHF$_2$, —CF$_3$, —CD$_3$, —OCD$_3$, cyclopropyl, cyclobutyl, cyclopentyl, or cyclohexyl. In some embodiments, each $R^2$ is independently H, D, F, Cl, —CN, —OH, —OCH$_3$, —OCH$_2$CH$_3$, —OCF$_3$, —NH$_2$, —NHCH$_3$, —N(CH$_3$)$_2$, —CH$_3$, —CH$_2$CH$_3$, —CH$_2$F, —CHF$_2$, —CF$_3$, —CD$_3$, or —OCD$_3$. In some embodiments, each $R^2$ is independently H, D, F, Cl, —CH$_3$, —CF$_3$, or -CD$_3$. In some embodiments, each $R^2$ is independently H, F, or —CH$_3$.

In some embodiments, $R^3$ is H or C$_1$-C$_6$alkyl. In some embodiments, $R^3$ is H or —CH$_3$. In some embodiments, $R^3$ is H.

In some embodiments, each $R^4$ is independently selected from C$_1$-C$_6$alkyl, C$_1$-C$_6$fluoroalkyl, C$_1$-C$_6$deuteroalkyl, C$_1$-C$_6$heteroalkyl, substituted or unsubstituted monocyclic C$_3$-C$_6$cycloalkyl, substituted or unsubstituted monocyclic C$_2$-C$_6$heterocycloalkyl, substituted or unsubstituted phenyl, substituted or unsubstituted benzyl and substituted or unsubstituted monocyclic heteroaryl. In some embodiments, each $R^4$ is independently selected from C$_1$-C$_6$alkyl, C$_1$-C$_6$heteroalkyl, substituted or unsubstituted monocyclic C$_3$-C$_6$cycloalkyl, substituted or unsubstituted monocyclic C$_2$-C$_6$heterocycloalkyl, substituted or unsubstituted phenyl, substituted or unsubstituted benzyl and substituted or unsubstituted monocyclic heteroaryl.

In some embodiments, each $R^5$ is independently selected from H, $C_1$-$C_6$alkyl, $C_1$-$C_6$fluoroalkyl, $C_1$-$C_6$deuteroalkyl, $C_1$-$C_6$heteroalkyl, substituted or unsubstituted monocyclic $C_3$-$C_6$cycloalkyl, substituted or unsubstituted monocyclic $C_2$-$C_6$heterocycloalkyl, substituted or unsubstituted phenyl, substituted or unsubstituted benzyl and substituted or unsubstituted monocyclic heteroaryl; or two $R^5$ on the same N atom are taken together with the N atom to which they are attached to a substituted or unsubstituted N-containing monocyclic heterocycle. In some embodiments, each $R^5$ is independently selected from H, $C_1$-$C_6$alkyl, $C_1$-$C_6$heteroalkyl, substituted or unsubstituted monocyclic $C_3$-$C_6$cycloalkyl, substituted or unsubstituted monocyclic $C_2$-$C_6$heterocycloalkyl, substituted or unsubstituted phenyl, substituted or unsubstituted benzyl and substituted or unsubstituted monocyclic heteroaryl; or two $R^5$ on the same N atom are taken together with the N atom to which they are attached to a substituted or unsubstituted N-containing monocyclic heterocycle.

In some embodiments, each $R^b$ is independently H, D, halogen, —CN, —$OR^5$, —$SR^5$, $C_1$-$C_6$alkyl, $C_1$-$C_6$fluoroalkyl, $C_1$-$C_6$deuteroalkyl, $C_1$-$C_6$heteroalkyl, or $C_3$-$C_6$cycloalkyl. In some embodiments, each $R^b$ is independently H, D, F, Cl, Br, —CN, —OH, —$OCH_3$, —$OCF_3$, —$CH_3$, —$CH_2F$, —$CHF_2$, —$CF_3$, —$CD_3$, or —$OCD_3$. In some embodiments, each $R^b$ is independently H, D, F, Cl, —CN, —OH, —$OCH_3$, —$OCF_3$, —$CH_3$, —$CH_2F$, —$CHF_2$, —$CF_3$, —$CD_3$, or —$OCD_3$. In some embodiments, each $R^b$ is independently H, D, F, —OH, —$OCH_3$, or —$CH_3$. In some embodiments, each $R^b$ is H.

In some embodiments, each $R^c$ is independently H, D, halogen, substituted or unsubstituted $C_1$-$C_6$alkyl, substituted or unsubstituted $C_1$-$C_6$fluoroalkyl, substituted or unsubstituted $C_1$-$C_6$deuteroalkyl, substituted or unsubstituted $C_1$-$C_6$heteroalkyl, or substituted or unsubstituted $C_3$-$C_6$cycloalkyl.

In some embodiments, each $R^c$ is independently H, D, F, Cl, —$CH_3$, —$CH_2CH_3$, —$CH_2CH_2CH_3$, —$CH(CH_3)_2$, —$CH(CD_3)_2$, —$CH(CF_3)_2$, —$CH(CH_2F)_2$, —$CH_2CH_2CH_2CH_3$, —$CH_2CH(CH_3)_2$, —$CH_2CH(CH_3)_2$, —$C(CH_3)_3$, —$CH(CH_2CH_3)_2$, —$CH(CH_3)(CH_2CH_3)$, —$CH_2OH$, —$CH(CH_2OH)_2$, —$CH(CH_3)(CH_2OH)$, —$CH(CH_3)(CH_2F)$, —$CH(CHF)_2$, —$CH(CH_2CF_3)_2$, —$CH_2OCH_3$, —$CH_2OCH_2CH_3$, —$CH_2CH_2OH$, —$CH_2CH_2OCH_3$, —$CH_2CH_2OCH_2CH_3$, —$CH_2NH_2$, —$CH_2NHCH_3$, —$CH_2N(CH_3)_2$, substituted or unsubstituted cyclopropyl, substituted or unsubstituted cyclobutyl, substituted or unsubstituted cyclopentyl, substituted or unsubstituted cyclohexyl. In some embodiments, each $R^c$ is independently H, D, F, Cl, —$CH_3$, —$CH_2CH_3$, —$CH(CH_3)_2$, —$CH(CD_3)_2$, —$CH(CF_3)_2$, —$CH(CH_2F)_2$, —$CH_2CH(CH_3)_2$, —$CH_2CH(CH_3)_2$, —$CH(CH_2CH_3)_2$, —$CH(CH_3)(CH_2CH_3)$, —$CH_2OH$, —$CH(CH_2OH)_2$, —$CH(CH_3)(CH_2OH)$, —$CH(CH_3)(CH_2F)$, —$CH(CH_2F)_2$, —$CH(CH_2CF_3)_2$, cyclopropyl, fluorocyclopropyl, deuterocyclopropyl, or hydroxycyclopropyl. In some embodiments, each $R^c$ is independently H, —$CH_3$, —$CH_2CH_3$, —$CH(CH_3)_2$, —$CH(CD_3)_2$, —$CH(CF_3)_2$, —$CH(CH_2F)_2$, —$CH_2CH(CH_3)_2$, —$CH_2CH(CH_3)_2$, —$CH_2CH_2CH_3$, —$CH(CH_3)(CH_2CH_3)$, —$CH_2OH$, —$CH(CH_2OH)_2$, —$CH(CH_3)(CH_2OH)$, —$CH(CH_3)(CH_2F)$, —$CH(CHF_2)_2$, —$CH(CH_2CF_3)_2$, cyclopropyl, fluorocyclopropyl, deuterocyclopropyl, or hydroxycyclopropyl. In some embodiments, each $R^c$ is independently —$CH(CH_3)_2$, —$CH(CD_3)_2$, —$CH(CF_3)_2$, —$CH(CH_2F)_2$, —$CH(CH_2CH_3)_2$, —$CH(CH_3)(CH_2CH_3)$, —$CH(CH_2OH)_2$, —$CH(CH_3)(CH_2OH)$, —$CH(CH_3)(CH_2F)$, or cyclopropyl. In some embodiments, each $R^c$ is independently —$CH(CH_3)_2$, or cyclopropyl.

In some embodiments, $L^2$ is —$CH_2$—, —CH=CH—, —C≡C—; $L^3$ is —$CH_2$—.

In some embodiments, $L^1$ is —$X^2$—, $L^2$, -$L^2$-$X^2$—, or —$X^2$-$L^3$-.

In some embodiments, $X^2$ is —O—, —S—, —S(=O)—, —S(=O)$_2$—, —C(=O)—, —C(=O)$NR^6$—, —$NR^6C(=O)$—, or —$NR^6$—.

In some embodiments, $X^2$ is —O—.

In some embodiments, $L^1$ is —O—, —O—$CH_2$—, —$CH_2$—, —CH=CH—, —C≡C—, —C(=O)—, —C(=O)$NHCH_2$—, —$NHC(=O)$—, —C(=O)$NH$—, or —$NHC(=O)CH_2$—. In some embodiments, $L^1$ is —O—.

In some embodiments, ring B is a 6-membered heteroaryl or phenyl.

In some embodiments, ring B is a pyridinyl, pyrimidinyl, pyrazinyl, pyridazinyl, or triazinyl.

In some embodiments, the groups

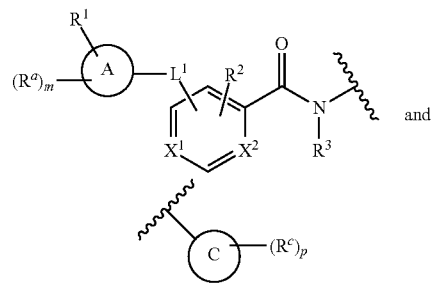

are in a 1,3-relationship or a 1,4-relationship on ring B. In some embodiments, the groups

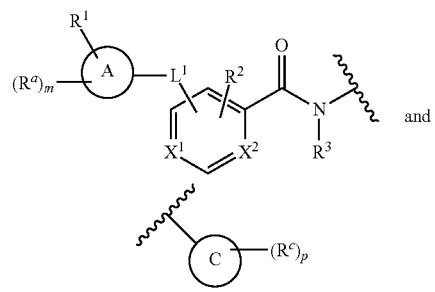

are in a 1,3-relationship on ring B.

In some embodiments,

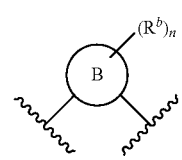

is

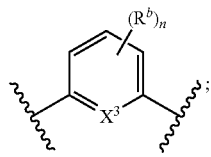

$X^3$ is N or $CR^b$. In some embodiments, $X^3$ is N. In some embodiments, $X^3$ is $CR^b$.

In some embodiments,

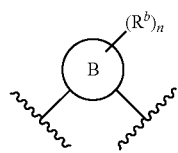

is

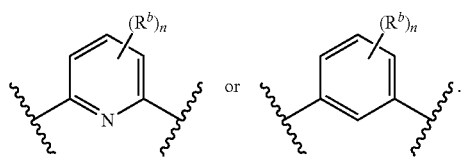

In some embodiments,

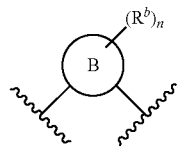

is

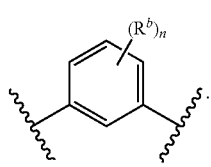

In some embodiments,

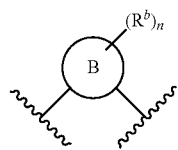

is

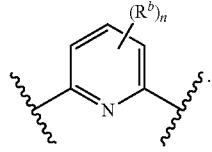

In some embodiments, the compound of Formula (I) has the following structure of Formula (II), or a pharmaceutically acceptable salt, or solvate thereof:

Formula (II)

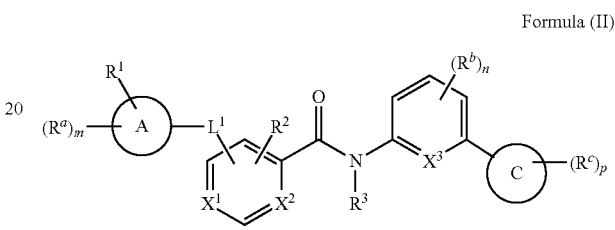

wherein, $X^3$ is N or $CR^b$.

In some embodiments, the compound of Formula (II) has one of the following structures, or a pharmaceutically acceptable salt, or solvate thereof:

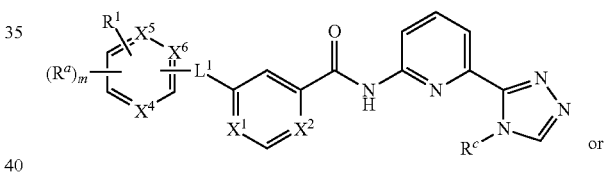

or

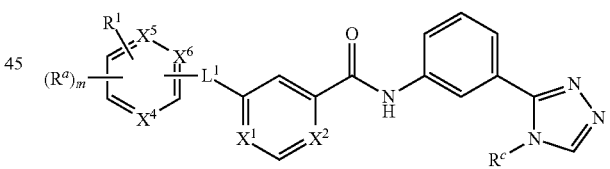

wherein, $X^4$ is N or $CR^a$; $X^5$ is N or $CR^a$; $X^6$ is N or $CR^a$.

In some embodiments, ring B is triazolyl, imidazolyl, pyrazolyl, tetrazolyl, furyl, thienyl, isoxazolyl, thiazolyl, oxazolyl, isothiazolyl, pyrrolyl, oxadiazolyl, thiadiazolyl, or furazanyl.

In some embodiments,

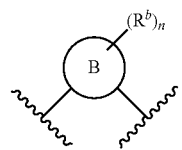

is
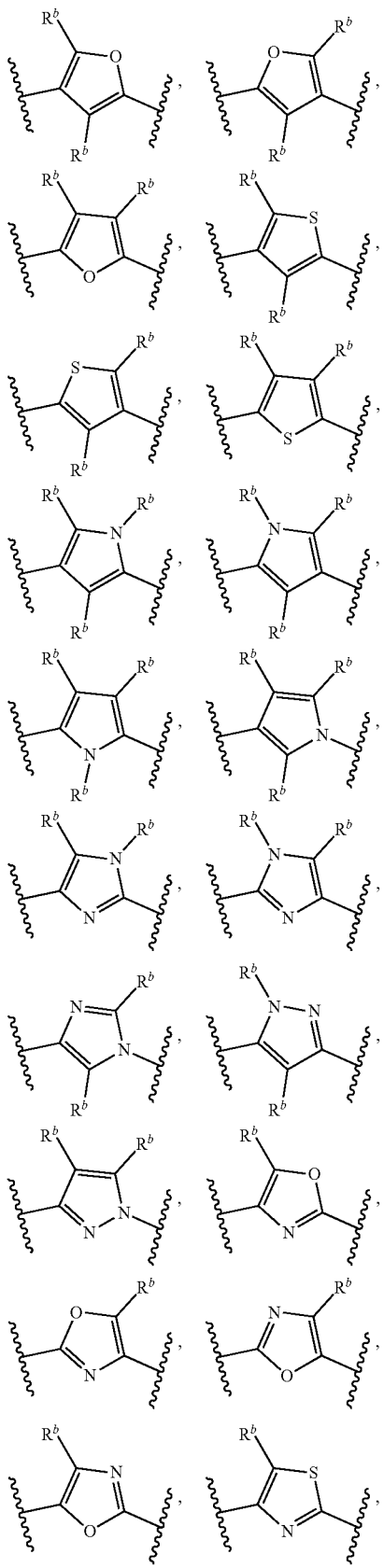
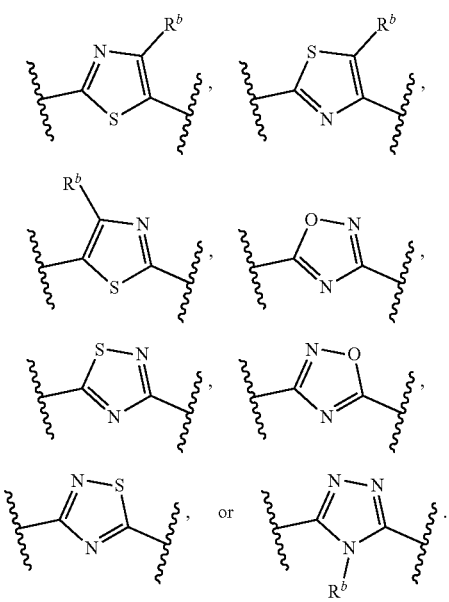
In some embodiments,
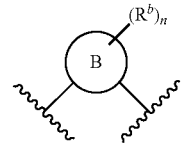
is
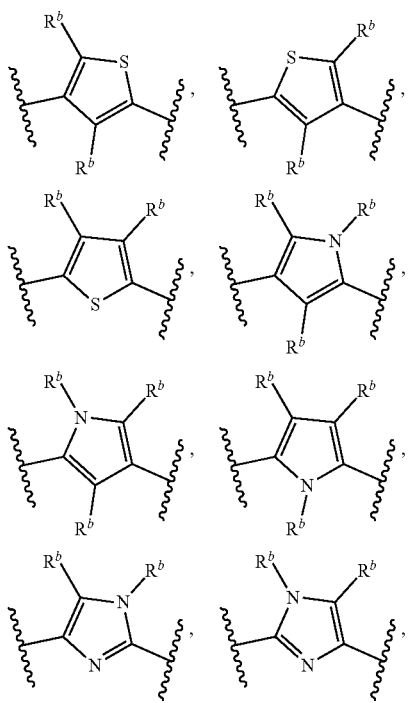

-continued

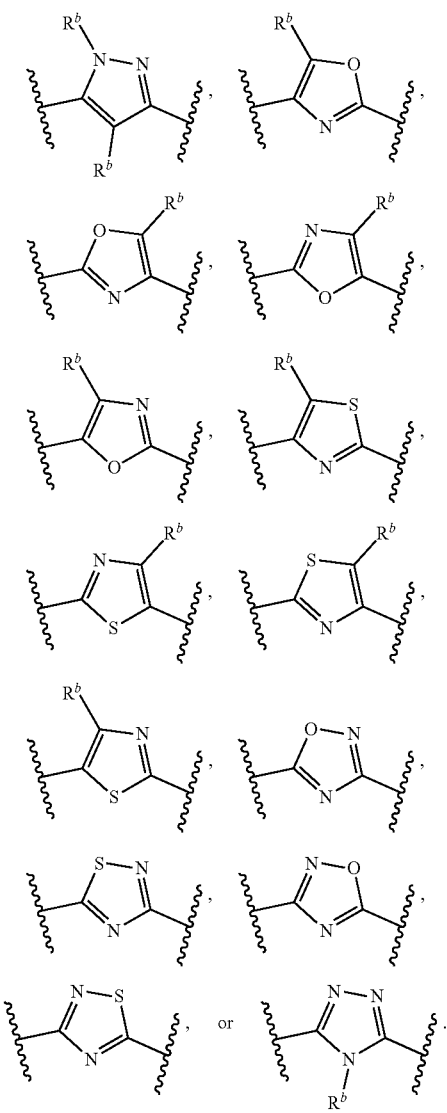

In some embodiments, ring C is a 5-membered heteroaryl containing 1-4 N atoms, 0-1 O atoms, and 0-1 S atoms, or a 5-membered heteroaryl containing 0-4 N atoms and 1 O or S atom.

In some embodiments, ring C is triazolyl, imidazolyl, pyrazolyl, tetrazolyl, furyl, thienyl, isoxazolyl, thiazolyl, oxazolyl, isothiazolyl, pyrrolyl, oxadiazolyl, thiadiazolyl, or furazanyl.

In some embodiments,

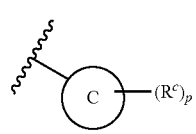

is

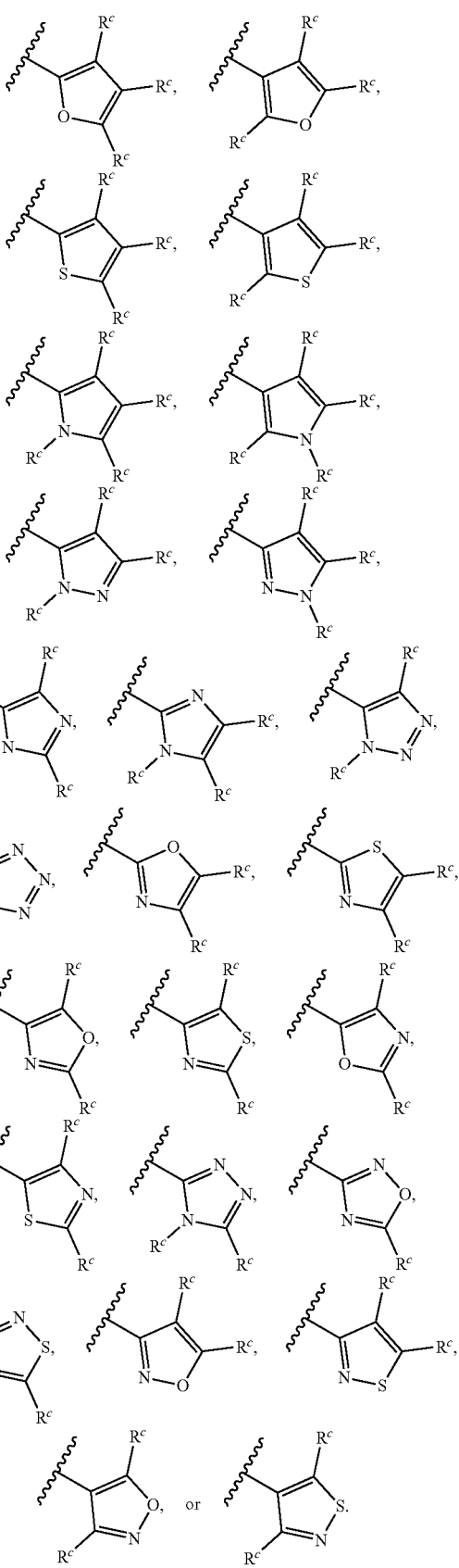

In some embodiments,

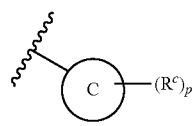

is

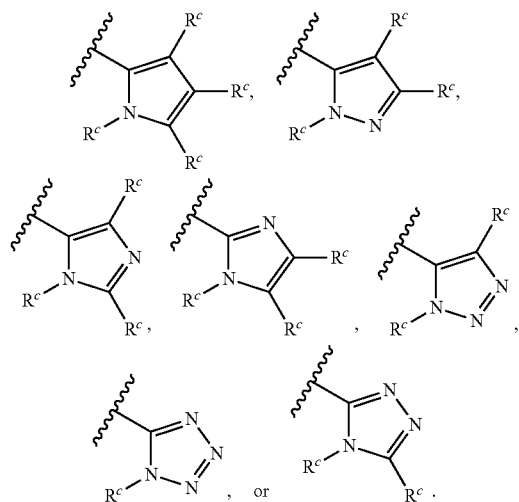

In some embodiments,

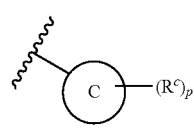

is

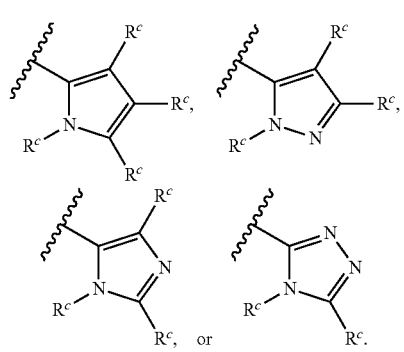

In some embodiments,

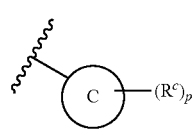

is

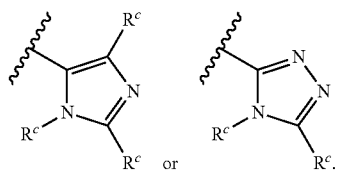

In some embodiments,

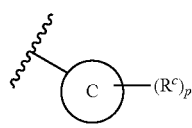

is

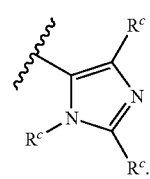

In some embodiments,

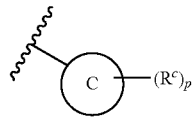

is

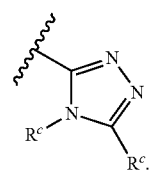

In some embodiments,

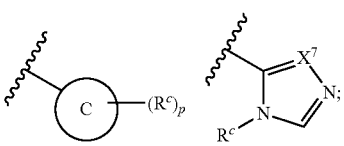

$X^7$ is N or $CR^c$.

In some embodiments, $X^7$ is N. In some embodiments, $X^7$ is $CR^c$.

In some embodiments, the compound of Formula (I) has the following structure of Formula (III), or a pharmaceutically acceptable salt, or solvate thereof:

Formula (III)

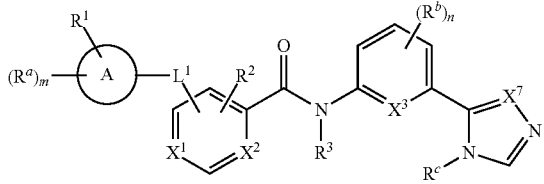

wherein,
X¹ is CR² or N;
X² is CR² or N;
X³ is N or CR$^b$; and
X⁷ is N or CR$^c$.

In one aspect, described herein is a compound that inhibits apoptosis signal-regulating kinase (ASK1) activity and lysyl oxidase like-2 (LOXL2) activity. In some embodiments, the compound is an aminoalkyl compound. In some embodiments, the compound is an aminomethyl compound. In some embodiments, the compound is an aminoalkylaryl or aminoalkylheteroaryl compound. In some embodiments, the compound is an aminomethylphenyl or aminomethylheteroaryl compound, where heteroaryl is ring A as described herein. In some embodiments, the compound has the structure of Formula (IV), or a pharmaceutically acceptable salt, or solvate thereof In some embodiments, described herein is a compound that has the structure of Formula (IV), or a pharmaceutically acceptable salt, or solvate thereof:

Formula (IV)

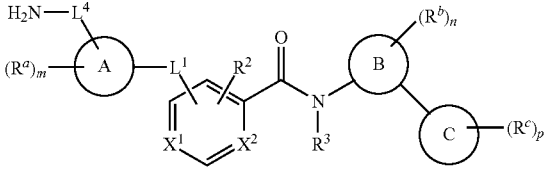

wherein,
ring A is a phenyl, 6-membered heteroaryl, or a 5-membered heteroaryl;
each R$^a$ is independently H, D, halogen, —CN, —OR⁵, —SR⁵, —S(═O)R⁴, —S(═O)₂R⁴, —S(═O)₂N(R⁵)₂, —NR⁵S(═O)₂R⁴, —C(═O)R⁴, —OC(═O)R⁴, —CO₂R⁵, —OCO₂R⁴, —N(R⁵)₂, —OC(═O)N(R⁵)₂, —C(═O)N(R⁵)₂, —NR⁵C(═O)R⁴, —NR⁵C(═O)OR⁴, —NR⁵C(═O)N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, substituted or unsubstituted C₃-C₆cycloalkyl;
m is 0, 1, 2, or 3;
L⁴ is C₁-C₄alkylene, C₁-C₄fluoroalkylene, or C₁-C₄deuteroalkylene;
L¹ is linker that is —X²—, L², -L²-X²—, —X²-L³-, or -L²-X²-L³-.
X² is —O—, —S—, —S(═O)—, —S(═O)₂—, —S(═O)₂NR⁶—, —C(═O)—, —C(═O)O—, —C(═O)NR⁶—, —OC(═O)NR⁶—, —NR⁶C(═O)O—, —NR⁶C(═O)NR⁶—, —OC(═O)—, —NR⁶C(═O)—, —NR⁶S(═O)₂—, or —NR⁶—;

R⁶ is H, C₁-C₆alkyl, C₁-C₆fluoroalkyl, or C₁-C₆deuteroalkyl;
L² is substituted or unsubstituted C₁-C₄alkylene, substituted or unsubstituted C₂-C₄alkenylene or substituted or unsubstituted C₂-C₄alkynylene;
L³ is C₁-C₄alkylene;
X¹ is CR² or N;
X² is CR² or N;
each R² is independently H, D, halogen, —CN, —OR⁵, —SR⁵, —S(═O)R⁴, —S(═O)₂R⁴, —N(R⁵)₂ substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, substituted or unsubstituted C₃-C₆cycloalkyl;
R³ is H, substituted or unsubstituted C₁-C₆alkyl, substituted or unsubstituted C₁-C₆fluoroalkyl, or substituted or unsubstituted C₁-C₆deuteroalkyl;
ring B is a 6-membered heteroaryl, phenyl, or a 5-membered heteroaryl;
each R$^b$ is independently H, D, halogen, —CN, —OR⁵, —SR⁵, —S(═O)R⁴, —S(═O)₂R⁴, —S(═O)₂N(R⁵)₂, —NR⁵S(═O)₂R⁴, —C(═O)R⁴, —OC(═O)R⁴, —CO₂R⁵, —OCO₂R⁴, —N(R⁵)₂, —OC(═O)N(R⁵)₂, —NR⁵C(═O)R⁴, —NR²C(═O)OR⁴, —C(═O)N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, substituted or unsubstituted C₃-C₆cycloalkyl;
n is 0, 1, 2, 3, or 4;
ring C is a 5-membered heteroaryl;
each R$^c$ is independently H, D, halogen, —CN, —OR⁵, —SR⁵, —S(═O)R⁴, —S(═O)₂R⁴, —S(═O)₂N(R⁵)₂, —NR⁵S(═O)₂R⁴, —C(═O)R⁴, —OC(═O)R⁴, —CO₂R⁵, —OCO₂R⁴, —N(R⁵)₂, —OC(═O)N(R⁵)₂, —NR⁵C(═O)R⁴, —NR⁵C(═O)OR⁴, —C(═O)N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, or substituted or unsubstituted C₃-C₆cycloalkyl;
p is 0, 1, 2, or 3;
each R⁴ is independently selected from C₁-C₆alkyl, C₁-C₆fluoroalkyl, C₁-C₆deuteroalkyl, C₁-C₆heteroalkyl, substituted or unsubstituted C₃-C₁₀cycloalkyl, substituted or unsubstituted C₂-C₁₀heterocycloalkyl, substituted or unsubstituted aryl, substituted or unsubstituted benzyl and substituted or unsubstituted heteroaryl;
each R⁵ is independently selected from H, C₁-C₆alkyl, C₁-C₆fluoroalkyl, C₁-C₆deuteroalkyl, C₁-C₆heteroalkyl, substituted or unsubstituted C₃-C₁₀cycloalkyl, substituted or unsubstituted C₂-C₁₀heterocycloalkyl, substituted or unsubstituted aryl, substituted or unsubstituted benzyl and substituted or unsubstituted heteroaryl; or two R⁵ on the same N atom are taken together with the N atom to which they are attached to a substituted or unsubstituted N-containing heterocycle.

In some embodiments, L⁴ is —CH₂—, —CH₂CH₂—, —CF₂—, or CD₂-. In some embodiments, L⁴ is —CH₂—, —CF₂—, or CD₂-. In some embodiments, L⁴ is —CH₂—.

In some embodiments, ring A is phenyl, a 6-membered heteroaryl containing 1-3 N-atoms, a 5-membered heteroaryl containing 1-4 N atoms, 0-1 O atoms, and 0-1 S atoms, or a 5-membered heteroaryl containing 0-4 N atoms and 1 O or S atom.

In some embodiments, ring A is phenyl, pyridinyl, pyrimidinyl, pyrazinyl, pyridazinyl, or triazinyl. In some embodiments, ring A is phenyl, pyridinyl, pyrimidinyl, pyrazinyl, or pyridazinyl. In some embodiments, ring A is phenyl, pyridinyl, or pyrimidinyl. In some embodiments, ring A is phenyl, or pyridinyl. In some embodiments, ring A is pyridinyl, pyrimidinyl, pyrazinyl, or pyridazinyl. In some embodiments, ring A is pyridinyl, pyrimidinyl, or pyrazinyl. In some embodiments, ring A is pyridinyl, or pyrimidinyl. In some embodiments, ring A is pyridinyl. In some embodiments, ring A is pyrimidinyl. In some embodiments, ring A is pyrazinyl. In some embodiments, ring A is pyridazinyl. In some embodiments, ring A is phenyl.

In some embodiments,

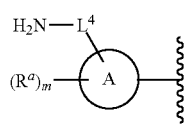

is

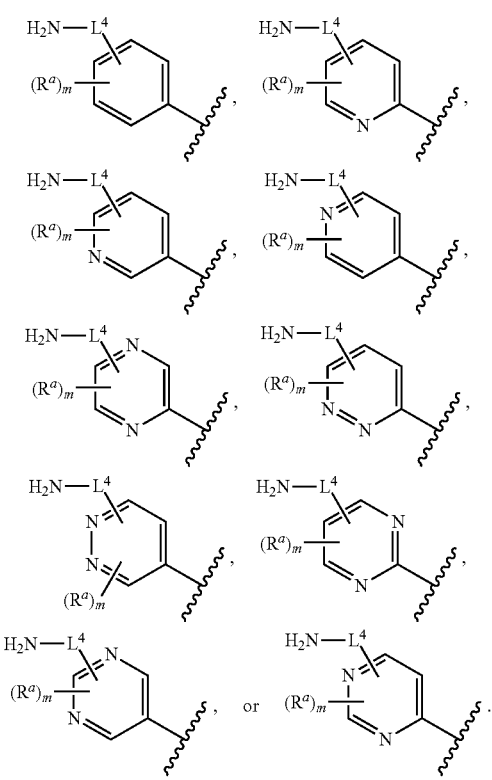

In some embodiments,

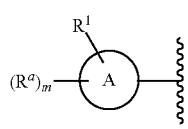

is

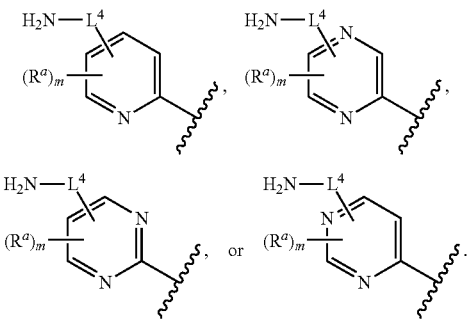

In some embodiments,

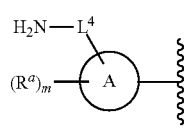

is

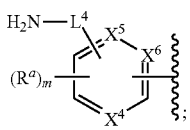

$X^4$ is N or $CR^a$; $X^5$ is N or $CR^a$; $X^6$ is N or $CR^a$.

In some embodiments, $X^4$ is N or $CR^a$; $X^5$ is $CR^a$; $X^6$ is $CR^a$. In some embodiments, $X^4$ is N; $X^5$ is $CR^a$; $X^6$ is $CR^a$. In some embodiments, $X^4$ is N; $X^5$ is N; $X^6$ is $CR^a$. In some embodiments, $X^4$ is N; $X^5$ is $CR^a$; $X^6$ is N. In some embodiments, $X^4$ is $CR^a$; $X^5$ is N; $X^6$ is N. In some embodiments, $X^4$ is N or $CR^a$; $X^5$ is N or $CR^a$; $X^6$ is N or $CR^a$. In some embodiments, $X^4$ is N or $CR^a$; $X^5$ is N or $CR^a$; $X^6$ is N or $CR^a$. In some embodiments, $X^4$ is N or $CR^a$; $X^5$ is N or $CR^a$; $X^6$ is N or $CR^a$. In some embodiments, $X^4$ is N or $CR^a$; $X^5$ is N or $CR^a$; $X^6$ is N or $CR^a$ In some embodiments, $X^4$ is N or $CR^a$; $X^5$ is N or $CR^a$; $X^6$ is N or $CR^a$.

In some embodiments, ring A is triazolyl, imidazolyl, pyrazolyl, tetrazolyl, furyl, thienyl, isoxazolyl, thiazolyl, oxazolyl, isothiazolyl, pyrrolyl, oxadiazolyl, thiadiazolyl, or furazanyl.

In some embodiments, the compound of Formula (IV) has one of the following structures, or a pharmaceutically acceptable salt, or solvate thereof:

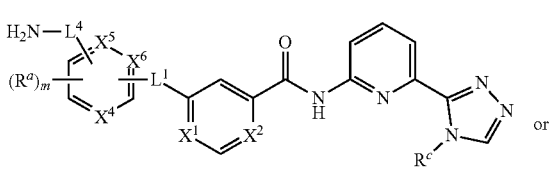

or

-continued

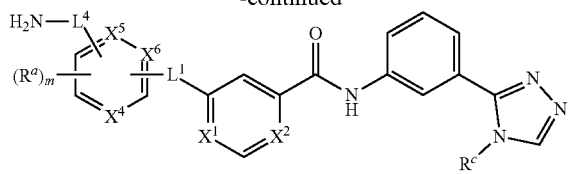

wherein, $X^4$ is N or $CR^a$; $X^5$ is N or $CR^a$; $X^6$ is N or $CR^a$.

In some embodiments, $R^c$, $X^2$, $X^1$, and $L^1$ are as described herein. In some embodiments, $R^c$, $X^2$, $X^1$, and $L^1$ are as described in Table 1 or Table 2. In some embodiments, $L^4$ is —CH$_2$—, —CH$_2$CH$_2$—, —CF$_2$—, or CD$_2$-. In some embodiments, $L^4$ is —CH$_2$—, —CF$_2$—, or CD$_2$-. In some embodiments, $L^4$ is —CH$_2$—.

In some embodiments, each $R^a$ is independently selected from the group consisting of H, D, F, Cl, Br, —CN, —OH, —OCH$_3$, —OCF$_3$, —CH$_3$, —CH$_2$F, —CHF$_2$, —CF$_3$, —CD$_3$, —OCD$_3$, cyclopropyl, cyclobutyl, cyclopentyl, and cyclohexyl. In some embodiments, each $R^a$ is independently selected from the group consisting of H and —CF$_3$. In some embodiments, $R^a$ is H or —CF$_3$.

In some embodiments, the compound of Formula (IV) has the following structure, or a pharmaceutically acceptable salt, or solvate thereof:

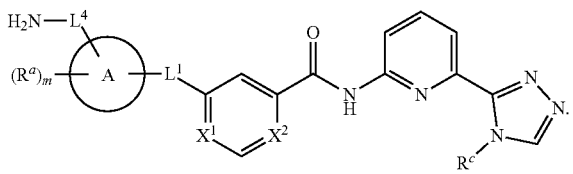

In some embodiments, $R^c$, $X^2$, $X^1$, and $L^1$ are as described herein. In some embodiments, $R^c$, $X^2$, $X^1$, and $L^1$ are as described in Table 1 or Table 2. In some embodiments, $L^4$ is —CH$_2$—, —CH$_2$CH$_2$—, —CF$_2$—, or CD$_2$-. In some embodiments, $L^4$ is —CH$_2$—, —CF$_2$—, or CD$_2$-. In some embodiments, $L^4$ is —CH$_2$—.

In some embodiments, the compound of Formula (IV) has the following structure, or a pharmaceutically acceptable salt, or solvate thereof:

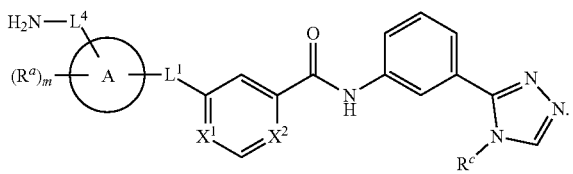

In some embodiments, $R^c$, $X^2$, $X^1$, and $L^1$ are as described herein. In some embodiments, $R^c$, $X^2$, $X^1$, and $L^1$ are as described in Table 1 or Table 2. In some embodiments, $L^4$ is —CH$_2$—, —CH$_2$CH$_2$—, —CF$_2$—, or CD$_2$-. In some embodiments, $L^4$ is —CH$_2$—, —CF$_2$—, or CD$_2$-. In some embodiments, $L^4$ is —CH$_2$—.

In some embodiments, the compound of Formula (I) has the following structure, or a pharmaceutically acceptable salt, or solvate thereof:

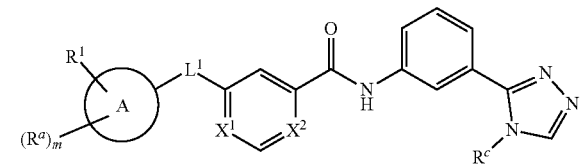

In some embodiments,

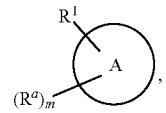

$R^c$, $X^2$, $X^1$, and $L^1$ are as described herein. In some embodiments,

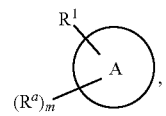

$R^c$, $X^2$, $X^1$, and $L^1$ are as described in Table 1 or Table 2.

In some embodiments, the compound of Formula (I) has the following structure, or a pharmaceutically acceptable salt, or solvate thereof:

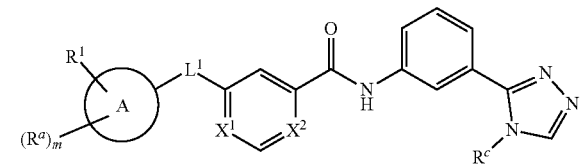

In some embodiments,

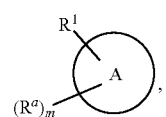

$R^c$, $X^2$, $X^1$, and $L^1$ are as described herein. In some embodiments

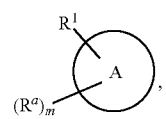

$R^c$, $X^2$, $X^1$, and $L^1$ are as described in Table 1 or Table 2.

Any combination of the groups described above for the various variables is contemplated herein. Throughout the specification, groups and substituents thereof are chosen by one skilled in the field to provide stable moieties and compounds.

Exemplary compounds described herein include the compounds described in the following Tables:

TABLE 1
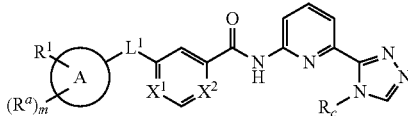
| Compound Number |  | L¹ | X¹ | X² | R^c |
|---|---|---|---|---|---|
| 1-1 |  | O | CH | CH |  |
| 1-2 |  | O | CH | CH |  |
| 1-3 |  | O | CH | CH |  |
| 1-4 |  | O | CH | CH |  |
| 1-5 |  | O | CH | CH |  |
| 1-6 |  | O | CH | CH |  |
| 1-7 |  | O | CH | CH |  |
| 1-8 |  | O | CH | CH |  |
| 1-9 |  | O | CH | CH |  |
| 1-10 |  | O | CH | CH | 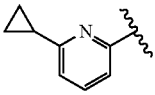 [SMILES: *c1cccc(C2CC2)n1] |
| 1-11 |  | O | CH | CH | 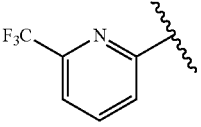 [SMILES: *c1cccc(C(F)(F)F)n1] |
| 1-12 |  | O | CH | CH | |

TABLE 1-continued

| Compound Number | (R¹)(Rᵃ)ₘ-A | L¹ | X¹ | X² | Rᶜ |
|---|---|---|---|---|---|
| 1-13 | 6-methoxypyridin-2-yl | O | CH | CH | isopropyl |
| 1-14 | 6-(pyrrolidin-1-yl)pyridin-2-yl | O | CH | CH | isopropyl |
| 1-15 | 6-(dimethylamino)pyridin-2-yl | O | CH | CH | isopropyl |
| 1-16 | 6-(dimethylamino)pyridin-3-yl | O | CH | CH | isopropyl |
| 1-17 | 5,6,7,8-tetrahydro-1,8-naphthyridin-2-yl | O | CH | CH | isopropyl |
| 1-18 | 6-carboxypyridin-2-yl | O | CH | CH | isopropyl |
| 1-19 | 5-cyclopropylpyridin-2-yl | O | CH | CH | isopropyl |
| 1-20 | 5-(trifluoromethyl)pyridin-2-yl | O | CH | CH | isopropyl |
| 1-21 | 5-methoxypyridin-2-yl | O | CH | CH | isopropyl |
| 1-22 | 5-carboxypyridin-2-yl | O | CH | CH | isopropyl |
| 1-23 | 4-cyano-6-(trifluoromethyl)pyridin-2-yl | O | CH | CH | isopropyl |

TABLE 1-continued

| Compound Number | ![A ring with R1 and (Ra)m] | L¹ | X¹ | X² | Rc |
|---|---|---|---|---|---|
| 1-24 | F₃C-pyridine-CO₂H | O | CH | CH | isopropyl |
| 1-25 | cyclopropyl-pyrimidine | O | CH | CH | isopropyl |
| 1-26 | F₃C-pyrimidine | O | CH | CH | isopropyl |
| 1-27 | MeO-pyrimidine | O | CH | CH | isopropyl |
| 1-28 | pyrrolidine-CH₂CH₂-pyrimidine | O | CH | CH | isopropyl |
| 1-29 | pyrrolidine-pyrimidine | O | CH | CH | isopropyl |
| 1-30 | HOOC-pyrimidine | O | CH | CH | isopropyl |
| 1-31 | cyclopropyl-pyrimidine | O | CH | CH | isopropyl |
| 1-32 | F₃C-pyrimidine | O | CH | CH | isopropyl |
| 1-33 | MeO-pyrimidine | O | CH | CH | isopropyl |
| 1-34 | pyrrolidine-CH₂-O-pyrimidine | O | CH | CH | isopropyl |

TABLE 1-continued

| Compound Number | (R^a)_m / A ring | L^1 | X^1 | X^2 | R^c |
|---|---|---|---|---|---|
| 1-35 | 2-(pyrrolidin-1-yl)pyrimidin-5-yl | O | CH | CH | isopropyl |
| 1-36 | 2-(carboxy)pyrimidin-5-yl (HOOC-) | O | CH | CH | isopropyl |
| 1-37 | phenyl | NH | CH | CH | isopropyl |
| 1-38 | pyridin-2-yl | NH | CH | CH | isopropyl |
| 1-39 | pyridin-3-yl | NH | CH | CH | isopropyl |
| 1-40 | pyridin-4-yl | NH | CH | CH | isopropyl |
| 1-41 | pyrimidin-4-yl | NH | CH | CH | isopropyl |
| 1-42 | pyrimidin-5-yl | NH | CH | CH | isopropyl |
| 1-43 | pyrimidin-2-yl | NH | CH | CH | isopropyl |
| 1-44 | pyrazin-2-yl | NH | CH | CH | isopropyl |
| 1-45 | pyridazin-3-yl | NH | CH | CH | isopropyl |
| 1-46 | pyridazin-4-yl | NH | CH | CH | isopropyl |

TABLE 1-continued

| Compound Number | (R^a)_m ⌬ A R^1 | L^1 | X^1 | X^2 | R^c |
|---|---|---|---|---|---|
| 1-47 | 2-cyclopropylpyridin-6-yl | NH | CH | CH | isopropyl |
| 1-48 | 2-(trifluoromethyl)pyridin-6-yl | NH | CH | CH | isopropyl |
| 1-49 | 2-methoxypyridin-6-yl | NH | CH | CH | isopropyl |
| 1-50 | 3-(pyrrolidin-1-yl)phenyl | NH | CH | CH | isopropyl |
| 1-51 | 1,2,3,4-tetrahydro-1,8-naphthyridin-7-yl | NH | CH | CH | isopropyl |
| 1-52 | 6-carboxypyridin-2-yl | NH | CH | CH | isopropyl |
| 1-53 | 5-cyclopropylpyridin-2-yl | NH | CH | CH | isopropyl |
| 1-54 | 5-(trifluoromethyl)pyridin-2-yl | NH | CH | CH | isopropyl |
| 1-55 | 5-methoxypyridin-2-yl | NH | CH | CH | isopropyl |
| 1-56 | 5-carboxypyridin-2-yl | NH | CH | CH | isopropyl |
| 1-57 | 2-cyclopropylpyrimidin-4-yl | NH | CH | CH | isopropyl |
| 1-58 | 2-(trifluoromethyl)pyrimidin-4-yl | NH | CH | CH | isopropyl |

TABLE 1-continued

| Compound Number | (R^a)_m [A with R^1] | L^1 | X^1 | X^2 | R^c |
|---|---|---|---|---|---|
| 1-59 | methoxy-pyrimidine | NH | CH | CH | isopropyl |
| 1-60 | pyrrolidinyl-methoxy-pyrimidine | NH | CH | CH | isopropyl |
| 1-61 | pyrrolidinyl-pyrimidine | NH | CH | CH | isopropyl |
| 1-62 | carboxy-pyrimidine | NH | CH | CH | isopropyl |
| 1-63 | cyclopropyl-pyrimidine | NH | CH | CH | isopropyl |
| 1-64 | trifluoromethyl-pyrimidine | NH | CH | CH | isopropyl |
| 1-65 | methoxy-pyrimidine | NH | CH | CH | isopropyl |
| 1-66 | pyrrolidinyl-methoxy-pyrimidine | NH | CH | CH | isopropyl |
| 1-67 | pyrrolidinyl-pyrimidine | NH | CH | CH | isopropyl |
| 1-68 | carboxy-pyrimidine | NH | CH | CH | isopropyl |
| 1-69 | pyrrole | NH | CH | CH | isopropyl |

TABLE 1-continued

| Compound Number | (Rᵃ)ₘ⟨A⟩R¹ | L¹ | X¹ | X² | Rᶜ |
|---|---|---|---|---|---|
| 1-70 | N-methylpyrrole | NH | CH | CH | isopropyl |
| 1-71 | furan | NH | CH | CH | isopropyl |
| 1-72 | thiophene | NH | CH | CH | isopropyl |
| 1-73 | 1-methylpyrazol-5-yl | NH | CH | CH | isopropyl |
| 1-74 | 1-methylpyrazol-3-yl | NH | CH | CH | isopropyl |
| 1-75 | 1H-imidazol-4-yl | NH | CH | CH | isopropyl |
| 1-76 | 1-methylimidazol-5-yl | NH | CH | CH | isopropyl |
| 1-77 | 1-methylimidazol-4-yl | NH | CH | CH | isopropyl |
| 1-78 | oxazol-4-yl | NH | CH | CH | isopropyl |
| 1-79 | oxazol-5-yl | NH | CH | CH | isopropyl |
| 1-80 | isoxazol-5-yl | NH | CH | CH | isopropyl |
| 1-81 | isoxazol-3-yl | NH | CH | CH | isopropyl |
| 1-82 | 1,3,4-oxadiazol-2-yl | NH | CH | CH | isopropyl |

TABLE 1-continued
| Compound Number | 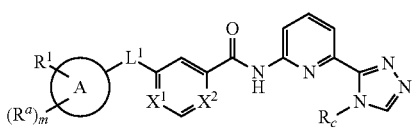 | L¹ | X¹ | X² | Rᶜ |
|---|---|---|---|---|---|
| 1-83 |  | NH | CH | CH |  |
| 1-84 |  | NH | CH | CH |  |
| 1-85 |  | S | CH | CH |  |
| 1-86 |  | S | CH | CH |  |
| 1-87 |  | S | CH | CH |  |
| 1-88 |  | S | CH | CH |  |
| 1-89 |  | S | CH | CH |  |
| 1-90 |  | S | CH | CH |  |
| 1-91 |  | S | CH | CH |  |
| 1-92 |  | S | CH | CH |  |
| 1-93 |  | S | CH | CH |  |
| 1-94 |  | S | CH | CH |  |

TABLE 1-continued
| Compound Number | 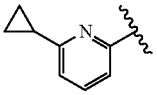 [SMILES: *c1cccc(C2CC2)n1] (A with R¹, (Rᵃ)ₘ) | L¹ | X¹ | X² | Rᶜ |
|---|---|---|---|---|---|
| 1-95 |  | S | CH | CH | 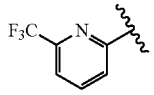 |
| 1-96 |  | S | CH | CH | |
| 1-97 | 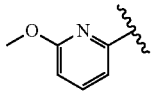 | S | CH | CH | |
| 1-98 |  | S | CH | CH | |
| 1-99 | 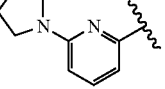 | S | CH | CH | |
| 1-100 |  | S | CH | CH | |
| 1-101 | 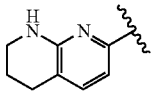 | S | CH | CH | |
| 1-102 |  | S | CH | CH | |
| 1-103 | 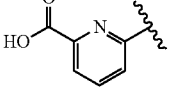 | S | CH | CH | |
| 1-104 |  | S | CH | CH | |
| 1-105 | 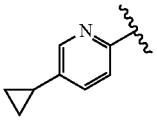 | S | CH | CH | |

TABLE 1-continued
| Compound Number | (Rᵃ)ₘ—A(R¹) | L¹ | X¹ | X² | Rᶜ |
|---|---|---|---|---|---|
| 1-106 | 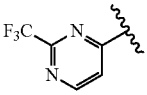 | S | CH | CH |  |
| 1-107 |  | S | CH | CH | |
| 1-108 |  | S | CH | CH | |
| 1-109 |  | S | CH | CH | |
| 1-110 |  | S | CH | CH | |
| 1-111 |  | S | CH | CH | |
| 1-112 |  | S | CH | CH | |
| 1-113 |  | S | CH | CH | |
| 1-114 |  | S | CH | CH | |
| 1-115 |  | S | CH | CH | |
| 1-116 |  | S | CH | CH | |

TABLE 1-continued

| Compound Number | A ring (R¹, (Rᵃ)ₘ) | L¹ | X¹ | X² | Rᶜ |
|---|---|---|---|---|---|
| 1-117 | phenyl | SO₂ | CH | CH | isopropyl |
| 1-118 | pyridin-2-yl | SO₂ | CH | CH | isopropyl |
| 1-119 | pyridin-3-yl | SO₂ | CH | CH | isopropyl |
| 1-120 | pyridin-4-yl | SO₂ | CH | CH | isopropyl |
| 1-121 | pyrimidin-4-yl | SO₂ | CH | CH | isopropyl |
| 1-122 | pyrimidin-5-yl | SO₂ | CH | CH | isopropyl |
| 1-123 | pyrimidin-2-yl | SO₂ | CH | CH | isopropyl |
| 1-124 | pyrazin-2-yl | SO₂ | CH | CH | isopropyl |
| 1-125 | pyridazin-3-yl | SO₂ | CH | CH | isopropyl |
| 1-126 | pyridazin-4-yl | SO₂ | CH | CH | isopropyl |
| 1-127 | phenyl | NHC(=O) | CH | CH | isopropyl |
| 1-128 | pyridin-2-yl | NHC(=O) | CH | CH | isopropyl |

TABLE 1-continued

| Compound Number | A (R¹, (Rᵃ)ₘ) | L¹ | X¹ | X² | Rᶜ |
|---|---|---|---|---|---|
| 1-129 | pyridin-3-yl | NHC(=O) | CH | CH | isopropyl |
| 1-130 | pyridin-4-yl | NHC(=O) | CH | CH | isopropyl |
| 1-131 | pyrimidin-4-yl | NHC(=O) | CH | CH | isopropyl |
| 1-132 | pyrimidin-5-yl | NHC(=O) | CH | CH | isopropyl |
| 1-133 | pyrimidin-2-yl | NHC(=O) | CH | CH | isopropyl |
| 1-134 | pyrazin-2-yl | NHC(=O) | CH | CH | isopropyl |
| 1-135 | pyridazin-3-yl | NHC(=O) | CH | CH | isopropyl |
| 1-136 | pyridazin-4-yl | NHC(=O) | CH | CH | isopropyl |
| 1-137 | 1H-pyrrol-2-yl | NHC(=O) | CH | CH | isopropyl |
| 1-138 | 1-methyl-1H-pyrrol-2-yl | NHC(=O) | CH | CH | isopropyl |
| 1-139 | furan-2-yl | NHC(=O) | CH | CH | isopropyl |
| 1-140 | thiophen-2-yl | NHC(=O) | CH | CH | isopropyl |

TABLE 1-continued

| Compound Number | (R^a)_m — A — R^1 | L^1 | X^1 | X^2 | R^c |
|---|---|---|---|---|---|
| 1-141 | 1-methylpyrazol-5-yl | NHC(=O) | CH | CH | isopropyl |
| 1-142 | 1-methylpyrazol-3-yl | NHC(=O) | CH | CH | isopropyl |
| 1-143 | 1H-imidazol-4-yl | NHC(=O) | CH | CH | isopropyl |
| 1-144 | 1-methylimidazol-5-yl | NHC(=O) | CH | CH | isopropyl |
| 1-145 | 1-methylimidazol-4-yl | NHC(=O) | CH | CH | isopropyl |
| 1-146 | oxazol-4-yl | NHC(=O) | CH | CH | isopropyl |
| 1-147 | oxazol-5-yl | NHC(=O) | CH | CH | isopropyl |
| 1-148 | isoxazol-5-yl | NHC(=O) | CH | CH | isopropyl |
| 1-149 | isoxazol-3-yl | NHC(=O) | CH | CH | isopropyl |
| 1-150 | 1,3,4-oxadiazol-2-yl | NHC(=O) | CH | CH | isopropyl |
| 1-151 | thiazol-5-yl | NHC(=O) | CH | CH | isopropyl |
| 1-152 | 1,3,4-thiadiazol-2-yl | NHC(=O) | CH | CH | isopropyl |

TABLE 1-continued

| Compound Number | A ring (R¹, (Rᵃ)ₘ) | L¹ | X¹ | X² | Rᶜ |
|---|---|---|---|---|---|
| 1-153 | phenyl | C(=O)NH | CH | CH | isopropyl |
| 1-154 | pyridin-2-yl | C(=O)NH | CH | CH | isopropyl |
| 1-155 | pyridin-3-yl | C(=O)NH | CH | CH | isopropyl |
| 1-156 | pyridin-4-yl | C(=O)NH | CH | CH | isopropyl |
| 1-157 | pyrimidin-4-yl | C(=O)NH | CH | CH | isopropyl |
| 1-158 | pyrimidin-5-yl | C(=O)NH | CH | CH | isopropyl |
| 1-159 | pyrimidin-2-yl | C(=O)NH | CH | CH | isopropyl |
| 1-160 | pyrazin-2-yl | C(=O)NH | CH | CH | isopropyl |
| 1-161 | pyridazin-3-yl | C(=O)NH | CH | CH | isopropyl |
| 1-162 | pyridazin-4-yl | C(=O)NH | CH | CH | isopropyl |
| 1-163 | 1H-pyrrol-2-yl | C(=O)NH | CH | CH | isopropyl |
| 1-164 | 1-methyl-pyrrol-2-yl | C(=O)NH | CH | CH | isopropyl |

TABLE 1-continued

| Compound Number | (R$^a$)$_m$ A R$^1$ | L$^1$ | X$^1$ | X$^2$ | R$^c$ |
|---|---|---|---|---|---|
| 1-165 | furan-2-yl | C(=O)NH | CH | CH | isopropyl |
| 1-166 | thiophen-2-yl | C(=O)NH | CH | CH | isopropyl |
| 1-167 | 1-methyl-1H-pyrazol-5-yl | C(=O)NH | CH | CH | isopropyl |
| 1-168 | 1-methyl-1H-pyrazol-3-yl | C(=O)NH | CH | CH | isopropyl |
| 1-169 | 1H-imidazol-4-yl | C(=O)NH | CH | CH | isopropyl |
| 1-170 | 1-methyl-1H-imidazol-5-yl | C(=O)NH | CH | CH | isopropyl |
| 1-171 | 1-methyl-1H-imidazol-4-yl | C(=O)NH | CH | CH | isopropyl |
| 1-172 | oxazol-4-yl | C(=O)NH | CH | CH | isopropyl |
| 1-173 | oxazol-5-yl | C(=O)NH | CH | CH | isopropyl |
| 1-174 | isoxazol-5-yl | C(=O)NH | CH | CH | isopropyl |
| 1-175 | isoxazol-3-yl | C(=O)NH | CH | CH | isopropyl |
| 1-176 | 1,3,4-oxadiazol-2-yl | C(=O)NH | CH | CH | isopropyl |
| 1-177 | thiazol-5-yl | C(=O)NH | CH | CH | isopropyl |

TABLE 1-continued
| Compound Number | (R^a)_m A R^1 | L^1 | X^1 | X^2 | R^c |
|---|---|---|---|---|---|
| 1-178 | 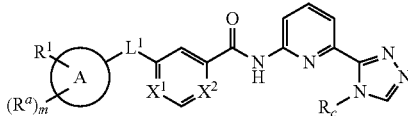 | C(=O)NH | CH | CH |  |
| 1-179 |  | CH_2O | CH | CH |  |
| 1-180 |  | CH_2O | CH | CH |  |
| 1-181 |  | CH_2O | CH | CH |  |
| 1-182 |  | CH_2O | CH | CH |  |
| 1-183 |  | CH_2O | CH | CH |  |
| 1-184 |  | CH_2O | CH | CH |  |
| 1-185 |  | CH_2O | CH | CH |  |
| 1-186 |  | CH_2O | CH | CH |  |
| 1-187 |  | CH_2O | CH | CH |  |
| 1-188 |  | CH_2O | CH | CH |  |
| 1-189 |  | CH_2NH | CH | CH |  |

TABLE 1-continued

| Compound Number | (R^a)_m A R^1 | L^1 | X^1 | X^2 | R^c |
|---|---|---|---|---|---|
| 1-190 | 2-pyridyl | CH_2NH | CH | CH | iPr |
| 1-191 | 3-pyridyl | CH_2NH | CH | CH | iPr |
| 1-192 | 4-pyridyl | CH_2NH | CH | CH | iPr |
| 1-193 | 4-pyrimidinyl | CH_2NH | CH | CH | iPr |
| 1-194 | 5-pyrimidinyl | CH_2NH | CH | CH | iPr |
| 1-195 | 2-pyrimidinyl | CH_2NH | CH | CH | iPr |
| 1-196 | 2-pyrazinyl | CH_2NH | CH | CH | iPr |
| 1-197 | 3-pyridazinyl | CH_2NH | CH | CH | iPr |
| 1-198 | 4-pyridazinyl | CH_2NH | CH | CH | iPr |
| 1-199 | phenyl | C≡C | CH | CH | iPr |
| 1-200 | 2-pyridyl | C≡C | CH | CH | iPr |
| 1-201 | 3-pyridyl | C≡C | CH | CH | iPr |

TABLE 1-continued
| Compound Number | 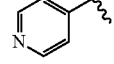 | L¹ | X¹ | X² | R^c |
|---|---|---|---|---|---|
| 1-202 |  | C≡C | CH | CH | 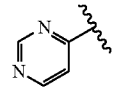 |
| 1-203 |  | C≡C | CH | CH | 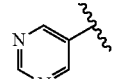 |
| 1-204 |  | C≡C | CH | CH | 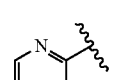 |
| 1-205 |  | C≡C | CH | CH | 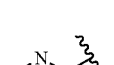 |
| 1-206 |  | C≡C | CH | CH | 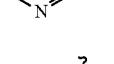 |
| 1-207 |  | C≡C | CH | CH | 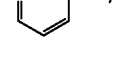 |
| 1-208 |  | C≡C | CH | CH | 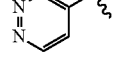 |
| 1-209 |  | O | CH | CF | 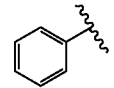 |
| 1-210 |  | O | CH | CF | 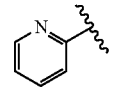 |
| 1-211 |  | O | CH | CF | 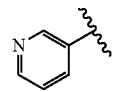 |
| 1-212 |  | O | CH | CF | 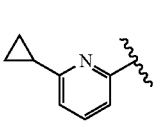 |
| 1-213 |  | O | CH | CF | 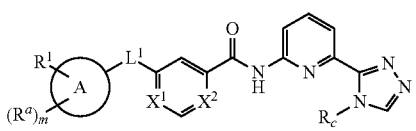 |

TABLE 1-continued
| Compound Number | (Rᵃ)ₘ—A—R¹ | L¹ | X¹ | X² | Rᶜ |
|---|---|---|---|---|---|
| 1-214 | 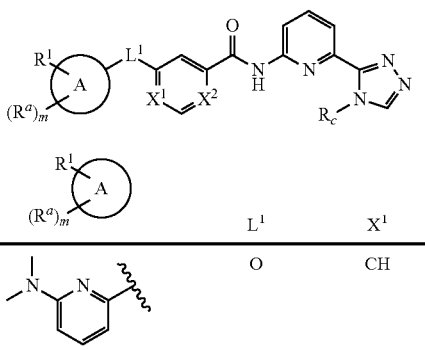 | O | CH | CF | 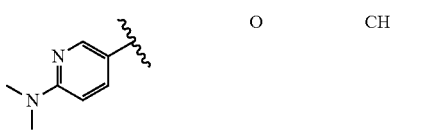 |
| 1-215 | 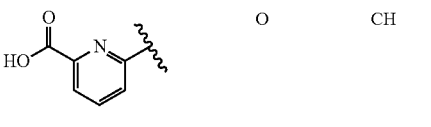 | O | CH | CF | |
| 1-216 | 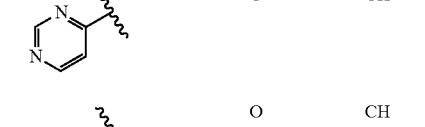 | O | CH | CF | |
| 1-217 | 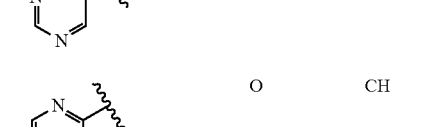 | O | CH | CF | |
| 1-218 | 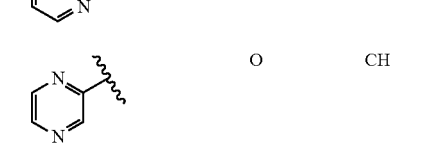 | O | CH | CF | |
| 1-219 | 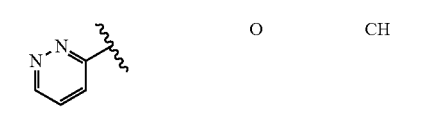 | O | CH | CF | |
| 1-220 | 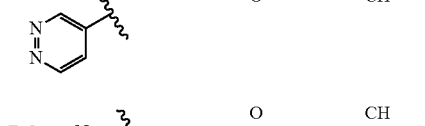 | O | CH | CF | |
| 1-221 | 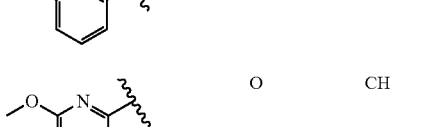 | O | CH | CF | |
| 1-222 | 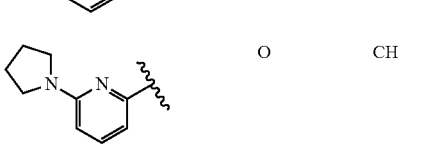 | O | CH | CF | |
| 1-223 |  | O | CH | CF | |
| 1-224 |  | O | CH | CF | |
| 1-225 | | O | CH | CF | |

TABLE 1-continued

| Compound Number | (R^a)_m ⌬A-R^1 | L^1 | X^1 | X^2 | R^c |
|---|---|---|---|---|---|
| 1-226 | 1,2,3,4-tetrahydro-1,8-naphthyridin-7-yl | O | CH | CF | isopropyl |
| 1-227 | 5-cyclopropylpyridin-2-yl | O | CH | CF | isopropyl |
| 1-228 | 5-(trifluoromethyl)pyridin-2-yl | O | CH | CF | isopropyl |
| 1-229 | 5-methoxypyridin-2-yl | O | CH | CF | isopropyl |
| 1-230 | 5-carboxypyridin-2-yl | O | CH | CF | isopropyl |
| 1-231 | 2-cyclopropylpyrimidin-4-yl | O | CH | CF | isopropyl |
| 1-232 | 2-(trifluoromethyl)pyrimidin-4-yl | O | CH | CF | isopropyl |
| 1-233 | 2-methoxypyrimidin-4-yl | O | CH | CF | isopropyl |
| 1-234 | 2-(2-(pyrrolidin-1-yl)ethoxy)pyrimidin-4-yl | O | CH | CF | isopropyl |
| 1-235 | 2-(pyrrolidin-1-yl)pyrimidin-4-yl | O | CH | CF | isopropyl |
| 1-236 | 2-carboxypyrimidin-4-yl | O | CH | CF | isopropyl |

TABLE 1-continued

| Compound Number | A with R¹ and (Rᵃ)ₘ | L¹ | X¹ | X² | Rᶜ |
|---|---|---|---|---|---|
| 1-237 | 2-cyclopropylpyrimidin-5-yl | O | CH | CF | isopropyl |
| 1-238 | 2-(trifluoromethyl)pyrimidin-5-yl | O | CH | CF | isopropyl |
| 1-239 | 2-methoxypyrimidin-5-yl | O | CH | CF | isopropyl |
| 1-240 | 2-(2-(pyrrolidin-1-yl)ethoxy)pyrimidin-5-yl | O | CH | CF | isopropyl |
| 1-241 | 2-(pyrrolidin-1-yl)pyrimidin-5-yl | O | CH | CF | isopropyl |
| 1-242 | 2-carboxypyrimidin-5-yl | O | CH | CF | isopropyl |
| 1-243 | phenyl | O | CH | N | isopropyl |
| 1-244 | pyridin-2-yl | O | CH | N | isopropyl |
| 1-245 | pyridin-3-yl | O | CH | N | isopropyl |
| 1-246 | pyridin-4-yl | O | CH | N | isopropyl |
| 1-247 | pyrimidin-4-yl | O | CH | N | isopropyl |

TABLE 1-continued

| Compound Number | (R¹, (Rᵃ)ₘ, A) | L¹ | X¹ | X² | Rᶜ |
|---|---|---|---|---|---|
| 1-248 | pyrimidin-5-yl | O | CH | N | isopropyl |
| 1-249 | pyrimidin-2-yl | O | CH | N | isopropyl |
| 1-250 | pyrazin-2-yl | O | CH | N | isopropyl |
| 1-251 | pyridazin-3-yl | O | CH | N | isopropyl |
| 1-252 | pyridazin-4-yl | O | CH | N | isopropyl |
| 1-253 | 6-cyclopropylpyridin-2-yl | O | CH | N | isopropyl |
| 1-254 | 6-(trifluoromethyl)pyridin-2-yl | O | CH | N | isopropyl |
| 1-255 | 6-methoxypyridin-2-yl | O | CH | N | isopropyl |
| 1-256 | 6-(pyrrolidin-1-yl)pyridin-2-yl | O | CH | N | isopropyl |
| 1-257 | 5,6,7,8-tetrahydro-1,8-naphthyridin-2-yl | O | CH | N | isopropyl |
| 1-258 | 6-carboxypyridin-2-yl | O | CH | N | isopropyl |
| 1-259 | 5-cyclopropylpyridin-2-yl | O | CH | N | isopropyl |

TABLE 1-continued

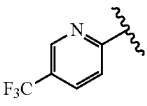

| Compound Number | (Rᵃ)ₘ⟨A⟩R¹ | L¹ | X¹ | X² | Rᶜ |
|---|---|---|---|---|---|
| 1-260 | 5-(trifluoromethyl)pyridin-2-yl | O | CH | N | isopropyl |
| 1-261 | 5-methoxypyridin-2-yl | O | CH | N | isopropyl |
| 1-262 | 5-carboxypyridin-2-yl | O | CH | N | isopropyl |
| 1-263 | 2-cyclopropylpyrimidin-4-yl | O | CH | N | isopropyl |
| 1-264 | 2-(trifluoromethyl)pyrimidin-4-yl | O | CH | N | isopropyl |
| 1-265 | 2-methoxypyrimidin-4-yl | O | CH | N | isopropyl |
| 1-266 | 2-(2-(pyrrolidin-1-yl)ethoxy)pyrimidin-4-yl | O | CH | N | isopropyl |
| 1-267 | 2-(pyrrolidin-1-yl)pyrimidin-4-yl | O | CH | N | isopropyl |
| 1-268 | 2-carboxypyrimidin-4-yl | O | CH | N | isopropyl |
| 1-269 | 2-cyclopropylpyrimidin-5-yl | O | CH | N | isopropyl |
| 1-270 | 2-(trifluoromethyl)pyrimidin-5-yl | O | CH | N | isopropyl |
| 1-271 | 2-methoxypyrimidin-5-yl | O | CH | N | isopropyl |

TABLE 1-continued

| Compound Number | (Rᵃ)ₘ⟨A⟩R¹ | L¹ | X¹ | X² | Rᶜ |
|---|---|---|---|---|---|
| 1-272 | pyrrolidine-CH₂CH₂-O-pyrimidin-5-yl | O | CH | N | isopropyl |
| 1-273 | 2-(pyrrolidin-1-yl)pyrimidin-5-yl | O | CH | N | isopropyl |
| 1-274 | 2-carboxypyrimidin-5-yl | O | CH | N | isopropyl |
| 1-275 | phenyl | O | CMe | CH | isopropyl |
| 1-276 | pyridin-2-yl | O | CMe | CH | isopropyl |
| 1-277 | pyridin-3-yl | O | CMe | CH | isopropyl |
| 1-278 | pyridin-4-yl | O | CMe | CH | isopropyl |
| 1-279 | pyrimidin-4-yl | O | CMe | CH | isopropyl |
| 1-280 | pyrimidin-5-yl | O | CMe | CH | isopropyl |
| 1-281 | pyrimidin-2-yl | O | CMe | CH | isopropyl |
| 1-282 | pyrazin-2-yl | O | CMe | CH | isopropyl |
| 1-283 | pyridazin-3-yl | O | CMe | CH | isopropyl |

TABLE 1-continued

| Compound Number | A ring (R¹, (Rᵃ)ₘ) | L¹ | X¹ | X² | Rᶜ |
|---|---|---|---|---|---|
| 1-284 | pyridazin-4-yl | O | CMe | CH | isopropyl |
| 1-285 | phenyl | O | CMe | CF | isopropyl |
| 1-286 | pyridin-2-yl | O | CMe | CF | isopropyl |
| 1-287 | pyridin-3-yl | O | CMe | CF | isopropyl |
| 1-288 | pyridin-4-yl | O | CMe | CF | isopropyl |
| 1-289 | pyrimidin-4-yl | O | CMe | CF | isopropyl |
| 1-290 | pyrimidin-5-yl | O | CMe | CF | isopropyl |
| 1-291 | pyrimidin-2-yl | O | CMe | CF | isopropyl |
| 1-292 | pyrazin-2-yl | O | CMe | CF | isopropyl |
| 1-293 | pyridazin-3-yl | O | CMe | CF | isopropyl |
| 1-294 | pyridazin-4-yl | O | CMe | CF | isopropyl |
| 1-295 | phenyl | NHC(=O) | CH | CF | isopropyl |

TABLE 1-continued

| Compound Number | (Rᵃ)ₘ A R¹ | L¹ | X¹ | X² | Rᶜ |
|---|---|---|---|---|---|
| 1-296 | 2-pyridyl | NHC(=O) | CH | CF | isopropyl |
| 1-297 | 3-pyridyl | NHC(=O) | CH | CF | isopropyl |
| 1-298 | 4-pyridyl | NHC(=O) | CH | CF | isopropyl |
| 1-299 | 4-pyrimidinyl | NHC(=O) | CH | CF | isopropyl |
| 1-300 | 5-pyrimidinyl | NHC(=O) | CH | CF | isopropyl |
| 1-301 | 2-pyrimidinyl | NHC(=O) | CH | CF | isopropyl |
| 1-302 | pyrazinyl | NHC(=O) | CH | CF | isopropyl |
| 1-303 | 3-pyridazinyl | NHC(=O) | CH | CF | isopropyl |
| 1-304 | 4-pyridazinyl | NHC(=O) | CH | CF | isopropyl |
| 1-305 | phenyl | C(=O)NH | CH | CF | isopropyl |
| 1-306 | 4-(aminomethyl)phenyl | C(=O)NH | CH | CF | isopropyl |
| 1-307 | 2-pyridyl | C(=O)NH | CH | CF | isopropyl |

TABLE 1-continued

| Compound Number | A with R¹, (Rᵃ)ₘ | L¹ | X¹ | X² | Rᶜ |
|---|---|---|---|---|---|
| 1-308 | pyridin-3-yl | C(=O)NH | CH | CF | isopropyl |
| 1-309 | pyridin-4-yl | C(=O)NH | CH | CF | isopropyl |
| 1-310 | 6-cyclopropylpyridin-2-yl | C(=O)NH | CH | CF | isopropyl |
| 1-311 | 5-bromopyridin-2-yl | C(=O)NH | CH | CF | isopropyl |
| 1-312 | pyrimidin-4-yl | C(=O)NH | CH | CF | isopropyl |
| 1-313 | pyrimidin-5-yl | C(=O)NH | CH | CF | isopropyl |
| 1-314 | pyrimidin-2-yl | C(=O)NH | CH | CF | isopropyl |
| 1-315 | pyrazin-2-yl | C(=O)NH | CH | CF | isopropyl |
| 1-316 | pyridazin-3-yl | C(=O)NH | CH | CF | isopropyl |
| 1-317 | pyridazin-4-yl | C(=O)NH | CH | CF | isopropyl |
| 1-318 | 2-methyl-1,3,4-oxadiazol-5-yl | C(=O)NH | CH | CF | isopropyl |
| 1-319 | phenyl | O | CH | CH | cyclopropyl |

TABLE 1-continued

| Compound Number | (Rᵃ)ₘ—A—R¹ | L¹ | X¹ | X² | Rᶜ |
|---|---|---|---|---|---|
| 1-320 | 2-pyridyl | O | CH | CH | cyclopropyl |
| 1-321 | 3-pyridyl | O | CH | CH | cyclopropyl |
| 1-322 | 4-pyridyl | O | CH | CH | cyclopropyl |
| 1-323 | 4-pyrimidinyl | O | CH | CH | cyclopropyl |
| 1-324 | 5-pyrimidinyl | O | CH | CH | cyclopropyl |
| 1-325 | 2-pyrimidinyl | O | CH | CH | cyclopropyl |
| 1-326 | 2-pyrazinyl | O | CH | CH | cyclopropyl |
| 1-327 | 3-pyridazinyl | O | CH | CH | cyclopropyl |
| 1-328 | 4-pyridazinyl | O | CH | CH | cyclopropyl |
| 1-329 | Boc-NH-CH₂-(CF₃-pyridyl) | O | CH | N | cyclopropyl |
| 1-330 | H₂N-CH₂-(CF₃-pyridyl) | O | CH | N | cyclopropyl |

TABLE 1-continued
| Compound Number | (Rᵃ)ₘ⟨A⟩R¹ | L¹ | X¹ | X² | Rᶜ |
|---|---|---|---|---|---|
| 1-331 | 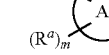 | O | CH | CH |  |
| 1-332 |  | C(=O)NH | CH | CF |  |
| 1-333 |  | CH₂C(=O)NH | CH | CF |  |
| 1-334 |  | C(=O)NH | CH | CF |  |
| 1-335 | 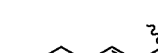 | C(=O)NH | CH | CF |  |
| 1-336 | 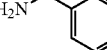 | O | CH | CF |  |
| 1-337 |  | O | CH | CF |  |
| 1-338 |  | C(=O)NH | CH | CF |  |
| 1-339 | 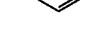 | C(=O)NH | CH | CF |  |
| 1-340 |  | C(=O)NH | CH | CF |  |
| 1-341 |  | C(=O)NH | CH | CF |  |
| 1-342 | 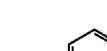 | NH | CH | CF |  |

TABLE 1-continued

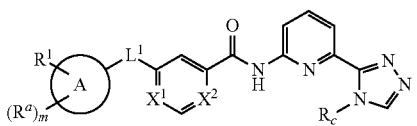

| Compound Number | (R^a)_m A R^1 | L^1 | X^1 | X^2 | R^c |
|---|---|---|---|---|---|
| 1-343 |  | CH$_2$NH | CH | CF |  |

Compounds in Table 1 are named:

N-(6-(4-Isopropyl-4H-1,2,4-triazol-3-yl)pyridin-2-yl)-3-phenoxybenzamide (Compound 1-1);

N-(6-(4-Isopropyl-4H-1,2,4-triazol-3-yl)pyridin-2-yl)-3-(pyridin-2-yloxy)benzamide (Compound 1-2);

N-(6-(4-Isopropyl-4H-1,2,4-triazol-3-yl)pyridin-2-yl)-3-(pyridin-3-yloxy)benzamide (Compound 1-3);

N-(6-(4-isopropyl-4H-1,2,4-triazol-3-yl)pyridin-2-yl)-3-(pyridin-4-yloxy)benzamide (Compound 1-4);

N-(6-(4-isopropyl-4H-1,2,4-triazol-3-yl)pyridin-2-yl)-3-(pyrimidin-4-yloxy)benzamide (Compound 1-5);

N-(6-(4-Isopropyl-4H-1,2,4-triazol-3-yl)pyridin-2-yl)-3-(pyrimidin-5-yloxy)benzamide (Compound 1-6);

N-(6-(4-Isopropyl-4H-1,2,4-triazol-3-yl)pyridin-2-yl)-3-(pyrimidin-2-yloxy)benzamide (Compound 1-7);

N-(6-(4-Isopropyl-4H-1,2,4-triazol-3-yl)pyridin-2-yl)-3-(pyrazin-2-yloxy)benzamide (Compound 1-8);

N-(6-(4-Isopropyl-4H-1,2,4-triazol-3-yl)pyridin-2-yl)-3-(pyridazin-3-yloxy)benzamide (Compound 1-9);

N-(6-(4-Isopropyl-4H-1,2,4-triazol-3-yl)pyridin-2-yl)-3-(pyridazin-4-yloxy)benzamide (Compound 1-10);

3-((6-Cyclopropylpyridin-2-yl)oxy)-N-(6-(4-isopropyl-4H-1,2,4-triazol-3-yl)pyridin-2-yl)benzamide (Compound 1-11);

N-(6-(4-Isopropyl-4H-1,2,4-triazol-3-yl)pyridin-2-yl)-3-((6-(trifluoromethyl)pyridin-2-yl)oxy)benzamide (Compound 1-12);

N-(6-(4-Isopropyl-4H-1,2,4-triazol-3-yl)pyridin-2-yl)-3-((6-methoxypyridin-2-yl)oxy)benzamide (Compound 1-13);

N-(6-(4-Isopropyl-4H-1,2,4-triazol-3-yl)pyridin-2-yl)-3-((6-(pyrrolidin-1-yl)pyridin-2-yl)oxy)benzamide (Compound 1-14);

3-((6-(Dimethylamino)pyridin-2-yl)oxy)-N-(6-(4-isopropyl-4H-1,2,4-triazol-3-yl)pyridin-2-yl)benzamide (Compound 1-15);

3-((6-(Dimethylamino)pyridin-3-yl)oxy)-N-(6-(4-isopropyl-4H-1,2,4-triazol-3-yl)pyridin-2-yl)benzamide (Compound 1-16);

N-(6-(4-Isopropyl-4H-1,2,4-triazol-3-yl)pyridin-2-yl)-3-((5,6,7,8-tetrahydro-1,8-naphthyridin-2-yl)oxy)benzamide (Compound 1-17);

6-(3-((6-(4-Isopropyl-4H-1,2,4-triazol-3-yl)pyridin-2-yl)carbamoyl)phenoxy)picolinic acid (Compound 1-18);

3-((5-Cyclopropylpyridin-2-yl)oxy)-N-(6-(4-isopropyl-4H-1,2,4-triazol-3-yl)pyridin-2-yl)benzamide (Compound 1-19);

N-(6-(4-Isopropyl-4H-1,2,4-triazol-3-yl)pyridin-2-yl)-3-((5-(trifluoromethyl)pyridin-2-yl)oxy)benzamide (Compound 1-20);

N-(6-(4-Isopropyl-4H-1,2,4-triazol-3-yl)pyridin-2-yl)-3-((5-methoxypyridin-2-yl)oxy)benzamide (Compound 1-21);

6-(3-((6-(4-Isopropyl-4H-1,2,4-triazol-3-yl)pyridin-2-yl)carbamoyl)phenoxy)nicotinic acid (Compound 1-22);

3-((4-Cyano-6-(trifluoromethyl)pyridin-2-yl)oxy)-N-(6-(4-isopropyl-4H-1,2,4-triazol-3-yl)pyridin-2-yl)benzamide (Compound 1-23);

2-(3-((6-(4-Isopropyl-4H-1,2,4-triazol-3-yl)pyridin-2-yl)carbamoyl)phenoxy)-6-(trifluoromethyl)isonicotinic acid (Compound 1-24);

3-((2-Cyclopropylpyrimidin-4-yl)oxy)-N-(6-(4-isopropyl-4H-1,2,4-triazol-3-yl)pyridin-2-yl)benzamide (Compound 1-25);

N-(6-(4-Isopropyl-4H-1,2,4-triazol-3-yl)pyridin-2-yl)-3-((2-(trifluoromethyl)pyrimidin-4-yl)oxy)benzamide (Compound 1-26);

N-(6-(4-Isopropyl-4H-1,2,4-triazol-3-yl)pyridin-2-yl)-3-((2-methoxypyrimidin-4-yl)oxy)benzamide (Compound 1-27);

N-(6-(4-Isopropyl-4H-1,2,4-triazol-3-yl)pyridin-2-yl)-3-((2-(2-(pyrrolidin-1-yl)ethoxy)pyrimidin-4-yl)oxy)benzamide (Compound 1-28);

N-(6-(4-Isopropyl-4H-1,2,4-triazol-3-yl)pyridin-2-yl)-3-((2-(pyrrolidin-1-yl)pyrimidin-4-yl)oxy)benzamide (Compound 1-29);

4-(3-((6-(4-Isopropyl-4H-1,2,4-triazol-3-yl)pyridin-2-yl)carbamoyl)phenoxy)pyrimidine-2-carboxylic acid (Compound 1-30);

3-((2-Cyclopropylpyrimidin-5-yl)oxy)-N-(6-(4-isopropyl-4H-1,2,4-triazol-3-yl)pyridin-2-yl)benzamide (Compound 1-31);

N-(6-(4-Isopropyl-4H-1,2,4-triazol-3-yl)pyridin-2-yl)-3-((2-(trifluoromethyl)pyrimidin-5-yl)oxy)benzamide (Compound 1-32);

N-(6-(4-Isopropyl-4H-1,2,4-triazol-3-yl)pyridin-2-yl)-3-((2-methoxypyrimidin-5-yl)oxy)benzamide (Compound 1-33);

N-(6-(4-Isopropyl-4H-1,2,4-triazol-3-yl)pyridin-2-yl)-3-((2-(2-(pyrrolidin-1-yl)ethoxy)pyrimidin-5-yl)oxy)benzamide (Compound 1-34);

N-(6-(4-Isopropyl-4H-1,2,4-triazol-3-yl)pyridin-2-yl)-3-((2-(pyrrolidin-1-yl)pyrimidin-5-yl)oxy)benzamide (Compound 1-35);

5-(3-((6-(4-Isopropyl-4H-1,2,4-triazol-3-yl)pyridin-2-yl)carbamoyl)phenoxy)pyrimidine-2-carboxylic acid (Compound 1-36);

N-(6-(4-Isopropyl-4H-1,2,4-triazol-3-yl)pyridin-2-yl)-3-(phenylamino)benzamide (Compound 1-37);

N-(6-(4-Isopropyl-4H-1,2,4-triazol-3-yl)pyridin-2-yl)-3-(pyridin-2-ylamino)benzamide (Compound 1-38);

N-(6-(4-Isopropyl-4H-1,2,4-triazol-3-yl)pyridin-2-yl)-3-(pyridin-3-ylamino)benzamide (Compound 1-39);

N-(6-(4-Isopropyl-4H-1,2,4-triazol-3-yl)pyridin-2-yl)-3-(pyridin-4-ylamino)benzamide (Compound 1-40);

N-(6-(4-Isopropyl-4H-1,2,4-triazol-3-yl)pyridin-2-yl)-3-(pyrimidin-4-ylamino)benzamide (Compound 1-41);

N-(6-(4-Isopropyl-4H-1,2,4-triazol-3-yl)pyridin-2-yl)-3-(pyrimidin-5-ylamino)benzamide (Compound 1-42);

N-(6-(4-Isopropyl-4H-1,2,4-triazol-3-yl)pyridin-2-yl)-3-(pyrimidin-2-ylamino)benzamide (Compound 1-43);

N-(6-(4-Isopropyl-4H-1,2,4-triazol-3-yl)pyridin-2-yl)-3-(pyrazin-2-ylamino)benzamide (Compound 1-44);

N-(6-(4-Isopropyl-4H-1,2,4-triazol-3-yl)pyridin-2-yl)-3-(pyridazin-3-ylamino)benzamide (Compound 1-45);

N-(6-(4-Isopropyl-4H-1,2,4-triazol-3-yl)pyridin-2-yl)-3-(pyridazin-4-ylamino)benzamide (Compound 1-46);

3-((6-Cyclopropylpyridin-2-yl)amino)-N-(6-(4-isopropyl-4H-1,2,4-triazol-3-yl)pyridin-2-yl)benzamide (Compound 1-47);

N-(6-(4-Isopropyl-4H-1,2,4-triazol-3-yl)pyridin-2-yl)-3-((6-(trifluoromethyl)pyridin-2-yl)amino)benzamide (Compound 1-48);

N-(6-(4-Isopropyl-4H-1,2,4-triazol-3-yl)pyridin-2-yl)-3-((6-methoxypyridin-2-yl)amino)benzamide (Compound 1-49);

N-(6-(4-Isopropyl-4H-1,2,4-triazol-3-yl)pyridin-2-yl)-3-((6-(pyrrolidin-1-yl)pyridin-2-yl)amino)benzamide (Compound 1-50);

N-(6-(4-Isopropyl-4H-1,2,4-triazol-3-yl)pyridin-2-yl)-3-((5,6,7,8-tetrahydro-1,8-naphthyridin-2-yl)amino)benzamide (Compound 1-51);

6-((3-((6-(4-Isopropyl-4H-1,2,4-triazol-3-yl)pyridin-2-yl)carbamoyl)phenyl)amino)picolinic acid (Compound 1-52);

3-((5-Cyclopropylpyridin-2-yl)amino)-N-(6-(4-isopropyl-4H-1,2,4-triazol-3-yl)pyridin-2-yl)benzamide (Compound 1-53);

N-(6-(4-Isopropyl-4H-1,2,4-triazol-3-yl)pyridin-2-yl)-3-((5-(trifluoromethyl)pyridin-2-yl)amino)benzamide (Compound 1-54);

N-(6-(4-Isopropyl-4H-1,2,4-triazol-3-yl)pyridin-2-yl)-3-((5-methoxypyridin-2-yl)amino)benzamide (Compound 1-55);

6-((3-((6-(4-Isopropyl-4H-1,2,4-triazol-3-yl)pyridin-2-yl)carbamoyl)phenyl)amino)nicotinic acid (Compound 1-56);

3-((2-Cyclopropylpyrimidin-4-yl)amino)-N-(6-(4-isopropyl-4H-1,2,4-triazol-3-yl)pyridin-2-yl)benzamide (Compound 1-57);

N-(6-(4-Isopropyl-4H-1,2,4-triazol-3-yl)pyridin-2-yl)-3-((2-(trifluoromethyl)pyrimidin-4-yl)amino)benzamide (Compound 1-58);

N-(6-(4-Isopropyl-4H-1,2,4-triazol-3-yl)pyridin-2-yl)-3-((2-methoxypyrimidin-4-yl)amino)benzamide (Compound 1-59);

N-(6-(4-Isopropyl-4H-1,2,4-triazol-3-yl)pyridin-2-yl)-3-((2-(2-(pyrrolidin-1-yl)ethoxy)pyrimidin-4-yl)amino)benzamide (Compound 1-60);

N-(6-(4-Isopropyl-4H-1,2,4-triazol-3-yl)pyridin-2-yl)-3-((2-(pyrrolidin-1-yl)pyrimidin-4-yl)amino)benzamide (Compound 1-61);

4-((3-((6-(4-Isopropyl-4H-1,2,4-triazol-3-yl)pyridin-2-yl)carbamoyl)phenyl)amino)pyrimidine-2-carboxylic acid (Compound 1-62);

3-((2-Cyclopropylpyrimidin-5-yl)amino)-N-(6-(4-isopropyl-4H-1,2,4-triazol-3-yl)pyridin-2-yl)benzamide (Compound 1-63);

N-(6-(4-Isopropyl-4H-1,2,4-triazol-3-yl)pyridin-2-yl)-3-((2-(trifluoromethyl)pyrimidin-5-yl)amino)benzamide (Compound 1-64);

N-(6-(4-Isopropyl-4H-1,2,4-triazol-3-yl)pyridin-2-yl)-3-((2-methoxypyrimidin-5-yl)amino)benzamide (Compound 1-65);

N-(6-(4-Isopropyl-4H-1,2,4-triazol-3-yl)pyridin-2-yl)-3-((2-(2-(pyrrolidin-1-yl)ethoxy)pyrimidin-5-yl)amino)benzamide (Compound 1-66);

N-(6-(4-Isopropyl-4H-1,2,4-triazol-3-yl)pyridin-2-yl)-3-((2-(pyrrolidin-1-yl)pyrimidin-5-yl)amino)benzamide (Compound 1-67);

5-((3-((6-(4-Isopropyl-4H-1,2,4-triazol-3-yl)pyridin-2-yl)carbamoyl)phenyl)amino)pyrimidine-2-carboxylic acid (Compound 1-68);

3-((1H-Pyrrol-2-yl)amino)-N-(6-(4-isopropyl-4H-1,2,4-triazol-3-yl)pyridin-2-yl)benzamide (Compound 1-69);

N-(6-(4-Isopropyl-4H-1,2,4-triazol-3-yl)pyridin-2-yl)-3-((1-methyl-1H-pyrrol-2-yl)amino)benzamide (Compound 1-70);

3-(Furan-2-ylamino)-N-(6-(4-isopropyl-4H-1,2,4-triazol-3-yl)pyridin-2-yl)benzamide (Compound 1-71);

N-(6-(4-Isopropyl-4H-1,2,4-triazol-3-yl)pyridin-2-yl)-3-(thiophen-2-ylamino)benzamide (Compound 1-72);

N-(6-(4-Isopropyl-4H-1,2,4-triazol-3-yl)pyridin-2-yl)-3-((1-methyl-1H-pyrazol-5-yl)amino)benzamide (Compound 1-73);

N-(6-(4-Isopropyl-4H-1,2,4-triazol-3-yl)pyridin-2-yl)-3-((1-methyl-1H-pyrazol-3-yl)amino)benzamide (Compound 1-74);

3-((1H-Imidazol-5-yl)amino)-N-(6-(4-isopropyl-4H-1,2,4-triazol-3-yl)pyridin-2-yl)benzamide (Compound 1-75);

N-(6-(4-Isopropyl-4H-1,2,4-triazol-3-yl)pyridin-2-yl)-3-((1-methyl-1H-imidazol-5-yl)amino)benzamide (Compound 1-76);

N-(6-(4-Isopropyl-4H-1,2,4-triazol-3-yl)pyridin-2-yl)-3-((1-methyl-1H-imidazol-4-yl)amino)benzamide (Compound 1-77);

N-(6-(4-Isopropyl-4H-1,2,4-triazol-3-yl)pyridin-2-yl)-3-(oxazol-4-ylamino)benzamide (Compound 1-78); N-(6-(4-Isopropyl-4H-1,2,4-triazol-3-yl)pyridin-2-yl)-3-(oxazol-5-ylamino)benzamide (Compound 1-79);

N-(6-(4-Isopropyl-4H-1,2,4-triazol-3-yl)pyridin-2-yl)-3-(isoxazol-5-ylamino)benzamide (Compound 1-80);

N-(6-(4-Isopropyl-4H-1,2,4-triazol-3-yl)pyridin-2-yl)-3-(isoxazol-3-ylamino)benzamide (Compound 1-81);

3-((1,3,4-Oxadiazol-2-yl)amino)-N-(6-(4-isopropyl-4H-1,2,4-triazol-3-yl)pyridin-2-yl)benzamide (Compound 1-82);

N-(6-(4-Isopropyl-4H-1,2,4-triazol-3-yl)pyridin-2-yl)-3-(thiazol-5-ylamino)benzamide (Compound 1-83);

3-((1,3,4-Thiadiazol-2-yl)amino)-N-(6-(4-isopropyl-4H-1,2,4-triazol-3-yl)pyridin-2-yl)benzamide (Compound 1-84);

N-(6-(4-Isopropyl-4H-1,2,4-triazol-3-yl)pyridin-2-yl)-3-(phenylthio)benzamide (Compound 1-85);

N-(6-(4-Isopropyl-4H-1,2,4-triazol-3-yl)pyridin-2-yl)-3-(pyridin-2-ylthio)benzamide (Compound 1-86);

N-(6-(4-Isopropyl-4H-1,2,4-triazol-3-yl)pyridin-2-yl)-3-(pyridin-3-ylthio)benzamide (Compound 1-87);

N-(6-(4-Isopropyl-4H-1,2,4-triazol-3-yl)pyridin-2-yl)-3-(pyridin-4-ylthio)benzamide (Compound 1-88);

N-(6-(4-Isopropyl-4H-1,2,4-triazol-3-yl)pyridin-2-yl)-3-(pyrimidin-4-ylthio)benzamide (Compound 1-89);

N-(6-(4-Isopropyl-4H-1,2,4-triazol-3-yl)pyridin-2-yl)-3-(pyrimidin-5-ylthio)benzamide (Compound 1-90);

N-(6-(4-Isopropyl-4H-1,2,4-triazol-3-yl)pyridin-2-yl)-3-(pyrimidin-2-ylthio)benzamide (Compound 1-91);

N-(6-(4-Isopropyl-4H-1,2,4-triazol-3-yl)pyridin-2-yl)-3-(pyrazin-2-ylthio)benzamide (Compound 1-92);

N-(6-(4-Isopropyl-4H-1,2,4-triazol-3-yl)pyridin-2-yl)-3-(pyridazin-3-ylthio)benzamide (Compound 1-93);

N-(6-(4-Isopropyl-4H-1,2,4-triazol-3-yl)pyridin-2-yl)-3-(pyridazin-4-ylthio)benzamide (Compound 1-94);

3-((6-Cyclopropylpyridin-2-yl)thio)-N-(6-(4-isopropyl-4H-1,2,4-triazol-3-yl)pyridin-2-yl)benzamide (Compound 1-95);

N-(6-(4-Isopropyl-4H-1,2,4-triazol-3-yl)pyridin-2-yl)-3-((6-(trifluoromethyl)pyridin-2-yl)thio)benzamide (Compound 1-96);

N-(6-(4-Isopropyl-4H-1,2,4-triazol-3-yl)pyridin-2-yl)-3-((6-methoxypyridin-2-yl)thio)benzamide (Compound 1-97);

N-(6-(4-Isopropyl-4H-1,2,4-triazol-3-yl)pyridin-2-yl)-3-((6-(pyrrolidin-1-yl)pyridin-2-yl)thio)benzamide (Compound 1-98);

N-(6-(4-Isopropyl-4H-1,2,4-triazol-3-yl)pyridin-2-yl)-3-((5,6,7,8-tetrahydro-1,8-naphthyridin-2-yl)thio)benzamide (Compound 1-99);

6-((3-((6-(4-Isopropyl-4H-1,2,4-triazol-3-yl)pyridin-2-yl)carbamoyl)phenyl)thio)picolinic acid (Compound 1-100);

3-((5-Cyclopropylpyridin-2-yl)thio)-N-(6-(4-isopropyl-4H-1,2,4-triazol-3-yl)pyridin-2-yl)benzamide (Compound 1-101);

N-(6-(4-Isopropyl-4H-1,2,4-triazol-3-yl)pyridin-2-yl)-3-((5-(trifluoromethyl)pyridin-2-yl)thio)benzamide (Compound 1-102);

N-(6-(4-Isopropyl-4H-1,2,4-triazol-3-yl)pyridin-2-yl)-3-((5-methoxypyridin-2-yl)thio)benzamide (Compound 1-103);

6-((3-((6-(4-Isopropyl-4H-1,2,4-triazol-3-yl)pyridin-2-yl)carbamoyl)phenyl)thio)nicotinic acid (Compound 1-104);

3-((2-Cyclopropylpyrimidin-4-yl)thio)-N-(6-(4-isopropyl-4H-1,2,4-triazol-3-yl)pyridin-2-yl)benzamide (Compound 1-105);

N-(6-(4-Isopropyl-4H-1,2,4-triazol-3-yl)pyridin-2-yl)-3-((2-(trifluoromethyl)pyrimidin-4-yl)thio)benzamide (Compound 1-106);

N-(6-(4-Isopropyl-4H-1,2,4-triazol-3-yl)pyridin-2-yl)-3-((2-methoxypyrimidin-4-yl)thio)benzamide (Compound 1-107);

N-(6-(4-Isopropyl-4H-1,2,4-triazol-3-yl)pyridin-2-yl)-3-((2-(2-(pyrrolidin-1-yl)ethoxy)pyrimidin-4-yl)thio)benzamide (Compound 1-108);

N-(6-(4-Isopropyl-4H-1,2,4-triazol-3-yl)pyridin-2-yl)-3-((2-(pyrrolidin-1-yl)pyrimidin-4-yl)thio)benzamide (Compound 1-109);

4-(3-((6-(4-Isopropyl-4H-1,2,4-triazol-3-yl)pyridin-2-yl)carbamoyl)phenyl)thio)pyrimidine-2-carboxylic acid (Compound 1-110);

3-((2-Cyclopropylpyrimidin-5-yl)thio)-N-(6-(4-isopropyl-4H-1,2,4-triazol-3-yl)pyridin-2-yl)benzamide (Compound 1-111);

N-(6-(4-Isopropyl-4H-1,2,4-triazol-3-yl)pyridin-2-yl)-3-((2-(trifluoromethyl)pyrimidin-5-yl)thio)benzamide (Compound 1-112);

N-(6-(4-Isopropyl-4H-1,2,4-triazol-3-yl)pyridin-2-yl)-3-((2-methoxypyrimidin-5-yl)thio)benzamide (Compound 1-113);

N-(6-(4-Isopropyl-4H-1,2,4-triazol-3-yl)pyridin-2-yl)-3-((2-(2-(pyrrolidin-1-yl)ethoxy)pyrimidin-5-yl)thio)benzamide (Compound 1-114);

N-(6-(4-Isopropyl-4H-1,2,4-triazol-3-yl)pyridin-2-yl)-3-((2-(pyrrolidin-1-yl)pyrimidin-5-yl)thio)benzamide (Compound 1-115);

5-((3-((6-(4-Isopropyl-4H-1,2,4-triazol-3-yl)pyridin-2-yl)carbamoyl)phenyl)thio)pyrimidine-2-carboxylic acid (Compound 1-116);

N-(6-(4-Isopropyl-4H-1,2,4-triazol-3-yl)pyridin-2-yl)-3-(phenylsulfonyl)benzamide (Compound 1-117);

N-(6-(4-Isopropyl-4H-1,2,4-triazol-3-yl)pyridin-2-yl)-3-(pyridin-2-ylsulfonyl)benzamide (Compound 1-118);

N-(6-(4-Isopropyl-4H-1,2,4-triazol-3-yl)pyridin-2-yl)-3-(pyridin-3-ylsulfonyl)benzamide (Compound 1-119);

N-(6-(4-Isopropyl-4H-1,2,4-triazol-3-yl)pyridin-2-yl)-3-(pyridin-4-ylsulfonyl)benzamide (Compound 1-120);

N-(6-(4-Isopropyl-4H-1,2,4-triazol-3-yl)pyridin-2-yl)-3-(pyrimidin-4-ylsulfonyl)benzamide (Compound 1-121);

N-(6-(4-Isopropyl-4H-1,2,4-triazol-3-yl)pyridin-2-yl)-3-(pyrimidin-5-ylsulfonyl)benzamide (Compound 1-122);

N-(6-(4-Isopropyl-4H-1,2,4-triazol-3-yl)pyridin-2-yl)-3-(pyrimidin-2-ylsulfonyl)benzamide (Compound 1-123);

N-(6-(4-Isopropyl-4H-1,2,4-triazol-3-yl)pyridin-2-yl)-3-(pyrazin-2-ylsulfonyl)benzamide (Compound 1-124);

N-(6-(4-Isopropyl-4H-1,2,4-triazol-3-yl)pyridin-2-yl)-3-(pyridazin-3-ylsulfonyl)benzamide (Compound 1-125);

N-(6-(4-Isopropyl-4H-1,2,4-triazol-3-yl)pyridin-2-yl)-3-(pyridazin-4-ylsulfonyl)benzamide (Compound 1-126);

$N^1$-(6-(4-Isopropyl-4H-1,2,4-triazol-3-yl)pyridin-2-yl)-$N^3$-phenylisophthalamide (Compound 1-127);

$N^1$-(6-(4-Isopropyl-4H-1,2,4-triazol-3-yl)pyridin-2-yl)-$N^3$-(pyridin-2-yl)isophthalamide (Compound 1-128);

$N^1$-(6-(4-Isopropyl-4H-1,2,4-triazol-3-yl)pyridin-2-yl)-$N^3$-(pyridin-3-yl)isophthalamide (Compound 1-129);

$N^1$-(6-(4-Isopropyl-4H-1,2,4-triazol-3-yl)pyridin-2-yl)-$N^3$-(pyridin-4-yl)isophthalamide (Compound 1-130);

$N^1$-(6-(4-Isopropyl-4H-1,2,4-triazol-3-yl)pyridin-2-yl)-$N^3$-(pyrimidin-4-yl)isophthalamide (Compound 1-131);

$N^1$-(6-(4-Isopropyl-4H-1,2,4-triazol-3-yl)pyridin-2-yl)-$N^3$-(pyrimidin-5-yl)isophthalamide (Compound 1-132);

$N^1$-(6-(4-Isopropyl-4H-1,2,4-triazol-3-yl)pyridin-2-yl)-$N^3$-(pyrimidin-2-yl)isophthalamide (Compound 1-133);

$N^1$-(6-(4-Isopropyl-4H-1,2,4-triazol-3-yl)pyridin-2-yl)-$N^3$-(pyrazin-2-yl)isophthalamide (Compound 1-134);

$N^1$-(6-(4-Isopropyl-4H-1,2,4-triazol-3-yl)pyridin-2-yl)-$N^3$-(pyridazin-3-yl)isophthalamide (Compound 1-135);

$N^1$-(6-(4-Isopropyl-4H-1,2,4-triazol-3-yl)pyridin-2-yl)-$N^3$-(pyridazin-4-yl)isophthalamide (Compound 1-136);

$N^1$-(6-(4-Isopropyl-4H-1,2,4-triazol-3-yl)pyridin-2-yl)-$N^3$-(1H-pyrrol-2-yl)isophthalamide (Compound 1-137);

$N^1$-(6-(4-Isopropyl-4H-1,2,4-triazol-3-yl)pyridin-2-yl)-$N^3$-(1-methyl-1H-pyrrol-2-yl)isophthalamide (Compound 1-138);

$N^1$-(Furan-2-yl)-$N^3$-(6-(4-isopropyl-4H-1,2,4-triazol-3-yl)pyridin-2-yl)isophthalamide (Compound 1-139);

$N^1$-(6-(4-Isopropyl-4H-1,2,4-triazol-3-yl)pyridin-2-yl)-$N^3$-(thiophen-2-yl)isophthalamide (Compound 1-140);

$N^1$-(6-(4-Isopropyl-4H-1,2,4-triazol-3-yl)pyridin-2-yl)-$N^3$-(1-methyl-1H-pyrazol-5-yl)isophthalamide (Compound 1-141);

$N^1$-(6-(4-Isopropyl-4H-1,2,4-triazol-3-yl)pyridin-2-yl)-$N^3$-(1-methyl-1H-pyrazol-3-yl)isophthalamide (Compound 1-142);

$N^1$-(1H-Imidazol-5-yl)-$N^3$-(6-(4-isopropyl-4H-1,2,4-triazol-3-yl)pyridin-2-yl)isophthalamide (Compound 1-143);

$N^1$-(6-(4-Isopropyl-4H-1,2,4-triazol-3-yl)pyridin-2-yl)-$N^3$-(1-methyl-1H-imidazol-5-yl)isophthalamide (Compound 1-144);

$N^1$-(6-(4-Isopropyl-4H-1,2,4-triazol-3-yl)pyridin-2-yl)-$N^3$-(1-methyl-1H-imidazol-4-yl)isophthalamide (Compound 1-145);

$N^1$-(6-(4-Isopropyl-4H-1,2,4-triazol-3-yl)pyridin-2-yl)-$N^3$-(oxazol-4-yl)isophthalamide (Compound 1-146);

$N^1$-(6-(4-Isopropyl-4H-1,2,4-triazol-3-yl)pyridin-2-yl)-$N^3$-(oxazol-5-yl)isophthalamide (Compound 1-147);

$N^1$-(6-(4-Isopropyl-4H-1,2,4-triazol-3-yl)pyridin-2-yl)-$N^3$-(isoxazol-5-yl)isophthalamide (Compound 1-148);

$N^1$-(6-(4-Isopropyl-4H-1,2,4-triazol-3-yl)pyridin-2-yl)-$N^3$-(isoxazol-3-yl)isophthalamide (Compound 1-149);

$N^1$-(6-(4-Isopropyl-4H-1,2,4-triazol-3-yl)pyridin-2-yl)-$N^3$-(1,3,4-oxadiazol-2-yl)isophthalamide (Compound 1-150);

$N^1$-(6-(4-Isopropyl-4H-1,2,4-triazol-3-yl)pyridin-2-yl)-$N^3$-(thiazol-5-yl)isophthalamide (Compound 1-151);

$N^1$-(6-(4-Isopropyl-4H-1,2,4-triazol-3-yl)pyridin-2-yl)-$N^3$-(1,3,4-thiadiazol-2-yl)isophthalamide (Compound 1-152);

3-Benzamido-N-(6-(4-isopropyl-4H-1,2,4-triazol-3-yl)pyridin-2-yl)benzamide (Compound 1-153);

N-(3-((6-(4-Isopropyl-4H-1,2,4-triazol-3-yl)pyridin-2-yl)carbamoyl)phenyl)picolinamide (Compound 1-154);

N-(3-((6-(4-Isopropyl-4H-1,2,4-triazol-3-yl)pyridin-2-yl)carbamoyl)phenyl)nicotinamide (Compound 1-155);

N-(3-((6-(4-Isopropyl-4H-1,2,4-triazol-3-yl)pyridin-2-yl)carbamoyl)phenyl)isonicotinamide (Compound 1-156);

N-(3-((6-(4-Isopropyl-4H-1,2,4-triazol-3-yl)pyridin-2-yl)carbamoyl)phenyl)pyrimidine-4-carboxamide (Compound 1-157);

N-(3-((6-(4-Isopropyl-4H-1,2,4-triazol-3-yl)pyridin-2-yl)carbamoyl)phenyl)pyrimidine-5-carboxamide (Compound 1-158);

N-(3-((6-(4-Isopropyl-4H-1,2,4-triazol-3-yl)pyridin-2-yl)carbamoyl)phenyl)pyrimidine-2-carboxamide (Compound 1-159);

N-(3-((6-(4-Isopropyl-4H-1,2,4-triazol-3-yl)pyridin-2-yl)carbamoyl)phenyl)pyrazine-2-carboxamide (Compound 1-160);

N-(3-((6-(4-Isopropyl-4H-1,2,4-triazol-3-yl)pyridin-2-yl)carbamoyl)phenyl)pyridazine-3-carboxamide (Compound 1-161);

N-(3-((6-(4-Isopropyl-4H-1,2,4-triazol-3-yl)pyridin-2-yl)carbamoyl)phenyl)pyridazine-4-carboxamide (Compound 1-162);

N-(3-((6-(4-Isopropyl-4H-1,2,4-triazol-3-yl)pyridin-2-yl)carbamoyl)phenyl)-1H-pyrrole-2-carboxamide (Compound 1-163);

N-(3-((6-(4-Isopropyl-4H-1,2,4-triazol-3-yl)pyridin-2-yl)carbamoyl)phenyl)-1-methyl-1H-pyrrole-2-carboxamide (Compound 1-164);

N-(3-((6-(4-Isopropyl-4H-1,2,4-triazol-3-yl)pyridin-2-yl)carbamoyl)phenyl)furan-2-carboxamide (Compound 1-165);

N-(3-((6-(4-Isopropyl-4H-1,2,4-triazol-3-yl)pyridin-2-yl)carbamoyl)phenyl)thiophene-2-carboxamide (Compound 1-166);

N-(3-((6-(4-Isopropyl-4H-1,2,4-triazol-3-yl)pyridin-2-yl)carbamoyl)phenyl)-1-methyl-1H-pyrazole-5-carboxamide (Compound 1-167);

N-(3-((6-(4-Isopropyl-4H-1,2,4-triazol-3-yl)pyridin-2-yl)carbamoyl)phenyl)-1-methyl-1H-pyrazole-3-carboxamide (Compound 1-168);

N-(3-((6-(4-Isopropyl-4H-1,2,4-triazol-3-yl)pyridin-2-yl)carbamoyl)phenyl)-1H-imidazole-5-carboxamide (Compound 1-169);

N-(3-((6-(4-Isopropyl-4H-1,2,4-triazol-3-yl)pyridin-2-yl)carbamoyl)phenyl)-1-methyl-1H-imidazole-5-carboxamide (Compound 1-170);

N-(3-((6-(4-Isopropyl-4H-1,2,4-triazol-3-yl)pyridin-2-yl)carbamoyl)phenyl)-1-methyl-1H-imidazole-4-carboxamide (Compound 1-171);

N-(3-((6-(4-Isopropyl-4H-1,2,4-triazol-3-yl)pyridin-2-yl)carbamoyl)phenyl)oxazole-4-carboxamide (Compound 1-172);

N-(3-((6-(4-Isopropyl-4H-1,2,4-triazol-3-yl)pyridin-2-yl)carbamoyl)phenyl)oxazole-5-carboxamide (Compound 1-173);

N-(3-((6-(4-Isopropyl-4H-1,2,4-triazol-3-yl)pyridin-2-yl)carbamoyl)phenyl)isoxazole-5-carboxamide (Compound 1-174);

N-(3-((6-(4-Isopropyl-4H-1,2,4-triazol-3-yl)pyridin-2-yl)carbamoyl)phenyl)isoxazole-3-carboxamide (Compound 1-175);

N-(3-((6-(4-Isopropyl-4H-1,2,4-triazol-3-yl)pyridin-2-yl)carbamoyl)phenyl)-1,3,4-oxadiazole-2-carboxamide (Compound 1-176);

N-(3-((6-(4-Isopropyl-4H-1,2,4-triazol-3-yl)pyridin-2-yl)carbamoyl)phenyl)thiazole-5-carboxamide (Compound 1-177);

N-(3-((6-(4-Isopropyl-4H-1,2,4-triazol-3-yl)pyridin-2-yl)carbamoyl)phenyl)-1,3,4-thiadiazole-2-carboxamide (Compound 1-178);

3-(Benzyloxy)-N-(6-(4-isopropyl-4H-1,2,4-triazol-3-yl)pyridin-2-yl)benzamide (Compound 1-179);

N-(6-(4-Isopropyl-4H-1,2,4-triazol-3-yl)pyridin-2-yl)-3-(pyridin-2-ylmethoxy)benzamide (Compound 1-180);

N-(6-(4-Isopropyl-4H-1,2,4-triazol-3-yl)pyridin-2-yl)-3-(pyridin-3-ylmethoxy)benzamide (Compound 1-181);

N-(6-(4-Isopropyl-4H-1,2,4-triazol-3-yl)pyridin-2-yl)-3-(pyridin-4-ylmethoxy)benzamide (Compound 1-182);

N-(6-(4-Isopropyl-4H-1,2,4-triazol-3-yl)pyridin-2-yl)-3-(pyrimidin-4-ylmethoxy)benzamide (Compound 1-183);

N-(6-(4-Isopropyl-4H-1,2,4-triazol-3-yl)pyridin-2-yl)-3-(pyrimidin-5-ylmethoxy)benzamide (Compound 1-184);

N-(6-(4-Isopropyl-4H-1,2,4-triazol-3-yl)pyridin-2-yl)-3-(pyrimidin-2-ylmethoxy)benzamide (Compound 1-185);

N-(6-(4-Isopropyl-4H-1,2,4-triazol-3-yl)pyridin-2-yl)-3-(pyrazin-2-ylmethoxy)benzamide (Compound 1-186);

N-(6-(4-Isopropyl-4H-1,2,4-triazol-3-yl)pyridin-2-yl)-3-(pyridazin-3-ylmethoxy)benzamide (Compound 1-187);

N-(6-(4-Isopropyl-4H-1,2,4-triazol-3-yl)pyridin-2-yl)-3-(pyridazin-4-ylmethoxy)benzamide (Compound 1-188);

3-(Benzylamino)-N-(6-(4-isopropyl-4H-1,2,4-triazol-3-yl)pyridin-2-yl)benzamide (Compound 1-189);

N-(6-(4-Isopropyl-4H-1,2,4-triazol-3-yl)pyridin-2-yl)-3-((pyridin-2-ylmethyl)amino)benzamide (Compound 1-190);

N-(6-(4-Isopropyl-4H-1,2,4-triazol-3-yl)pyridin-2-yl)-3-((pyridin-3-ylmethyl)amino)benzamide (Compound 1-191);

N-(6-(4-Isopropyl-4H-1,2,4-triazol-3-yl)pyridin-2-yl)-3-((pyridin-4-ylmethyl)amino)benzamide (Compound 1-192);

N-(6-(4-Isopropyl-4H-1,2,4-triazol-3-yl)pyridin-2-yl)-3-((pyrimidin-4-ylmethyl)amino)benzamide (Compound 1-193);
N-(6-(4-Isopropyl-4H-1,2,4-triazol-3-yl)pyridin-2-yl)-3-((pyrimidin-5-ylmethyl)amino)benzamide (Compound 1-194);
N-(6-(4-Isopropyl-4H-1,2,4-triazol-3-yl)pyridin-2-yl)-3-((pyrimidin-2-ylmethyl)amino)benzamide (Compound 1-195);
N-(6-(4-Isopropyl-4H-1,2,4-triazol-3-yl)pyridin-2-yl)-3-((pyrazin-2-ylmethyl)amino)benzamide (Compound 1-196);
N-(6-(4-Isopropyl-4H-1,2,4-triazol-3-yl)pyridin-2-yl)-3-((pyridazin-3-ylmethyl)amino)benzamide (Compound 1-197);
N-(6-(4-Isopropyl-4H-1,2,4-triazol-3-yl)pyridin-2-yl)-3-((pyridazin-4-ylmethyl)amino)benzamide (Compound 1-198);
N-(6-(4-Isopropyl-4H-1,2,4-triazol-3-yl)pyridin-2-yl)-3-(phenylethynyl)benzamide (Compound 1-199);
N-(6-(4-Isopropyl-4H-1,2,4-triazol-3-yl)pyridin-2-yl)-3-(pyridin-2-ylethynyl)benzamide (Compound 1-200);
N-(6-(4-Isopropyl-4H-1,2,4-triazol-3-yl)pyridin-2-yl)-3-(pyridin-3-ylethynyl)benzamide (Compound 1-201);
N-(6-(4-Isopropyl-4H-1,2,4-triazol-3-yl)pyridin-2-yl)-3-(pyridin-4-ylethynyl)benzamide (Compound 1-202);
N-(6-(4-Isopropyl-4H-1,2,4-triazol-3-yl)pyridin-2-yl)-3-(pyrimidin-4-ylethynyl)benzamide (Compound 1-203);
N-(6-(4-Isopropyl-4H-1,2,4-triazol-3-yl)pyridin-2-yl)-3-(pyrimidin-5-ylethynyl)benzamide (Compound 1-204);
N-(6-(4-Isopropyl-4H-1,2,4-triazol-3-yl)pyridin-2-yl)-3-(pyrimidin-2-ylethynyl)benzamide (Compound 1-205);
N-(6-(4-Isopropyl-4H-1,2,4-triazol-3-yl)pyridin-2-yl)-3-(pyrazin-2-ylethynyl)benzamide (Compound 1-206);
N-(6-(4-Isopropyl-4H-1,2,4-triazol-3-yl)pyridin-2-yl)-3-(pyridazin-3-ylethynyl)benzamide (Compound 1-207);
N-(6-(4-Isopropyl-4H-1,2,4-triazol-3-yl)pyridin-2-yl)-3-(pyridazin-4-ylethynyl)benzamide (Compound 1-208);
2-Fluoro-N-(6-(4-isopropyl-4H-1,2,4-triazol-3-yl)pyridin-2-yl)-5-phenoxybenzamide (Compound 1-209);
2-Fluoro-N-(6-(4-isopropyl-4H-1,2,4-triazol-3-yl)pyridin-2-yl)-5-(pyridin-2-yloxy)benzamide (Compound 1-210);
2-Fluoro-N-(6-(4-isopropyl-4H-1,2,4-triazol-3-yl)pyridin-2-yl)-5-(pyridin-3-yloxy)benzamide (Compound 1-211);
2-Fluoro-N-(6-(4-isopropyl-4H-1,2,4-triazol-3-yl)pyridin-2-yl)-5-(pyridin-4-yloxy)benzamide (Compound 1-212);
5-((6-Cyclopropylpyridin-2-yl)oxy)-2-fluoro-N-(6-(4-isopropyl-4H-1,2,4-triazol-3-yl)pyridin-2-yl)benzamide (Compound 1-213);
5-((6-(Dimethylamino)pyridin-2-yl)oxy)-2-fluoro-N-(6-(4-isopropyl-4H-1,2,4-triazol-3-yl)pyridin-2-yl)benzamide (Compound 1-214);
5-((6-(Dimethylamino)pyridin-3-yl)oxy)-2-fluoro-N-(6-(4-isopropyl-4H-1,2,4-triazol-3-yl)pyridin-2-yl)benzamide (Compound 1-215);
6-(4-Fluoro-3-((6-(4-isopropyl-4H-1,2,4-triazol-3-yl)pyridin-2-yl)carbamoyl)phenoxy)picolinic acid (Compound 1-216);
2-Fluoro-N-(6-(4-isopropyl-4H-1,2,4-triazol-3-yl)pyridin-2-yl)-5-(pyrimidin-4-yloxy)benzamide (Compound 1-217);
2-Fluoro-N-(6-(4-isopropyl-4H-1,2,4-triazol-3-yl)pyridin-2-yl)-5-(pyrimidin-5-yloxy)benzamide (Compound 1-218);
2-Fluoro-N-(6-(4-isopropyl-4H-1,2,4-triazol-3-yl)pyridin-2-yl)-5-(pyrimidin-2-yloxy)benzamide (Compound 1-219);
2-Fluoro-N-(6-(4-isopropyl-4H-1,2,4-triazol-3-yl)pyridin-2-yl)-5-(pyrazin-2-yloxy)benzamide (Compound 1-220);
2-Fluoro-N-(6-(4-isopropyl-4H-1,2,4-triazol-3-yl)pyridin-2-yl)-5-(pyridazin-3-yloxy)benzamide (Compound 1-221);
2-Fluoro-N-(6-(4-isopropyl-4H-1,2,4-triazol-3-yl)pyridin-2-yl)-5-(pyridazin-4-yloxy)benzamide (Compound 1-222);
2-Fluoro-N-(6-(4-isopropyl-4H-1,2,4-triazol-3-yl)pyridin-2-yl)-5-((6-(trifluoromethyl)pyridin-2-yl)oxy)benzamide (Compound 1-223);
2-Fluoro-N-(6-(4-isopropyl-4H-1,2,4-triazol-3-yl)pyridin-2-yl)-5-((6-methoxypyridin-2-yl)oxy)benzamide (Compound 1-224);
2-Fluoro-N-(6-(4-isopropyl-4H-1,2,4-triazol-3-yl)pyridin-2-yl)-5-((6-(pyrrolidin-1-yl)pyridin-2-yl)oxy)benzamide (Compound 1-225);
2-Fluoro-N-(6-(4-isopropyl-4H-1,2,4-triazol-3-yl)pyridin-2-yl)-5-((5,6,7,8-tetrahydro-1,8-naphthyridin-2-yl)oxy)benzamide (Compound 1-226);
5-((5-Cyclopropylpyridin-2-yl)oxy)-2-fluoro-N-(6-(4-isopropyl-4H-1,2,4-triazol-3-yl)pyridin-2-yl)benzamide (Compound 1-227);
2-Fluoro-N-(6-(4-isopropyl-4H-1,2,4-triazol-3-yl)pyridin-2-yl)-5-((5-(trifluoromethyl)pyridin-2-yl)oxy)benzamide (Compound 1-228);
2-Fluoro-N-(6-(4-isopropyl-4H-1,2,4-triazol-3-yl)pyridin-2-yl)-5-((5-methoxypyridin-2-yl)oxy)benzamide (Compound 1-229);
6-(4-Fluoro-3-((6-(4-isopropyl-4H-1,2,4-triazol-3-yl)pyridin-2-yl)carbamoyl)phenoxy)nicotinic acid (Compound 1-230);
5-((2-Cyclopropylpyrimidin-4-yl)oxy)-2-fluoro-N-(6-(4-isopropyl-4H-1,2,4-triazol-3-yl)pyridin-2-yl)benzamide (Compound 1-231);
2-Fluoro-N-(6-(4-isopropyl-4H-1,2,4-triazol-3-yl)pyridin-2-yl)-5-((2-(trifluoromethyl)pyrimidin-4-yl)oxy)benzamide (Compound 1-232);
2-Fluoro-N-(6-(4-isopropyl-4H-1,2,4-triazol-3-yl)pyridin-2-yl)-5-((2-methoxypyrimidin-4-yl)oxy)benzamide (Compound 1-233);
2-Fluoro-N-(6-(4-isopropyl-4H-1,2,4-triazol-3-yl)pyridin-2-yl)-5-((2-(2-(pyrrolidin-1-yl)ethoxy)pyrimidin-4-yl)oxy)benzamide (Compound 1-234);
2-Fluoro-N-(6-(4-isopropyl-4H-1,2,4-triazol-3-yl)pyridin-2-yl)-5-((2-(pyrrolidin-1-yl)pyrimidin-4-yl)oxy)benzamide (Compound 1-235);
4-(4-Fluoro-3-((6-(4-isopropyl-4H-1,2,4-triazol-3-yl)pyridin-2-yl)carbamoyl)phenoxy)pyrimidine-2-carboxylic acid (Compound 1-236);
5-((2-Cyclopropylpyrimidin-5-yl)oxy)-2-fluoro-N-(6-(4-isopropyl-4H-1,2,4-triazol-3-yl)pyridin-2-yl)benzamide (Compound 1-237);
2-Fluoro-N-(6-(4-isopropyl-4H-1,2,4-triazol-3-yl)pyridin-2-yl)-5-((2-(trifluoromethyl)pyrimidin-5-yl)oxy)benzamide (Compound 1-238);
2-Fluoro-N-(6-(4-isopropyl-4H-1,2,4-triazol-3-yl)pyridin-2-yl)-5-((2-methoxypyrimidin-5-yl)oxy)benzamide (Compound 1-239);
2-Fluoro-N-(6-(4-isopropyl-4H-1,2,4-triazol-3-yl)pyridin-2-yl)-5-((2-(2-(pyrrolidin-1-yl)ethoxy)pyrimidin-5-yl)oxy)benzamide (Compound 1-240);
2-Fluoro-N-(6-(4-isopropyl-4H-1,2,4-triazol-3-yl)pyridin-2-yl)-5-((2-(pyrrolidin-1-yl)pyrimidin-5-yl)oxy)benzamide (Compound 1-241);

5-(4-Fluoro-3-((6-(4-isopropyl-4H-1,2,4-triazol-3-yl)pyridin-2-yl)carbamoyl)phenoxy)pyrimidine-2-carboxylic acid (Compound 1-242);

N-(6-(4-Isopropyl-4H-1,2,4-triazol-3-yl)pyridin-2-yl)-4-phenoxypicolinamide (Compound 1-243);

N-(6-(4-Isopropyl-4H-1,2,4-triazol-3-yl)pyridin-2-yl)-4-(pyridin-2-yloxy)picolinamide (Compound 1-244);

N-(6-(4-Isopropyl-4H-1,2,4-triazol-3-yl)pyridin-2-yl)-4-(pyridin-3-yloxy)picolinamide (Compound 1-245);

N-(6-(4-Isopropyl-4H-1,2,4-triazol-3-yl)pyridin-2-yl)-4-(pyridin-4-yloxy)picolinamide (Compound 1-246);

N-(6-(4-Isopropyl-4H-1,2,4-triazol-3-yl)pyridin-2-yl)-4-(pyrimidin-4-yloxy)picolinamide (Compound 1-247);

N-(6-(4-Isopropyl-4H-1,2,4-triazol-3-yl)pyridin-2-yl)-4-(pyrimidin-5-yloxy)picolinamide (Compound 1-248);

N-(6-(4-Isopropyl-4H-1,2,4-triazol-3-yl)pyridin-2-yl)-4-(pyrimidin-2-yloxy)picolinamide (Compound 1-249);

N-(6-(4-Isopropyl-4H-1,2,4-triazol-3-yl)pyridin-2-yl)-4-(pyrazin-2-yloxy)picolinamide (Compound 1-250);

N-(6-(4-Isopropyl-4H-1,2,4-triazol-3-yl)pyridin-2-yl)-4-(pyridazin-3-yloxy)picolinamide (Compound 1-251);

N-(6-(4-Isopropyl-4H-1,2,4-triazol-3-yl)pyridin-2-yl)-4-(pyridazin-4-yloxy)picolinamide (Compound 1-252);

4-((6-Cyclopropylpyridin-2-yl)oxy)-N-(6-(4-isopropyl-4H-1,2,4-triazol-3-yl)pyridin-2-yl)picolinamide (Compound 1-253);

N-(6-(4-Isopropyl-4H-1,2,4-triazol-3-yl)pyridin-2-yl)-4-((6-(trifluoromethyl)pyridin-2-yl)oxy)picolinamide (Compound 1-254);

N-(6-(4-Isopropyl-4H-1,2,4-triazol-3-yl)pyridin-2-yl)-4-((6-methoxypyridin-2-yl)oxy)picolinamide (Compound 1-255);

N-(6-(4-Isopropyl-4H-1,2,4-triazol-3-yl)pyridin-2-yl)-4-((6-(pyrrolidin-1-yl)pyridin-2-yl)oxy)picolinamide (Compound 1-256);

N-(6-(4-Isopropyl-4H-1,2,4-triazol-3-yl)pyridin-2-yl)-4-((5,6,7,8-tetrahydro-1,8-naphthyridin-2-yl)oxy)picolinamide (Compound 1-257);

6-((2-((6-(4-Isopropyl-4H-1,2,4-triazol-3-yl)pyridin-2-yl)carbamoyl)pyridin-4-yl)oxy)picolinic acid (Compound 1-258);

4-((5-Cyclopropylpyridin-2-yl)oxy)-N-(6-(4-isopropyl-4H-1,2,4-triazol-3-yl)pyridin-2-yl)picolinamide (Compound 1-259);

N-(6-(4-Isopropyl-4H-1,2,4-triazol-3-yl)pyridin-2-yl)-4-((5-(trifluoromethyl)pyridin-2-yl)oxy)picolinamide (Compound 1-260);

N-(6-(4-Isopropyl-4H-1,2,4-triazol-3-yl)pyridin-2-yl)-4-((5-methoxypyridin-2-yl)oxy)picolinamide (Compound 1-261);

6-((2-((6-(4-Isopropyl-4H-1,2,4-triazol-3-yl)pyridin-2-yl)carbamoyl)pyridin-4-yl)oxy)nicotinic acid (Compound 1-262);

4-((2-Cyclopropylpyrimidin-4-yl)oxy)-N-(6-(4-isopropyl-4H-1,2,4-triazol-3-yl)pyridin-2-yl)picolinamide (Compound 1-263);

N-(6-(4-Isopropyl-4H-1,2,4-triazol-3-yl)pyridin-2-yl)-4-((2-(trifluoromethyl)pyrimidin-4-yl)oxy)picolinamide (Compound 1-264);

N-(6-(4-Isopropyl-4H-1,2,4-triazol-3-yl)pyridin-2-yl)-4-((2-methoxypyrimidin-4-yl)oxy)picolinamide (Compound 1-265);

N-(6-(4-Isopropyl-4H-1,2,4-triazol-3-yl)pyridin-2-yl)-4-((2-(2-(pyrrolidin-1-yl)ethoxy)pyrimidin-4-yl)oxy)picolinamide (Compound 1-266);

N-(6-(4-Isopropyl-4H-1,2,4-triazol-3-yl)pyridin-2-yl)-4-((2-(pyrrolidin-1-yl)pyrimidin-4-yl)oxy)picolinamide (Compound 1-267);

4-((2-((6-(4-Isopropyl-4H-1,2,4-triazol-3-yl)pyridin-2-yl)carbamoyl)pyridin-4-yl)oxy)pyrimidine-2-carboxylic acid (Compound 1-268);

4-((2-Cyclopropylpyrimidin-5-yl)oxy)-N-(6-(4-isopropyl-4H-1,2,4-triazol-3-yl)pyridin-2-yl)picolinamide (Compound 1-269);

N-(6-(4-Isopropyl-4H-1,2,4-triazol-3-yl)pyridin-2-yl)-4-((2-(trifluoromethyl)pyrimidin-5-yl)oxy)picolinamide (Compound 1-270);

N-(6-(4-Isopropyl-4H-1,2,4-triazol-3-yl)pyridin-2-yl)-4-((2-methoxypyrimidin-5-yl)oxy)picolinamide (Compound 1-271);

N-(6-(4-Isopropyl-4H-1,2,4-triazol-3-yl)pyridin-2-yl)-4-((2-(2-(pyrrolidin-1-yl)ethoxy)pyrimidin-5-yl)oxy)picolinamide (Compound 1-272);

N-(6-(4-Isopropyl-4H-1,2,4-triazol-3-yl)pyridin-2-yl)-4-((2-(pyrrolidin-1-yl)pyrimidin-5-yl)oxy)picolinamide (Compound 1-273);

5-((2-((6-(4-Isopropyl-4H-1,2,4-triazol-3-yl)pyridin-2-yl)carbamoyl)pyridin-4-yl)oxy)pyrimidine-2-carboxylic acid (Compound 1-274);

N-(6-(4-Isopropyl-4H-1,2,4-triazol-3-yl)pyridin-2-yl)-4-methyl-3-phenoxybenzamide (Compound 1-275);

N-(6-(4-Isopropyl-4H-1,2,4-triazol-3-yl)pyridin-2-yl)-4-methyl-3-(pyridin-2-yloxy)benzamide (Compound 1-276);

N-(6-(4-Isopropyl-4H-1,2,4-triazol-3-yl)pyridin-2-yl)-4-methyl-3-(pyridin-3-yloxy)benzamide (Compound 1-277);

N-(6-(4-Isopropyl-4H-1,2,4-triazol-3-yl)pyridin-2-yl)-4-methyl-3-(pyridin-4-yloxy)benzamide (Compound 1-278);

N-(6-(4-Isopropyl-4H-1,2,4-triazol-3-yl)pyridin-2-yl)-4-methyl-3-(pyrimidin-4-yloxy)benzamide (Compound 1-279);

N-(6-(4-Isopropyl-4H-1,2,4-triazol-3-yl)pyridin-2-yl)-4-methyl-3-(pyrimidin-5-yloxy)benzamide (Compound 1-280);

N-(6-(4-Isopropyl-4H-1,2,4-triazol-3-yl)pyridin-2-yl)-4-methyl-3-(pyrimidin-2-yloxy)benzamide (Compound 1-281);

N-(6-(4-Isopropyl-4H-1,2,4-triazol-3-yl)pyridin-2-yl)-4-methyl-3-(pyrazin-2-yloxy)benzamide (Compound 1-282);

N-(6-(4-Isopropyl-4H-1,2,4-triazol-3-yl)pyridin-2-yl)-4-methyl-3-(pyridazin-3-yloxy)benzamide (Compound 1-283);

N-(6-(4-Isopropyl-4H-1,2,4-triazol-3-yl)pyridin-2-yl)-4-methyl-3-(pyridazin-4-yloxy)benzamide (Compound 1-284);

2-Fluoro-N-(6-(4-isopropyl-4H-1,2,4-triazol-3-yl)pyridin-2-yl)-4-methyl-5-phenoxybenzamide (Compound 1-285);

2-Fluoro-N-(6-(4-isopropyl-4H-1,2,4-triazol-3-yl)pyridin-2-yl)-4-methyl-5-(pyridin-2-yloxy)benzamide (Compound 1-286);

2-Fluoro-N-(6-(4-isopropyl-4H-1,2,4-triazol-3-yl)pyridin-2-yl)-4-methyl-5-(pyridin-3-yloxy)benzamide (Compound 1-287);

2-Fluoro-N-(6-(4-isopropyl-4H-1,2,4-triazol-3-yl)pyridin-2-yl)-4-methyl-5-(pyridin-4-yloxy)benzamide (Compound 1-288);

2-Fluoro-N-(6-(4-isopropyl-4H-1,2,4-triazol-3-yl)pyridin-2-yl)-4-methyl-5-(pyrimidin-4-yloxy)benzamide (Compound 1-289);

2-Fluoro-N-(6-(4-isopropyl-4H-1,2,4-triazol-3-yl)pyridin-2-yl)-4-methyl-5-(pyrimidin-5-yloxy)benzamide (Compound 1-290);

2-Fluoro-N-(6-(4-isopropyl-4H-1,2,4-triazol-3-yl)pyridin-2-yl)-4-methyl-5-(pyrimidin-2-yloxy)benzamide (Compound 1-291);

2-Fluoro-N-(6-(4-isopropyl-4H-1,2,4-triazol-3-yl)pyridin-2-yl)-4-methyl-5-(pyrazin-2-yloxy)benzamide (Compound 1-292);

2-Fluoro-N-(6-(4-isopropyl-4H-1,2,4-triazol-3-yl)pyridin-2-yl)-4-methyl-5-(pyridazin-3-yloxy)benzamide (Compound 1-293);

2-Fluoro-N-(6-(4-isopropyl-4H-1,2,4-triazol-3-yl)pyridin-2-yl)-4-methyl-5-(pyridazin-4-yloxy)benzamide (Compound 1-294);

4-Fluoro-$N^3$-(6-(4-isopropyl-4H-1,2,4-triazol-3-yl)pyridin-2-yl)-$N^1$-phenylisophthalamide (Compound 1-295);

4-Fluoro-$N^3$-(6-(4-isopropyl-4H-1,2,4-triazol-3-yl)pyridin-2-yl)-$N^1$-(pyridin-2-yl)isophthalamide (Compound 1-296);

4-Fluoro-$N^3$-(6-(4-isopropyl-4H-1,2,4-triazol-3-yl)pyridin-2-yl)-$N^1$-(pyridin-3-yl)isophthalamide (Compound 1-297);

4-Fluoro-$N^3$-(6-(4-isopropyl-4H-1,2,4-triazol-3-yl)pyridin-2-yl)-$N^1$-(pyridin-4-yl)isophthalamide (Compound 1-298);

4-Fluoro-$N^3$-(6-(4-isopropyl-4H-1,2,4-triazol-3-yl)pyridin-2-yl)-$N^1$-(pyrimidin-4-yl)isophthalamide (Compound 1-299);

4-Fluoro-$N^3$-(6-(4-isopropyl-4H-1,2,4-triazol-3-yl)pyridin-2-yl)-$N^1$-(pyrimidin-5-yl)isophthalamide (Compound 1-300);

4-Fluoro-$N^3$-(6-(4-isopropyl-4H-1,2,4-triazol-3-yl)pyridin-2-yl)-$N^1$-(pyrimidin-2-yl)isophthalamide (Compound 1-301);

4-Fluoro-$N^3$-(6-(4-isopropyl-4H-1,2,4-triazol-3-yl)pyridin-2-yl)-$N^1$-(pyrazin-2-yl)isophthalamide (Compound 1-302);

4-Fluoro-$N^3$-(6-(4-isopropyl-4H-1,2,4-triazol-3-yl)pyridin-2-yl)-$N^1$-(pyridazin-3-yl)isophthalamide (Compound 1-303);

4-Fluoro-$N^3$-(6-(4-isopropyl-4H-1,2,4-triazol-3-yl)pyridin-2-yl)-$N^1$-(pyridazin-4-yl)isophthalamide (Compound 1-304);

5-Benzamido-2-fluoro-N-(6-(4-isopropyl-4H-1,2,4-triazol-3-yl)pyridin-2-yl)benzamide (Compound 1-305);

5-(4-(Aminomethyl)benzamido)-2-fluoro-N-(6-(4-isopropyl-4H-1,2,4-triazol-3-yl)pyridin-2-yl)benzamide (Compound 1-306);

N-(4-Fluoro-3-((6-(4-isopropyl-4H-1,2,4-triazol-3-yl)pyridin-2-yl)carbamoyl)phenyl)picolinamide (Compound 1-307);

N-(4-Fluoro-3-((6-(4-isopropyl-4H-1,2,4-triazol-3-yl)pyridin-2-yl)carbamoyl)phenyl)nicotinamide (Compound 1-308);

N-(4-Fluoro-3-((6-(4-isopropyl-4H-1,2,4-triazol-3-yl)pyridin-2-yl)carbamoyl)phenyl)isonicotinamide (Compound 1-309);

6-Cyclopropyl-N-(4-fluoro-3-((6-(4-isopropyl-4H-1,2,4-triazol-3-yl)pyridin-2-yl)carbamoyl)phenyl)picolinamide (Compound 1-310);

5-Bromo-N-(4-fluoro-3-((6-(4-isopropyl-4H-1,2,4-triazol-3-yl)pyridin-2-yl)carbamoyl)phenyl)picolinamide (Compound 1-311);

N-(4-Fluoro-3-((6-(4-isopropyl-4H-1,2,4-triazol-3-yl)pyridin-2-yl)carbamoyl)phenyl)pyrimidine-4-carboxamide (Compound 1-312);

N-(4-Fluoro-3-((6-(4-isopropyl-4H-1,2,4-triazol-3-yl)pyridin-2-yl)carbamoyl)phenyl)pyrimidine-5-carboxamide (Compound 1-313);

N-(4-Fluoro-3-((6-(4-isopropyl-4H-1,2,4-triazol-3-yl)pyridin-2-yl)carbamoyl)phenyl)pyrimidine-2-carboxamide (Compound 1-314);

N-(4-Fluoro-3-((6-(4-isopropyl-4H-1,2,4-triazol-3-yl)pyridin-2-yl)carbamoyl)phenyl)pyrazine-2-carboxamide (Compound 1-315);

N-(4-Fluoro-3-((6-(4-isopropyl-4H-1,2,4-triazol-3-yl)pyridin-2-yl)carbamoyl)phenyl)pyridazine-3-carboxamide (Compound 1-316);

N-(4-Fluoro-3-((6-(4-isopropyl-4H-1,2,4-triazol-3-yl)pyridin-2-yl)carbamoyl)phenyl)pyridazine-4-carboxamide (Compound 1-317);

N-(4-Fluoro-3-((6-(4-isopropyl-4H-1,2,4-triazol-3-yl)pyridin-2-yl)carbamoyl)phenyl)-5-methyl-1,3,4-oxadiazole-2-carboxamide (Compound 1-318);

N-(6-(4-Cyclopropyl-4H-1,2,4-triazol-3-yl)pyridin-2-yl)-3-phenoxybenzamide (Compound 1-319);

N-(6-(4-Cyclopropyl-4H-1,2,4-triazol-3-yl)pyridin-2-yl)-3-(pyridin-2-yloxy) benzamide (Compound 1-320);

N-(6-(4-Cyclopropyl-4H-1,2,4-triazol-3-yl)pyridin-2-yl)-3-(pyridin-3-yloxy)benzamide (Compound 1-321);

N-(6-(4-Cyclopropyl-4H-1,2,4-triazol-3-yl)pyridin-2-yl)-3-(pyridin-4-yloxy)benzamide (Compound 1-322);

N-(6-(4-Cyclopropyl-4H-1,2,4-triazol-3-yl)pyridin-2-yl)-3-(pyrimidin-4-yloxy)benzamide (Compound 1-323);

N-(6-(4-Cyclopropyl-4H-1,2,4-triazol-3-yl)pyridin-2-yl)-3-(pyrimidin-5-yloxy)benzamide (Compound 1-324);

N-(6-(4-Cyclopropyl-4H-1,2,4-triazol-3-yl)pyridin-2-yl)-3-(pyrimidin-2-yloxy)benzamide (Compound 1-325);

N-(6-(4-Cyclopropyl-4H-1,2,4-triazol-3-yl)pyridin-2-yl)-3-(pyrazin-2-yloxy)benzamide (Compound 1-326);

N-(6-(4-Cyclopropyl-4H-1,2,4-triazol-3-yl)pyridin-2-yl)-3-(pyridazin-3-yloxy)benzamide (Compound 1-327);

N-(6-(4-Cyclopropyl-4H-1,2,4-triazol-3-yl)pyridin-2-yl)-3-(pyridazin-4-yloxy)benzamide (Compound 1-328);

tert-Butyl ((2-((2-((6-(4-cyclopropyl-4H-1,2,4-triazol-3-yl)pyridin-2-yl)carbamoyl)pyridin-4-yl)oxy)-6-(trifluoromethyl)pyridin-4-yl)methyl)carbamate (Compound 1-329);

4-((4-(Aminomethyl)-6-(trifluoromethyl)pyridin-2-yl)oxy)-N-(6-(4-cyclopropyl-4H-1,2,4-triazol-3-yl)pyridin-2-yl)picolinamide (Compound 1-330);

3-((4-(Aminomethyl)-6-(trifluoromethyl)pyridin-2-yl)oxy)-N-(6-(4-isopropyl-4H-1,2,4-triazol-3-yl)pyridin-2-yl)benzamide (Compound 1-331);

4-(Aminomethyl)-N-(4-fluoro-3-((6-(4-isopropyl-4H-1,2,4-triazol-3-yl)pyridin-2-yl)carbamoyl)phenyl)picolinamide (Compound 1-332);

2-Fluoro-N-(6-(4-isopropyl-4H-1,2,4-triazol-3-yl)pyridin-2-yl)-5-(2-phenylacetamido)benzamide (Compound 1-333);

5-(3,4-Difluorobenzamido)-2-fluoro-N-(6-(4-isopropyl-4H-1,2,4-triazol-3-yl)pyridin-2-yl)benzamide (Compound 1-334);

4-((4-(Fluoro-3-((6-(4-isopropyl-4H-1,2,4-triazol-3-yl)pyridin-2-yl)carbamoyl)phenyl)carbamoyl)benzoic acid (Compound 1-335);

5-((6-Bromopyridin-2-yl)oxy)-2-fluoro-N-(6-(4-isopropyl-4H-1,2,4-triazol-3-yl)pyridin-2-yl)benzamide (Compound 1-336);

5-((5-Bromopyridin-2-yl)oxy)-2-fluoro-N-(6-(4-isopropyl-4H-1,2,4-triazol-3-yl)pyridin-2-yl)benzamide (Compound 1-337);

5-Benzamido-N-(6-(4-cyclopropyl-4H-1,2,4-triazol-3-yl)pyridin-2-yl)-2-fluorobenzamide (Compound 1-338);

N-(6-(4-Cyclopropyl-4H-1,2,4-triazol-3-yl)pyridin-2-yl)-5-(3,4-difluorobenzamido)-2-fluorobenzamide (Compound 1-339);

5-Benzamido-N-(6-(4-(1,3-difluoropropan-2-yl)-4H-1,2,4-triazol-3-yl)pyridin-2-yl)-2-fluorobenzamide (Compound 1-340);

(R)-5-Benzamido-2-fluoro-N-(6-(4-(1-hydroxypropan-2-yl)-4H-1,2,4-triazol-3-yl)pyridin-2-yl)benzamide (Compound 1-341);

(R)-2-Fluoro-5-((4-fluorophenyl)amino)-N-(6-(4-(1-hydroxypropan-2-yl)-4H-1,2,4-triazol-3-yl)pyridin-2-yl)benzamide (Compound 1-342);

(R)-2-Fluoro-5-((4-fluorobenzyl)amino)-N-(6-(4-(1-hydroxypropan-2-yl)-4H-1,2,4-triazol-3-yl)pyridin-2-yl)benzamide (Compound 1-343).

In some embodiments, provided herein is a pharmaceutically acceptable salt or solvate of a compound that is described in Table 1.

TABLE 2

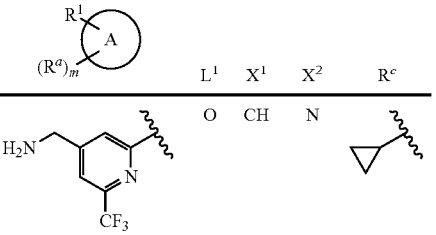

Compounds in Table 2 are named:

4-((4-(Aminomethyl)-6-(trifluoromethyl)pyridin-2-yl)oxy)-N-(3-(4-cyclopropyl-4H-1,2,4-triazol-3-yl)phenyl)picolinamide (Compound 2-1)

In some embodiments, provided herein is a pharmaceutically acceptable salt or solvate of a compound that is described in Table 2.

Any combination of the groups described above for the various variables is contemplated herein. Throughout the specification, groups and substituents thereof are chosen by one skilled in the field to provide stable moieties and compounds.

In one aspect, compounds described herein are in the form of pharmaceutically acceptable salts. As well, active metabolites of these compounds having the same type of activity are included in the scope of the present disclosure. In addition, the compounds described herein can exist in unsolvated as well as solvated forms with pharmaceutically acceptable solvents such as water, ethanol, and the like. The solvated forms of the compounds presented herein are also considered to be disclosed herein.

"Pharmaceutically acceptable," as used herein, refers a material, such as a carrier or diluent, which does not abrogate the biological activity or properties of the compound, and is relatively nontoxic, i.e., the material is administered to an individual without causing undesirable biological effects or interacting in a deleterious manner with any of the components of the composition in which it is contained.

The term "pharmaceutically acceptable salt" refers to a form of a therapeutically active agent that consists of a cationic form of the therapeutically active agent in combination with a suitable anion, or in alternative embodiments, an anionic form of the therapeutically active agent in combination with a suitable cation. Handbook of Pharmaceutical Salts: Properties, Selection and Use. International Union of Pure and Applied Chemistry, Wiley-VCH 2002. S. M. Berge, L. D. Bighley, D. C. Monkhouse, J. Pharm. Sci. 1977, 66, 1-19. P. H. Stahl and C. G. Wermuth, editors, *Handbook of Pharmaceutical Salts: Properties, Selection and Use,* Weinheim/Zurich: Wiley-VCH/VHCA, 2002. Pharmaceutical salts typically are more soluble and more rapidly soluble in stomach and intestinal juices than non-ionic species and so are useful in solid dosage forms. Furthermore, because their solubility often is a function of pH, selective dissolution in one or another part of the digestive tract is possible and this capability can be manipulated as one aspect of delayed and sustained release behaviours. Also, because the salt-forming molecule can be in equilibrium with a neutral form, passage through biological membranes can be adjusted.

In some embodiments, pharmaceutically acceptable salts are obtained by reacting a compound described herein with an acid. In some embodiments, the compound described herein (i.e. free base form) is basic and is reacted with an organic acid or an inorganic acid. Inorganic acids include, but are not limited to, hydrochloric acid, hydrobromic acid, sulfuric acid, phosphoric acid, nitric acid, and metaphosphoric acid. Organic acids include, but are not limited to, 1-hydroxy-2-naphthoic acid; 2,2-dichloroacetic acid; 2-hydroxyethanesulfonic acid; 2-oxoglutaric acid; 4-acetamidobenzoic acid; 4-aminosalicylic acid; acetic acid; adipic acid; ascorbic acid (L); aspartic acid (L); benzenesulfonic acid; benzoic acid; camphoric acid (+); camphor-10-sulfonic acid (+); capric acid (decanoic acid); caproic acid (hexanoic acid); caprylic acid (octanoic acid); carbonic acid; cinnamic acid; citric acid; cyclamic acid; dodecylsulfuric acid; ethane-1,2-disulfonic acid; ethanesulfonic acid; formic acid; fumaric acid; galactaric acid; gentisic acid; glucoheptonic acid (D); gluconic acid (D); glucuronic acid (D); glutamic acid; glutaric acid; glycerophosphoric acid; glycolic acid; hippuric acid; isobutyric acid; lactic acid (DL); lactobionic acid; lauric acid; maleic acid; malic acid (−L); malonic acid; mandelic acid (DL); methanesulfonic acid; monomethyl fumarate, naphthalene-1,5-disulfonic acid; naphthalene-2-sulfonic acid; nicotinic acid; oleic acid; oxalic acid; palmitic acid; pamoic acid; phosphoric acid; proprionic acid; pyroglutamic acid (−L); salicylic acid; sebacic acid; stearic acid; succinic acid; sulfuric acid; tartaric acid (+L); thiocyanic acid; toluenesulfonic acid (p); and undecylenic acid.

In some embodiments, a compound described herein is prepared as a chloride salt, sulfate salt, bromide salt, mesylate salt, maleate salt, citrate salt or phosphate salt. In some embodiments, a compound described herein is prepared as a hydrochloride salt.

In some embodiments, pharmaceutically acceptable salts are obtained by reacting a compound described herein with a base. In some embodiments, the compound described herein is acidic and is reacted with a base. In such situations, an acidic proton of the compound described herein is replaced by a metal ion, e.g., lithium, sodium, potassium, magnesium, calcium, or an aluminum ion. In some cases, compounds described herein coordinate with an organic base, such as, but not limited to, ethanolamine, diethanolamine, triethanolamine, tromethamine, meglumine, N-methylglucamine, dicyclohexylamine, tris(hydroxymethyl)methylamine. In other cases, compounds described herein form salts with amino acids such as, but not limited to, arginine, lysine, and the like. Acceptable inorganic bases used to form salts with compounds that include an acidic proton, include, but are not limited to, aluminum hydroxide, calcium hydroxide, potassium hydroxide, sodium carbonate, potassium carbonate, sodium hydroxide, lithium hydroxide, and the like. In some embodiments, the compounds provided herein are prepared as a sodium salt, calcium salt, potassium salt, magnesium salt, meglumine salt, N-methylglucamine salt or ammonium salt. In some embodiments, the compounds provided herein are prepared as a sodium salt.

It should be understood that a reference to a pharmaceutically acceptable salt includes the solvent addition forms. In some embodiments, solvates contain either stoichiometric or non-stoichiometric amounts of a solvent, and are formed during the process of crystallization with pharmaceutically acceptable solvents such as water, ethanol, and the like. Hydrates are formed when the solvent is water, or alcoholates are formed when the solvent is alcohol. Solvates of compounds described herein are conveniently prepared or formed during the processes described herein. In addition, the compounds provided herein optionally exist in unsolvated as well as solvated forms.

The methods and formulations described herein include the use of N-oxides (if appropriate), crystalline forms (also known as polymorphs), or pharmaceutically acceptable salts of compounds described herein, as well as active metabolites of these compounds having the same type of activity.

In some embodiments, sites on the organic radicals (e.g. alkyl groups, aromatic rings) of compounds described herein are susceptible to various metabolic reactions. Incorporation of appropriate substituents on the organic radicals will reduce, minimize or eliminate this metabolic pathway. In specific embodiments, the appropriate substituent to decrease or eliminate the susceptibility of the aromatic ring to metabolic reactions is, by way of example only, a halogen, deuterium, an alkyl group, a haloalkyl group, or a deuteroalkyl group.

In another embodiment, the compounds described herein are labeled isotopically (e.g. with a radioisotope) or by another other means, including, but not limited to, the use of chromophores or fluorescent moieties, bioluminescent labels, or chemiluminescent labels.

Compounds described herein include isotopically-labeled compounds, which are identical to those recited in the various formulae and structures presented herein, but for the fact that one or more atoms are replaced by an atom having an atomic mass or mass number different from the atomic mass or mass number usually found in nature. Examples of isotopes that can be incorporated into the present compounds include isotopes of hydrogen, carbon, nitrogen, oxygen, fluorine and chlorine, such as, for example, $^{2}H$, $^{3}H$, $^{13}C$, $^{14}C$, $^{15}N$, $^{18}O$, $^{17}O$, $^{35}S$, $^{18}F$, $^{36}Cl$. In one aspect, isotopically-labeled compounds described herein, for example those into which radioactive isotopes such as $^{3}H$ and $^{14}C$ are incorporated, are useful in drug and/or substrate tissue distribution assays. In one aspect, substitution with isotopes such as deuterium affords certain therapeutic advantages resulting from greater metabolic stability, such as, for example, increased in vivo half-life or reduced dosage requirements.

In some embodiments, the compounds described herein possess one or more stereocenters and each stereocenter exists independently in either the R or S configuration. The compounds presented herein include all diastereomeric, enantiomeric, atropisomers, and epimeric forms as well as the appropriate mixtures thereof. The compounds and methods provided herein include all cis, trans, syn, anti, entgegen (E), and zusammen (Z) isomers as well as the appropriate mixtures thereof.

Individual stereoisomers are obtained, if desired, by methods such as, stereoselective synthesis and/or the separation of stereoisomers by chiral chromatographic columns. In certain embodiments, compounds described herein are prepared as their individual stereoisomers by reacting a racemic mixture of the compound with an optically active resolving agent to form a pair of diastereoisomeric compounds/salts, separating the diastereomers and recovering the optically pure enantiomers. In some embodiments, resolution of enantiomers is carried out using covalent diastereomeric derivatives of the compounds described herein. In another embodiment, diastereomers are separated by separation/resolution techniques based upon differences in solubility. In other embodiments, separation of steroisomers is performed by chromatography or by the forming diastereomeric salts and separation by recrystallization, or chromatography, or any combination thereof. Jean Jacques, Andre Collet, Samuel H. Wilen, "Enantiomers, Racemates and Resolutions", John Wiley and Sons, Inc., 1981. In some embodiments, stereoisomers are obtained by stereoselective synthesis.

In some embodiments, compounds described herein are prepared as prodrugs. A "prodrug" refers to an agent that is converted into the parent drug in vivo. Prodrugs are often useful because, in some situations, they are easier to administer than the parent drug. They are, for instance, bioavailable by oral administration whereas the parent is not. The prodrug may be a substrate for a transporter. Further or alternatively, the prodrug also has improved solubility in pharmaceutical compositions over the parent drug. In some embodiments, the design of a prodrug increases the effective water solubility. An example, without limitation, of a prodrug is a compound described herein, which is administered as an ester (the "prodrug") but then is metabolically hydrolyzed to provide the active entity. A further example of a prodrug is a short peptide (polyaminoacid) bonded to an acid group where the peptide is metabolized to reveal the active moiety. In certain embodiments, upon in vivo administration, a prodrug is chemically converted to the biologically, pharmaceutically or therapeutically active form of the compound. In certain embodiments, a prodrug is enzymatically metabolized by one or more steps or processes to the biologically, pharmaceutically or therapeutically active form of the compound.

Prodrugs of the compounds described herein include, but are not limited to, esters, ethers, carbonates, thiocarbonates, N-acyl derivatives, N-acyloxyalkyl derivatives, quaternary derivatives of tertiary amines, N-Mannich bases, Schiff bases, amino acid conjugates, phosphate esters, and sulfonate esters. See for example Design of Prodrugs, Bundgaard, A. Ed., Elseview, 1985 and Method in Enzymology, Widder, K. et al., Ed.; Academic, 1985, vol. 42, p. 309-396; Bundgaard, H. "Design and Application of Prodrugs" in A Textbook of Drug Design and Development, Krosgaard-Larsen and H. Bundgaard, Ed., 1991, Chapter 5, p. 113-191; and Bundgaard, H., Advanced Drug Delivery Review, 1992, 8, 1-38, each of which is incorporated herein by reference. In some embodiments, a hydroxyl group in the compounds disclosed herein is used to form a prodrug, wherein the hydroxyl group is incorporated into an acyloxyalkyl ester, alkoxycarbonyloxyalkyl ester, alkyl ester, aryl ester, phosphate ester, sugar ester, ether, and the like. In some embodiments, a hydroxyl group in the compounds disclosed herein is a prodrug wherein the hydroxyl is then metabolized in vivo to provide a carboxylic acid group. In some embodiments, a carboxyl group is used to provide an ester or amide (i.e. the prodrug), which is then metabolized in vivo to provide a carboxylic acid group. In some embodiments, compounds described herein are prepared as alkyl ester prodrugs.

Prodrug forms of the herein described compounds, wherein the prodrug is metabolized in vivo to produce a compound described herein as set forth herein are included within the scope of the claims. In some cases, some of the herein-described compounds is a prodrug for another derivative or active compound.

In additional or further embodiments, the compounds described herein are metabolized upon administration to an organism in need to produce a metabolite that is then used to produce a desired effect, including a desired therapeutic effect.

A "metabolite" of a compound disclosed herein is a derivative of that compound that is formed when the compound is metabolized. The term "active metabolite" refers to a biologically active derivative of a compound that is formed when the compound is metabolized. The term "metabolized," as used herein, refers to the sum of the processes (including, but not limited to, hydrolysis reactions and reactions catalyzed by enzymes) by which a particular substance is changed by an organism. Thus, enzymes may produce specific structural alterations to a compound. For example, cytochrome P450 catalyzes a variety of oxidative and reductive reactions while uridine diphosphate glucuronyltransferases catalyze the transfer of an activated glucuronic-acid molecule to aromatic alcohols, aliphatic alcohols, carboxylic acids, amines and free sulphydryl groups. Metabolites of the compounds disclosed herein are optionally identified either by administration of compounds to a host and analysis of tissue samples from the host, or by incubation of compounds with hepatic cells in vitro and analysis of the resulting compounds.

Synthesis of Compounds

Compounds of Formula (I) described herein are synthesized using standard synthetic techniques or using methods known in the art in combination with methods described herein. Unless otherwise indicated, conventional methods of mass spectroscopy, NMR, HPLC, protein chemistry, biochemistry, recombinant DNA techniques and pharmacology are employed. Compounds are prepared using standard organic chemistry techniques such as those described in, for example, March's Advanced Organic Chemistry, 6$^{th}$ Edition, John Wiley and Sons, Inc. Alternative reaction conditions for the synthetic transformations described herein may be employed such as variation of solvent, reaction temperature, reaction time, as well as different chemical reagents and other reaction conditions. As necessary, the use of appropriate protecting groups may be required. The incorporation and cleavage of such groups may be carried out using standard methods described in Theodora W. Green and Peter G. M. Wuts, Protecting Groups in Organic Synthesis, 3$^{rd}$ Edition, John Wiley and Sons, Inc. (1999). The starting materials are available from commercial sources or are readily prepared.

In some embodiments, (4H-[1,2,4]-triazol-3-yl)arylamide derivatives 1-6 or (1H-imidazol-5-yl)arylamide 1-7 are synthesized as shown in Scheme 1.

Scheme 1

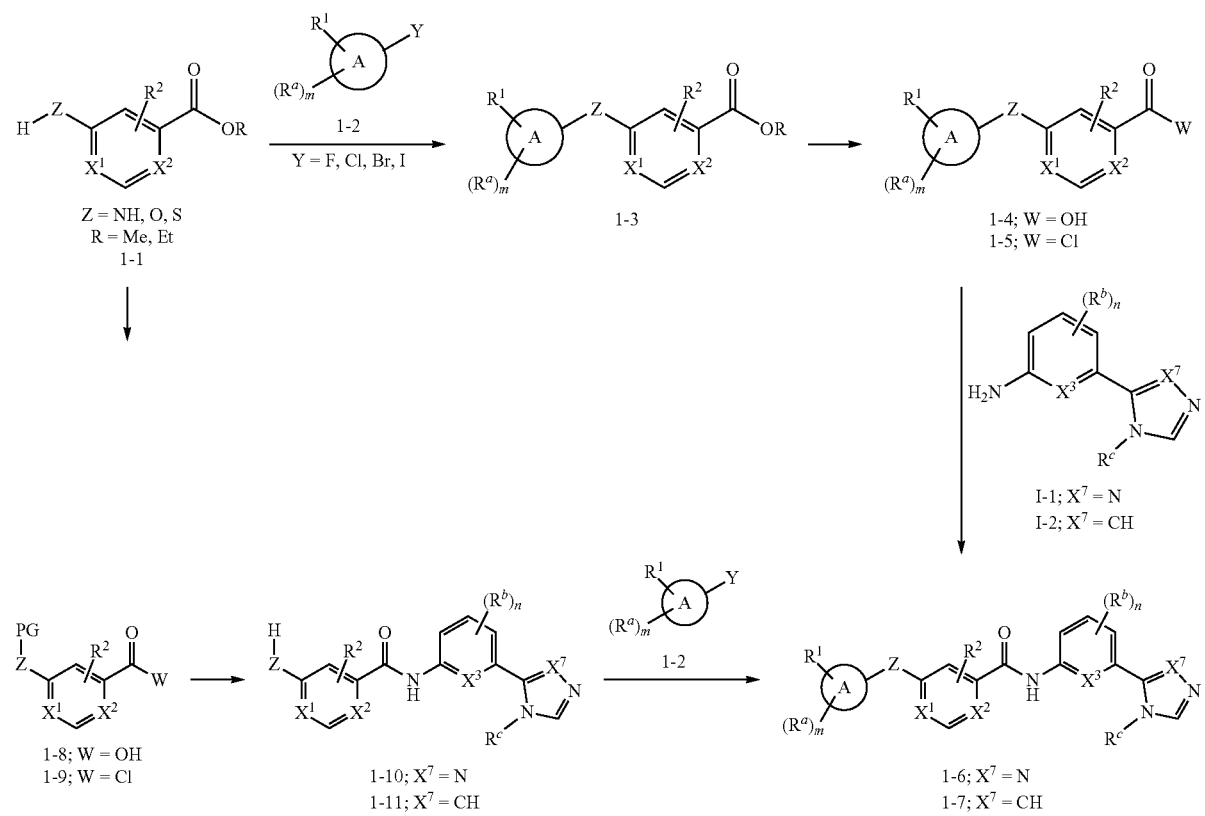

In some embodiments, treatment of a hydroxyaryl derivative (Z=O) or thioaryl derivative (Z=S) 1-1 with haloheteroaryl derivative 1-2 in the presence of a base such as $K_2CO_3$, KO$^t$Bu, or NaH, and in a suitable solvent such as THF, DMF, or DMSO with or without heating will afford 1-3. Alternatively, when Z=O treatment of 1-1 with I-2 in the presence of a transition metal catalyst such as Cu, CuI, or CuBr[PPh$_3$]$_3$ and in the presence of a base such as $K_3PO_4$ or $Cs_2CO_3$, and in the presence of a ligand such as 2-pyridinecarboxylic acid, 1-methyl-1H-imidazole, N,N,N',N'-tertamethylethylenediamine, or 2,2,6,6-tetramethylheptane-3,5-dione, and heating in a suitable solvent such as DMSO, DMA, NMP, or isobutyramide can also afford 1-3 (Z=O). Alternatively, when Z=NH treatment of 1-1 with I-2 in the presence of a transition metal catalyst such as Pd(OAC)$_2$ or Pd$_2$(dba)$_3$, and in the presence of a base such as $K_2CO_3$, $Cs_2CO_3$, $K_3PO_4$, or NaO$^t$Bu, and in the presence of a ligand such as XantPhos, BINAP, or JosiPhos, and heating in a suitable solvent such as DME, toluene, tert-BuOH, with or without water, can afford 1-3 (Z=NH). Subsequent treatment of ester derivative 1-3 with LiOH in aqueous THF will give carboxylic acid derivative 1-4. Treatment of 1-4 with I-1 or I-2 (prepared as described in Schemes 8 through 11) under standard amide coupling conditions, will give 1-6 or 1-7, respectively. Alternatively, treatment of carboxylic acid 1-4 with, for example, SOCl$_2$ or oxalyl chloride and catalytic DMF, in a suitable solvent such as DCM or THF will afford acid chloride 1-5. Subsequent treatment of acid chloride 1-5 with either I-1 or I-2 in the presence of a suitable base such as TEA, Hunig's base, NaHCO$_3$, or $K_2CO_3$, and in a suitable solvent such as DCM or THF, with or without an activating agent such as DMAP, with or without heating will afford 1-6 or 1-7, respectively. Alternatively, compounds 1-6 and 1-7 may be prepared from 1-1 as follows. Introduction of a suitable protecting group (PG) for ZH resistant to alkali cleavage, followed by ester hydrolysis will afford 1-8. Treatment of 1-8 with I-1 or I-2 (prepared as described in Schemes 8 through 11) under standard amide coupling conditions, followed by deprotection of Z will give 1-10 or 1-11, respectively. Alternatively, treatment of carboxylic acid 1-8 with, for example, SOCl$_2$ or oxalyl chloride and catalytic DMF, in a suitable solvent such as DCM or THF will afford acid chloride 1-9. Subsequent treatment of acid chloride 1-9 with either I-1 or I-2 in the presence of a suitable base such as TEA, Hunig's base, NaHCO$_3$, or $K_2CO_3$, and in a suitable solvent such as DCM or THF, with or without an activating agent such as DMAP, with or without heating, followed by deprotection of Z will afford 1-10 or 1-11, respectively. Treatment of 1-10 or 1-11 with 1-2 using methods described above, will give 1-6 or 1-7, respectively.

In some embodiments, (4H-[1,2,4]-triazol-3-yl)arylamide derivatives 2-6 or (1H-imidazol-5-yl)arylamide derivatives 2-7 are synthesized as shown in Scheme 2.

Scheme 2

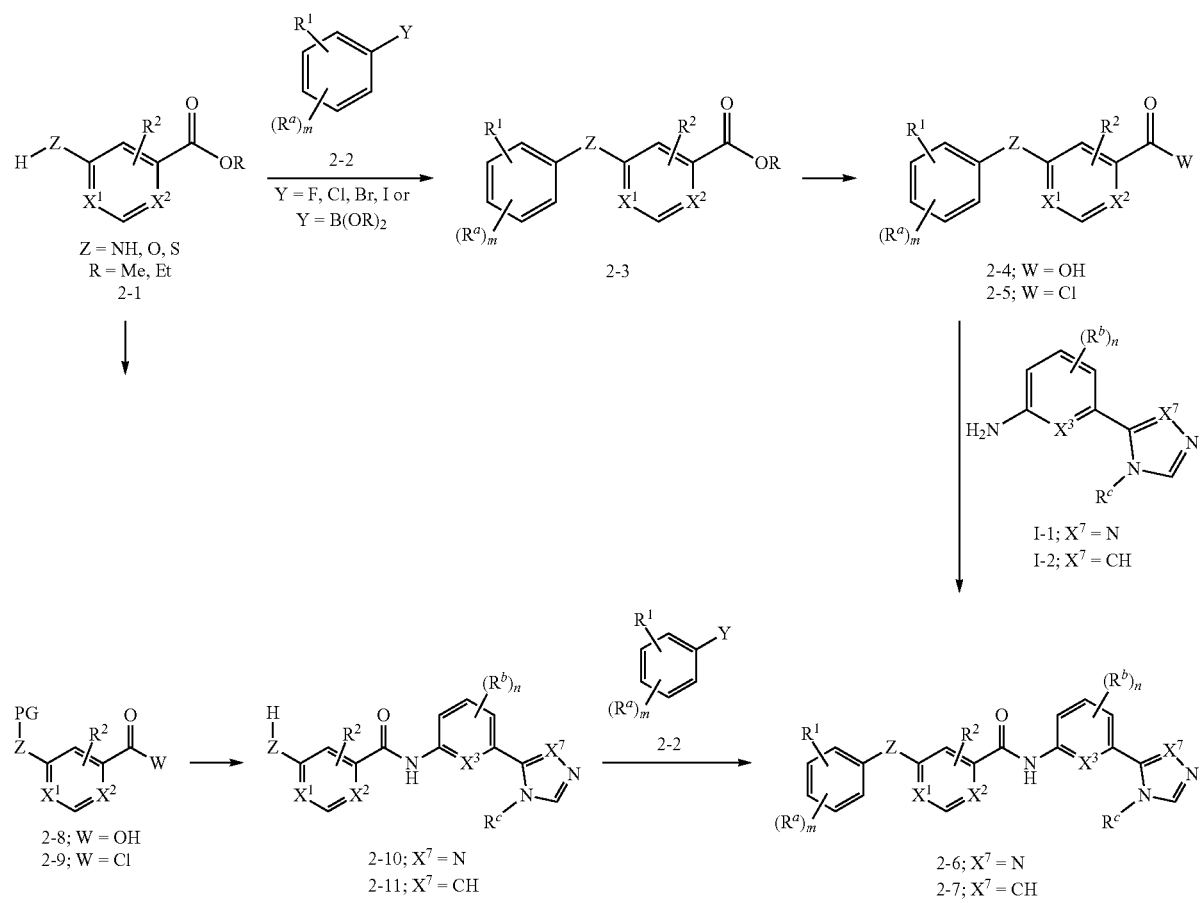

In some embodiments, treatment of a hydroxyaryl derivative 2-1 with phenyl derivative 2-2 (Y=halide) in the presence of a palladium catalyst such as Pd(OAc)$_2$ or Pd$_2$(dba)$_3$, in the presence of a base such as K$_3$PO$_4$ or Cs$_2$CO$_3$, and in the presence of a ligand such as BINAP, or biphenyl-2-yl-di-tert-butylphospane, or XantPhos, heating in a suitable solvent such as toluene, or 1,4-dioxane and/or tert-butanol, can afford 2-3. Alternatively, treatment of 2-1 with a copper catalyst such as CuO or Cu(OAc)$_2$, in the presence of a base such as pyridine or TEA, and heating in a suitable solvent such as DCM, DCE, or pyridine, can also afford 2-3. Conversion of 2-3 to 2-6 or 2-7, may be carried out using methods described in Scheme 1 (see conversion of 1-3 to 1-6 and 1-7). Alternatively, compounds 2-6 and 2-7 may be prepared from 2-1 as follows. Introduction of a suitable protecting group (PG) for ZH resistant to alkali cleavage, followed by ester hydrolysis will afford 2-8. Treatment of 2-8 with I-1 or I-2 (prepared as described in Schemes 8 through 11) under standard amide coupling conditions, followed by deprotection of Z will give 2-10 or 2-11, respectively. Alternatively, treatment of carboxylic acid 2-8 with, for example, SOCl$_2$ or oxalyl chloride and catalytic DMF, in a suitable solvent such as DCM or THF will afford acid chloride 2-9. Subsequent treatment of acid chloride 2-9 with either I-1 or I-2 in the presence of a suitable base such as TEA, Hunig's base, NaHCO$_3$, or K$_2$CO$_3$, and in a suitable solvent such as DCM or THF, with or without an activating agent such as DMAP, with or without heating, followed by deprotection of Z will afford 2-10 or 2-11, respectively. Treatment of 2-10 or 2-11 with 2-2 using methods described above, will give 2-6 or 2-7, respectively.

In some embodiments, (4H-[1,2,4]-triazol-3-yl)arylamide derivatives 3-3 and 3-5 or (1H-imidazol-5-yl)arylamide derivatives 3-4 and 3-6 are synthesized as shown in Scheme 3.

Scheme 3

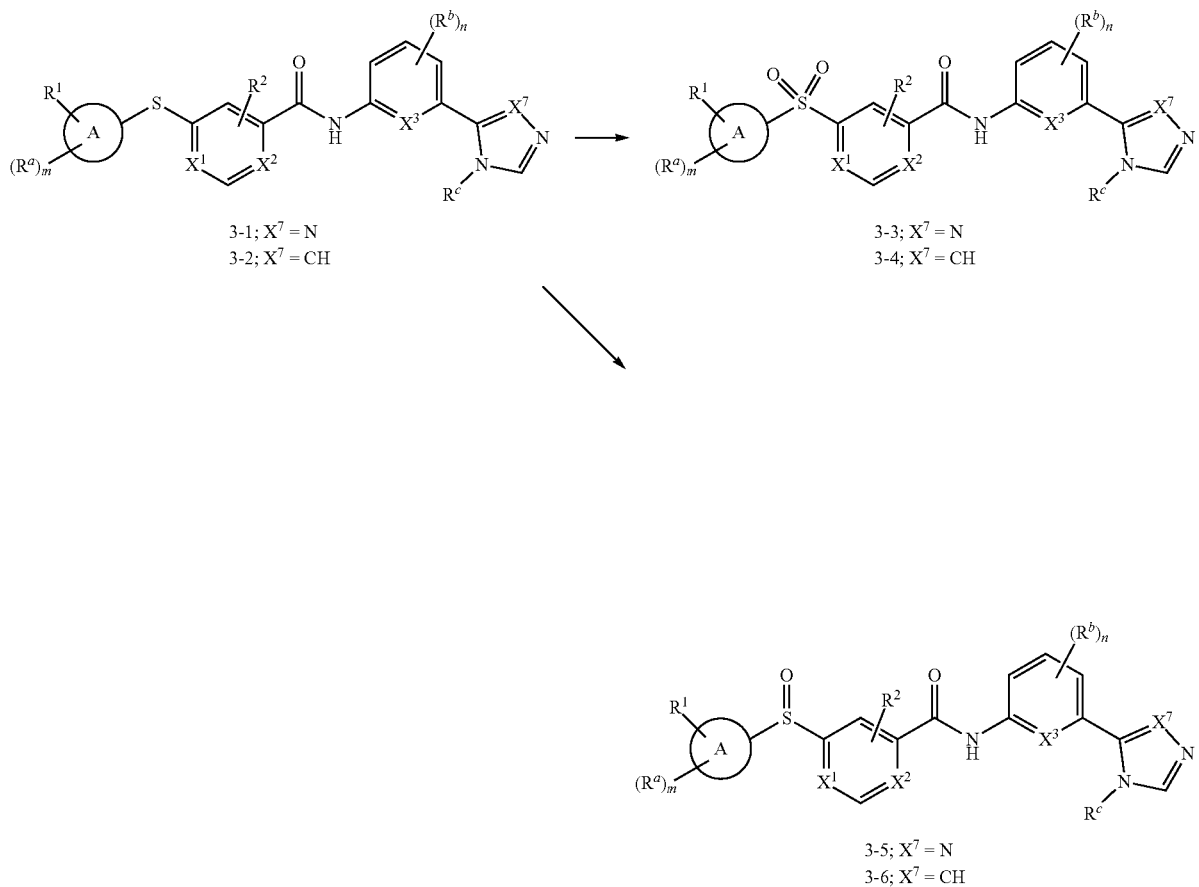

3-1; X$^7$ = N
3-2; X$^7$ = CH 3-3; X$^7$ = N
3-4; X$^7$ = CH 3-5; X$^7$ = N
3-6; X$^7$ = CH

In some embodiments, treatment of sulfenyl derivatives 3-1 or 3-2 (prepared as described in Schemes 1 and 2) with excess of a suitable oxidizing agent such as mCPBA in a suitable solvent such as DCM, will give the corresponding sulfonyl-derivatives 3-3 and 3-4, respectively. Using approximately 1 equivalent of the oxidizing agent will give predominantly the corresponding sulfoxide derivatives 3-5 and 3-6, respectively.

In some embodiments, (4H-[1,2,4]-triazol-3-yl)arylamide derivatives 4-7 or (1H-imidazol-5-yl)arylamide derivatives 4-8 are synthesized as shown in Scheme 4.

Scheme 4
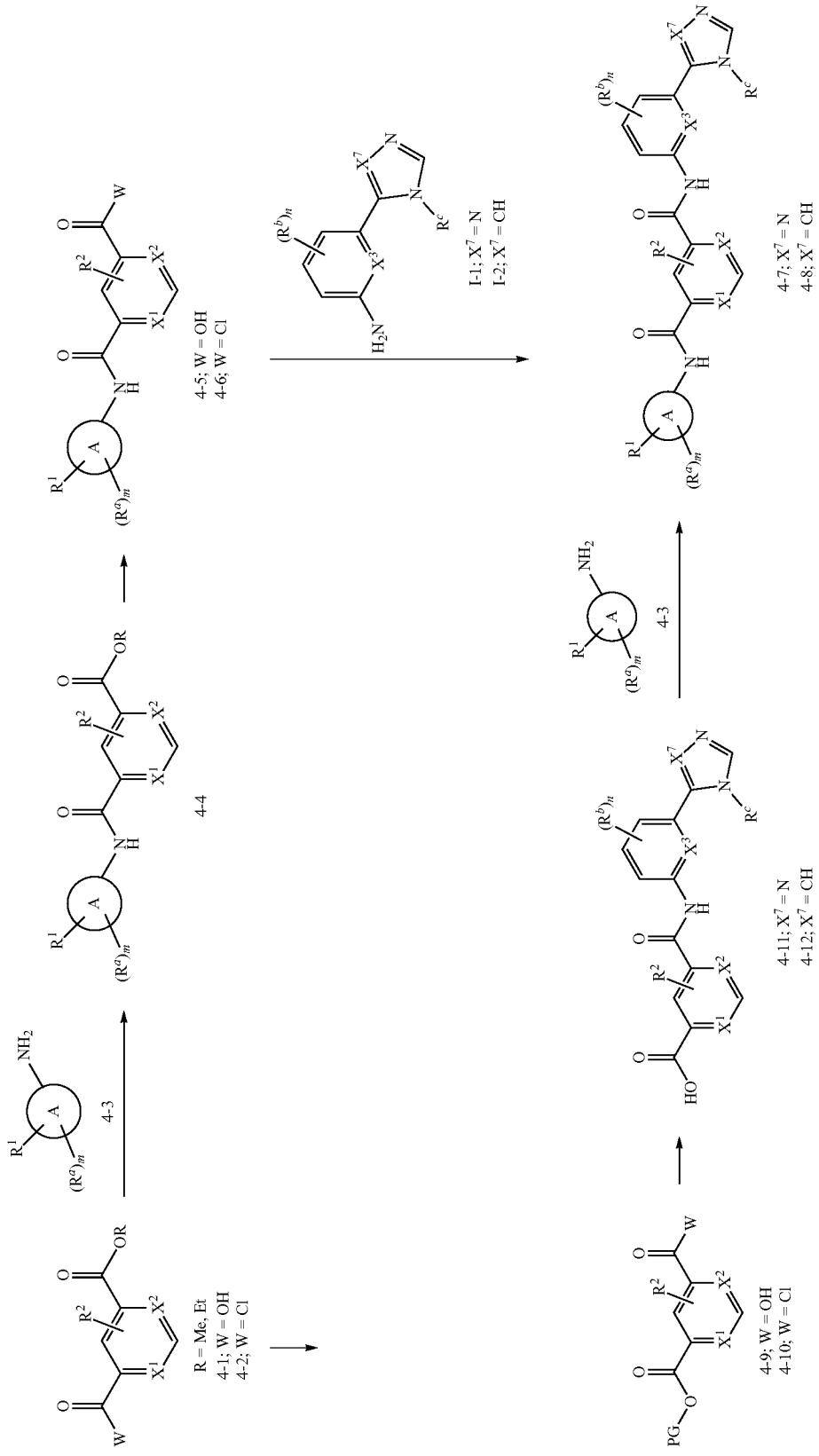

In some embodiments, treatment of carboxylic acid derivative 4-1 with a substituted aniline or heteroarylamine 4-3 using standard amide coupling conditions will afford amide-derivative 4-4. Alternatively, treatment of carboxylic acid 4-1 with, for example, $SOCl_2$ or oxalyl chloride and catalytic DMF, in a suitable solvent such as DCM or THF will afford acid chloride 4-2. Subsequent treatment of acid chloride 4-2 with 4-3 in the presence of a suitable base such as TEA, Hunig's base, $NaHCO_3$, or $K_2CO_3$, and in a suitable solvent such as DCM or THF, with or without an activating agent such as DMAP, with or without heating, will afford 4-4. Subsequent treatment of 4-4 with LiOH in aqueous THF will give carboxylic acid derivative 4-5. Acid derivative 4-5 may be converted to either 4-7 or 4-8 via reaction with I-1 or I-2 (prepared as described in Schemes 8 through 11), respectively, using methods described in Scheme 1. Alternatively, compounds 4-7 and 4-8 may be prepared from 4-1 as follows. Introduction of a suitable carboxylic protecting group (PG) resistant to alkali cleavage (for instance THP ester, allyl ester, or tert-butyl ester), followed by ester (R=Me, Et) hydrolysis will afford 4-9. Treatment of 4-9 with I-1 or I-2 (prepared as described in Schemes 8 through 11) under standard amide coupling conditions, followed by PG-ester deprotection will give 4-11 or 4-12, respectively. Alternatively, treatment of carboxylic acid 4-9 with, for example, $SOCl_2$ or oxalyl chloride and catalytic DMF, in a suitable solvent such as DCM or THF will afford acid chloride 4-10. Subsequent treatment of acid chloride 4-10 with either I-1 or I-2 in the presence of a suitable base such as TEA, Hunig's base, $NaHCO_3$, or $K_2CO_3$, and in a suitable solvent such as DCM or THF, with or without an activating agent such as DMAP, with or without heating, followed by PG-ester deprotection will afford 4-11 or 4-12, respectively. Treatment of 4-11 or 4-12 with 4-3 using methods described above, will give 4-7 or 4-8, respectively.

In some embodiments, (4H-[1,2,4]-triazol-3-yl)arylamide derivatives 5-7 or (1H-imidazol-5-yl)arylamide derivatives 5-8 are synthesized as shown in Scheme 5.

Scheme 5
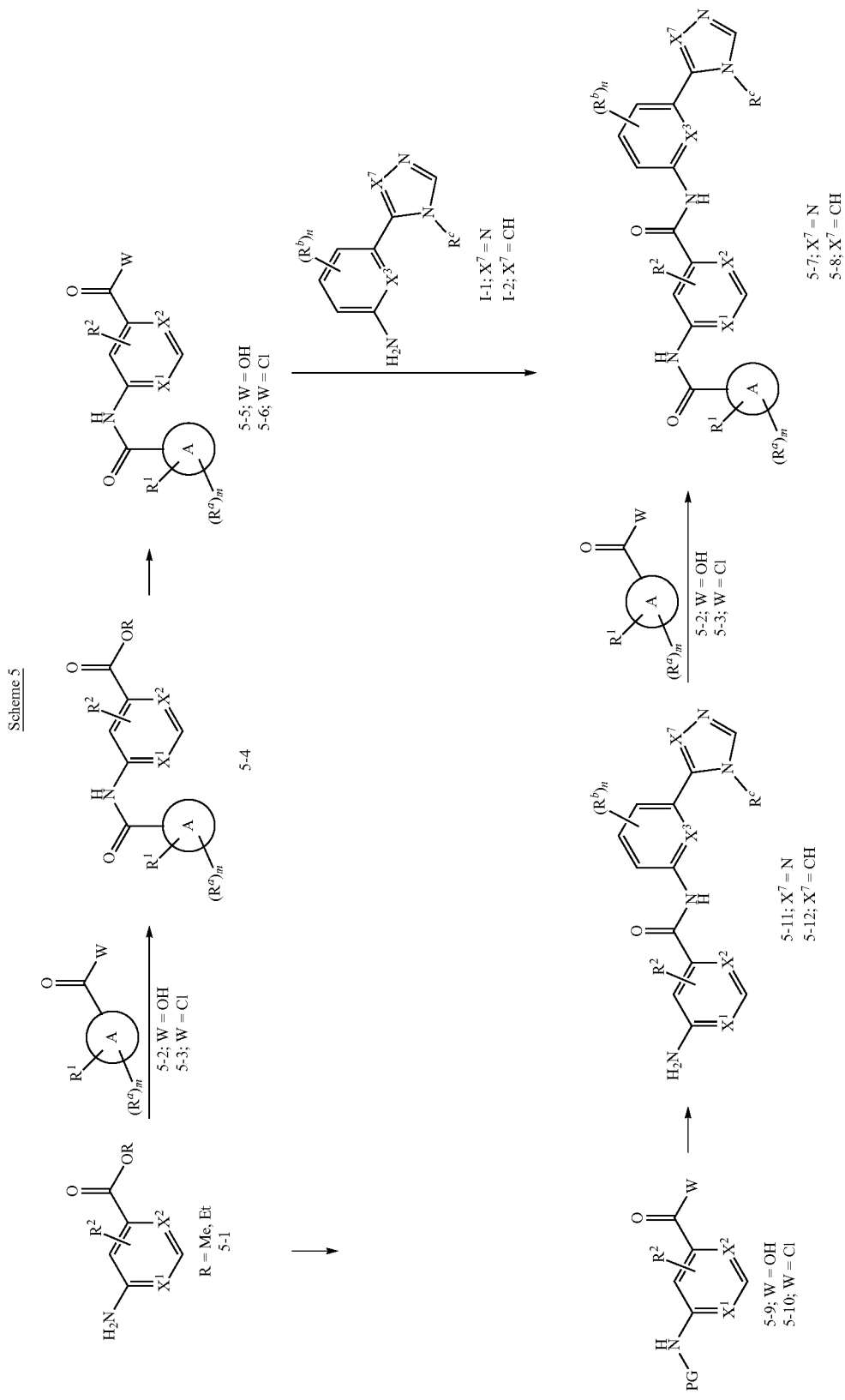

In some embodiments, treatment of amino-derivative 5-1 with a heteroarylcarboxylic acid or benzoic acid 5-2 using standard amide coupling conditions will afford amide-derivative 5-4. Alternatively, treatment of amino-derivative 5-1 with heteroaryl acid chloride or benzoyl chloride 5-3 in the presence of a suitable base such as TEA, Hunig's base, NaHCO$_3$, or K$_2$CO$_3$, and in a suitable solvent such as DCM or THF, with or without an activating agent such as DMAP, with or without heating, will afford 5-4. Subsequent treatment of 5-4 with LiOH in aqueous THF will give carboxylic acid derivative 5-5. Acid derivative 5-5 may be converted to either 5-7 or 5-8 via reaction with I-1 or I-2 (prepared as described in Schemes 8 through 11), respectively, using methods described in Scheme 1. Alternatively, compounds 5-7 and 5-8 may be prepared from 5-1 as follows. Introduction of a suitable amine protecting group (PG) resistant to alkali cleavage (for instance BOC), followed by ester (R=Me, Et) hydrolysis will afford 5-9. Treatment of 5-9 with aminopyridine derivatives I-1 or I-2 (prepared as described in Schemes 8 through 11) under standard amide coupling conditions, followed by amine deprotection will give 5-11 or 5-12, respectively. Alternatively, treatment of carboxylic acid 5-9 with, for example, oxalyl chloride and catalytic DMF, in a suitable solvent such as DCM or THF will afford acid chloride 5-10. Subsequent treatment of acid chloride 5-10 with either I-1 or I-2 in the presence of a suitable base such as TEA, Hunig's base, NaHCO$_3$, or K$_2$CO$_3$, and in a suitable solvent such as DCM or THF, with or without an activating agent such as DMAP, with or without heating, followed by amine deprotection will afford 5-11 or 5-12, respectively. Treatment of 5-11 or 5-12 with 5-2 or 5-3 using methods described above, will give 5-7 or 5-8, respectively.

In some embodiments, (4H-[1,2,4]-triazol-3-yl)arylamide derivatives 6-6 or (1H-imidazol-5-yl)arylamide derivatives 6-7 are synthesized as shown in Scheme 6.

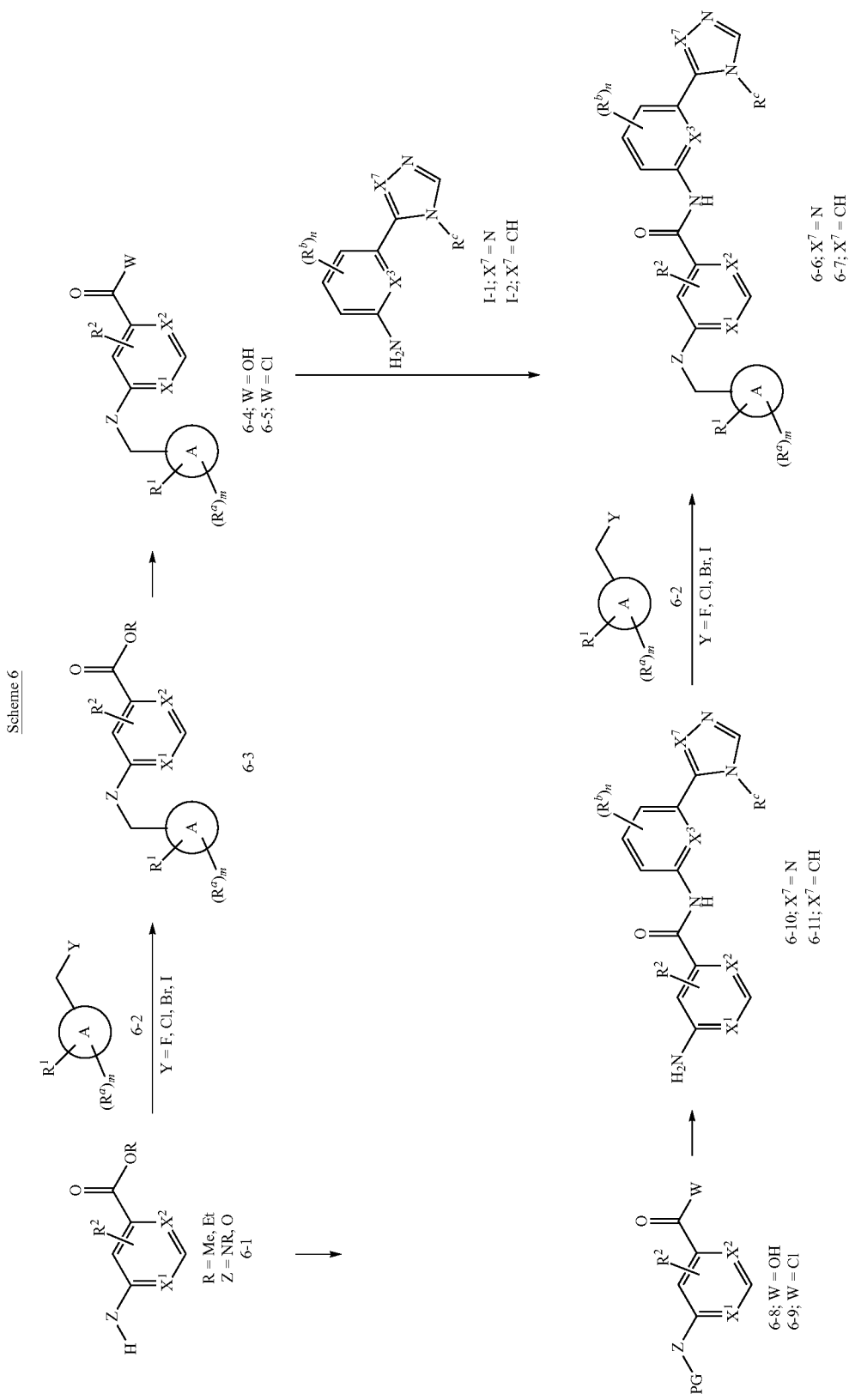

In some embodiments, treatment of amino-derivative 6-1 (Z=NR) with methyl halide derivative 6-2 in the presence of a suitable base such as TEA, Hunig's base, NaH, $K_2CO_3$, NaOH, $NaHCO_3$, and in a suitable solvent such as DMF, DMA, DMSO, MeCN, 1,4-dioxane, or THF, with or without an activating agent such as TBAI, $AgNO_3$, or a crown ether, with or without heating, will afford 6-3. Subsequent treatment of 6-3 with LiOH in aqueous THF will give carboxylic acid derivative 6-4. Acid derivative 6-4 may be converted to either 6-6 or 6-7 via reaction with I-1 or I-2 (prepared as described in Schemes 8 through 11), respectively, using methods described in Scheme 1. Alternatively, compounds 6-6 and 6-7 may be prepared from 6-1 as follows. Introduction of a suitable protecting group (PG) resistant to alkali cleavage, followed by ester (R=Me, Et) hydrolysis will afford 6-8. Treatment of 6-8 with aminopyridine derivatives I-1 or I-2 (prepared as described in Schemes 8 through 11) under standard amide coupling conditions, followed by deprotection of Z will give 6-10 or 6-11, respectively. Alternatively, treatment of carboxylic acid 6-8 with, for example, oxalyl chloride and catalytic DMF, in a suitable solvent such as DCM or THF will afford acid chloride 6-9. Subsequent treatment of acid chloride 6-9 with either I-1 or I-2 in the presence of a suitable base such as TEA, Hunig's base, $NaHCO_3$, or $K_2CO_3$, and in a suitable solvent such as DCM or THF, with or without an activating agent such as DMAP, with or without heating, and followed by deprotection of Z will afford 6-10 or 6-11, respectively. Treatment of 6-10 or 6-11 with 6-2 using methods described above, will give 6-6 or 6-7, respectively.

In some embodiments, (4H-[1,2,4]-triazol-3-yl)arylamide derivatives 7-7 or (1H-imidazol-5-yl)arylamide derivatives 7-8 are synthesized as shown in Scheme 7.

Scheme 7
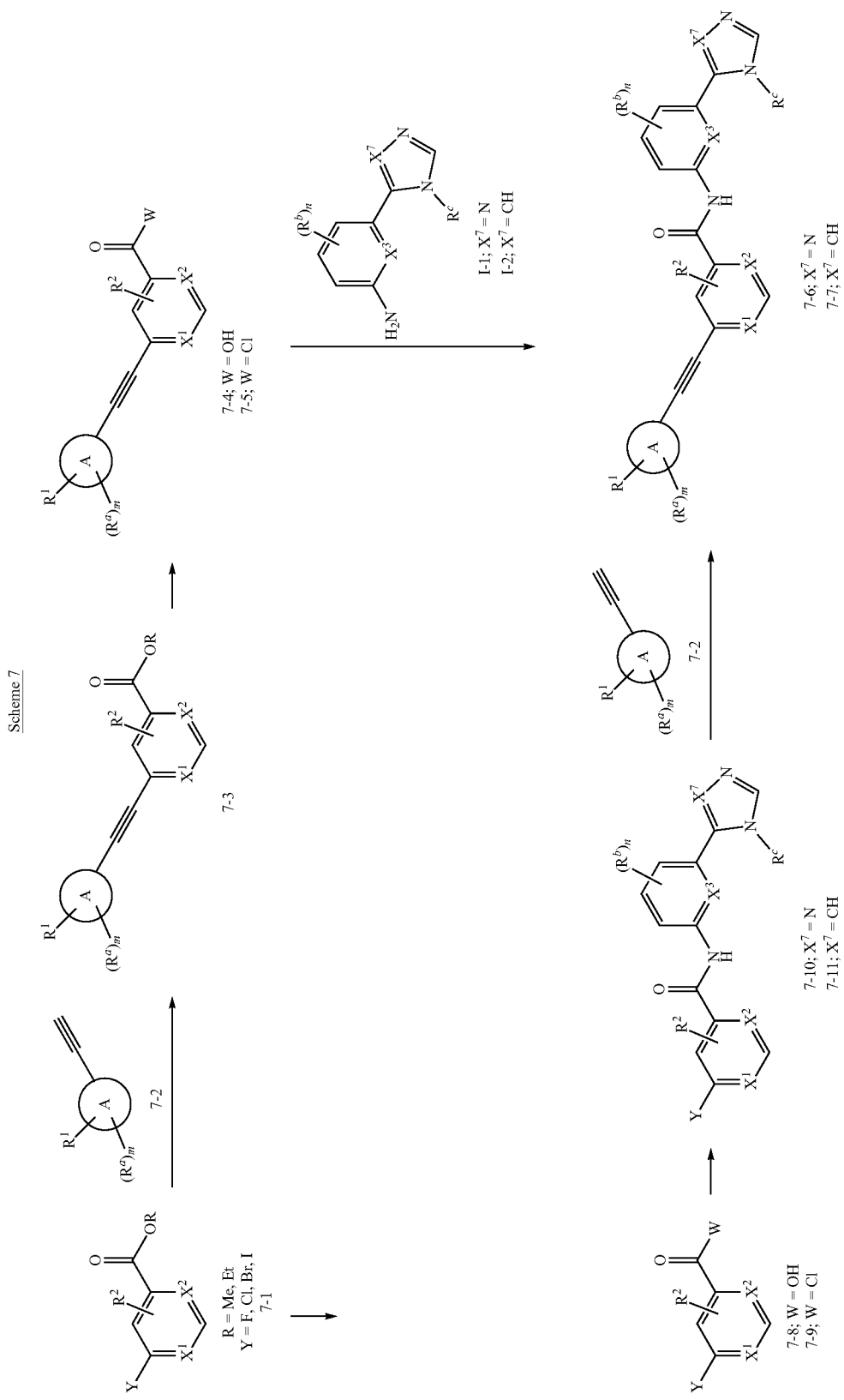

In some embodiments, heating aryl halide derivative 7-1 with acetylene derivative 7-2, in the presence of a palladium catalyst such as for example Pd[PPh$_3$]$_4$ or Pd[PPh$_3$]$_2$Cl$_2$, and in the presence of CuI, and in the presence of a base such as TEA or hunig's base, and in a suitable solvent such as toluene, DMF, DMA, MeCN, or THF, will give 7-3. Subsequent treatment of 7-3 with LiOH in aqueous THF will give carboxylic acid derivative 7-4. Acid derivative 7-4 may be converted to either 7-6 or 7-7 via reaction with aminopyridine derivatives I-1 or I-2 (prepared as described in Schemes 8 through 11), respectively, using methods described in Scheme 1. Alternatively, compounds 7-6 and 7-7 may be prepared from 7-1 as follows. Treatment of 7-1 with LiOH in aqueous THF, will afford carboxylic acid derivative 7-8. Treatment of 7-8 with I-1 or I-2 (prepared as described in Schemes 8 through 11) under standard amide coupling conditions, will give 7-10 or 7-11, respectively. Alternatively, treatment of carboxylic acid 7-8 with, for example, oxalyl chloride and catalytic DMF, in a suitable solvent such as DCM or THF will afford acid chloride 7-9. Subsequent treatment of acid chloride 7-9 with either I-1 or I-2 in the presence of a suitable base such as TEA, Hunig's base, NaHCO$_3$, or K$_2$CO$_3$, and in a suitable solvent such as DCM or THF, with or without an activating agent such as DMAP, with or without heating, will afford 7-10 or 7-11, respectively. Treatment of 7-10 or 7-11 with 7-2 using methods described above, will give 7-6 or 7-7, respectively.

In some embodiments, (4H-[1,2,4]-triazol-3-yl)arylamine derivatives I-1 are synthesized as shown in Scheme 8.

Scheme 8

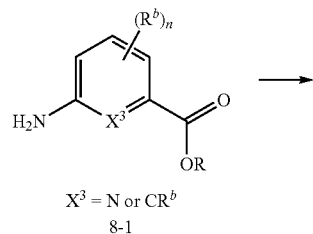

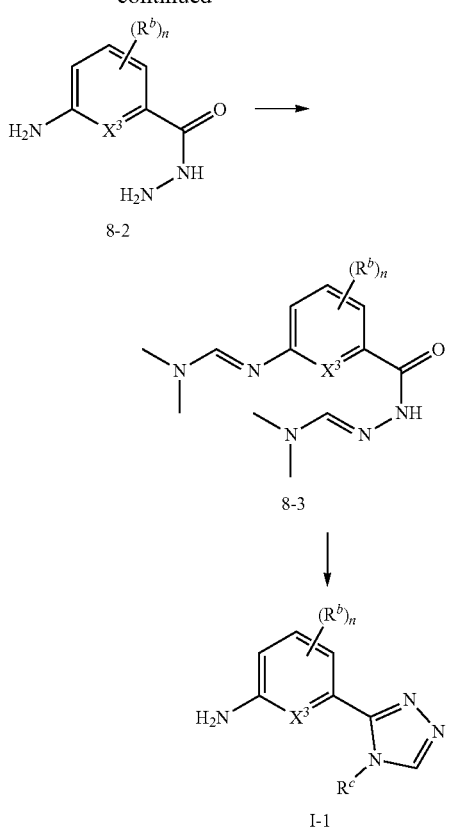

In some embodiments, aryl-ester derivatives 8-1 can be converted to the corresponding hydrazides 8-2, via treatment of 8-1 with hydrazine in a suitable solvent such as MeOH or EtOH with heating. Hydrazide derivatives 8-2 upon heating with DMF-DMA can afford 8-3. Reaction of 8-3 with a primary amine (R$^c$NH$_2$) in the presence of HOAc and in a suitable solvent such as MeCN with heating, will give I-1.

In some embodiments, (4H-[1,2,4]-triazol-3-yl)arylamine derivatives I-1 are synthesized as shown in Scheme 9.

Scheme 9

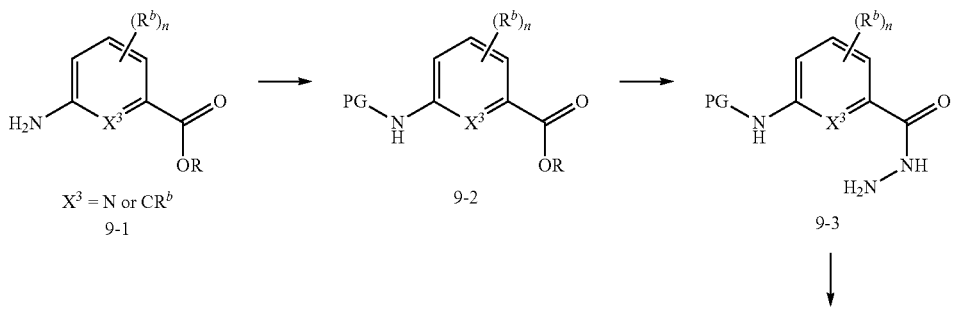

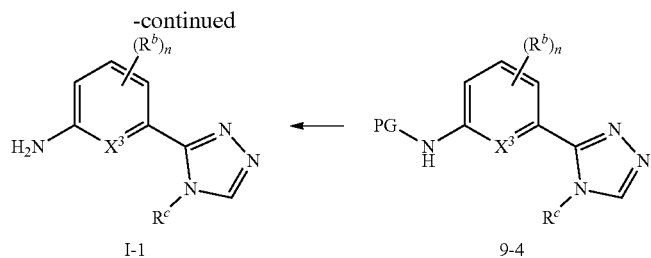

In some embodiments, the amino group of 9-1 may be protected with appropriate protecting groups (PG) to give 9-2. Treatment of 9-2 with hydrazine in a suitable solvent such as MeOH or EtOH with heating, will afford hydrazides 9-3. Heating of 9-3 with a primary amine (R<sup>c</sup>NH$_2$) and a formamide of formula R<sup>c</sup>NHCHO, in the presence of a suitable acid such as TFA, and in a suitable solvent such as toluene, will give 9-4. Subsequent amine deprotection of 9-4 will afford I-1.

In some embodiments, (4H-[1,2,4]-triazol-3-yl)arylamine derivatives I-1 are synthesized as shown in Scheme 10.

Scheme 10

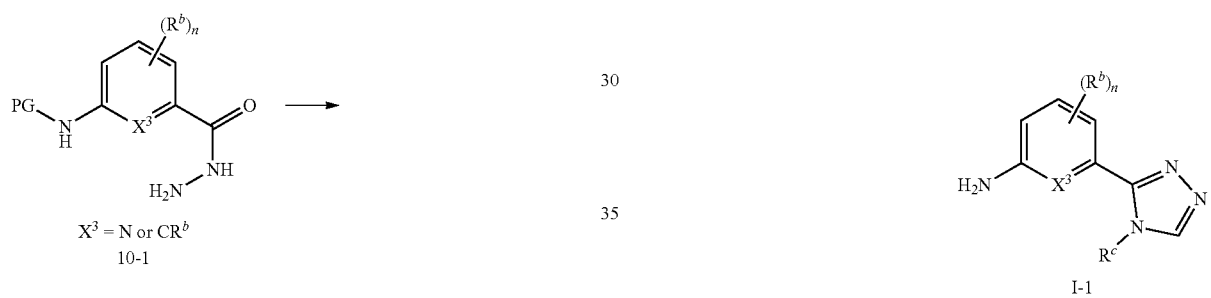

In some embodiments, treatment of hydrazide derivatives 10-1 (prepared as described in Scheme 9) with triethylorthoformate in the presence of para-toluenesulfonic acid with heating, either neat or in a suitable solvent such as DMA, will give [1,2,4]-oxadiazol derivatives 10-2. Heating of 10-2 with a primary amine (R<sup>c</sup>NH$_2$) in the presence of a suitable acid such as TFA or para-toluenesulfonic acid, either neat or in a suitable solvent such as 1-butanol or xylene, will give 10-3. Subsequent amine deprotection of 10-3 will afford I-1.

In some embodiments, (1H-imidazol-5-yl)arylamine derivatives 1-2 are synthesized as shown in Scheme 11.

Scheme 11

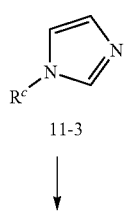

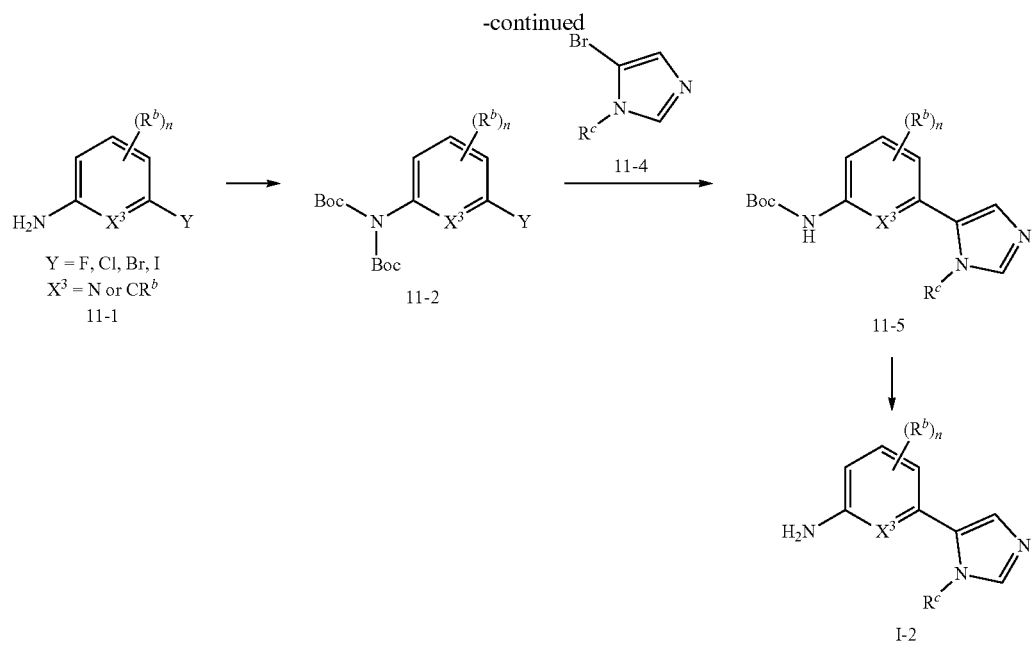

In some embodiments, treatment of arylamine derivative 11-1 with di-tert-butyl dicarbonate, in the presence of a suitable base such as TEA or Hunig's base, and in the presence of an activating agent such as DMAP, and in a suitable solvent such as THF, DCM, or tert-butanol, with or without heating, will afford 11-2. Treatment of imidazole derivative 11-3 with a suitable brominating agent such as 1,3-dibromo-5,5-dimethyl-hydantoin, in a suitable solvent such as DCM, will give bromoimidazole derivative 11-4. Compound 11-4 upon treatment with n-butyl lithium at low temperature in a suitable solvent such as THF, followed by treatment with $ZnBr_2$ at low to room temperature, followed by treatment with 11-2 in the presence of a palladium catalyst such as $Pd[PPh_3]_4$ at elevated temperature, will afford 11-5. Subsequent N-boc deprotection of 11-5 with TFA or HCl will give I-2.

In some embodiments, compounds are prepared as described in the Examples.

Certain Terminology

Unless otherwise stated, the following terms used in this application have the definitions given below. The use of the term "including" as well as other forms, such as "include", "includes," and "included," is not limiting. The section headings used herein are for organizational purposes only and are not to be construed as limiting the subject matter described.

As used herein, $C_1$-$C_x$ includes $C_1$-$C_2$, $C_1$-$C_3$ . . . $C_1$-$C_x$. By way of example only, a group designated as "$C_1$-$C_4$" indicates that there are one to four carbon atoms in the moiety, i.e. groups containing 1 carbon atom, 2 carbon atoms, 3 carbon atoms or 4 carbon atoms. Thus, by way of example only, "$C_1$-$C_4$ alkyl" indicates that there are one to four carbon atoms in the alkyl group, i.e., the alkyl group is selected from among methyl, ethyl, propyl, iso-propyl, n-butyl, iso-butyl, sec-butyl, and t-butyl.

An "alkyl" group refers to an aliphatic hydrocarbon group. The alkyl group is branched or straight chain. In some embodiments, the "alkyl" group has 1 to 10 carbon atoms, i.e. a $C_1$-$C_{10}$alkyl. Whenever it appears herein, a numerical range such as "1 to 10" refers to each integer in the given range; e.g., "1 to 10 carbon atoms" means that the alkyl group consist of 1 carbon atom, 2 carbon atoms, 3 carbon atoms, etc., up to and including 10 carbon atoms, although the present definition also covers the occurrence of the term "alkyl" where no numerical range is designated. In some embodiments, an alkyl is a $C_1$-$C_6$alkyl. In one aspect the alkyl is methyl, ethyl, propyl, iso-propyl, n-butyl, iso-butyl, sec-butyl, or t-butyl. Typical alkyl groups include, but are in no way limited to, methyl, ethyl, propyl, isopropyl, butyl, isobutyl, sec-butyl, tertiary butyl, pentyl, neopentyl, or hexyl.

An "alkylene" group refers refers to a divalent alkyl radical. Any of the above mentioned monovalent alkyl groups may be an alkylene by abstraction of a second hydrogen atom from the alkyl. In some embodiments, an alkelene is a $C_1$-$C_6$alkylene. In other embodiments, alkylene is a $C_1$-$C_4$alkylene. Typical alkylene groups include, but are not limited to, —$CH_2$—, —$CH(CH_3)$—, —$C(CH_3)_2$—, —$CH_2CH_2$—, —$CH_2CH(CH_3)$—, —$CH_2C(CH_3)_2$—, —$CH_2CH_2CH_2$—, —$CH_2CH_2CH_2CH_2$—, and the like.

"Deuteroalkyl" refers to an alkyl group where 1 or more hydrogen atoms of an alkyl are replaced with deuterium.

The term "alkenyl" refers to a type of alkyl group in which at least one carbon-carbon double bond is present. In one embodiment, an alkenyl group has the formula —C(R)=$CR_2$, wherein The term "alkenyl" refers to a type of alkyl group in which at least one carbon-carbon double bond is present. In one embodiment, an alkenyl group has the formula —C≡C—$R_2$, wherein R refers to the remaining portions of the alkenyl group, which may be the same or different. In some embodiments, R is H or an alkyl. Non-limiting examples of an alkenyl group include —CH=$CH_2$, —C($CH_3$)=$CH_2$, —CH=$CHCH_3$, —C($CH_3$)=$CHCH_3$, and —$CH_2$CH=$CH_2$.

The term "alkynyl" refers to a type of alkyl group in which at least one carbon-carbon triple bond is present. In one embodiment, an alkynyl group has the formula —C≡C—R, wherein R refers to the remaining portions of the alkynyl group. In some embodiments, R is H or an alkyl. Non-limiting examples of an alkynyl group include —C≡CH, —C≡CCH$_3$—C≡CCH$_2$CH$_3$, —CH$_2$C≡CH.

An "alkoxy" group refers to a (alkyl)O— group, where alkyl is as defined herein.

The term "alkylamine" refers to the —N(alkyl)$_x$H$_y$ group, where x is 0 and y is 2, or where x is 1 and y is 1, or where x is 2 and y is 0.

The term "aromatic" refers to a planar ring having a delocalized π-electron system containing 4n+2 π electrons, where n is an integer. The term "aromatic" includes both carbocyclic aryl ("aryl", e.g., phenyl) and heterocyclic aryl (or "heteroaryl" or "heteroaromatic") groups (e.g., pyridine). The term includes monocyclic or fused-ring polycyclic (i.e., rings which share adjacent pairs of carbon atoms) groups.

The term "carbocyclic" or "carbocycle" refers to a ring or ring system where the atoms forming the backbone of the ring are all carbon atoms. The term thus distinguishes carbocyclic from "heterocyclic" rings or "heterocycles" in which the ring backbone contains at least one atom which is different from carbon. In some embodiments, at least one of the two rings of a bicyclic carbocycle is aromatic. In some embodiments, both rings of a bicyclic carbocycle are aromatic. In some embodiments, bicyclic carbocycles are fused, bridged or spirocyclic.

As used herein, the term "aryl" refers to an aromatic ring wherein each of the atoms forming the ring is a carbon atom. In one aspect, aryl is phenyl or a naphthyl. In some embodiments, an aryl is a phenyl. In some embodiments, an aryl is a C$_6$-C$_{10}$aryl. Depending on the structure, an aryl group is a monoradical or a diradical (i.e., an arylene group).

The term "cycloalkyl" refers to a monocyclic or polycyclic aliphatic, non-aromatic radical, wherein each of the atoms forming the ring (i.e. skeletal atoms) is a carbon atom. In some embodiments, cycloalkyls are spirocyclic or bridged compounds. In some embodiments, cycloalkyls are optionally fused with an aromatic ring, and the point of attachment is at a carbon that is not an aromatic ring carbon atom. Cycloalkyl groups include groups having from 3 to 10 ring atoms. In some embodiments, cycloalkyl groups are selected from among cyclopropyl, cyclobutyl, cyclopentyl, cyclopentenyl, cyclohexyl, cyclohexenyl, cycloheptyl, cyclooctyl, spiro[2.2]pentyl, norbornyl and bicycle[1.1.1] pentyl. In some embodiments, a cycloalkyl is a C$_3$-C$_6$cycloalkyl.

The term "halo" or, alternatively, "halogen" or "halide" means fluoro, chloro, bromo or iodo. In some embodiments, halo is fluoro, chloro, or bromo.

The term "fluoroalkyl" refers to an alkyl in which one or more hydrogen atoms are replaced by a fluorine atom. In one aspect, a fluoralkyl is a C$_1$-C$_6$fluoroalkyl.

The term "heteroalkyl" refers to an alkyl group in which one or more skeletal atoms of the alkyl are selected from an atom other than carbon, e.g., oxygen, nitrogen (e.g. —NH—, —N(alkyl)-, sulfur, or combinations thereof. A heteroalkyl is attached to the rest of the molecule at a carbon atom of the heteroalkyl. In one aspect, a heteroalkyl is a C$_1$-C$_6$heteroalkyl.

The term "heterocycle" or "heterocyclic" refers to heteroaromatic rings (also known as heteroaryls) and heterocycloalkyl rings (also known as heteroalicyclic groups) containing one to four heteroatoms in the ring(s), where each heteroatom in the ring(s) is selected from O, S and N, wherein each heterocyclic group has from 3 to 10 atoms in its ring system, and with the proviso that any ring does not contain two adjacent O or S atoms. Non-aromatic heterocyclic groups (also known as heterocycloalkyls) include rings having 3 to 10 atoms in its ring system and aromatic heterocyclic groups include rings having 5 to 10 atoms in its ring system. The heterocyclic groups include benzo-fused ring systems. Examples of non-aromatic heterocyclic groups are pyrrolidinyl, tetrahydrofuranyl, dihydrofuranyl, tetrahydrothienyl, oxazolidinonyl, tetrahydropyranyl, dihydropyranyl, tetrahydrothiopyranyl, piperidinyl, morpholinyl, thiomorpholinyl, thioxanyl, piperazinyl, aziridinyl, azetidinyl, oxetanyl, thietanyl, homopiperidinyl, oxepanyl, thiepanyl, oxazepinyl, diazepinyl, thiazepinyl, 1,2,3,6-tetrahydropyridinyl, pyrrolin-2-yl, pyrrolin-3-yl, indolinyl, 2H-pyranyl, 4H-pyranyl, dioxanyl, 1,3-dioxolanyl, pyrazolinyl, dithianyl, dithiolanyl, dihydropyranyl, dihydrothienyl, dihydrofuranyl, pyrazolidinyl, imidazolinyl, imidazolidinyl, 3-azabicyclo[3.1.0]hexanyl, 3-azabicyclo[4.1.0]heptanyl, 3H-indolyl, indolin-2-onyl, isoindolin-1-onyl, isoindoline-1,3-dionyl, 3,4-dihydroisoquinolin-1 (2H)-onyl, 3,4-dihydroquinolin-2 (1H)-onyl, isoindoline-1,3-dithionyl, benzo[d]oxazol-2 (3H)-onyl, 1H-benzo[d]imidazol-2 (3H)-onyl, benzo[d]thiazol-2 (3H)-onyl, and quinolizinyl. Examples of aromatic heterocyclic groups are pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, quinolinyl, isoquinolinyl, indolyl, benzimidazolyl, benzofuranyl, cinnolinyl, indazolyl, indolizinyl, phthalazinyl, pyridazinyl, triazinyl, isoindolyl, pteridinyl, purinyl, oxadiazolyl, thiadiazolyl, furazanyl, benzofurazanyl, benzothiophenyl, benzothiazolyl, benzoxazolyl, quinazolinyl, quinoxalinyl, naphthyridinyl, and furopyridinyl. The foregoing groups are either C-attached (or C-linked) or N-attached where such is possible. For instance, a group derived from pyrrole includes both pyrrol-1-yl (N-attached) or pyrrol-3-yl (C-attached). Further, a group derived from imidazole includes imidazol-1-yl or imidazol-3-yl (both N-attached) or imidazol-2-yl, imidazol-4-yl or imidazol-5-yl (all C-attached). The heterocyclic groups include benzo-fused ring systems. Non-aromatic heterocycles are optionally substituted with one or two oxo (═O) moieties, such as pyrrolidin-2-one. In some embodiments, at least one of the two rings of a bicyclic heterocycle is aromatic. In some embodiments, both rings of a bicyclic heterocycle are aromatic. In some embodiments, bicyclic heterocycles are fused, bridged or spirocyclic.

The terms "heteroaryl" or, alternatively, "heteroaromatic" refers to an aryl group that includes one or more ring heteroatoms selected from nitrogen, oxygen and sulfur. Illustrative examples of heteroaryl groups include monocyclic heteroaryls and bicyclcic heteroaryls. Monocyclic heteroaryls include pyridinyl, imidazolyl, pyrimidinyl, pyrazolyl, triazolyl, pyrazinyl, tetrazolyl, furyl, thienyl, isoxazolyl, thiazolyl, oxazolyl, isothiazolyl, pyrrolyl, pyridazinyl, triazinyl, oxadiazolyl, thiadiazolyl, and furazanyl. Monocyclic heteroaryls include indolizine, indole, benzofuran, benzothiophene, indazole, benzimidazole, purine, quinolizine, quinoline, isoquinoline, cinnoline, phthalazine, quinazoline, quinoxaline, 1,8-naphthyridine, and pteridine. In some embodiments, a heteroaryl contains 0-4 N atoms in the ring. In some embodiments, a heteroaryl contains 1-4 N atoms in the ring. In some embodiments, a heteroaryl contains 0-4 N atoms, 0-1 O atoms, and 0-1 S atoms in the ring. In some embodiments, a heteroaryl contains 1-4 N atoms, 0-1 O atoms, and 0-1 S atoms in the ring. In some embodiments, heteroaryl is a C$_1$-C$_9$heteroaryl. In some embodiments, monocyclic heteroaryl is a C$_1$-C$_5$heteroaryl.

In some embodiments, monocyclic heteroaryl is a 5-membered or 6-membered heteroaryl. In some embodiments, bicyclic heteroaryl is a $C_6$-$C_9$heteroaryl.

A "heterocycloalkyl" or "heteroalicyclic" group refers to a cycloalkyl group that includes at least one heteroatom selected from nitrogen, oxygen and sulfur. In some embodiments, a heterocycloalkyl is fused with an aryl or heteroaryl. In some embodiments, the heterocycloalkyl is oxazolidinonyl, pyrrolidinyl, tetrahydrofuranyl, tetrahydrothienyl, tetrahydropyranyl, tetrahydrothiopyranyl, piperidinyl, morpholinyl, thiomorpholinyl, piperazinyl, piperidin-2-onyl, pyrrolidine-2,5-dithionyl, pyrrolidine-2,5-dionyl, pyrrolidinonyl, imidazolidinyl, imidazolidin-2-onyl, or thiazolidin-2-onyl. The term heteroalicyclic also includes all ring forms of the carbohydrates, including but not limited to the monosaccharides, the disaccharides and the oligosaccharides. In one aspect, a heterocycloalkyl is a $C_2$-$C_{10}$heterocycloalkyl. In another aspect, a heterocycloalkyl is a $C_4$-$C_{10}$heterocycloalkyl. In some embodiments, a heterocycloalkyl contains 0-2 N atoms in the ring. In some embodiments, a heterocycloalkyl contains 0-2 N atoms, 0-2 O atoms and 0-1 S atoms in the ring. In some embodiments, bicyclic heterocycloalkyls are fused, bridged or spirocyclic.

The term "bond" or "single bond" refers to a chemical bond between two atoms, or two moieties when the atoms joined by the bond are considered to be part of larger substructure. In one aspect, when a group described herein is a bond, the referenced group is absent thereby allowing a bond to be formed between the remaining identified groups.

The term "moiety" refers to a specific segment or functional group of a molecule. Chemical moieties are often recognized chemical entities embedded in or appended to a molecule.

The term "optionally substituted" or "substituted" means that the referenced group is optionally substituted with one or more additional group(s) individually and independently selected from D, halogen, —CN, —N($R^y$)$_2$, —O$R^y$, —S$R^y$, —S(=O)$R^y$, —S(=O)$_2R^y$, —CO$_2R^y$, —OC(=O)$R^x$, —C(=O)N($R^y$)$_2$, —N$R^y$C(=O)$R^x$, —OC(=O)N($R^y$)$_2$, —N$R^y$C(=O)N($R^y$)$_2$, —N$R^y$C(=O)O$R^x$, —S(=O)$_2$N($R^y$)$_2$, —N$R^y$S(=O)$_2R^x$, alkyl, cycloalkyl, fluoroalkyl, heteroalkyl, heterocycloalkyl, aryl, and heteroaryl; each $R^x$ is independently selected from alkyl, $C_1$-$C_6$fluoroalkyl, deuteroalkyl, heteroalkyl, cycloalkyl, heterocycloalkyl, aryl, benzyl and heteroaryl; each $R^y$ is independently selected from H, alkyl, fluoroalkyl, deuteroalkyl, heteroalkyl, cycloalkyl, heterocycloalkyl, aryl, benzyl and heteroaryl; or two $R^5$ on the same N atom are taken together with the N atom to which they are attached to a N-containing heterocycle. In some other embodiments, optional substituents are independently selected from D, halogen, —CN, —NH$_2$, —NH(alkyl), —N(alkyl)$_2$, —OH, —CO$_2$H, —CO$_2$alkyl, —C(=O)NH$_2$, —C(=O)NH(alkyl), —C(=O)N(alkyl)$_2$, —S(=O)$_2$NH$_2$, —S(=O)$_2$NH(alkyl), —S(=O)$_2$N(alkyl)$_2$, alkyl, cycloalkyl, fluoroalkyl, heteroalkyl, alkoxy, fluoroalkoxy, heterocycloalkyl, aryl, heteroaryl, aryloxy, alkylthio, arylthio, alkylsulfoxide, arylsulfoxide, alkylsulfone, and arylsulfone. In some other embodiments, optional substituents are independently selected from halogen, —CN, —NH$_2$, —NH(CH$_3$), —N(CH$_3$)$_2$, —OH, —CO$_2$H, —CO$_2$($C_1$-$C_4$alkyl), —C(=O)NH$_2$, —C(=O)NH($C_1$-$C_4$alkyl), —C(=O)N($C_1$-$C_4$alkyl)$_2$, —S(=O)$_2$NH$_2$, —S(=O)$_2$NH($C_1$-$C_4$alkyl), —S(=O)$_2$N($C_1$-$C_4$alkyl)$_2$, $C_1$-$C_4$alkyl, $C_3$-$C_6$cycloalkyl, $C_1$-$C_4$fluoroalkyl, $C_1$-$C_4$heteroalkyl, $C_1$-$C_4$alkoxy, $C_1$-$C_4$fluoroalkoxy, —S$C_1$-$C_4$alkyl, —S(=O)$C_1$-$C_4$alkyl, and —S(=O)$_2C_1$-$C_4$alkyl. In yet some embodiments, optional substituents are independently selected from halogen, —CN, —NH$_2$, —OH, —NH(CH$_3$), —N(CH$_3$)$_2$, —CH$_3$, —CH$_2$CH$_3$, —CF$_3$, —OCH$_3$, and —OCF$_3$. In some embodiments, substituted groups are substituted with one or two of the preceding groups. In some embodiments, an optional substituent on an aliphatic carbon atom (acyclic or cyclic) includes oxo (=O).

The term "acceptable" with respect to a formulation, composition or ingredient, as used herein, means having no persistent detrimental effect on the general health of the subject being treated.

The term "modulate" as used herein, means to interact with a target either directly or indirectly so as to alter the activity of the target, including, by way of example only, to enhance the activity of the target, to inhibit the activity of the target, to limit the activity of the target, or to extend the activity of the target.

The term "modulator" as used herein, refers to a molecule that interacts with a target either directly or indirectly. The interactions include, but are not limited to, the interactions of an agonist, partial agonist, an inverse agonist, antagonist, degrader, or combinations thereof. In some embodiments, a modulator is an antagonist. In some embodiments, a modulator is a degrader.

The terms "administer," "administering", "administration," and the like, as used herein, refer to the methods that may be used to enable delivery of compounds or compositions to the desired site of biological action. These methods include, but are not limited to oral routes, intraduodenal routes, parenteral injection (including intravenous, subcutaneous, intraperitoneal, intramuscular, intravascular or infusion), topical and rectal administration. Those of skill in the art are familiar with administration techniques that can be employed with the compounds and methods described herein. In some embodiments, the compounds and compositions described herein are administered orally.

The terms "co-administration" or the like, as used herein, are meant to encompass administration of the selected therapeutic agents to a single patient, and are intended to include treatment regimens in which the agents are administered by the same or different route of administration or at the same or different time.

The terms "effective amount" or "therapeutically effective amount," as used herein, refer to a sufficient amount of an agent or a compound being administered, which will relieve to some extent one or more of the symptoms of the disease or condition being treated. The result includes reduction and/or alleviation of the signs, symptoms, or causes of a disease, or any other desired alteration of a biological system. For example, an "effective amount" for therapeutic uses is the amount of the composition comprising a compound as disclosed herein required to provide a clinically significant decrease in disease symptoms. An appropriate "effective" amount in any individual case is optionally determined using techniques, such as a dose escalation study.

The terms "enhance" or "enhancing," as used herein, means to increase or prolong either in potency or duration a desired effect. Thus, in regard to enhancing the effect of therapeutic agents, the term "enhancing" refers to the ability to increase or prolong, either in potency or duration, the effect of other therapeutic agents on a system. An "enhancing-effective amount," as used herein, refers to an amount adequate to enhance the effect of another therapeutic agent in a desired system.

The term "pharmaceutical combination" as used herein, means a product that results from the mixing or combining of more than one active ingredient and includes both fixed and non-fixed combinations of the active ingredients. The term "fixed combination" means that the active ingredients, e.g. a compound described herein, or a pharmaceutically acceptable salt thereof, and a co-agent, are both administered to a patient simultaneously in the form of a single entity or dosage. The term "non-fixed combination" means that the active ingredients, e.g. a compound described herein, or a pharmaceutically acceptable salt thereof, and a co-agent, are administered to a patient as separate entities either simultaneously, concurrently or sequentially with no specific intervening time limits, wherein such administration provides effective levels of the two compounds in the body of the patient. The latter also applies to cocktail therapy, e.g. the administration of three or more active ingredients.

The terms "kit" and "article of manufacture" are used as synonyms.

The term "subject" or "patient" encompasses mammals. Examples of mammals include, but are not limited to, any member of the Mammalian class: humans, non-human primates such as chimpanzees, and other apes and monkey species; farm animals such as cattle, horses, sheep, goats, swine; domestic animals such as rabbits, dogs, and cats; laboratory animals including rodents, such as rats, mice and guinea pigs, and the like. In one aspect, the mammal is a human.

The terms "treat," "treating" or "treatment," as used herein, include alleviating, abating or ameliorating at least one symptom of a disease or condition, preventing additional symptoms, inhibiting the disease or condition, e.g., arresting the development of the disease or condition, relieving the disease or condition, causing regression of the disease or condition, relieving a condition caused by the disease or condition, or stopping the symptoms of the disease or condition either prophylactically and/or therapeutically.

Pharmaceutical Compositions

In some embodiments, the compounds described herein are formulated into pharmaceutical compositions. Pharmaceutical compositions are formulated in a conventional manner using one or more pharmaceutically acceptable inactive ingredients that facilitate processing of the active compounds into preparations that are used pharmaceutically. Proper formulation is dependent upon the route of administration chosen. A summary of pharmaceutical compositions described herein is found, for example, in Remington: The Science and Practice of Pharmacy, Nineteenth Ed (Easton, Pa.: Mack Publishing Company, 1995); Hoover, John E., Remington's Pharmaceutical Sciences, Mack Publishing Co., Easton, Pa. 1975; Liberman, H. A. and Lachman, L., Eds., Pharmaceutical Dosage Forms, Marcel Decker, New York, N.Y., 1980; and Pharmaceutical Dosage Forms and Drug Delivery Systems, Seventh Ed. (Lippincott Williams & Wilkins 1999), herein incorporated by reference for such disclosure.

In some embodiments, the compounds described herein are administered either alone or in combination with pharmaceutically acceptable carriers, excipients or diluents, in a pharmaceutical composition. Administration of the compounds and compositions described herein can be effected by any method that enables delivery of the compounds to the site of action. These methods include, though are not limited to delivery via enteral routes (including oral, gastric or duodenal feeding tube, rectal suppository and rectal enema), parenteral routes (injection or infusion, including intraarterial, intracardiac, intradermal, intraduodenal, intramedullary, intramuscular, intraosseous, intraperitoneal, intrathecal, intravascular, intravenous, intravitreal, epidural and subcutaneous), inhalational, transdermal, transmucosal, sublingual, buccal and topical (including epicutaneous, dermal, enema, eye drops, ear drops, intranasal, vaginal) administration, although the most suitable route may depend upon for example the condition and disorder of the recipient. By way of example only, compounds described herein can be administered locally to the area in need of treatment, by for example, local infusion during surgery, topical application such as creams or ointments, injection, catheter, or implant. The administration can also be by direct injection at the site of a diseased tissue or organ.

In some embodiments, pharmaceutical compositions suitable for oral administration are presented as discrete units such as capsules, cachets or tablets each containing a predetermined amount of the active ingredient; as a powder or granules; as a solution or a suspension in an aqueous liquid or a non-aqueous liquid; or as an oil-in-water liquid emulsion or a water-in-oil liquid emulsion. In some embodiments, the active ingredient is presented as a bolus, electuary or paste.

Pharmaceutical compositions which can be used orally include tablets, push-fit capsules made of gelatin, as well as soft, sealed capsules made of gelatin and a plasticizer, such as glycerol or sorbitol. Tablets may be made by compression or molding, optionally with one or more accessory ingredients. Compressed tablets may be prepared by compressing in a suitable machine the active ingredient in a free-flowing form such as a powder or granules, optionally mixed with binders, inert diluents, or lubricating, surface active or dispersing agents. Molded tablets may be made by molding in a suitable machine a mixture of the powdered compound moistened with an inert liquid diluent. In some embodiments, the tablets are coated or scored and are formulated so as to provide slow or controlled release of the active ingredient therein. All formulations for oral administration should be in dosages suitable for such administration. The push-fit capsules can contain the active ingredients in admixture with filler such as lactose, binders such as starches, and/or lubricants such as talc or magnesium stearate and, optionally, stabilizers. In soft capsules, the active compounds may be dissolved or suspended in suitable liquids, such as fatty oils, liquid paraffin, or liquid polyethylene glycols. In some embodiments, stabilizers are added. Dragee cores are provided with suitable coatings. For this purpose, concentrated sugar solutions may be used, which may optionally contain gum arabic, talc, polyvinyl pyrrolidone, carbopol gel, polyethylene glycol, and/or titanium dioxide, lacquer solutions, and suitable organic solvents or solvent mixtures. Dyestuffs or pigments may be added to the tablets or Dragee coatings for identification or to characterize different combinations of active compound doses.

In some embodiments, pharmaceutical compositions are formulated for parenteral administration by injection, e.g., by bolus injection or continuous infusion. Formulations for injection may be presented in unit dosage form, e.g., in ampoules or in multi-dose containers, with an added preservative. The compositions may take such forms as suspensions, solutions or emulsions in oily or aqueous vehicles, and may contain formulatory agents such as suspending, stabilizing and/or dispersing agents. The compositions may be presented in unit-dose or multi-dose containers, for example sealed ampoules and vials, and may be stored in powder form or in a freeze-dried (lyophilized) condition requiring only the addition of the sterile liquid carrier, for example, saline or sterile pyrogen-free water, immediately prior to use. Extemporaneous injection solutions and suspensions may be prepared from sterile powders, granules and tablets of the kind previously described.

Pharmaceutical compositions for parenteral administration include aqueous and non-aqueous (oily) sterile injection solutions of the active compounds which may contain antioxidants, buffers, bacteriostats and solutes which render the formulation isotonic with the blood of the intended recipient; and aqueous and non-aqueous sterile suspensions which may include suspending agents and thickening agents. Suitable lipophilic solvents or vehicles include fatty oils such as sesame oil, or synthetic fatty acid esters, such as ethyl oleate or triglycerides, or liposomes. Aqueous injection suspensions may contain substances which increase the viscosity of the suspension, such as sodium carboxymethyl cellulose, sorbitol, or dextran. Optionally, the suspension may also contain suitable stabilizers or agents which increase the solubility of the compounds to allow for the preparation of highly concentrated solutions.

Pharmaceutical compositions may also be formulated as a depot preparation. Such long acting formulations may be administered by implantation (for example subcutaneously or intramuscularly) or by intramuscular injection. Thus, for example, the compounds may be formulated with suitable polymeric or hydrophobic materials (for example, as an emulsion in an acceptable oil) or ion exchange resins, or as sparingly soluble derivatives, for example, as a sparingly soluble salt.

For buccal or sublingual administration, the compositions may take the form of tablets, lozenges, pastilles, or gels formulated in conventional manner. Such compositions may comprise the active ingredient in a flavored basis such as sucrose and acacia or tragacanth.

Pharmaceutical compositions may also be formulated in rectal compositions such as suppositories or retention enemas, e.g., containing conventional suppository bases such as cocoa butter, polyethylene glycol, or other glycerides.

Pharmaceutical compositions may be administered topically, that is by non-systemic administration. This includes the application of a compound of the present invention externally to the epidermis or the buccal cavity and the instillation of such a compound into the ear, eye and nose, such that the compound does not significantly enter the blood stream. In contrast, systemic administration refers to oral, intravenous, intraperitoneal and intramuscular administration.

Pharmaceutical compositions suitable for topical administration include liquid or semi-liquid preparations suitable for penetration through the skin to the site of inflammation such as gels, liniments, lotions, creams, ointments or pastes, and drops suitable for administration to the eye, ear or nose. The active ingredient may comprise, for topical administration, from 0.001% to 10% w/w, for instance from 1% to 2% by weight of the formulation.

Pharmaceutical compositions for administration by inhalation are conveniently delivered from an insufflator, nebulizer pressurized packs or other convenient means of delivering an aerosol spray. Pressurized packs may comprise a suitable propellant such as dichlorodifluoromethane, trichlorofluoromethane, dichlorotetrafluoroethane, carbon dioxide or other suitable gas. In the case of a pressurized aerosol, the dosage unit may be determined by providing a valve to deliver a metered amount. Alternatively, for administration by inhalation or insufflation, pharmaceutical preparations may take the form of a dry powder composition, for example a powder mix of the compound and a suitable powder base such as lactose or starch. The powder composition may be presented in unit dosage form, in for example, capsules, cartridges, gelatin or blister packs from which the powder may be administered with the aid of an inhalator or insufflator.

It should be understood that in addition to the ingredients particularly mentioned above, the compounds and compositions described herein may include other agents conventional in the art having regard to the type of formulation in question, for example those suitable for oral administration may include flavoring agents.

Methods of Dosing and Treatment Regimens

In one embodiment, the compounds described herein, or a pharmaceutically acceptable salt thereof, are used in the preparation of medicaments for the treatment of diseases or conditions in a mammal that would benefit from inhibition or reduction of ASK1 activity. Methods for treating any of the diseases or conditions described herein in a mammal in need of such treatment, involves administration of pharmaceutical compositions that include at least one compound described herein or a pharmaceutically acceptable salt, active metabolite, prodrug, or pharmaceutically acceptable solvate thereof, in therapeutically effective amounts to said mammal.

In certain embodiments, the compositions containing the compound(s) described herein are administered for prophylactic and/or therapeutic treatments. In certain therapeutic applications, the compositions are administered to a patient already suffering from a disease or condition, in an amount sufficient to cure or at least partially arrest at least one of the symptoms of the disease or condition. Amounts effective for this use depend on the severity and course of the disease or condition, previous therapy, the patient's health status, weight, and response to the drugs, and the judgment of the treating physician. Therapeutically effective amounts are optionally determined by methods including, but not limited to, a dose escalation and/or dose ranging clinical trial.

In prophylactic applications, compositions containing the compounds described herein are administered to a patient susceptible to or otherwise at risk of a particular disease, disorder or condition. Such an amount is defined to be a "prophylactically effective amount or dose." In this use, the precise amounts also depend on the patient's state of health, weight, and the like. When used in patients, effective amounts for this use will depend on the severity and course of the disease, disorder or condition, previous therapy, the patient's health status and response to the drugs, and the judgment of the treating physician. In one aspect, prophylactic treatments include administering to a mammal, who previously experienced at least one symptom of the disease being treated and is currently in remission, a pharmaceutical composition comprising a compound described herein, or a pharmaceutically acceptable salt thereof, in order to prevent a return of the symptoms of the disease or condition.

In certain embodiments wherein the patient's condition does not improve, upon the doctor's discretion the administration of the compounds are administered chronically, that is, for an extended period of time, including throughout the duration of the patient's life in order to ameliorate or otherwise control or limit the symptoms of the patient's disease or condition.

In certain embodiments wherein a patient's status does improve, the dose of drug being administered is temporarily reduced or temporarily suspended for a certain length of time (i.e., a "drug holiday"). In specific embodiments, the length of the drug holiday is between 2 days and 1 year, including by way of example only, 2 days, 3 days, 4 days, 5 days, 6 days, 7 days, 10 days, 12 days, 15 days, 20 days, 28 days, or more than 28 days. The dose reduction during a drug holiday is, by way of example only, by 10%-100%, including by way of example only 10%, 15%, 20%, 25%, 30%, 35%, 40%, 45%, 50%, 55%, 60%, 65%, 70%, 75%, 80%, 85%, 90%, 95%, and 100%.

Once improvement of the patient's conditions has occurred, a maintenance dose is administered if necessary. Subsequently, in specific embodiments, the dosage or the frequency of administration, or both, is reduced, as a function of the symptoms, to a level at which the improved disease, disorder or condition is retained. In certain embodiments, however, the patient requires intermittent treatment on a long-term basis upon any recurrence of symptoms.

The amount of a given agent that corresponds to such an amount varies depending upon factors such as the particular compound, disease condition and its severity, the identity (e.g., weight, sex) of the subject or host in need of treatment, but nevertheless is determined according to the particular circumstances surrounding the case, including, e.g., the specific agent being administered, the route of administration, the condition being treated, and the subject or host being treated.

In general, however, doses employed for adult human treatment are typically in the range of 0.01 mg-5000 mg per day. In one aspect, doses employed for adult human treatment are from about 1 mg to about 1000 mg per day. In one embodiment, the desired dose is conveniently presented in a single dose or in divided doses administered simultaneously or at appropriate intervals, for example as two, three, four or more sub-doses per day.

In one embodiment, the daily dosages appropriate for the compound described herein, or a pharmaceutically acceptable salt thereof, are from about 0.01 to about 50 mg/kg per body weight. In some embodiments, the daily dosage or the amount of active in the dosage form are lower or higher than the ranges indicated herein, based on a number of variables in regard to an individual treatment regime. In various embodiments, the daily and unit dosages are altered depending on a number of variables including, but not limited to, the activity of the compound used, the disease or condition to be treated, the mode of administration, the requirements of the individual subject, the severity of the disease or condition being treated, and the judgment of the practitioner.

Toxicity and therapeutic efficacy of such therapeutic regimens are determined by standard pharmaceutical procedures in cell cultures or experimental animals, including, but not limited to, the determination of the $LD_{50}$ and the $ED_{50}$. The dose ratio between the toxic and therapeutic effects is the therapeutic index and it is expressed as the ratio between $LD_{50}$ and $ED_{50}$. In certain embodiments, the data obtained from cell culture assays and animal studies are used in formulating the therapeutically effective daily dosage range and/or the therapeutically effective unit dosage amount for use in mammals, including humans. In some embodiments, the daily dosage amount of the compounds described herein lies within a range of circulating concentrations that include the $ED_{50}$ with minimal toxicity. In certain embodiments, the daily dosage range and/or the unit dosage amount varies within this range depending upon the dosage form employed and the route of administration utilized.

In any of the aforementioned aspects are further embodiments in which the effective amount of the compound described herein, or a pharmaceutically acceptable salt thereof, is: (a) systemically administered to the mammal; and/or (b) administered orally to the mammal; and/or (c) intravenously administered to the mammal; and/or (d) administered by injection to the mammal; and/or (e) administered topically to the mammal; and/or (f) administered non-systemically or locally to the mammal.

In any of the aforementioned aspects are further embodiments comprising single administrations of the effective amount of the compound, including further embodiments in which (i) the compound is administered once a day; or (ii) the compound is administered to the mammal multiple times over the span of one day.

In any of the aforementioned aspects are further embodiments comprising multiple administrations of the effective amount of the compound, including further embodiments in which (i) the compound is administered continuously or intermittently: as in a single dose; (ii) the time between multiple administrations is every 6 hours; (iii) the compound is administered to the mammal every 8 hours; (iv) the compound is administered to the mammal every 12 hours; (v) the compound is administered to the mammal every 24 hours. In further or alternative embodiments, the method comprises a drug holiday, wherein the administration of the compound is temporarily suspended or the dose of the compound being administered is temporarily reduced; at the end of the drug holiday, dosing of the compound is resumed. In one embodiment, the length of the drug holiday varies from 2 days to 1 year.

In certain instances, it is appropriate to administer at least one compound described herein, or a pharmaceutically acceptable salt thereof, in combination with one or more other therapeutic agents. In certain embodiments, the pharmaceutical composition further comprises one or more anti-cancer agents.

In one embodiment, the therapeutic effectiveness of one of the compounds described herein is enhanced by administration of an adjuvant (i.e., by itself the adjuvant has minimal therapeutic benefit, but in combination with another therapeutic agent, the overall therapeutic benefit to the patient is enhanced). Or, in some embodiments, the benefit experienced by a patient is increased by administering one of the compounds described herein with another agent (which also includes a therapeutic regimen) that also has therapeutic benefit.

In one specific embodiment, a compound described herein, or a pharmaceutically acceptable salt thereof, is co-administered with a second therapeutic agent, wherein the compound described herein, or a pharmaceutically acceptable salt thereof, and the second therapeutic agent modulate different aspects of the disease, disorder or condition being treated, thereby providing a greater overall benefit than administration of either therapeutic agent alone.

In any case, regardless of the disease, disorder or condition being treated, the overall benefit experienced by the patient may be additive of the two therapeutic agents or the patient may experience a synergistic benefit.

In certain embodiments, different therapeutically-effective dosages of the compounds disclosed herein will be utilized in formulating pharmaceutical composition and/or in treatment regimens when the compounds disclosed herein are administered in combination with one or more additional agent, such as an additional therapeutically effective drug, an adjuvant or the like. Therapeutically-effective dosages of drugs and other agents for use in combination treatment regimens is optionally determined by means similar to those set forth hereinabove for the actives themselves. Furthermore, the methods of prevention/treatment described herein encompasses the use of metronomic dosing, i.e., providing more frequent, lower doses in order to minimize toxic side effects. In some embodiments, a combination treatment regimen encompasses treatment regimens in which administration of a compound described herein, or a pharmaceutically acceptable salt thereof, is initiated prior to, during, or after treatment with a second agent described herein, and continues until any time during treatment with the second agent or after termination of treatment with the second agent. It also includes treatments in which a compound described herein, or a pharmaceutically acceptable salt thereof, and the second agent being used in combination are administered simultaneously or at different times and/or at decreasing or increasing intervals during the treatment period. Combination treatment further includes periodic treatments that start and stop at various times to assist with the clinical management of the patient.

It is understood that the dosage regimen to treat, prevent, or ameliorate the condition(s) for which relief is sought, is modified in accordance with a variety of factors (e.g. the disease, disorder or condition from which the subject suffers; the age, weight, sex, diet, and medical condition of the subject). Thus, in some instances, the dosage regimen actually employed varies and, in some embodiments, deviates from the dosage regimens set forth herein.

For combination therapies described herein, dosages of the co-administered compounds vary depending on the type of co-drug employed, on the specific drug employed, on the disease or condition being treated and so forth. In additional embodiments, when co-administered with one or more other therapeutic agents, the compound provided herein is administered either simultaneously with the one or more other therapeutic agents, or sequentially.

In combination therapies, the multiple therapeutic agents (one of which is one of the compounds described herein) are administered in any order or even simultaneously. If administration is simultaneous, the multiple therapeutic agents are, by way of example only, provided in a single, unified form, or in multiple forms (e.g., as a single pill or as two separate pills).

The compounds described herein, or a pharmaceutically acceptable salt thereof, as well as combination therapies, are administered before, during or after the occurrence of a disease or condition, and the timing of administering the composition containing a compound varies. Thus, in one embodiment, the compounds described herein are used as a prophylactic and are administered continuously to subjects with a propensity to develop conditions or diseases in order to prevent the occurrence of the disease or condition. In another embodiment, the compounds and compositions are administered to a subject during or as soon as possible after the onset of the symptoms. In specific embodiments, a compound described herein is administered as soon as is practicable after the onset of a disease or condition is detected or suspected, and for a length of time necessary for the treatment of the disease. In some embodiments, the length required for treatment varies, and the treatment length is adjusted to suit the specific needs of each subject. For example, in specific embodiments, a compound described herein or a formulation containing the compound is administered for at least 2 weeks, about 1 month to about 5 years.

In some embodiments, a compound described herein, or a pharmaceutically acceptable salt thereof, is administered in combination with chemotherapy, hormone blocking therapy, radiation therapy, monoclonal antibodies, or combinations thereof. Chemotherapy includes the use of anti-cancer agents.

In one aspect, the compound described herein, or a pharmaceutically acceptable salt thereof, is administered or formulated in combination with one or more anti-cancer agents.

EXAMPLES

The following examples are provided for illustrative purposes only and not to limit the scope of the claims provided herein.

Synthesis of Int-A

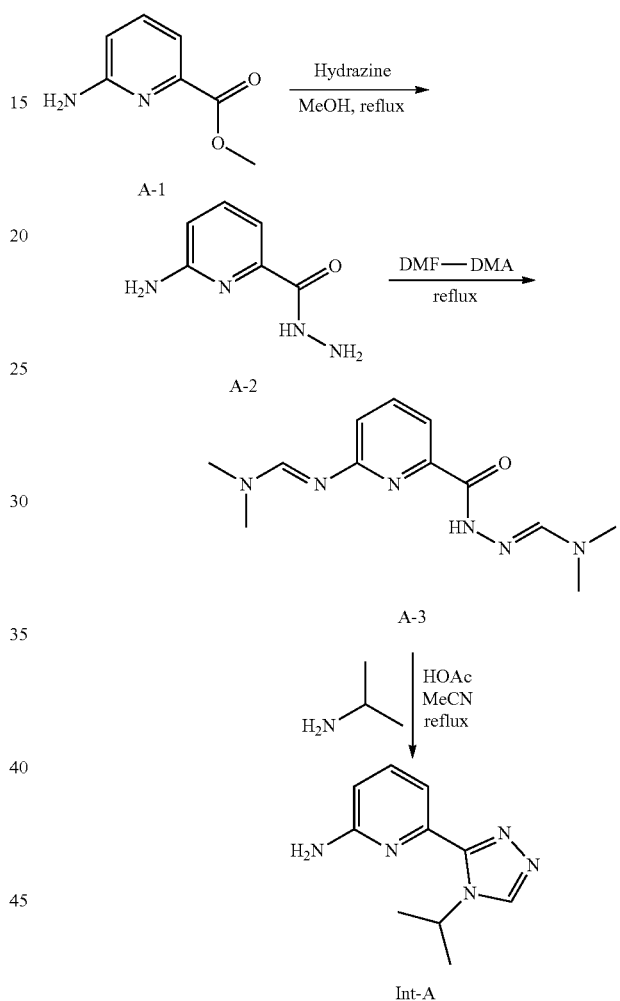

Step 1: 6-Aminopicolinohydrazide (A-2)

To a solution of 6-aminopicolinic acid methyl ester A-1 (25 g, 164 mmol) in MeOH (300 mL), was added hydrazine monohydrate (16.47 g, 329 mmol). The mixture was heated at 78° C. for 2 h. Additional hydrazine monohydrate (2.46 g, 50 mmol) and MeOH (100 mL) were added and the mixture stirred at 78° C. for a further 1 h. The mixture was cooled to rt then concentrated to approximately two-thirds volume. EtOAc (30 mL) and Et$_2$O (100 mL) were added. The resulting precipitate was collected via filtration, washed with Et$_2$O, and dried, to afford compound A-2 (23 g, 92%) as an off-white solid. $^1$H NMR (400 MHz, DMSO-d$_6$): δ 9.14 (s, 1H), 7.50 (m, 1H), 7.15 (m, 1H), 6.57 (m, 1H), 6.06 (s, 2H), 4.46 (s, 2H); LCMS Mass: 153.0 (M$^+$+1).

Step 2: (E)-N'-(6-((E)-2-((Dimethylamino)methylene)hydrazinecarbonyl)pyridin-2-yl)-N,N-dimethylformimidamide (A-3)

A stirred mixture of A-2 (23 g, 151 mmol) in DMF-DMA (200 mL) was heated at 110° C. for 24 h. The mixture was cooled to rt then concentrated under reduced pressure. The solid residue was re-suspended in EtOAc (150 mL) and stirred at 50° C. for 20 min. The mixture was cooled to rt and Et$_2$O (100 mL) was added. The solids were collected via filtration, washed with Et$_2$O, and dried to afford compound A-3 (36.5 g, 92%) as a light yellow solid. $^1$H NMR (400 MHz, DMSO-d$_6$): δ 10.67 (s, 1H), 8.85 (s, 1H), 8.06 (s, 1H), 7.69 (m, 1H), 7.45 (m, 1H), 6.91 (m, 1H), 3.13 (s, 3H), 2.99 (s, 3H), 2.87 (s, 6H); LCMS Mass: 263.0 (M$^+$+1).

Step 3: 6-(4-Isopropyl-4H-1,2,4-triazol-3-yl)pyridin-2-amine (Int-A)

To a stirred solution of A-3 (36.5 g, 139 mmol) in a mixture of MeCN (184 mL) and HOAc (46 mL), was added isopropylamine (60 mL, 696 mmol). The mixture was heated at 100° C. for 16 h. The mixture was cooled to rt and concentrated under reduced pressure. The residue was diluted with water (180 mL) and the pH was adjusted to 8 with aq. 1M NaOH. The obtained precipitate was collected via filtration and dried to afford Int-A (18.1 g, 64%) as an off-white solid. $^1$H NMR (400 MHz, DMSO-d$_6$): δ 8.78 (s, 1H), 7.52 (m, 1H), 7.15 (m, 1H), 6.50 (m, 1H), 6.15 (s, 2H), 5.51 (m, 1H), 1.44 (m, 6H); LCMS Mass: 204.0 (M$^+$+1).

Synthesis of Int-B

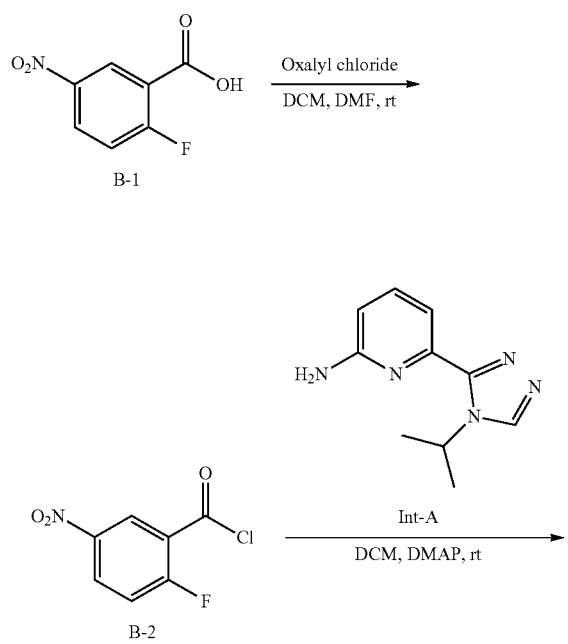

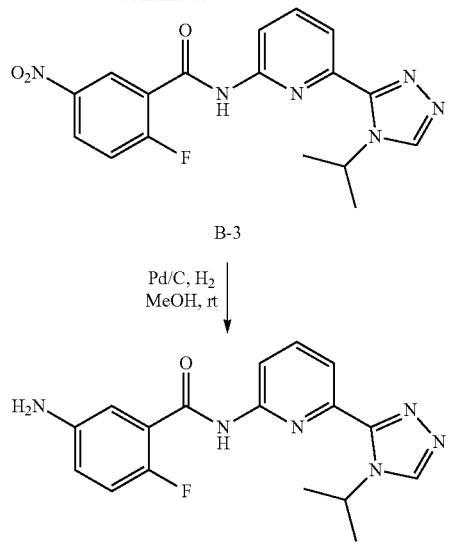

Step 1: 2-Fluoro-5-nitrobenzoyl chloride (B-2)

To a stirred solution of 2-fluoro-5-nitrobenzoic acid B-1 (1 g, 5.40 mmol) in DCM (35 mL) at rt under an inert atmosphere, was added oxalyl chloride (600 μL, 7.02 mmol) and DMF (catalytic). The mixture was stirred at rt for 2 h. The mixture was concentrated under reduced pressure to afford compound B-2 (1.09 g, 100%) as an oil, which was taken on to the next step without further purification.

Step 2: 2-Fluoro-N-(6-(4-isopropyl-4H-1,2,4-triazol-3-yl)pyridin-2-yl)-5-nitrobenzamide (B-3)

To a stirred solution of compound B-2 (1.09 g, 5.40 mmol) in DCM (35 mL) at rt under an inert atmosphere, was added Int-A (1.09 g, 5.40 mmol) and DMAP (659 mg, 5.40 mmol). The mixture was stirred at rt for 2 h. The mixture was concentrated under reduced pressure and the residue purified via trituration with a mixture of MeOH and MeCN, to afford compound B-3 (1.4 g, 70%) as a solid. LCMS Mass: 371.0 (M$^+$+1).

Step 3: 5-Amino-2-fluoro-N-(6-(4-isopropyl-4H-1,2,4-triazol-3-yl)pyridin-2-yl)benzamide (Int-B)

To a stirred solution of B-3 (1.3 g, 3.52 mmol) in MeOH (75 mL) at rt, was added 10% palladium on activated carbon (138 mg), and the mixture stirred under hydrogen (1 atmosphere) at rt for 1 h. The mixture was diluted with MeOH, then filtered through celite. The filtrate was concentrated under reduced pressure to afford compound Int-B (1.2 g, 100%) as a yellow solid. $^1$H NMR (400 MHz, DMSO-d$_6$): δ 10.66 (s, 1H), 8.88 (s, 1H), 8.19 (m, 1H), 8.01 (m, 1H), 7.87 (m, 1H), 7.02 (m, 1H), 6.85 (m, 1H), 6.71 (m, 1H), 5.70 (m, 1H), 5.24 (s, 2H), 1.42 (m, 6H); LCMS Mass: 341.0 (M$^+$+1).

Synthesis of Int-C

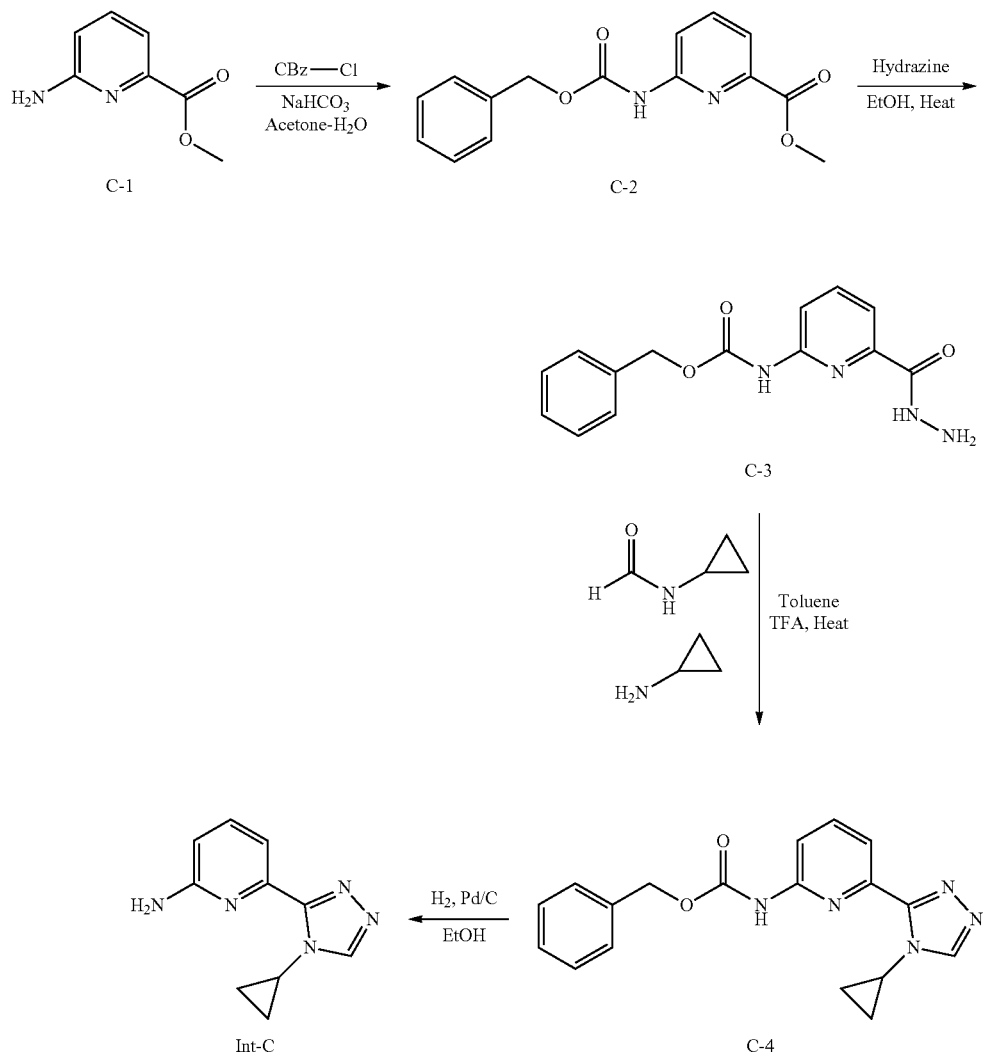

Step 1: Methyl 6-(((benzyloxy)carbonyl)amino)picolinate (C-2)

To a stirred solution of 6-aminopicolinic acid methyl ester C-1 (1 g, 6.6 mmol) and NaHCO$_3$ (1.1 g, 13.2 mmol) in a mixture of acetone (6 mL) and water (4 mL) at 0° C., was added dropwise benzyl chloroformate (1 mL, 7.3 mmol). The mixture was warmed to rt and stirred for an additional 18 h. The mixture was diluted with water and the resulting solids were collected via filtration and dried to afford compound C-2 (1.36 g, 72%) as a white solid. LCMS Mass: 287.0 (M$^+$+1).

Step 2: Benzyl (6-(hydrazinecarbonyl)pyridin-2-yl)carbamate (C-3)

To a stirred mixture of C-2 (1.36 g, 4.75 mmol) in EtOH (10 mL) was added hydrazine hydrate (1.5 g) and the mixture heated at 80° C. for 2 h. The mixture was cooled to rt and concentrated under reduced pressure to afford compound C-3 (1.36 g, 100%) as an off-white solid. LCMS Mass: 287.0 (M$^+$+1).

Step 3: Benzyl (6-(4-cyclopropyl-4H-1,2,4-triazol-3-yl)pyridin-2-yl)carbamate (C-4)

To a stirred mixture of C-3 (570 mg, 2.0 mmol), N-cyclopropylformamide (0.51 mg, 6.0 mmol), cyclopropylamine (0.42 mL, 6.0 mmol), and anhydrous toluene (10 mL), was added TFA (0.15 mL, 2.0 mmol). The mixture was heated at 100° C. for 18 h. The mixture was cooled to rt and concentrated under reduced pressure. The residue was purified (silica; eluting with 0-20% MeOH in DCM) to afford compound C-4 (460 mg) as an oil which was taken on to the next step without further purification. LCMS Mass: 336.0 (M$^+$+1).

Step 4: 6-(4-Cyclopropyl-4H-1,2,4-triazol-3-yl)pyridin-2-amine (Int-C)

To a stirred solution of C-4 (460 mg) in EtOH (10 mL) at rt, was added 10% palladium on activated carbon (50 mg), and the mixture stirred under hydrogen (1 atmosphere). Upon completion of reaction, the mixture was filtered through celite and the filtrate was concentrated under reduced pressure to afford compound Int-C (270 mg) as a light yellow solid. LCMS Mass: 202.0 (M$^+$+1).

Synthesis of Int-D

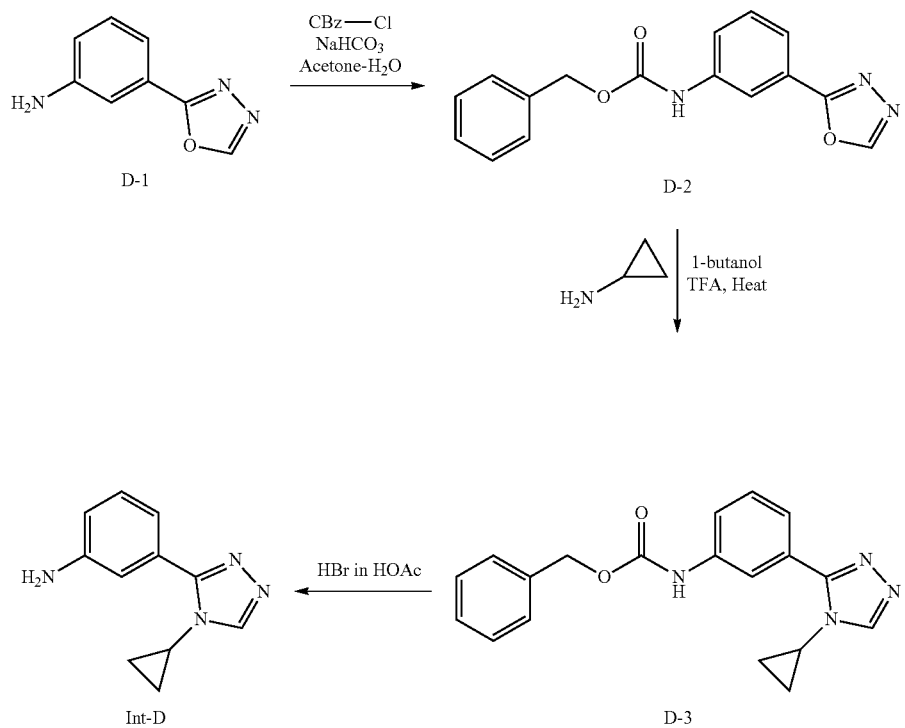

Step 1: Benzyl (3-(1,3,4-oxadiazol-2-yl)phenyl) carbamate (D-2)

The title compound (1.5 g, 82%) was prepared from 3-(1,3,4-oxadiazol-2-yl)aniline D-1 using the procedure described for Int-C, Step 1. LCMS Mass: 296.0 (M$^+$+1).

Step 2: Benzyl (3-(4-cyclopropyl-4H-1,2,4-triazol-3-yl)phenyl)carbamate (D-3)

A stirred mixture of D-2 (590 mg, 2.0 mmol), cyclopropylamine (1.4 mL, 20 mmol), TFA (0.15 mL, 2.0 mmol), and anhydrous 1-butanol (10 mL) was heated at 100° C. for 18 h. The mixture was cooled to rt and concentrated under reduced pressure. The residue was purified (silica; eluting with 0-10% MeOH in DCM) to afford compound D-2 (480 mg, 72%) as a yellow solid. LCMS Mass: 335.0 (M$^+$+1).

Step 3: 3-(4-Cyclopropyl-4H-1,2,4-triazol-3-yl)aniline (Int-D)

A mixture of D-2 (480 mg, 1.44 mmol) and 33% HBr in HOAc (3 mL) was stirred at rt for 18 h. The mixture was concentrated under reduced pressure and the residue diluted with water. The mixture was basified to pH 12 with 1M aq. NaOH solution, then repeatedly extracted with EtOAc. The combined organic layers were dried (Na$_2$SO$_4$), filtered, and concentrated under reduced pressure to afford compound Int-D (171 mg, 59%) as a light brown solid. LCMS Mass: 201.0 (M$^+$+1).

Synthesis of Int-E

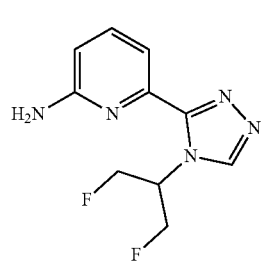

Int-E was prepared using the procedure described for Int-A, using 1,3-difluoropropan-2-amine hydrochloride in Step 3. LCMS Mass: 240.0 (M$^+$+1).

Synthesis of Int-F

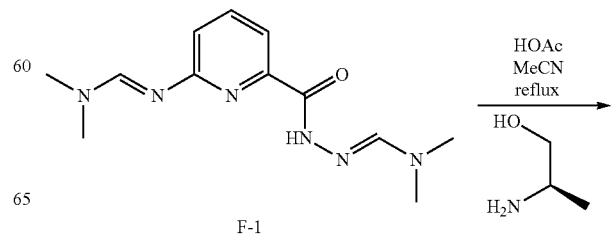

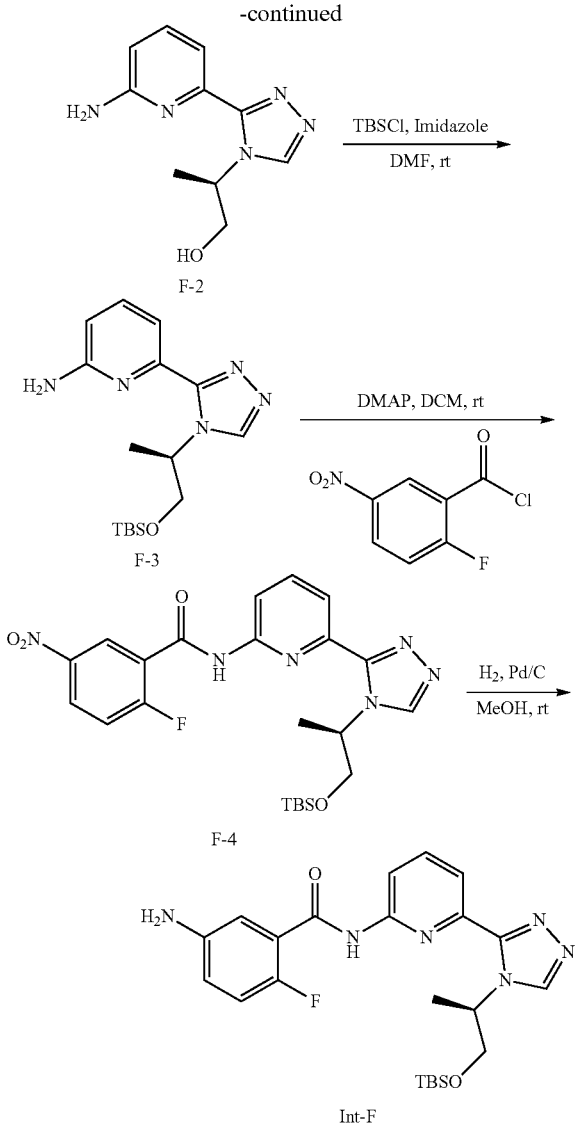

Step 1: (R)-2-(3-(6-Aminopyridin-2-yl)-4H-1,2,4-triazol-4-yl)propan-1-ol (F-2)

To a solution of F-1 (20.0 g, 76.2 mmol) (from the synthesis of Int-A, Step 2) in MeCN (200 mL) was added (R)-(−)-2-amino-1-propanol (28.6 g, 381 mmol) and HOAc (25 mL). The reaction mixture was heated at reflux for 8 h. The mixture was concentrated under reduced pressure and the residue purified (silica gel; eluting with 3% MeOH in DCM) to afford compound F-2 (15 g, 90%) as a yellow solid. $^1$H NMR (400 MHz, DMSO-$d_6$): δ 8.43 (s, 1H), 7.51 (m, 1H), 7.24 (m, 1H), 6.51 (m, 1H), 6.13 (s, 2H), 4.94 (br s, 1H), 4.62 (m, 1H), 4.26 (m, 1H), 3.86 (m, 1H), 1.00-1.05 (m, 3H).

Step 2: (R)-6-(4-(1-((tert-Butyldimethylsilyl)oxy)propan-2-yl)-4H-1,2,4-triazol-3-yl)pyridin-2-amine (F-3)

To a solution of compound F-2 (500 mg, 2.3 mmol) in DMF (10 mL) was added TBDMS-Cl (413 mg, 2.3 mmol) and imidazole (233 mg, 3.4 mmol). The reaction mixture was stirred at rt for 12 h. The mixture was filtered through celite and the filtrate concentrated under reduced pressure. The residue was purified (silica gel; eluting with 3% MeOH in DCM) to afford compound F-3 (600 mg, 79%) as a white solid. $^1$H NMR (400 MHz, DMSO-$d_6$): δ 8.64 (s, 1H), 7.50 (m, 1H), 7.16 (m, 1H), 6.52 (m, 1H), 6.11 (s, 2H), 5.56 (br m, 1H), 3.76-3.78 (m, 2H), 1.45-1.47 (m, 3H), 0.73 (s, 9H), −0.12 (s, 3H), −0.16 (s, 3H); LCMS Mass: 334.2 (M$^+$+1).

Step 3: (R)—N-(6-(4-(1-((tert-butyldimethylsilyl)oxy)propan-2-yl)-4H-1,2,4-triazol-3-yl)pyridin-2-yl)-2-fluoro-5-nitrobenzamide (F-4)

To a solution of F-3 (406 mg, 2.0 mmol) in DCM (15 mL) was added 2-fluoro-5-nitrobenzoyl chloride (600 mg, 1.8 mmol) and DMAP (219 mg, 1.8 mmol). The reaction mixture was stirred at rt overnight. Water was added and the aqueous layer extracted several times with DCM. The combined organic layers were dried (MgSO$_4$), filtered, and the filtrate concentrated under reduced pressure. The residue was purified (silica gel; eluting with 50% EtOAc in hexane) to afford compound F-4 (530 mg, 30%) as a white solid. LCMS Mass: 501.0 (M$^+$+1).

Step 4: (R)-5-Amino-N-(6-(4-(1-((tert-butyldimethylsilyl)oxy)propan-2-yl)-4H-1,2,4-triazol-3-yl)pyridin-2-yl)-2-fluorobenzamide (Int-F)

To a solution of F-4 (500 mg, 1 mmol) in MeOH (15 mL) was added Pd/C (50 mg). The reaction was stirred at rt under H$_2$ (1 atmosphere) for 16 h. The mixture was filtered through Celite and the filtrate concentrated under reduced pressure to afford Int-F (460 mg, 98%) as a brown solid. $^1$H NMR (400 MHz, DMSO-$d_6$): δ 10.54 (s, 1H), 8.47 (s, 1H), 8.15 (m, 1H), 8.01 (m, 1H), 7.90 (m, 1H), 7.02 (m, 1H), 6.89 (s, 1H), 6.74 (s, 1H), 5.23 (s, 2H), 4.96 (m, 1H), 4.32 (m, 1H), 3.95 (s, 1H), 1.13-1.15 (m, 3H), 0.71 (s, 9H), −0.20 (s, 3H), −0.44 (s, 3H); LCMS Mass: 471.2 (M$^+$+1).

Example 1: 3-((4-Cyano-6-(trifluoromethyl)pyridin-2-yl)oxy)-N-(6-(4-isopropyl-4H-1,2,4-triazol-3-yl)pyridin-2-yl)benzamide (Compound 1-179)

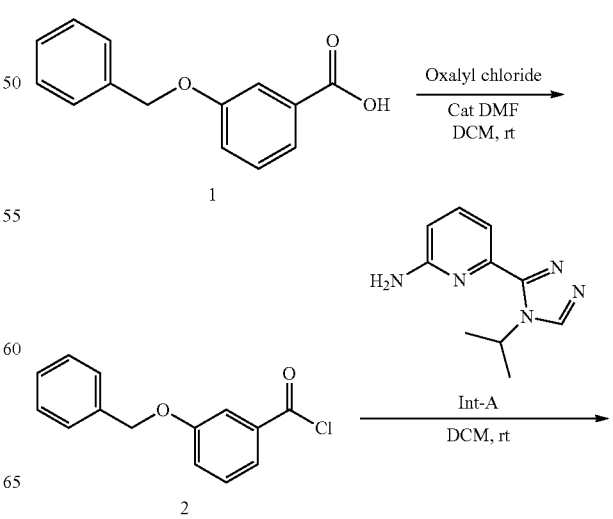

155

-continued

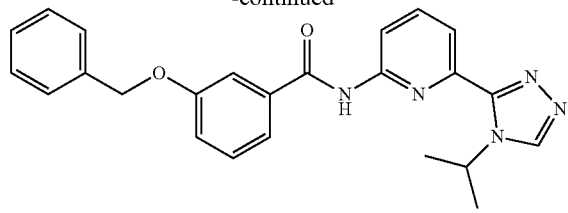

Compound 1-179

Step 1: 3-(Benzyloxy)benzoyl chloride (2)

To a stirred solution of 3-(benzyloxy)benzoic acid 1 (1 g, 4.38 mmol) in DCM (30 mL) at rt under an inert atmosphere, was added oxalyl chloride (525 μL, 6.13 mmol) and DMF (catalytic). The mixture was stirred at rt for 1.5 h. The mixture was concentrated under reduced pressure to afford compound 2 (1.08 g, 100%) as an oil, which was taken on to the next step without further purification.

Step 2: 3-(Benzyloxy)-N-(6-(4-isopropyl-4H-1,2,4-triazol-3-yl)pyridin-2-yl)benzamide (Compound 1-179)

To a stirred solution of compound 2 (1.08 g, 4.38 mmol) in DCM (30 mL) at 0° C. under an argon atmosphere, was added Int-A (890 mg, 4.38 mmol) and DIEA (1.5 mL, 8.76 mmol). The mixture was allowed to warm to rt and stirred for a further 1 h. The mixture was concentrated under reduced pressure and the residue purified (silica; eluting with 100% EtOAc followed by 0-20% MeOH in DCM; followed by trituration with a mixture of MeOH/MeCN/EtOAc) to afford compound 3 (840 mg, 47%) as a white solid. $^1$H NMR (400 MHz, DMSO-$d_6$): δ 10.74 (s, 1H), 8.86 (s, 1H), 8.16 (m, 1H), 8.01 (m, 1H), 7.86 (m, 1H), 7.56-7.60 (m, 2H), 7.49-7.50 (m, 3H), 7.40-7.47 (m, 2H), 7.34 (m, 1H), 7.27 (m, 1H), 5.71 (m, 1H), 5.21 (s, 2H), 1.43 (m, 6H); LCMS Mass: 414.0 (M$^+$+1).

Example 2: 3-((4-Cyano-6-(trifluoromethyl)pyridin-2-yl)oxy)-N-(6-(4-isopropyl-4H-1,2,4-triazol-3-yl)pyridin-2-yl)benzamide (Compound 1-23)

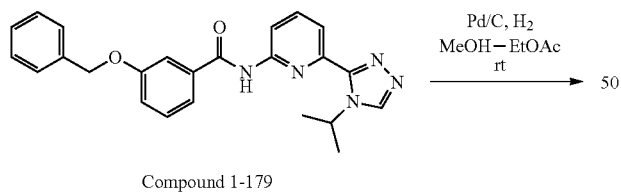

156

-continued

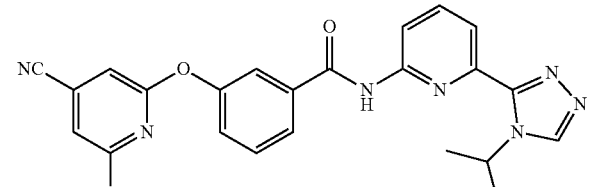

Compound 1-23

Step 1: 3-Hydroxy-N-(6-(4-isopropyl-4H-1,2,4-triazol-3-yl)pyridin-2-yl)benzamide (1)

To a stirred mixture of compound 1-179 (840 mg, 2.03 mmol) (from Example 1), MeOH (10 mL), and EtOAc (10 mL) was added 10% palladium on activated carbon (90 mg), and the mixture stirred under hydrogen (1 atmosphere) at rt for 4 h. The mixture was diluted with MeOH and EtOAc, then filtered through celite. The filtrate was concentrated under reduced pressure to afford compound 1 (656 mg, 100%) as a yellow solid. $^1$H NMR (400 MHz, DMSO-$d_6$): δ 10.66 (s, 1H), 8.86 (s, 1H), 8.15 (m, 1H), 8.01 (m, 1H), 7.83 (m, 1H), 7.30-7.40 (m, 3H), 7.00 (m, 1H), 5.76 (m, 1H), 1.42 (m, 6H); LCMS Mass: 324.0 (M+1).

Step 2: 3-((4-Cyano-6-(trifluoromethyl)pyridin-2-yl)oxy)-N-(6-(4-isopropyl-4H-1,2,4-triazol-3-yl)pyridin-2-yl)benzamide (Compound 1-23)

A mixture of compound 1 (100 mg, 0.309 mmol), K$_2$CO$_3$ (128 mg, 0.927 mmol), and DMF (2 mL) was stirred at rt for 2 h then heated at 50° C. for a further 18 h. The mixture was concentrated under reduced pressure and the residue was purified (silica; eluting with 100% EtOAc followed by 10% MeOH in DCM) to afford compound 1-23 (89 mg, 59%) as an off-white solid. $^1$H NMR (400 MHz, DMSO-$d_6$): δ 10.86 (s, 1H), 8.86 (s, 1H), 8.25 (m, 1H), 8.17 (m, 1H), 8.11 (s, 1H), 8.02 (m, 1H), 7.82-7.93 (m, 3H), 7.66 (m, 1H), 7.51 (m, 1H), 5.70 (m, 1H), 1.43 (m, 6H); LCMS Mass: 494.0 (M$^+$+1).

Example 3: 2-(3-((6-(4-Isopropyl-4H-1,2,4-triazol-3-yl)pyridin-2-yl)carbamoyl)phenoxy)-6-(trifluoromethyl)isonicotinic acid trifluoroacetate (Compound 1-24)

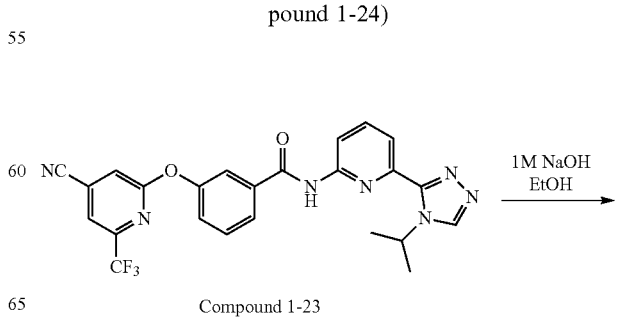

Compound 1-23

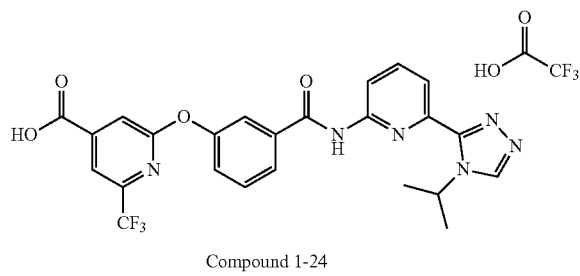

Compound 1-24

To a stirred solution of compound 1-23 (70 mg, 0.142 mmol) (from Example 2) in EtOH (0.7 mL) at rt, was added 1M aq. NaOH solution (0.5 mL). The mixture was stirred at rt for 4 h, then heated at 45° C. for 2 h. The mixture was concentrated under reduced pressure and the residue purified via reverse-phase preparative HPLC (Waters XTerra® Prep MS C-18 OBD 5 μm 50×100 mm column; eluting with 10-90% MeCN/H$_2$O containing 0.1% TFA, over 20 min) to afford compound 1-24 (15 mg, 17%) as a solid. $^1$H NMR (400 MHz, DMSO-d$_6$): δ 10.86 (s, 1H), 8.98 (s, 1H), 8.19 (m, 1H), 8.04 (m, 1H), 7.83-7.92 (m, 4H), 7.71 (s, 1H), 7.67 (m, 1H), 7.54 (m, 1H), 5.72 (m, 1H), 1.44 (m, 6H); LCMS Mass: 513.0 (M$^+$+1).

Example 4: N-(6-(4-Isopropyl-4H-1,2,4-triazol-3-yl) pyridin-2-yl)-3-(pyridin-3-ylmethoxy)benzamide hydrochloride (Compound 1-181)

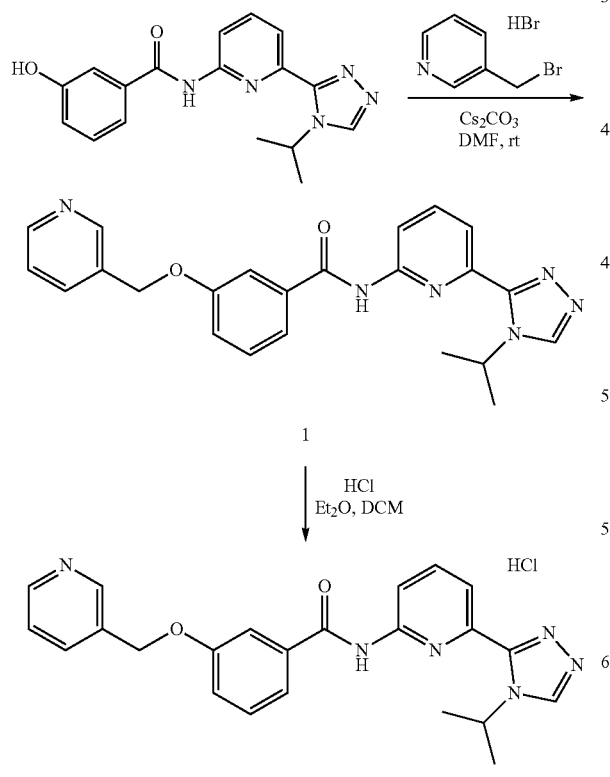

Step 1: N-(6-(4-Isopropyl-4H-1,2,4-triazol-3-yl) pyridin-2-yl)-3-(pyridin-3-ylmethoxy)benzamide (1)

A stirred mixture of 3-hydroxy-N-(6-(4-isopropyl-4H-1,2,4-triazol-3-yl)pyridin-2-yl)benzamide (32 mg, 0.098 mmol) (from Step 1 of Example 2), 2-(bromomethyl)pyridine hydrobromide (32 mg, 0.127 mmol), Cs$_2$CO$_3$ (64 mg, 0.196 mmol), and DMF (1.96 mL) was stirred at rt for 3 h then heated at 65° C. for a further 30 min. The mixture was cooled to rt and partitioned between DCM and water. The organic layer was separated, dried (MgSO$_4$), filtered, and concentrated under reduced pressure to afford compound 1 (36 mg, 89%) as a brown solid which did not require further purification. LCMS Mass: 415.0 (M$^+$+1).

Step 2: N-(6-(4-Isopropyl-4H-1,2,4-triazol-3-yl) pyridin-2-yl)-3-(pyridin-3-ylmethoxy)benzamide hydrochloride (Compound 1-181)

To a stirred solution of compound 1 (35 mg, 0.085 mmol), was added 2M HCl in ether (1.72 mL) and DCM (1.72 mL), and the mixture was stirred at rt for 15 min. The mixture was filtered and the obtained solid was purified via trituration with Et$_2$O to afford compound 1-181 (38 mg, 100%) as a beige solid. $^1$H NMR (400 MHz, DMSO-d$_6$): δ 10.90 (s, 1H), 9.46 (s, 1H), 8.76 (m, 1H), 8.20-8.24 (m, 2H), 8.08 (m, 1H), 7.90 (m, 1H), 7.85 (m, 1H), 7.60-7.70 (m, 3H), 7.52 (m, 1H), 7.34 (m, 1H), 5.81 (m, 1H), 5.46 (s, 2H), 1.46 (m, 6H); LCMS Mass: 415.0 (M$^+$+1).

Example 5: 2-Fluoro-N-(6-(4-isopropyl-4H-1,2,4-triazol-3-yl)pyridin-2-yl)-5-(pyridin-2-yloxy)benzamide hydrochloride (Compound 1-210)

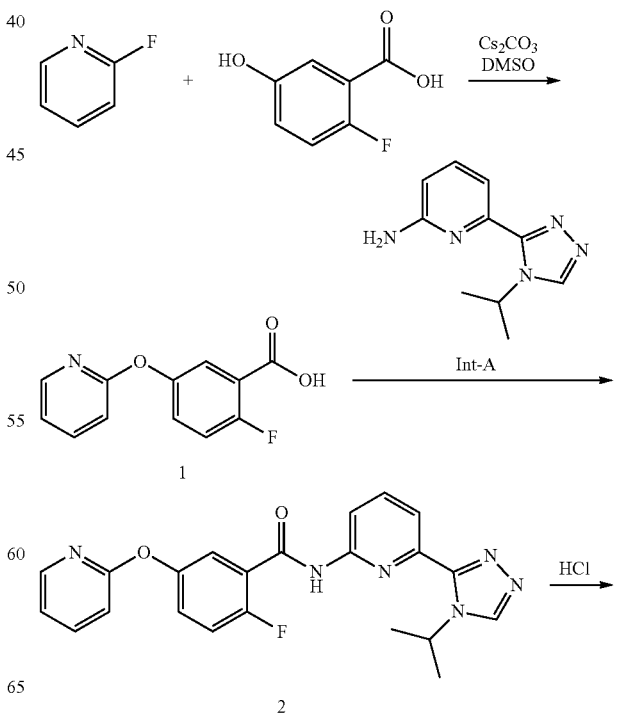

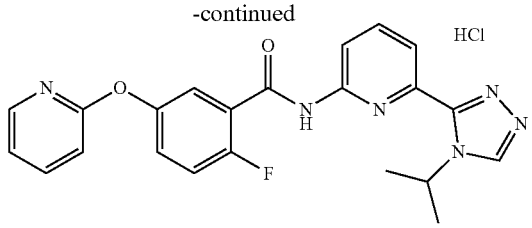

Compound 1-210

Step 1: 2-Fluoro-5-(pyridin-2-yloxy)benzoic acid (1)

A stirred mixture of 2-fluoropyridine (1 g, 6.41 mmol) and 2-fluoro-5-hydroxybenzoic acid (750 mg, 7.69 mmol), $Cs_2CO_3$ (4.1 g, 12.8 mmol), and DMSO (10 mL) was sealed under an inert atmosphere and heated at 95° C. for 24 h. The mixture was cooled to rt then diluted with water (10 mL) and extracted with EtOAc (2×50 mL). The aq. layer was acidified with aq. citric acid solution and extracted with EtOAc (2×50 mL). The combined organic layers were washed with brine (50 mL), dried ($Na_2SO_4$), filtered, then concentrated under reduced pressure. Purification via trituration with n-pentane afforded compound 1 (1.1 g, 78%) as an off-white solid.

$^1$H NMR (400 MHz, DMSO-$d_6$): δ 13.42 (br s, 1H), 8.13 (m, 1H), 7.86 (m, 1H), 7.52 (m, 1H), 7.30-7.45 (m, 2H), 7.15 (m, 1H), 7.08 (m, 1H).

Step 2: 2-Fluoro-N-(6-(4-isopropyl-4H-1,2,4-triazol-3-yl)pyridin-2-yl)-5-(pyridin-2-yloxy) benzamide (2)

To a stirred solution of 1 (600 mg, 25.7 mmol) in DCM (20 mL) at 0° C. under an inert atmosphere, were added $PPh_3$ (1.4 g, 51.5 mmol) and hexachloroacetone (0.56 mL, 3.09 mmol), and the mixture was stirred for 30 min. To this was added Int-A (522 mg, 25.7 mmol) and the mixture was stirred at 0° C. for 2 h. The reaction mixture was quenched with 2N aq. $Na_2CO_3$ (10 mL) and washed with DCM (2×10 mL). The aq. layer was acidified with aq. citric acid solution and extracted with EtOAc (2×20 mL). The combined organic layers were washed with brine (20 mL), dried ($Na_2SO_4$), filtered, and concentrated under reduced pressure. The residue was purified by (silica gel; eluting with 100% EtOAc) to afford compound 2 (210 mg, 21%) as a pale brown solid. $^1$H NMR (400 MHz, DMSO-$d_6$): δ 10.94 (s, 1H), 8.86 (s, 1H), 8.12-8.23 (m, 2H), 8.02 (m, 1H), 7.85-7.93 (m, 2H), 7.37-7.49 (m, 3H), 7.16 (m, 1H), 7.11 (m, 1H), 5.69 (m, 1H), 1.43 (m, 6H); LCMS Mass: 419.0 (M$^+$+1).

Step 3: 2-Fluoro-N-(6-(4-isopropyl-4H-1,2,4-triazol-3-yl)pyridin-2-yl)-5-(pyridin-2-yloxy) benzamide hydrochloride (Compound 1-210)

To a stirred solution of compound 2 (130 mg, 0.311 mmol) in 1,4-dioxane (2 mL) at 0° C., was added 4M HCl in 1,4-dioxane (2 mL, 8 mmol), and the mixture stirred at 0° C. for 3 h. The mixture was concentrated under reduced pressure and the residue was purified via trituration with $Et_2O$/n-pentane to afford compound 1-210 (70 g, 49%) as an off-white solid.

$^1$H NMR (400 MHz, DMSO-$d_6$): δ 11.01 (s, 1H), 9.13 (s, 1H), 8.22 (m, 1H), 8.15 (m, 1H), 8.05 (s, 1H), 7.86-7.94 (m, 2H), 7.38-7.53 (m, 3H), 7.17 (m, 1H), 7.12 (m, 1H), 5.73 (m, 1H), 1.45 (m, 6H); LCMS Mass: 419.6 (M$^+$+1).

Example 6: 2-Fluoro-N-(6-(4-isopropyl-4H-1,2,4-triazol-3-yl)pyridin-2-yl)-5-(pyridin-3-yloxy)benzamide hydrochloride (Compound 1-211)

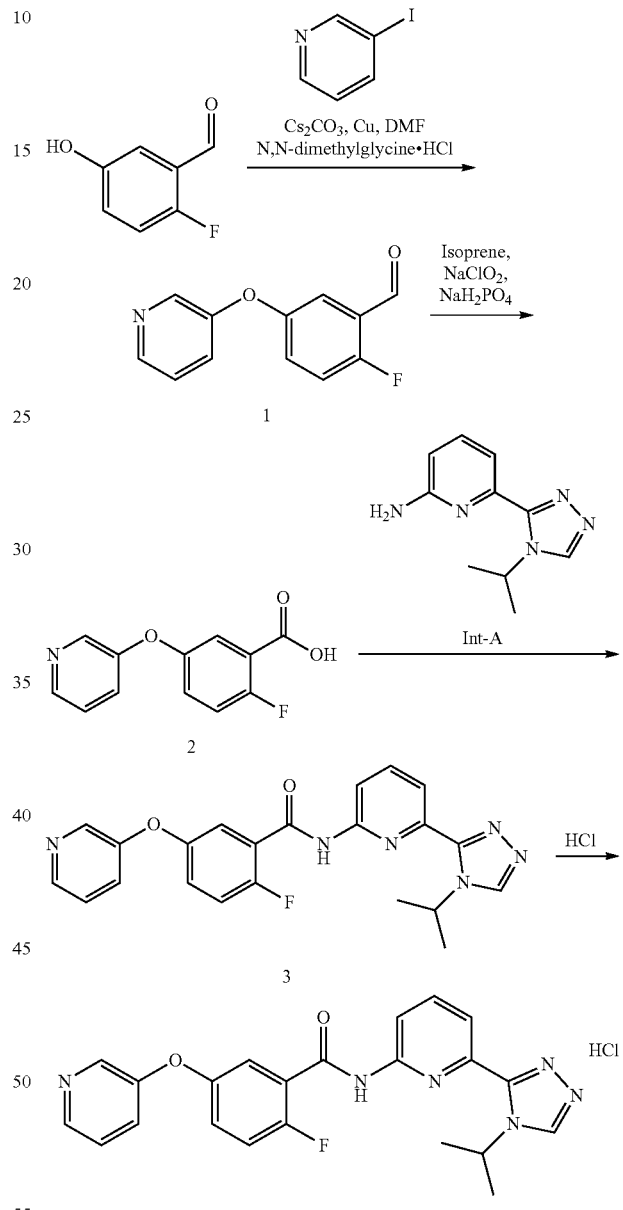

Compound 1-211

Step 1: 2-Fluoro-5-(pyridin-3-yloxy)benzaldehyde (1)

To a stirred solution of 2-fluoro-5-hydroxybenzaldehyde (3 g, 21.4 mmol) in 1,4-dioxane (30 mL) at rt, were added 3-iodopyridine (4.85 g, 23.5 mmol), $Cs_2CO_3$ (12.9 g, 42.8 mmol), CuI (910 mg, 4.28 mmol) and N,N-dimethylglycine hydrochloride (2.62 g, 18.7 mmol). The reaction mixture was sealed under an inert atmosphere and heated at 90° C.

for 16 h. The reaction mixture was cooled to rt and filtered through a pad of celite. The celite was further washed with EtOAc (2×100 mL). The combined filtrates were dried (Na₂SO₄), filtered, and concentrated under reduced pressure. The residue was purified (silica gel; eluting with 0-100% EtOAc in hexane) to afford compound 1 (660 mg, 14%) as an off-white solid. $^1$H NMR (400 MHz, CDCl₃) δ 10.33 (s, 1H), 8.39-8.45 (m, 2H), 7.46 (m, 1H), 7.28-7.34 (m, 3H), 7.23 (m, 1H).

Step 2: 2-Fluoro-5-(pyridin-3-yloxy)benzoic acid (2)

To a stirred solution of compound 1 (300 mg, 1.38 mmol) in THF (20 mL) at rt, were added isoprene (1 g, 1.38 mmol), NaH₂PO₄ (2.7 M aqueous buffer, 4 mL, 11.05 mmol) and sodium chlorite (500 mg, 5.52 mmol) and stirred for 2 h. The reaction mixture was diluted with water (10 mL) and extracted with CH₂Cl₂ (2×50 mL). The combined organic layers were dried (Na₂SO₄) and concentrated under reduced pressure to afford compound 2 (245 mg, 76%) as an off-white solid.

$^1$H NMR (500 MHz, DMSO-d₆) δ 8.41 (m, 2H), 7.40-7.50 (m, 3H), 7.34-7.37 (m, 2H); LCMS Mass: 233.8 (M$^+$+1).

Step 3: 2-Fluoro-N-(6-(4-isopropyl-4H-1,2,4-triazol-3-yl)pyridin-2-yl)-5-(pyridin-3-yloxy)benzamide (3)

To a stirred solution of 2 (250 mg, 1.07 mmol) in DCM (25 mL) at rt under an inert atmosphere, were added oxalyl chloride (0.6 mL, 1.61 mmol) and DMF (cat.) and the mixture stirred at rt for 2 h. The reaction mixture was concentrated under reduced pressure. The residue was dissolved in DCM (25 mL) and to this were added Int-A (200 mg, 1.18 mmol), TEA (1 mL, 2.14 mmol), and DMAP (6 mg, 0.053 mmol) and the mixture stirred at rt for 16 h. The mixture was washed with water (2×10 mL) and the organic layer was separated, dried (Na₂SO₄), filtered, and concentrated under reduced pressure. The residue was purified via preparative reverse-phase HPLC to afford compound 3 (70 mg, 16%) as a brown solid. LCMS Mass: 419.1 (M$^+$+1).

Step 4: 2-Fluoro-N-(6-(4-isopropyl-4H-1,2,4-triazol-3-yl)pyridin-2-yl)-5-(pyridin-3-yloxy)benzamide hydrochloride (Compound 1-211)

To a stirred solution of compound 3 (70 mg, 0.167 mmol) in DCM (7 mL) at 0° C., was added 4M HCl in 1,4-dioxane (0.5 mL) and the mixture was stirred for 1 h. The reaction mixture was concentrated under reduced pressure and the residue was purified via trituration with a mixture of Et₂O and n-pentane to afford compound 1-211 (56 mg, 74%) as a brown solid.

$^1$H NMR (400 MHz, DMSO-d₆) δ 11.02 (s, 1H), 9.27 (s, 1H), 8.58 (m, 1H), 8.51 (m, 1H), 8.22 (m, 1H), 8.07 (m, 1H), 7.92 (m, 1H), 7.77 (m, 1H), 7.68 (m, 1H), 7.48-7.54 (m, 2H), 7.42 (m, 1H), 5.73 (m, 1H), 1.46 (m, 6H); LCMS Mass: 419.3 (M$^+$+1).

Example 7: 5-((6-Cyclopropylpyridin-2-yl)oxy)-2-fluoro-N-(6-(4-isopropyl-4H-1,2,4-triazol-3-yl)pyridin-2-yl)benzamide trifluoroacetate (Compound 1-213)

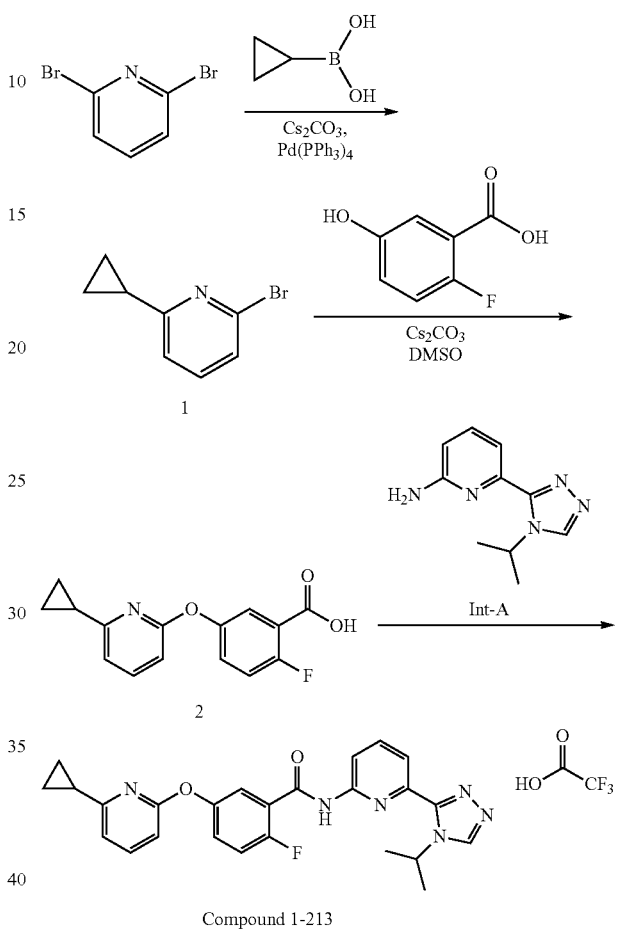

Step 1: 2-Bromo-6-cyclopropylpyridine (1)

A stirred mixture of 2,6-dibromopyridine (1.9 g, 8.08 mmol), cyclopropylboronic acid (1.37 g, 16.17 mmol), Cs₂CO₃ (7.8 g, 24.2 mmol), Pd(PPh₃)₄ (464 mg, 0.401 mmol), and 1,4-dioxane (32 mL) under an inert atmosphere, was heated at 100° C. for 1 h. The mixture was cooled to rt and filtered through a pad of celite, and the celite further washed with EtOAc (2×75 mL). The filtrate was concentrated under reduced pressure and the residue was purified (silica gel; eluting with 100% hexanes) to afford compound 1 (700 mg, 44%) as a pale brown solid. $^1$H NMR (400 MHz, CDCl₃): δ 7.36 (m, 1H), 7.20 (m, 1H), 7.04 (m, 1H), 1.98 (m, 1H), 0.96-1.05 (m, 4H); LCMS Mass: 199.7 (M$^+$+1).

Step 2: 5-((6-Cyclopropylpyridin-2-yl)oxy)-2-fluorobenzoic acid (2)

A stirred mixture A stirred mixture of 2,6-dibromopyridine (1.9 g, 8.08 mmol), cyclopropylboronic acid (1.37 g, 16.17 mmol), Cs₂CO₃ (7.8 g, 24.2 mmol), Pd(PPh₃)₄ (464 mg, 0.401 mmol), and 1,4-dioxane (32 mL) under an inert atmosphere, was heated at 100° C. for 1 h. The mixture was cooled to rt and filtered through a pad of celite, and the celite further washed with EtOAc (2×75 mL). The filtrate was concentrated under reduced pressure and the residue was purified (silica gel; eluting with 100% hexanes) to afford compound 1 (700 mg, 44%) as a pale brown solid. $^1$H NMR (400 MHz, CDCl$_3$): δ 7.36 (m, 1H), 7.20 (m, 1H), 7.04 (m, 1H), 1.98 (m, 1H), 0.96-1.05 (m, 4H); LCMS Mass: 199.7 (M$^+$+1) of compound 1 (700 mg, 3.55 mmol), 2-fluoro-5-hydroxybenzoic acid (610 mg, 3.91 mmol), Cs$_2$CO$_3$ (2.3 g, 7.05 mmol), and DMSO (10 mL) was sealed under an inert atmosphere and heated at 120° C. for 16 h. The mixture was cooled to rt then diluted with water (20 mL). The mixture was acidified with aq. citric acid solution and extracted with EtOAc (2×20 mL). The combined organic layers were washed with brine (20 mL), dried (Na$_2$SO$_4$), filtered, and concentrated under reduced pressure. The residue was purified (silica gel; eluting with 20% EtOAc in hexanes) to afford compound 2 (310 mg, 32%) as an off-white solid. $^1$H NMR (400 MHz, DMSO-d$_6$) δ 13.35 (s, 1H), 7.70 (m, 1H), 7.53 (m, 1H), 7.31-7.41 (m, 2H), 7.07 (m, 1H), 6.76 (m, 1H), 1.97 (m, 1H), 0.81-0.89 (m, 2H), 0.62-0.67 (m, 2H); LCMS Mass: 273.9 (M$^+$+1).

Step 3: 5-((6-Cyclopropylpyridin-2-yl)oxy)-2-fluoro-N-(6-(4-isopropyl-4H-1,2,4-triazol-3-yl)pyridin-2-yl)benzamide trifluoroacetate (Compound 1-213)

The title compound (1-213) (60 mg, 18%) was prepared from compound 2 using the procedure described for Example 5, Step 2. Purification via reverse-phase preparative HPLC (X-Select CSH C18 250×19 mm, 5 m column; eluting with 10-90% MeCN/H$_2$O containing 0.05% TFA, over 30 min) afforded the title compound as the trifluoroacetate salt. $^1$H NMR (400 MHz, DMSO-d$_6$): δ 10.89 (s, 1H), 8.90 (s, 1H), 8.20 (m, 1H), 8.03 (m, 1H), 7.90 (m, 1H), 7.71 (m, 1H), 7.33-7.48 (m, 3H), 7.07 (m, 1H), 6.78 (m, 1H), 5.68 (m, 1H), 2.01 (m, 1H), 1.44 (m, 6H), 0.82-0.89 (m, 2H), 0.67-0.73 (m, 2H); LCMS Mass: 459.2 (M$^+$+1).

Example 8: 2-Fluoro-N-(6-(4-isopropyl-4H-1,2,4-triazol-3-yl)pyridin-2-yl)-5-(pyrimidin-4-yloxy)benzamide hydrochloride (Compound 1-217)

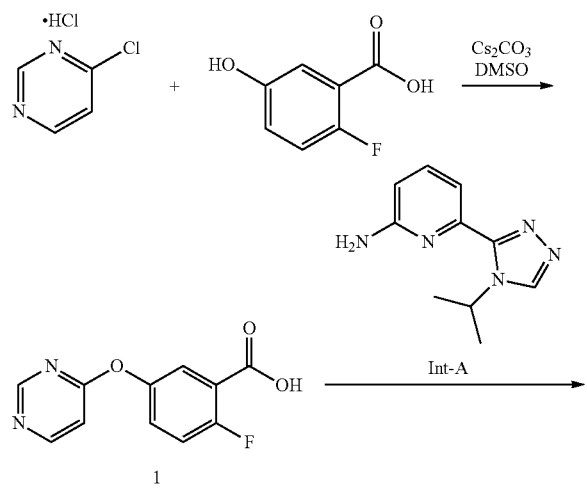

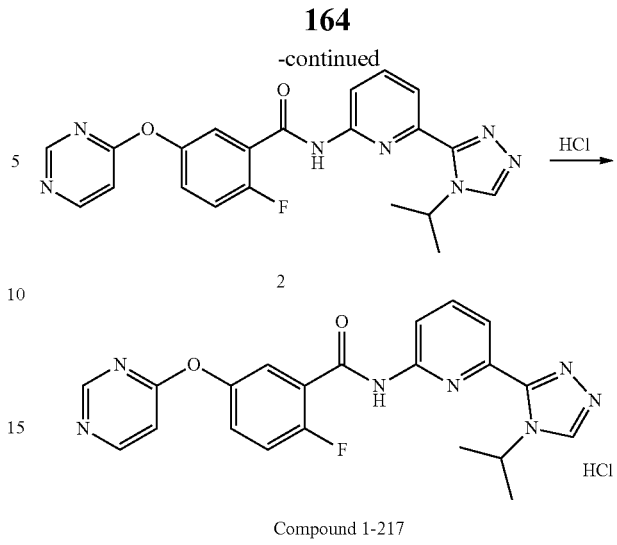

Compound 1-217

Step 1: 2-Fluoro-5-(pyrimidin-4-yloxy)benzoic acid (1)

A stirred mixture of 4-chloropyrimidine hydrochloride (500 mg, 3.31 mmol), 2-fluoro-5-hydroxybenzoic acid (620 mg, 3.97 mmol), Cs$_2$CO$_3$ (2.15 g, 7.69 mmol), and DMSO (10 mL) was sealed under an inert atmosphere and heated at 80° C. for 48 h. The reaction mixture was cooled to rt, acidified with aq. 1N HCl and extracted with EtOAc (2×100 mL). The combined organic layers were washed with brine (50 mL), dried (Na$_2$SO$_4$), filtered, and concentrated under reduced pressure to afford compound 1 (320 mg, 45%) as a pale brown solid.

$^1$H NMR (400 MHz, DMSO-d$_6$): δ 13.41 (br s, 1H), 8.77 (s, 1H), 8.70 (m, 1H), 7.66 (m, 1H), 7.53 (m, 1H), 7.41 (m, 1H), 7.20 (m, 1H); LCMS Mass: 235.2 (M$^+$+1).

Step 2: 2-Fluoro-N-(6-(4-isopropyl-4H-1,2,4-triazol-3-yl)pyridin-2-yl)-5-(pyrimidin-4-yloxy)benzamide (2)

The title compound (90 mg, 13%) was prepared from compound 1 using the procedure described for Example 5, Step 2. $^1$H NMR (400 MHz, CDCl$_3$): δ 9.10 (br m, 1H), 8.77 (s, 1H), 8.64 (m, 1H), 8.36-8.43 (m, 2H), 8.09 (m, 1H), 8.01 (m, 1H), 7.93 (m, 1H), 7.40 (m, 1H), 7.32 (m, 1H), 7.03 (m, 1H), 5.52 (m, 1H), 1.61 (m, 6H); LCMS Mass: 420.1 (M$^+$+1).

Step 3: 2-Fluoro-N-(6-(4-isopropyl-4H-1,2,4-triazol-3-yl)pyridin-2-yl)-5-(pyrimidin-4-yloxy) benzamide hydrochloride (Compound 1-217)

To a stirred solution of compound 2 (90 mg, 0.214 mmol) in DCM (5 mL) at 0° C., was added 4M HCl in 1,4-dioxane (2 mL), and the mixture stirred at rt for 1 h. The reaction mixture was concentrated under reduced pressure and the residue was purified via trituration with Et$_2$O/n-pentane to afford compound 1-217 (60 mg, 61%) as an off-white solid. $^1$H NMR (400 MHz, DMSO-d$_6$): δ 11.12 (s, 1H), 9.56 (s, 1H), 8.81 (s, 1H), 8.74 (m, 1H), 8.27 (m, 1H), 8.10 (m, 1H), 7.95 (m, 1H), 7.62 (m, 1H), 7.47-7.55 (m, 2H), 7.28 (m, 1H), 5.80 (m, 1H), 1.48 (m, 6H); LCMS Mass: 420.0 (M$^+$+1).

Example 9: 5-Benzamido-2-fluoro-N-(6-(4-isopropyl-4H-1,2,4-triazol-3-yl)pyridin-2-yl) benzamide hydrochloride (Compound 1-305)

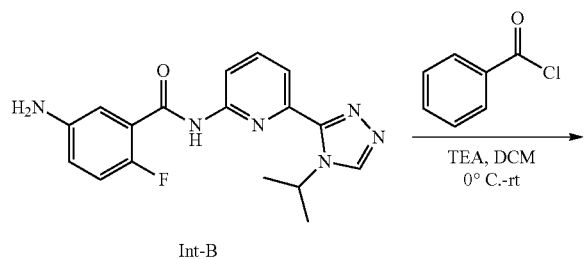

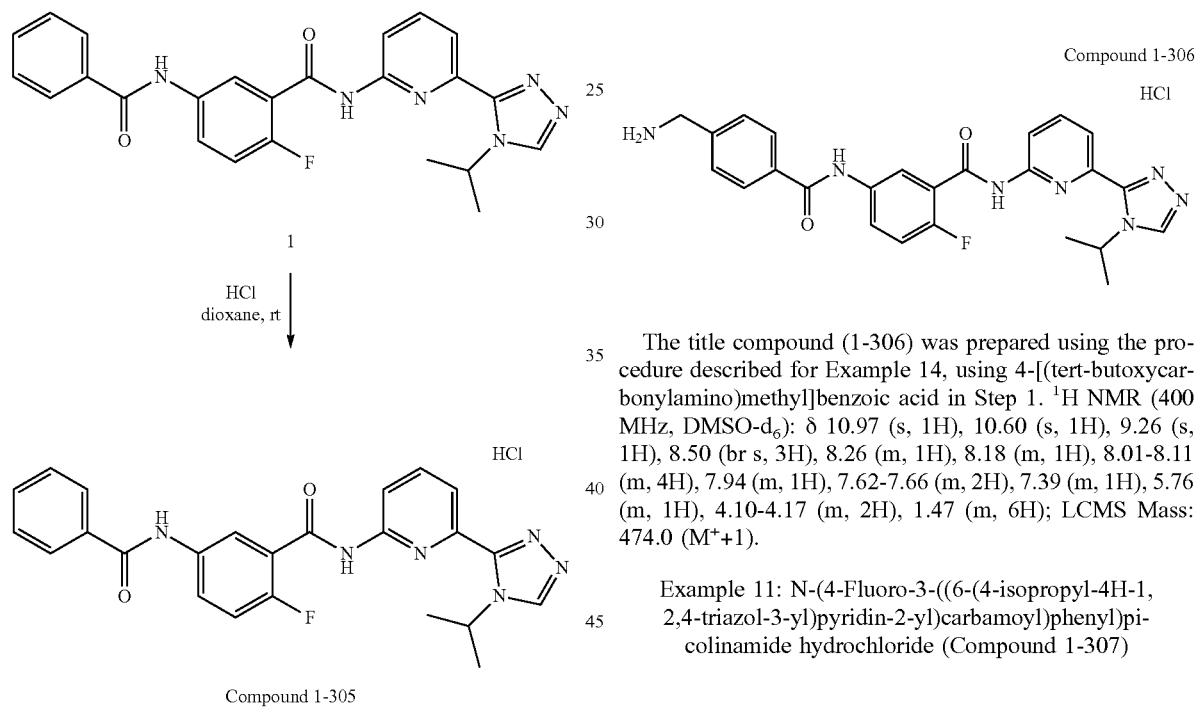

Step 1: 5-Benzamido-2-fluoro-N-(6-(4-isopropyl-4H-1,2,4-triazol-3-yl)pyridin-2-yl) benzamide (1)

To a stirred mixture of Int-B (80 mg, 0.235 mmol) in DCM (2 mL) at 0° C., was added benzoyl chloride (35 μL, 0.305 mmol) and TEA (98 μL, 0.705 mmol). The mixture was stirred at 0° C. for 15 min then allowed to warm to rt and stirred for a further 1 h. The mixture was concentrated under reduced pressure and the residue purified via trituration with a 1:1 mixture EtOAc and H$_2$O to afford compound 1 (48 mg, 46%) as a solid. $^1$H NMR (400 MHz, DMSO-d$_6$): δ 10.91 (s, 1H), 10.50 (s, 1H), 8.87 (s, 1H), 8.23 (m, 1H), 8.14 (m, 1H), 7.98-8.08 (m, 4H), 7.91 (m, 1H), 7.53-7.65 (m, 3H), 7.40 (m, 1H), 5.68 (m, 1H), 1.43 (m, 6H); LCMS Mass: 445.0 (M$^+$+1).

Step 2: 5-Benzamido-2-fluoro-N-(6-(4-isopropyl-4H-1,2,4-triazol-3-yl)pyridin-2-yl) benzamide hydrochloride (Compound 1-305)

A mixture of compound 1 (46 mg, 0.103 mmol) and 4M HCl in 1,4-dioxane (1 mL, 4.0 mmol) was stirred at rt for 2 h. The mixture was concentrated under reduced pressure. The residue was purified via trituration with Et$_2$O to afford compound 1-305 (30 mg, 60%) as a white solid. $^1$H NMR (400 MHz, DMSO-d$_6$): δ 10.98 (s, 1H), 10.53 (s, 1H), 9.33 (s, 1H), 8.27 (m, 1H), 8.18 (m, 1H), 8.09 (m, 1H), 7.99-8.05 (m, 3H), 7.91 (m, 1H), 7.61 (m, 1H), 7.53-7.58 (m, 2H), 7.41 (m, 1H), 5.77 (m, 1H), 1.47 (m, 6H); LCMS Mass: 445.0 (M$^+$+1).

Example 10: 5-(4-(Aminomethyl)benzamido)-2-fluoro-N-(6-(4-isopropyl-4H-1,2,4-triazol-3-yl)pyridin-2-yl)benzamide hydrochloride (Compound 1-306)

The title compound (1-306) was prepared using the procedure described for Example 14, using 4-[(tert-butoxycarbonylamino)methyl]benzoic acid in Step 1. $^1$H NMR (400 MHz, DMSO-d$_6$): δ 10.97 (s, 1H), 10.60 (s, 1H), 9.26 (s, 1H), 8.50 (br s, 3H), 8.26 (m, 1H), 8.18 (m, 1H), 8.01-8.11 (m, 4H), 7.94 (m, 1H), 7.62-7.66 (m, 2H), 7.39 (m, 1H), 5.76 (m, 1H), 4.10-4.17 (m, 2H), 1.47 (m, 6H); LCMS Mass: 474.0 (M$^+$+1).

Example 11: N-(4-Fluoro-3-((6-(4-isopropyl-4H-1,2,4-triazol-3-yl)pyridin-2-yl)carbamoyl)phenyl)picolinamide hydrochloride (Compound 1-307)

The title compound (1-307) was prepared using the procedure described for Example 9, using pyridine-2-carbonyl chloride hydrochloride in Step 1. $^1$H NMR (400 MHz, DMSO-d$_6$): δ 11.04 (s, 1H), 10.97 (s, 1H), 9.55 (m, 1H), 8.76 (m, 1H), 8.35 (m, 1H), 8.29 (m, 1H), 8.19 (m, 1H), 8.08-8.15 (m, 3H), 7.93 (m, 1H), 7.70 (m, 1H), 7.40 (m, 1H), 5.80 (m, 1H), 1.49 (m, 6H); LCMS Mass: 446.0 (M$^+$+1).

Example 12: N-(4-Fluoro-3-((6-(4-isopropyl-4H-1,2,4-triazol-3-yl)pyridin-2-yl) carbamoyl)phenyl) nicotinamide hydrochloride (Compound 1-308)

Compound 1-308

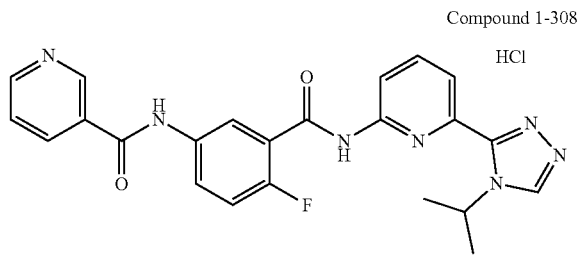 [SMILES: CC(C)n1cnnc1-c1cccc(NC(=O)c2cc(NC(=O)c3cccnc3)ccc2F)n1 ; Cl]

The title compound (1-308) was prepared using the procedure described for Example 9, using nicotinoyl chloride in Step 1. $^1$H NMR (400 MHz, DMSO-$d_6$): δ 11.00-11.03 (m, 2H), 9.44 (m, 1H), 9.30 (m, 1H), 8.90 (m, 1H), 8.63 (m, 1H), 8.26 (m, 1H), 8.19 (m, 1H), 8.09 (m, 1H), 8.05 (m, 1H), 7.93 (m, 1H), 7.83 (m, 1H), 7.43 (m, 1H), 5.78 (m, 1H), 1.47 (m, 6H); LCMS Mass: 446.0 (M$^+$+1).

Example 13: N-(4-Fluoro-3-((6-(4-isopropyl-4H-1,2,4-triazol-3-yl)pyridin-2-yl) carbamoyl)phenyl) isonicotinamide dihydrochloride (Compound 1-309)

Compound 1-309

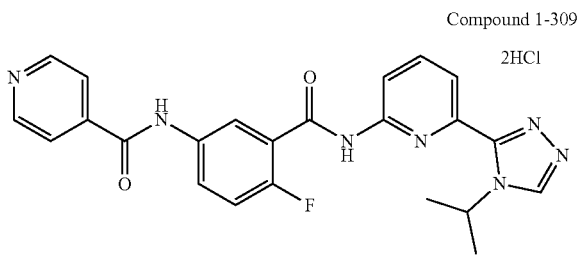 [SMILES: CC(C)n1cnnc1-c1cccc(NC(=O)c2cc(NC(=O)c3ccncc3)ccc2F)n1 ; "2HCl"]

The title compound (1-309) was prepared using the procedure described for Example 9, using isonicotinoyl chloride hydrochloride in Step 1. $^1$H NMR (400 MHz, DMSO-$d_6$): δ 11.01 (s, 1H), 10.99 (s, 1H), 9.34 (s, 1H), 8.90-8.96 (m, 2H), 8.87 (m, 1H), 8.28 (m, 1H), 8.13-8.21 (m, 3H), 8.02-8.12 (m, 2H), 7.98 (m, 1H), 7.94 (m, 1H), 7.44 (m, 1H), 5.76 (m, 1H), 1.47 (m, 6H); LCMS Mass: 446.0 (M$^+$+1).

Example 14: 5-Bromo-N-(4-fluoro-3-((6-(4-isopropyl-4H-1,2,4-triazol-3-yl)pyridin-2-yl) carbamoyl)phenyl)picolinamide hydrochloride (Compound 1-311)

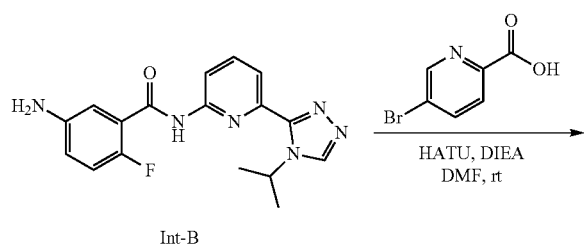

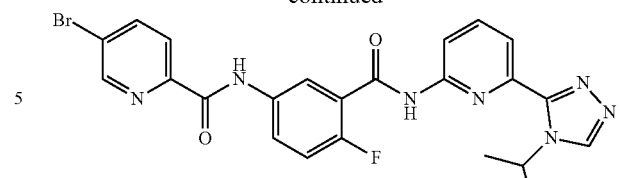

1

HCl
dioxane
DCM, rt

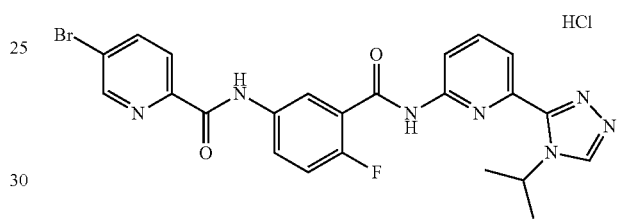

Compound 1-311

Step 1: 5-Bromo-N-(4-fluoro-3-((6-(4-isopropyl-4H-1,2,4-triazol-3-yl)pyridin-2-yl) carbamoyl)phenyl) picolinamide (1)

A mixture of 5-bromopyridine-2-carboxylic acid (33 mg, 0.163 mmol), HATU (61 mg, 0.160 mmol), and DMF (1 mL) was stirred at rt for 1 h. DIEA (76 μL, 0.441 mmol) and Int-B (50 mg, 0.147 mmol) were added and the mixture stirred at rt for 18 h. The mixture was concentrated under reduced pressure and the residue was purified via trituration with 5% H$_2$O in EtOAc, followed by 5% MeOH in EtOAc, to afford compound 1 (48 mg, 62%) as an off-white solid. LCMS Mass: 524.0 (M$^+$+1).

Step 2: 5-Bromo-N-(4-fluoro-3-((6-(4-isopropyl-4H-1,2,4-triazol-3-yl)pyridin-2-yl) carbamoyl)phenyl) picolinamide hydrochloride (Compound 1-311)

A mixture of compound 1 (48 mg, 0.091 mmol), 4M HCl in 1,4-dioxane (60 μL, 0.24 mmol), and DCM (1.5 mL) was stirred at rt for 3 h. The mixture was concentrated under reduced pressure. The residue was purified via trituration with Et$_2$O to afford compound 1-311 (51 mg, 100%) as an off-white solid. $^1$H NMR (400 MHz, DMSO-$d_6$): δ 11.02 (s, 1H), 10.99 (s, 1H), 9.54 (s, 1H), 8.88 (m, 1H), 8.34-8.38 (m, 2H), 8.29 (m, 1H), 8.08-8.15 (m, 3H), 7.94 (m, 1H), 7.40 (m, 1H), 5.80 (m, 1H), 1.47 (m, 6H); LCMS Mass: 524.0 (M$^+$+1).

Example 15: N-(4-Fluoro-3-((6-(4-isopropyl-4H-1,2,4-triazol-3-yl)pyridin-2-yl)carbamoyl)phenyl)pyrimidine-5-carboxamide hydrochloride (Compound 1-313)

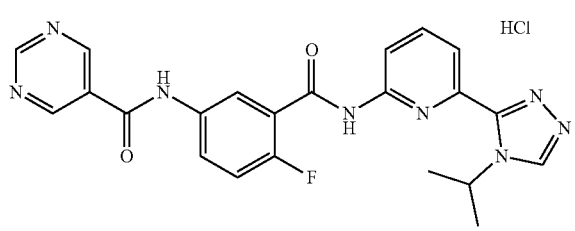

Compound 1-313

The title compound (1-313) was prepared using the procedure described for Example 9, using 5-pyrimidinecarbonyl chloride in Step 1. $^1$H NMR (400 MHz, DMSO-d$_6$): δ 10.92 (s, 1H), 10.82 (s, 1H), 9.38 (m, 1H), 9.30 (s, 2H), 8.88 (s, 1H), 8.22 (m, 1H), 8.12 (m, 1H), 7.97-8.08 (m, 2H), 7.91 (m, 1H), 7.43 (m, 1H), 5.68 (m, 1H), 1.42 (m, 6H); LCMS Mass: 447.0 (M$^+$+1).

Example 16: N-(4-Fluoro-3-((6-(4-isopropyl-4H-1,2,4-triazol-3-yl)pyridin-2-yl)carbamoyl)phenyl)pyrimidine-2-carboxamide trifluoroacetate (Compound 1-314)

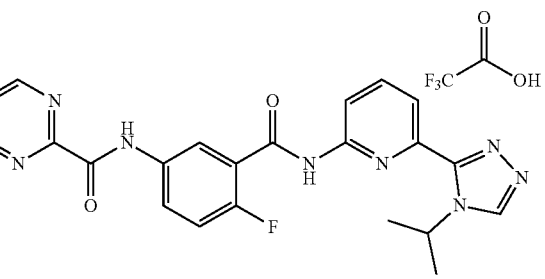

Compound 1-314

The title compound (1-314) was prepared using the procedure described for Example 14 Step 1, using 2-pyrimidinecarboxylic acid in Step 1. $^1$H NMR (400 MHz, DMSO-d$_6$): δ 11.07 (s, 1H), 10.92 (s, 1H), 9.06-9.08 (m, 2H), 9.01 (s, 1H), 8.29 (m, 1H), 8.24 (m, 1H), 8.03-8.10 (m, 2H), 7.91 (m, 1H), 7.76 (m, 1H), 7.39 (m, 1H), 5.69 (m, 1H), 1.42 (m, 6H); LCMS Mass: 447.0 (M$^+$+1).

Example 17: tert-Butyl ((2-((2-((6-(4-cyclopropyl-4H-1,2,4-triazol-3-yl)pyridin-2-yl)carbamoyl)pyridin-4-yl)oxy)-6-(trifluoromethyl)pyridin-4-yl)methyl)carbamate (Compound 1-329)

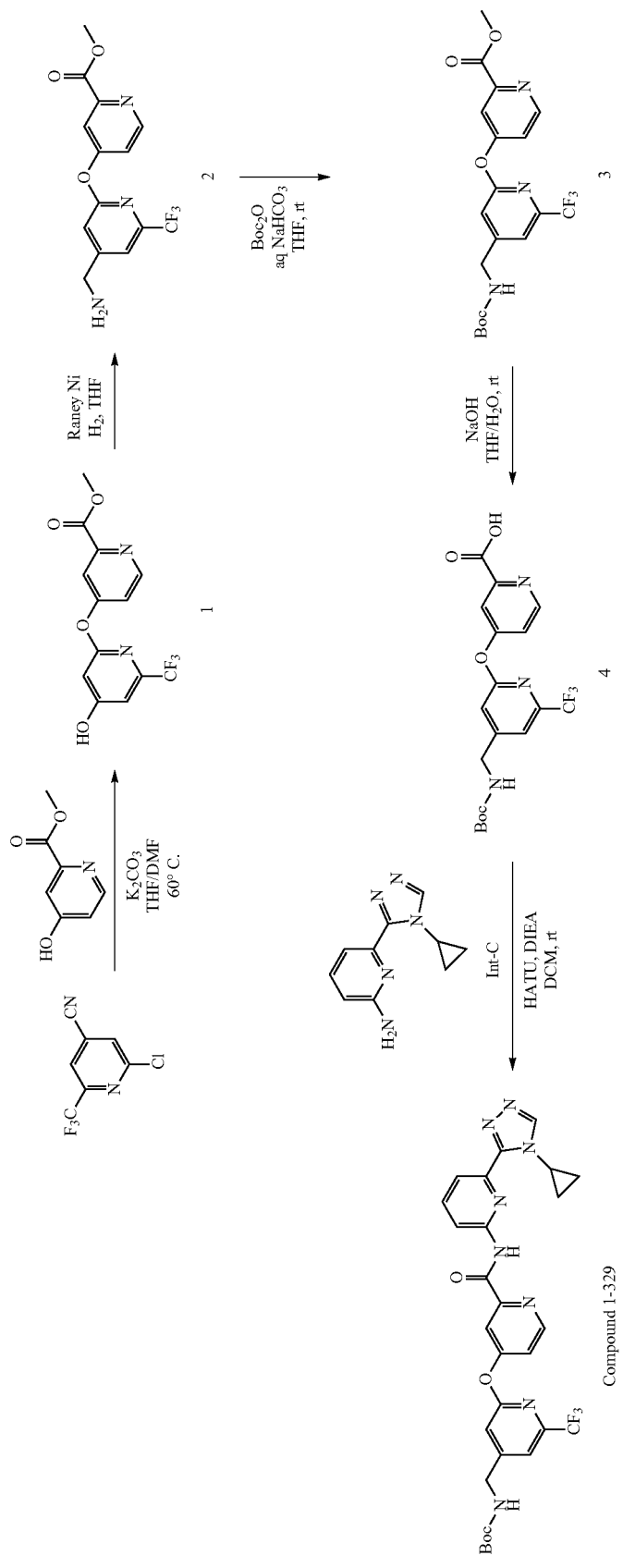

Step 1: Methyl 4-((4-cyano-6-(trifluoromethyl)pyridin-2-yl)oxy)picolinate (1)

The title compound 1 (667 mg, 53%) was prepared using the procedure described for Example 19 Step 1, using methyl 4-hydroxypicolinate in Step 1. LCMS Mass: 324.0 (M$^+$+1).

Step 2: Methyl 4-((4-(aminomethyl)-6-(trifluoromethyl)pyridin-2-yl)oxy)picolinate (2)

The title compound 2 was prepared from compound 1 using the procedure described for Example 19 Step 2. LCMS Mass: 328.0 (M$^+$+1).

Step 3: Methyl 4-((4-(((tert-butoxycarbonyl)amino)methyl)-6-(trifluoromethyl)pyridin-2-yl)oxy)picolinate (3)

The title compound 3 (240 mg) was prepared from compound 2 using the procedure described for Example 19 Step 3. LCMS Mass: 428.0 (M$^+$+1).

Step 4: 4-((4-(((tert-Butoxycarbonyl)amino)methyl)-6-(trifluoromethyl)pyridin-2-yl)oxy)picolinic acid (4)

The title compound 4 was prepared from compound 3 (232 mg, 100%) using the procedure described for Example 19 Step 4. LCMS Mass: 414.0 (M$^+$+1).

Step 5: tert-Butyl ((2-((2-((6-(4-cyclopropyl-4H-1,2,4-triazol-3-yl)pyridin-2-yl)carbamoyl)pyridin-4-yl)oxy)-6-(trifluoromethyl)pyridin-4-yl)methyl)carbamate (Compound 1-329)

The title compound 1-329 (15 mg, 21%) was prepared from compound 4 and Int-C using the procedure described for Example 19 Step 5. $^1$H NMR (400 MHz, DMSO-d$_6$): δ 10.64 (s, 1H), 8.79 (m, 1H), 8.69 (m, 1H), 8.34 (m, 1H), 8.08 (m, 1H), 7.99 (s, 1H), 7.88 (m, 1H), 7.60-7.70 (m, 3H), 7.37 (m, 1H), 4.30-4.35 (m, 2H), 4.10 (m, 1H), 1.40 (s, 9H), 1.00-1.10 (m, 2H), 0.95-1.00 (m, 2H); LCMS Mass: 597.0 (M$^+$+1).

Example 18: 4-((4-(Aminomethyl)-6-(trifluoromethyl)pyridin-2-yl)oxy)-N-(6-(4-cyclopropyl-4H-1,2,4-triazol-3-yl)pyridin-2-yl)picolinamide hydrochloride (Compound 1-330)

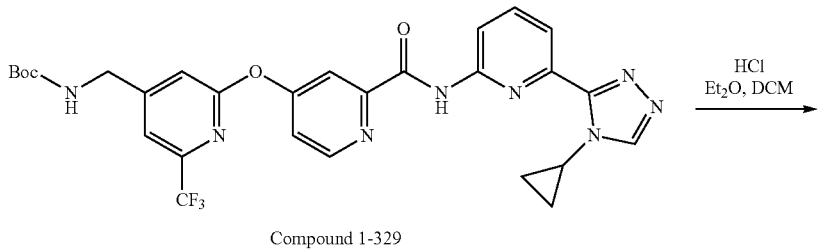

Compound 1-329

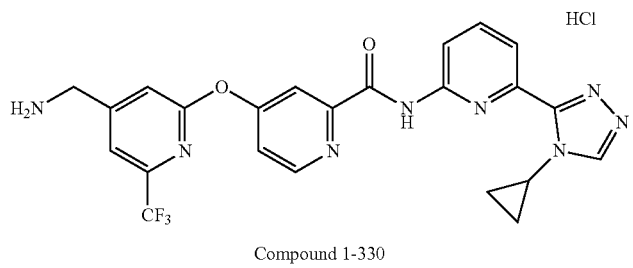

Compound 1-330

The title compound 1-330 was prepared from compound 1-329 (Example 17) using the procedure described for Example 19 Step 6. $^1$H NMR (400 MHz, DMSO-d$_6$): δ 10.68 (s, 1H), 8.90 (s, 1H), 8.81 (m, 1H), 8.71 (br s, 3H), 8.35 (m, 1H), 8.09 (m, 1H), 8.02 (m, 1H), 7.98 (m, 1H), 7.90 (m, 1H), 7.73 (m, 1H), 7.62 (m, 1H), 4.24-4.30 (m, 2H), 4.11 (m, 1H), 0.98-1.08 (m, 4H); LCMS Mass: 497.0 (M$^+$+1).

Example 19: 3-((4-(Aminomethyl)-6-(trifluoromethyl)pyridin-2-yl)oxy)-N-(6-(4-isopropyl-4H-1,2,4-triazol-3-yl)pyridin-2-yl)benzamide hydrochloride (Compound 1-331)

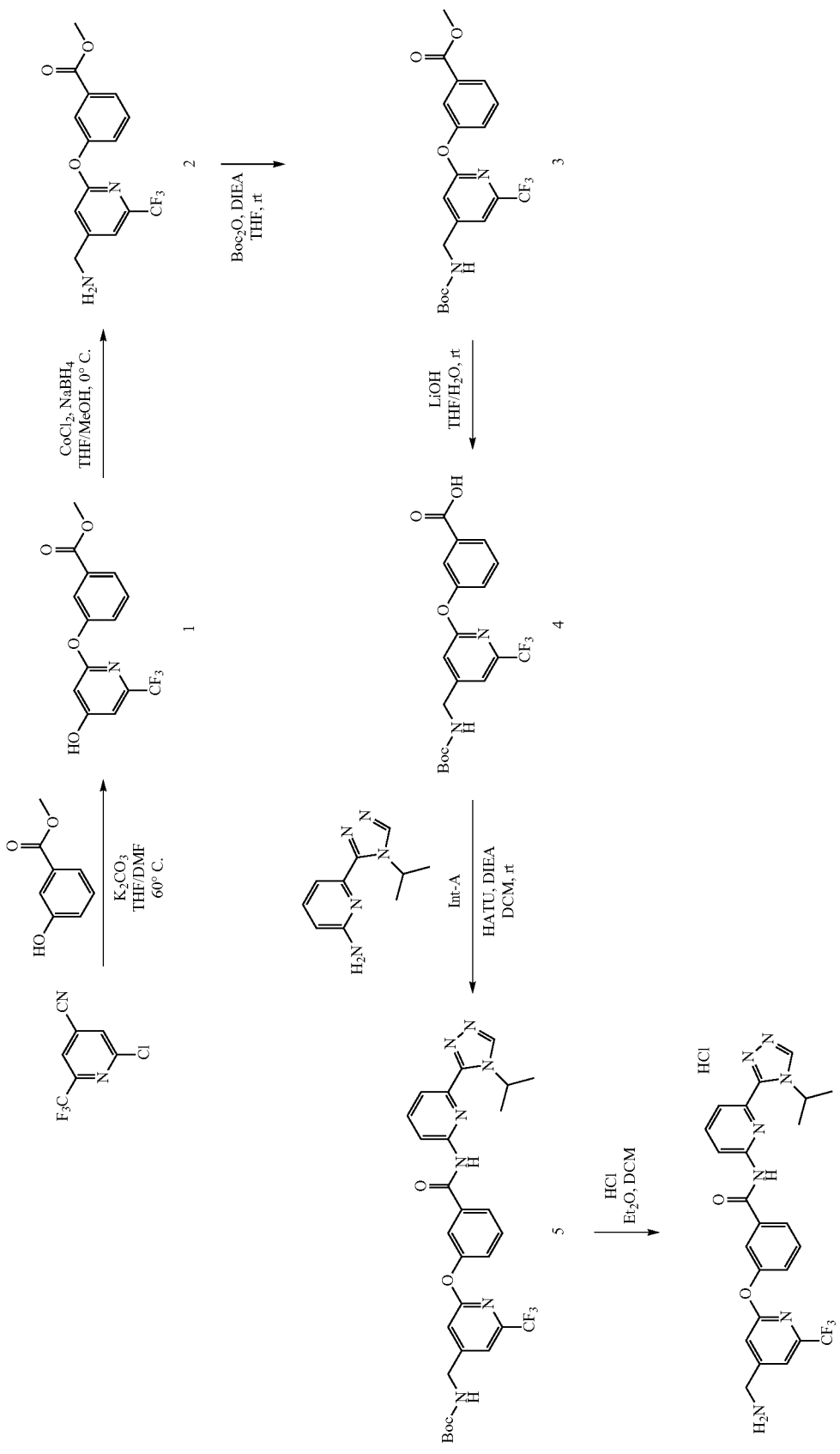

Step 1: Methyl 3-((4-cyano-6-(trifluoromethyl)pyridin-2-yl)oxy)benzoate (1)

To a solution of 2-chloro-6-(trifluoromethyl)isonicotinonitrile (4.0 g, 19.4 mmol) and methyl 3-hydroxybenzoate (3.24 g, 21.3 mmol) in a mixture of THF/DMF (4:1, 55 ml), was added potassium carbonate (8.0 g, 58 mmol). The reaction mixture was heated at 60° C. for 2 h. The THF was evaporated under reduced pressure and the remaining reaction mixture was partitioned between water (200 mL) and ethyl acetate (100 mL). The organic layer was separated and the aqueous layer was re-extracted with EtOAc (1×100 ml). The combined organic layers were dried ($Na_2SO_4$), filtered, and then concentrated under reduced pressure. The crude residue was purified (silica gel; eluting with 0-50% EtOAc in hexanes), to afford compound 1 as a light yellow solid (5.63 g, 91%). $^1$H NMR (300 MHz, DMSO-$d_6$): δ 8.21 (m, 1H), 8.07 (m, 1H), 7.87 (m, 1H), 7.77 (m, 1H), 7.64 (m, 1H), 7.55 (m, 1H), 3.85 (s, 3H); LCMS Mass: 323.0 ($M^+$+1).

Step 2: Methyl 3-((4-(aminomethyl)-6-(trifluoromethyl)pyridin-2-yl)oxy)benzoate (2)

To a stirred solution of compound 1 (1.5 g, 4.65 mmol) in THF/MeOH (1:1, 140 mL) at 0° C., was added portion-wise $CoCl_2$ (1.8 g, 13.98 mmol) followed by $NaBH_4$ (1.77 g, 46.5 mmol). The reaction mixture was stirred at 0° C. for 20 minutes. The mixture was diluted with EtOAc (100 mL) and filtered through celite. The filtrate was concentrated and the resulting residue was partitioned between water (200 mL) and EtOAc (200 mL). The water-organic layer was filtered through celite and the organic layer was separated, dried ($Na_2SO_4$), filtered, and then concentrated under reduced pressure to obtain compound 2 as an amber oil (1.38 g, 92%) which did not require further purification. $^1$H NMR (300 MHz, DMSO-$d_6$): δ 7.83 (m, 1H), 7.67 (m, 1H), 7.65 (br m, 1H), 7.60 (m, 1H), 7.47 (m, 1H), 7.33 (br m, 1H), 3.80-3.83 (m, 5H); LCMS Mass: 327.0 ($M^+$+1).

Step 3: Methyl 3-((4-(((tert-butoxycarbonyl)amino)methyl)-6-(trifluoromethyl)pyridin-2-yl)oxy)benzoate (3)

To a stirred solution of compound 2 (1.38 g, 4.24 mmol) in THF (25 mL) at 0° C., was added di-tert-butyl dicarbonate (1.29 g, 5.94 mmol) and DIEA (2.21 mL, 12.74 mmol). The mixture was warmed to RT and stirred for a further 4 h. The mixture was concentrated and the residue partitioned between EtOAc (50 mL) and water (50 mL). The organic layer was separated, dried ($Na_2SO_4$), filtered, and concentrated in vacuo. The residue was purified (silica gel; 0-60% EtOAc in hexanes), to afford compound 3 as an amber oil (1.42 g, 78%). $^1$H NMR (300 MHz, DMSO-$d_6$): δ 7.85 (m, 1H), 7.69 (m, 1H), 7.58-7.62 (m, 2H), 7.48-7.51 (m, 2H), 7.13 (br m, 1H), 4.20 (m, 2H), 3.84 (s, 3H), 1.36 (s, 9H); LCMS Mass: 427.0 ($M^+$+1).

Step 4: 3-((4-(((tert-Butoxycarbonyl)amino)methyl)-6-(trifluoromethyl)pyridin-2-yl)oxy)benzoic acid (4)

To a stirred solution of compound 3 (1.42 g, 3.34 mmol) in a mixture of THF/$H_2O$ (6:1, 21 mL) was added aqueous 4M LiOH (17 mL, 68 mmol). The mixture was stirred at rt for 16 h, then diluted with water (30 ml) and acidified to pH 3-4 using aq. sat. citric acid. The mixture was extracted with EtOAc (2×50 mL), and the combined organic layers were dried ($Na_2SO_4$), filtered, and concentrated under reduced pressure to afford compound 4 as an off white solid (1.2 g, 87%). $^1$H NMR (300 MHz, DMSO-$d_6$): δ 13.17 (br s, 1H), 7.83 (m, 1H), 7.66 (br m, 1H), 7.53-7.62 (m, 2H), 7.44-7.51 (m, 2H), 7.12 (br m, 1H), 4.25 (m, 2H), 1.36 (s, 9H); LCMS Mass: 413.0 ($M^+$+1).

Step 5: tert-Butyl ((2-(3-((6-(4-isopropyl-4H-1,2,4-triazol-3-yl)pyridin-2-yl)carbamoyl)phenoxy)-6-(trifluoromethyl)pyridin-4-yl)methyl)carbamate (5)

A mixture of compound 4 (250 mg, 0.606 mmol), HATU (346 mg, 0.909 mmol), and DMF (2.5 mL) was stirred at rt for 20 min. DIEA (156 mg, 1.21 mmol) and Int-A (123 mg, 0.606 mmol) were added and the mixture stirred at rt for 72 h. Water (40 mL) was added and the mixture extracted with EtOAc (3×20 mL). The combined organic layers were dried ($MgSO_4$), filtered, and concentrated under reduced pressure. The residue was purified (silica gel; eluting with 0-100% EtOAc in hexanes, followed by 0-10% MeOH in DCM) to afford compound 5 (138 mg, 38%) as a yellow oil. LCMS Mass: 598.0 ($M^+$+1).

Step 6: 3-((4-(Aminomethyl)-6-(trifluoromethyl)pyridin-2-yl)oxy)-N-(6-(4-isopropyl-4H-1,2,4-triazol-3-yl)pyridin-2-yl)benzamide hydrochloride (Compound 1-331)

A mixture of compound 5 (138 mg, 0.231 mmol), 2M HCl in $Et_2O$ (2 mL), and DCM (2 mL) was stirred at rt for 18 h. The mixture was concentrated under reduced pressure. The residue was purified via trituration with $Et_2O$ to afford compound 1-331 (110 mg, 89%) as an off-white solid. $^1$H NMR (400 MHz, DMSO-$d_6$): δ 10.90 (s, 1H), 9.08 (s, 1H), 8.65 (br s, 3H), 8.20 (m, 1H), 8.05 (m, 1H), 7.86-7.92 (m, 3H), 7.80 (m, 1H), 7.67 (m, 1H), 7.59 (m, 1H), 7.48 (m, 1H), 5.70 (m, 1H), 4.21-4.27 (m, 2H), 1.45 (m, 6H); LCMS Mass: 498.0 ($M^+$+1).

Example 20: 4-(Aminomethyl)-N-(4-fluoro-3-((6-(4-isopropyl-4H-1,2,4-triazol-3-yl)pyridin-2-yl)carbamoyl)phenyl)picolinamide hydrochloride (Compound 1-332)

Compound 1-332

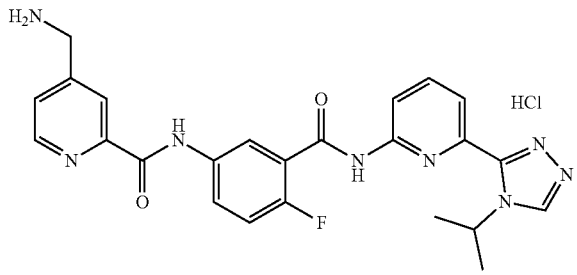

The title compound (1-332) was prepared using the procedure described for Example 14, using 4-[(tert-butoxycarbonylamino)methyl]pyridine-2-carboxylic acid in Step 1. $^1$H NMR (400 MHz, DMSO-$d_6$): δ 11.00 (s, 2H), 9.38 (s, 1H), 8.81 (m, 1H), 8.69 (br s, 3H), 8.25-8.37 (m, 3H), 8.08-8.13 (m, 2H), 7.95 (m, 1H), 7.81 (m, 1H), 7.42 (m, 1H), 5.78 (m, 1H), 4.20-4.25 (m, 2H), 1.45 (m, 6H); LCMS Mass: 475.0 ($M^+$+1).

Example 21: 2-Fluoro-N-(6-(4-isopropyl-4H-1,2,4-triazol-3-yl)pyridin-2-yl)-5-(2-phenylacetamido)benzamide trifluoroacetate (Compound 1-333)

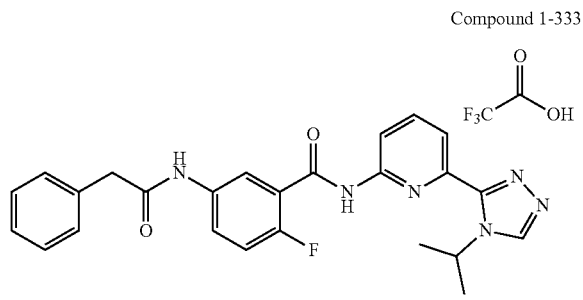

Compound 1-333

The title compound (1-333) was prepared using the procedure described for Example 9, using phenylacetyl chloride in Step 1. $^1$H NMR (400 MHz, DMSO-d$_6$): δ 10.87 (s, 1H), 10.40 (s, 1H), 8.99 (s, 1H), 8.20 (m, 1H), 8.04 (m, 1H), 7.96 (m, 1H), 7.91 (m, 1H), 7.78 (m, 1H), 7.33-7.39 (m, 5H), 7.26 (m, 1H), 5.69 (m, 1H), 3.65 (s, 2H), 1.43 (m, 6H); LCMS Mass: 459.0 (M$^+$+1).

Example 22: 4-((4-(Aminomethyl)-6-(trifluoromethyl)pyridin-2-yl)oxy)-N-(3-(4-cyclopropyl-4H-1,2,4-triazol-3-yl)phenyl)picolinamide hydrochloride (Compound 2-1)

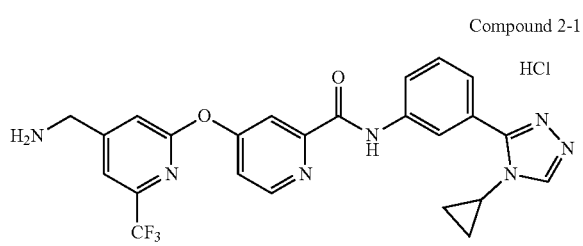 [SMILES: NCc1cc(Oc2ccnc(C(=O)Nc3cccc(-c4nncn4C4CC4)c3)c2)nc(C(F)(F)F)c1 ; Cl]

Compound 2-1

The title compound (2-1) was prepared using the procedure described for Example 19, using methyl 4-hydroxypicolinate in Step 1, and Int-D in Step 5. $^1$H NMR (400 MHz, DMSO-d$_6$): δ 11.04 (s, 1H), 9.18 (s, 1H), 8.80 (m, 1H), 8.74 (br s, 3H), 8.59 (m, 1H), 8.10 (m, 1H), 8.02 (m, 1H), 7.92 (m, 1H), 7.68-7.75 (m, 2H), 7.55-7.62 (m, 2H), 4.22-4.30 (m, 2H), 3.73 (m, 1H), 1.00-1.12 (m, 4H); LCMS Mass: 496.0 (M$^+$+1).

Example 23: 2-Fluoro-N-(3-(4-isopropyl-4H-1,2,4-triazol-3-yl)phenyl)-5-((6-(trifluoromethyl)pyridin-2-yl)oxy)benzamide hydrochloride (Compound 1-223)

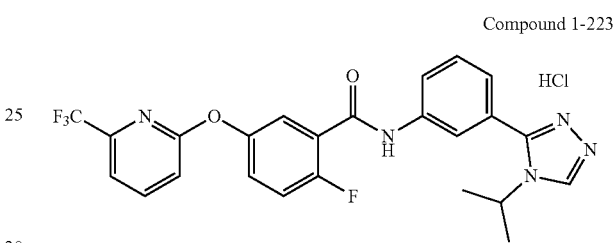

Compound 1-223

The title compound (1-223) was prepared using the procedure described for Example 5, using 6-chloro-2-(trifluoromethyl)pyridine in Step 1. $^1$H NMR (400 MHz, DMSO-d$_6$): δ 11.00 (s, 1H), 9.06 (s, 1H), 8.13-8.25 (m, 2H), 8.05 (m, 1H), 7.92 (m, 1H), 7.67 (m, 1H), 7.60 (m, 1H), 7.47-7.52 (m, 2H), 7.42 (m, 1H), 7.15 (m, 1H), 5.72 (m, 1H), 1.45 (m, 6H); LCMS Mass: 487.1 (M$^+$+1).

Example 24: 2-Fluoro-N-(6-(4-isopropyl-4H-1,2,4-triazol-3-yl)pyridin-2-yl)-5-((6-(pyrrolidin-1-yl)pyridin-2-yl)oxy)benzamide hydrochloride (Compound 1-225)

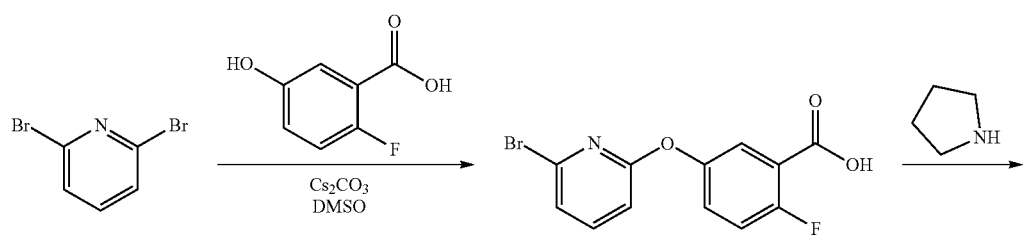

-continued

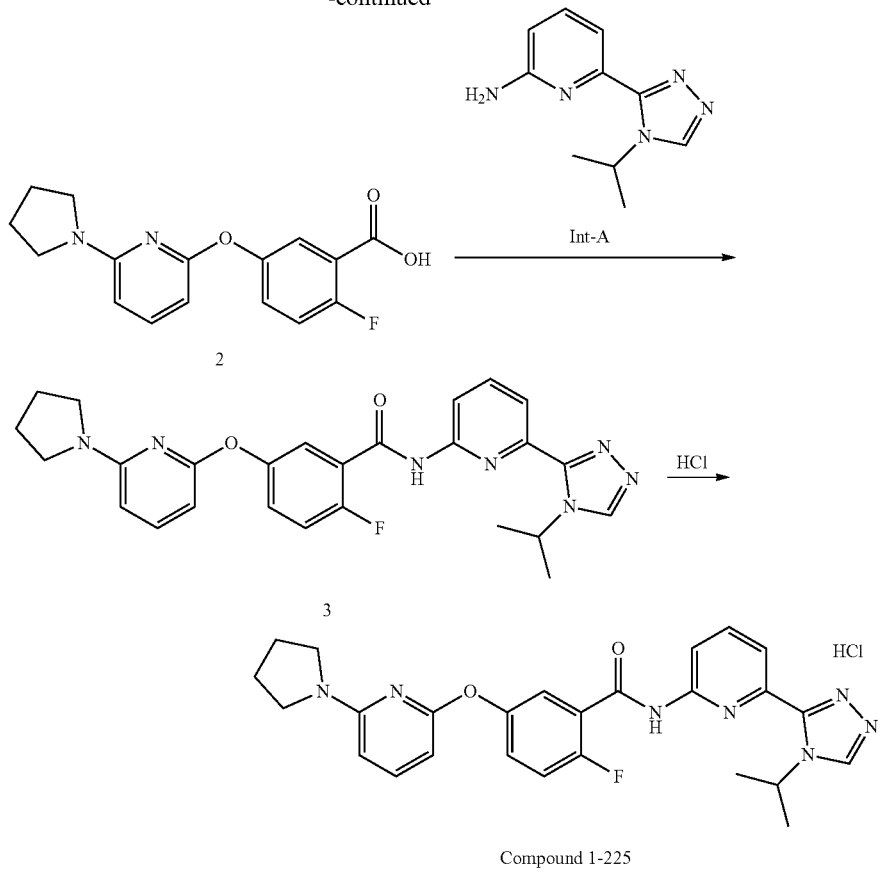

Compound 1-225

Step 1: 5-((6-Bromopyridin-2-yl)oxy)-2-fluorobenzoic acid (1)

A stirred mixture of 2,6-dibromopyridine (1 g, 4.23 mmol), 2-fluoro-5-hydroxybenzoic acid (600 mg, 4.23 mmol), $Cs_2CO_3$ (2.75 g, 8.47 mmol), and DMSO (15 mL) were heated in a sealed tube at 120° C. for 16 h. The reaction mixture was cooled to rt and poured into water (50 mL) then extracted with EtOAc (2×100 mL). The combined organic layers were washed with aqueous citric acid, dried ($Na_2SO_4$) and concentrated under reduced pressure. The residue was purified (silica gel; eluting with 10% MeOH in DCM) to afford compound 1 (850 mg, 65%) as an off-white solid. $^1$H NMR (400 MHz, DMSO-$d_6$): δ 7.82 (m, 1H), 7.59 (m, 1H), 7.49 (m, 1H), 7.39-7.44 (m, 2H), 7.11 (m, 1H); LCMS Mass: 313.1 ($M^+$+1).

Step 2: 2-Fluoro-5-(((6-(pyrrolidin-1-yl)pyridin-2-yl)oxy)benzoic acid (2)

A mixture of 1 (300 mg, 0.96 mmol) and pyrrolidine (4 mL) was stirred at rt under for 16 h. The mixture was poured into water (30 mL) and extracted with EtOAc (2×50 mL). The combined organic layers were washed with aqueous citric acid, dried ($Na_2SO_4$) and concentrated under reduced pressure to afford compound 5 (230 mg, 78%) as an off-white solid. $^1$H NMR (400 MHz, CDCl$_3$): δ 7.85 (m, 1H), 7.35-7.47 (m, 2H), 7.14 (m, 1H), 6.03 (m, 2H), 3.28-3.37 (m, 4H), 1.91-1.98 (m, 4H); LCMS Mass: 303.1 ($M^+$+1).

Step 3: 2-Fluoro-N-(6-(4-isopropyl-4H-1,2,4-triazol-3-yl)pyridin-2-yl)-5-((6-(pyrrolidin-1-yl)pyridin-2-yl)oxy)benzamide (3)

To a stirred solution of 2 (150 mg, 0.496 mmol) in DCM (15 mL) at rt and under an inert atmosphere, were added PPh$_3$ (162 mg, 0.621 mmol) and hexachloroacetone (0.14 mL, 0.745 mmol). The mixture was stirred at rt for 40 min. Int-A (100 mg, 0.496 mmol) was added and stirring continued at rt for 16 h. The residue was purified (silica gel; eluting with 2% MeOH in DCM) to afford compound 3 (60 mg, 25%) as an off-white solid. $^1$H NMR (400 MHz, DMSO-$d_6$): δ 10.87 (s, 1H), 8.85 (s, 1H), 8.19 (m, 1H), 8.02 (m, 1H), 7.90 (m, 1H), 7.53 (m, 1H), 7.48 (m, 1H), 7.36-7.41 (m, 2H), 6.09-6.19 (m, 2H), 5.68 (m, 1H), 3.20-3.29 (m, 4H), 1.83-1.92 (m, 4H), 1.43 (m, 6H); LCMS Mass: 488.1 ($M^+$+1).

Step 4: 2-Fluoro-N-(6-(4-isopropyl-4H-1,2,4-triazol-3-yl)pyridin-2-yl)-5-((6-(pyrrolidin-1-yl)pyridin-2-yl)oxy)benzamide hydrochloride (Compound 1-225)

To a stirred solution of 3 (50 mg, 0.102 mmol) in DCM (5 mL), at 0° C., was added 4M HCl in 1,4-dioxane (0.5 mL), and the mixture stirred for 1 h. The reaction mixture was concentrated under reduced pressure, and the residue was purified via trituration with a mixture of Et$_2$O and n-pentane to afford compound 1-225 (46 mg, 86%) as an off-white solid. $^1$H NMR (400 MHz, DMSO-$d_6$): δ 10.95 (s, 1H), 9.30 (s, 1H), 8.23 (m, 1H), 8.07 (m, 1H), 7.92 (m, 1H), 7.53 (m, 1H), 7.48 (m, 1H), 7.36-7.41 (m, 2H), 6.04-6.21

(m, 2H), 5.75 (m, 1H), 4.54 (br s, 1H), 3.18-3.27 (m, 4H), 1.82-1.91 (m, 4H), 1.47 (m, 6H); LCMS Mass: 488.1 (M⁺+1).

Example 25: 5-((5-Cyclopropylpyridin-2-yl)oxy)-2-fluoro-N-(6-(4-isopropyl-4H-1,2,4-triazol-3-yl)pyridin-2-yl)benzamide hydrochloride (Compound 1-227)

mL). The combined organic layers were washed with brine (20 mL), dried (Na₂SO₄) and concentrated under reduced pressure. The residue was purified (silica gel; eluting with 20% EtOAc in hexane) to afford compound 1 (1.5 g, 56%) as an off-white solid. ¹H NMR (500 MHz, DMSO-d₆): δ 13.42 (br s, 1H), 8.28 (m, 1H), 8.08 (m, 1H), 7.56 (m, 1H), 7.45 (m, 1H), 7.37 (m, 1H), 7.11 (m, 1H); LCMS Mass: 311.9 (M⁺+1).

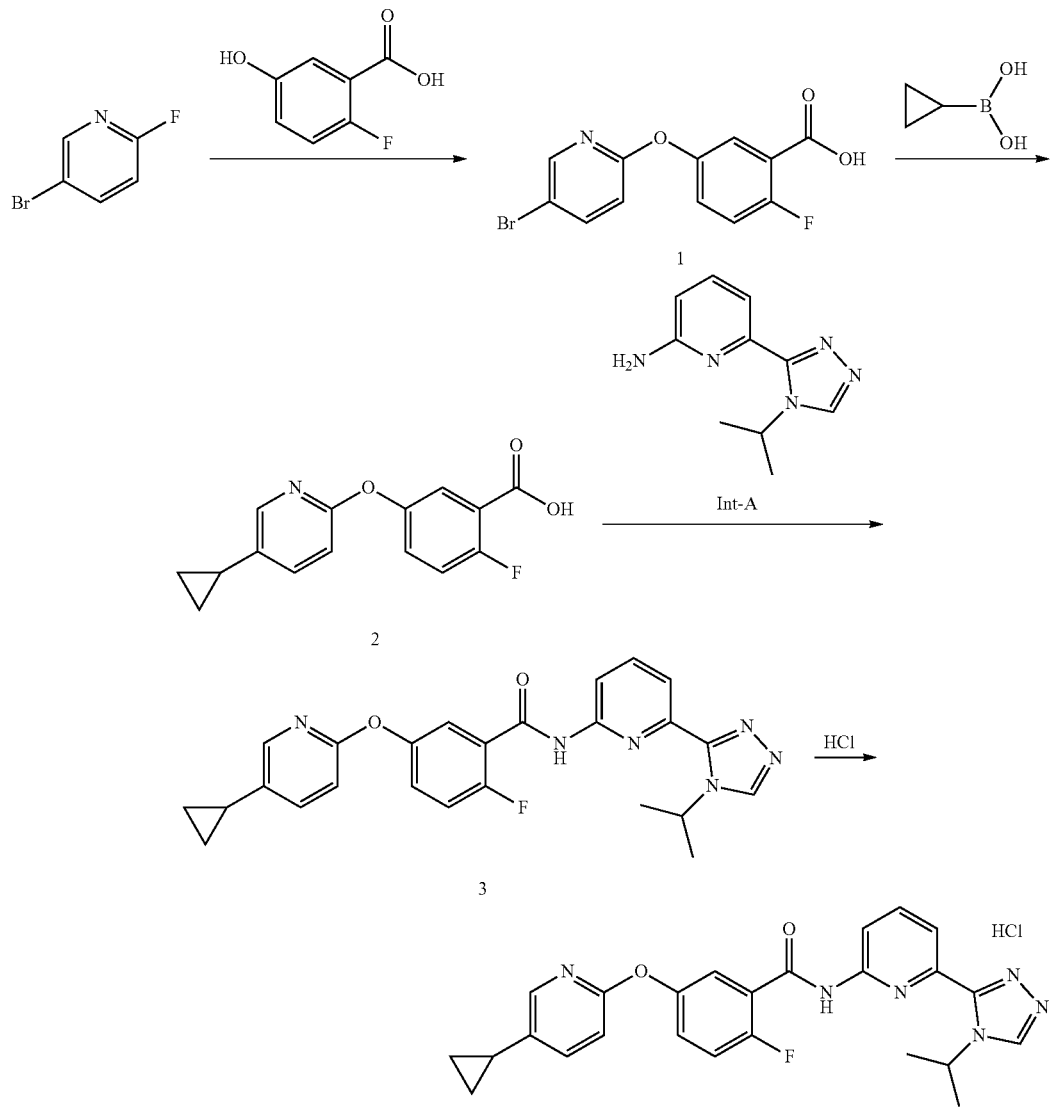

Step 1: 5-((5-Bromopyridin-2-yl)oxy)-2-fluorobenzoic acid (1)

A stirred solution of 5-bromo-2-fluoropyridine (1.5 g, 8.52 mmol), 2-fluoro-5-hydroxybenzoic acid (1.35 g, 8.52 mmol), Cs₂CO₃ (5.5 g, 17.04 mmol) in DMSO (25 mL), was heated at 120° C. for 12 h. The reaction mixture was cooled to rt and poured into water (50 mL). The aqueous layer was acidified with citric acid and extracted with EtOAc (2×100

Step 2: 5-((5-Cyclopropylpyridin-2-yl)oxy)-2-fluorobenzoic acid (2)

To a stirred solution of 1 (300 mg, 0.96 mmol) in 1,4-dioxane (17 mL) at rt and under an inert atmosphere, was added cyclopropylboronic acid (165 mg, 1.82 mmol), Cs₂CO₃ (940 mg, 2.88 mmol) and Pd(PPh₃)₄ (55 mg, 0.48 mmol). The reaction mixture was heated at 120° C. for 3 h. The reaction mixture was cooled to rt, washed with aqueous citric acid, and extracted with EtOAc (2×100 mL). The combined organic layers were dried (Na₂SO₄) and concentrated under reduced pressure to afford compound 2 (237 mg, 90%) as a pale brown solid. LCMS Mass: 273.9 (M$^+$+1).

Step 3: 5-((5-Cyclopropylpyridin-2-yl)oxy)-2-fluoro-N-(6-(4-isopropyl-4H-1,2,4-triazol-3-yl)pyridin-2-yl)benzamide (3)

To a stirred solution of 2 (200 mg, 0.732 mmol) in DCM (20 mL) at 0° C. and under an inert atmosphere, was added PPh$_3$ (239 mg, 0.915 mmol) and hexachloroacetone (0.2 mL, 1.09 mmol). The mixture was stirred at rt for 40 min. Int-A (148 mg, 0.732 mmol) was added to the mixture and stirring continued at rt for 14 h. The mixture was concentrated under reduced pressure and the residue was purified (silica gel; eluting with 2% MeOH in DCM) to afford compound 3 (68 mg, 20%) as an off-white solid. $^1$H NMR (500 MHz, DMSO-d$_6$): δ 10.93 (s, 1H), 8.86 (s, 1H), 8.19 (m, 1H), 8.02 (m, 1H), 7.97 (m, 1H), 7.90 (m, 1H), 7.54 (m, 1H), 7.29-7.45 (m, 3H), 7.00 (m, 1H), 5.69 (m, 1H), 1.92 (m, 1H), 1.43 (m, 6H), 0.90-0.99 (m, 2H), 0.61-0.75 (m, 2H); LCMS Mass: 459.2 (M$^+$+1).

Step 4: 5-((5-Cyclopropylpyridin-2-yl)oxy)-2-fluoro-N-(6-(4-isopropyl-4H-1,2,4-triazol-3-yl)pyridin-2-yl)benzamide hydrochloride (Compound 1-227)

To a stirred solution of 3 (68 mg, 0.15 mmol) in DCM (2 mL) at 0° C., was added 4M HCl in 1,4-Dioxane (0.3 mL). The mixture was stirred at rt for 30 min. The reaction mixture was concentrated under reduced pressure and the residue was purified via trituration with a mixture of Et$_2$O and n-pentane to afford compound 1-227 (65 mg, 89%) as an off-white solid. $^1$H NMR (400 MHz, DMSO-d$_6$): δ 11.03 (s, 1H), 9.41 (s, 1H), 8.25 (m, 1H), 8.08 (m, 1H), 7.89-8.00 (m, 2H), 7.54 (m, 1H), 7.39-7.48 (m, 2H), 7.35 (m, 1H), 7.00 (m, 1H), 5.79 (m, 1H), 4.87 (br s, 1H), 1.91 (m, 1H), 1.47 (m, 6H), 0.89-0.99 (m, 2H), 0.63-0.74 (m, 2H); LCMS Mass: 459.1 (M$^+$+1).

Example 26: 5-(3,4-Difluorobenzamido)-2-fluoro-N-(6-(4-isopropyl-4H-1,2,4-triazol-3-yl)pyridin-2-yl)benzamide hydrochloride (Compound 1-334)

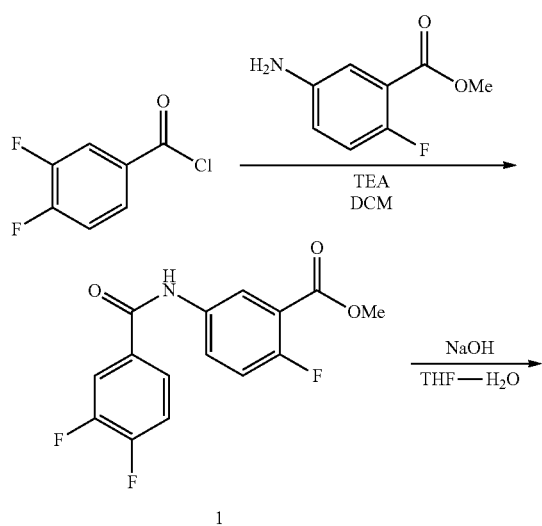

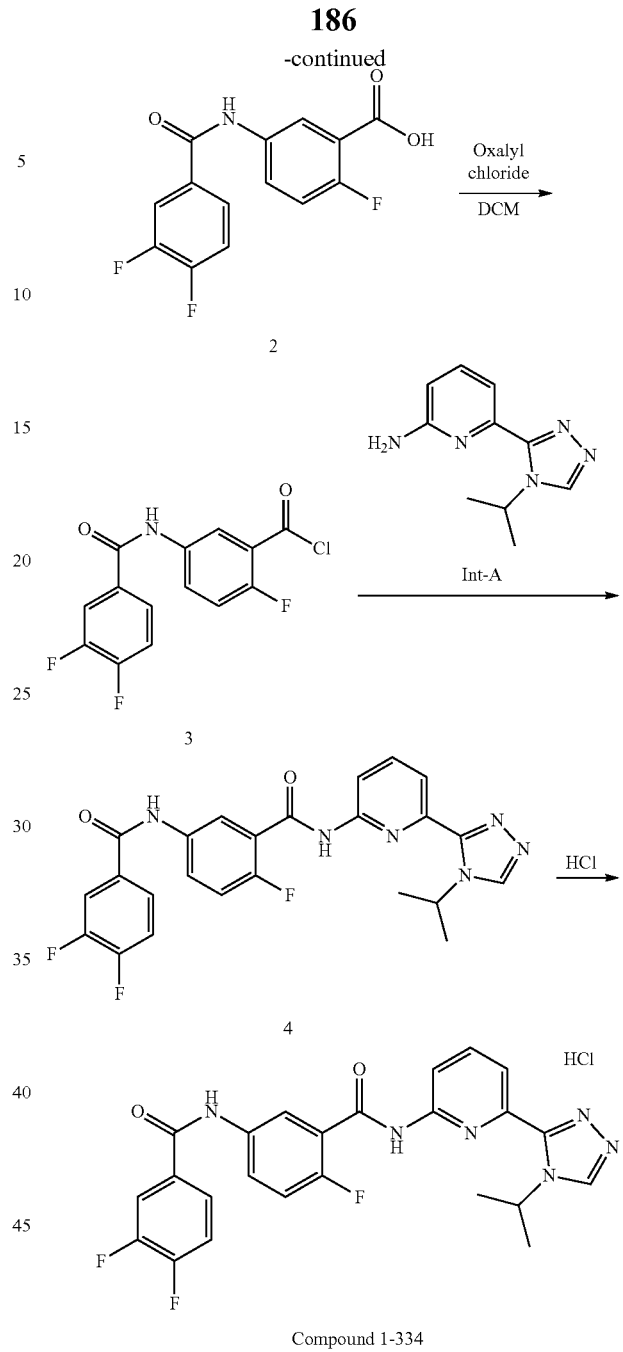

Step 1: Methyl 5-(3,4-difluorobenzamido)-2-fluorobenzoate (1)

To a stirred solution of methyl 5-amino-2-fluorobenzoate (500 mg, 2.99 mmol) in DCM (20 mL) at 0° C., was added 3,4-difluorobenzoyl chloride (410 μL, 3.26 mmol) followed by TEA (1.0 mL, 7.48 mmol). The mixture was allowed to warm to rt and stirred for 72 h. The mixture was diluted with water and the organic layer separated and concentrated under reduced pressure. The obtained solid was purified via trituration with Et$_2$O to afford compound 1 (782 mg, 84%) as a white solid. $^1$H NMR (400 MHz, DMSO-d$_6$): δ 10.53 (s, 1H), 8.35 (m, 1H), 8.00-8.10 (m, 2H), 7.88 (m, 1H), 7.66 (m, 1H), 7.38 (m, 1H), 3.85 (s, 3H); LCMS Mass: 310.0 (M$^+$+1).

Step 2: 5-(3,4-Difluorobenzamido)-2-fluorobenzoic acid (2)

To a stirred solution of 1 (782 mg, 2.53 mmol) in THF (18 mL) and water (4.58 mL), was added aq. 4M NaOH (4.42 mL). The mixture was stirred at rt for 16 h. The THF was removed via concentration under reduced pressure, and the remaining aq. solution was acidified to pH 2 with aq. 3M HCl. The obtained solid was collected via filtration and dried under high vacuum to afford compound 2 (782 mg, 100%) as a white solid. LCMS Mass: 296.0 ($M^+$+1).

Step 3: 5-(3,4-Difluorobenzamido)-2-fluorobenzoyl chloride (3)

To a stirred mixture of 2 (270 mg, 0.914 mmol) in DCM (4.6 mL) at 0° C., was added oxalyl chloride (157 µL, 1.83 mmol) followed by 6 to 7 drops DMF. The mixture was allowed to warm to rt and stirred for 15 min. The mixture was concentrated under reduced pressure and the residue dried under high vacuum for 1.5 h, to afford compound 3 (290 mg) as an off-white solid which was not purified further.

Step 4: 5-(3,4-Difluorobenzamido)-2-fluoro-N-(6-(4-isopropyl-4H-1,2,4-triazol-3-yl)pyridin-2-yl)benzamide (4)

To a stirred solution of 3 (80 mg, 0.26 mmol) in DCM (2 mL) at rt under an inert atmosphere, were added TEA (71 µL, 0.51 mmol) and Int-A (52 mg, 0.26 mmol). The mixture was stirred at rt for 16 h. Water was added and the obtained precipitate was isolated via filtration and dried to afford compound 4 (40 mg, 32%) as a white solid which did not require further purification. LCMS Mass: 481.0 ($M^+$+1).

Step 5: 5-(3,4-Difluorobenzamido)-2-fluoro-N-(6-(4-isopropyl-4H-1,2,4-triazol-3-yl)pyridin-2-yl)benzamide hydrochloride (Compound 1-334)

To a stirred solution of 4 (40 mg, 0.083 mmol) in DCM (1 mL) at rt, was added 2M HCl in diethyl ether (0.5 mL) and the mixture stirred at rt for 1 h. The reaction mixture was concentrated under reduced pressure and the residue purified via trituration with a mixture of $Et_2O$ and n-pentane to afford compound 1-334 (40 mg, 100%) as an off-white solid. $^1$H NMR (400 MHz, DMSO-$d_6$): δ 10.94 (s, 1H), 10.60 (s, 1H), 9.21 (s, 1H), 8.25 (m, 1H), 7.89-8.14 (m, 6H), 7.63 (m, 1H), 7.40 (m, 1H), 5.74 (m, 1H), 5.38 (br s, 1H), 1.46 (m, 6H); LCMS Mass: 481.0 ($M^+$+1).

Example 27: 4-((4-Fluoro-3-((6-(4-isopropyl-4H-1,2,4-triazol-3-yl)pyridin-2-yl)carbamoyl)phenyl)carbamoyl)benzoic acid sodium salt (Compound 1-335)

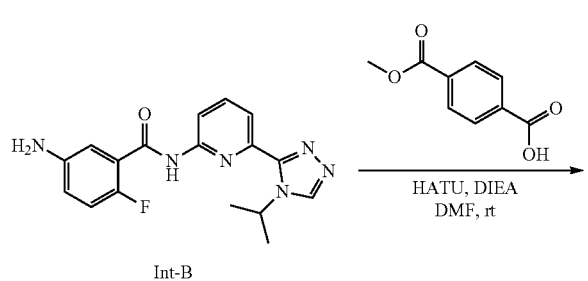

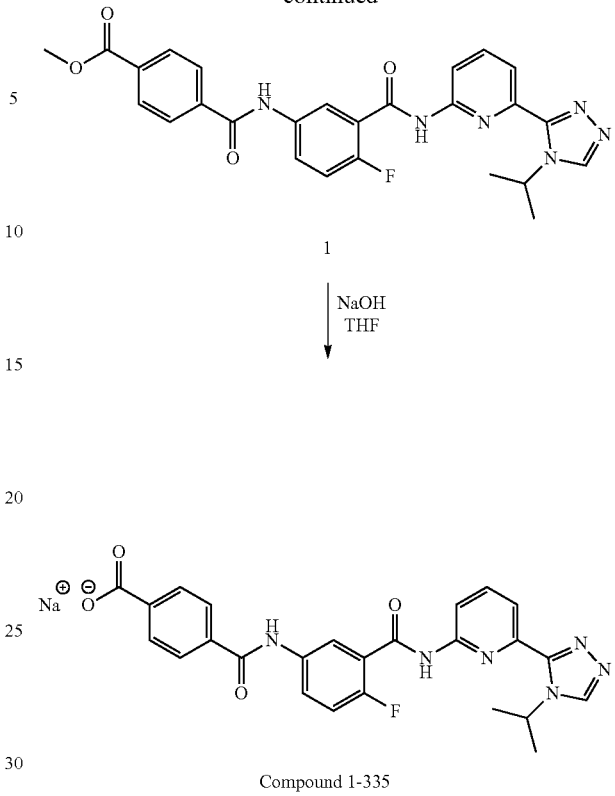

Compound 1-335

Step 1: Methyl 4-((4-fluoro-3-((6-(4-isopropyl-4H-1,2,4-triazol-3-yl)pyridin-2-yl)carbamoyl)phenyl)carbamoyl)benzoate (1)

A mixture of 4-(methoxycarbonyl)benzoic acid (40 mg, 0.221 mmol), HATU (90 mg, 0.235 mmol), and DMF (1.2 mL) was stirred at rt for 10 min. DIEA (107 µL, 0.615 mmol) and Int-B (70 mg, 0.205 mmol) was added and the mixture stirred at rt for 16 h. The mixture was concentrated under reduced pressure and purified via reverse-phase preparative HPLC (Waters XTerra® Prep MS C-18 OBD 5 µm 50×100 mm column; eluting with 10-90% MeCN/$H_2O$ containing 0.1% TFA, over 20 min) to afford compound 1 (54 mg, 52%) as an off-white solid. $^1$H NMR (400 MHz, DMSO-$d_6$): δ 10.92 (s, 1H), 10.68 (s, 1H), 9.00 (s, 1H), 8.23 (m, 1H), 8.16 (m, 1H), 8.01-8.11 (m, 6H), 7.91 (m, 1H), 7.42 (m, 1H), 5.69 (m, 1H), 3.90 (s, 3H), 1.44 (m, 6H); LCMS Mass: 503.0 ($M^+$+1).

Step 2: 4-((4-Fluoro-3-((6-(4-isopropyl-4H-1,2,4-triazol-3-yl)pyridin-2-yl)carbamoyl)phenyl)carbamoyl)benzoic acid sodium salt (Compound 1-335)

A mixture of 1 (54 mg, 0.107 mmol), THF (1.5 mL), and aq. 1M NaOH (220 µL) was stirred at rt for 3 h. The mixture was concentrated under reduced pressure and dried under high vacuum to afford compound 1-335 (23 mg, 43%) as an off-white solid. $^1$H NMR (400 MHz, DMSO-$d_6$): δ 10.93 (s, 1H), 10.48 (s, 1H), 8.87 (s, 1H), 8.18-8.22 (m, 2H), 8.00-8.10 (m, 2H), 7.85-7.95 (m, 5H), 7.37 (m, 1H), 5.70 (m, 1H), 1.42 (m, 6H); LCMS Mass: 489.0 ($M^+$+1).

Example 28: 5-((6-Bromopyridin-2-yl)oxy)-2-fluoro-N-(6-(4-isopropyl-4H-1,2,4-triazol-3-yl)pyridin-2-yl)benzamide hydrochloride (Compound 1-336)

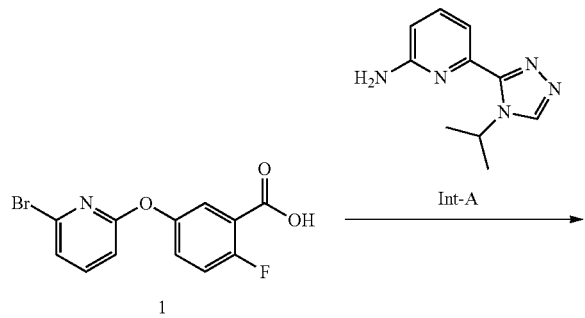

Step 1: 5-((6-Bromopyridin-2-yl)oxy)-2-fluoro-N-(6-(4-isopropyl-4H-1,2,4-triazol-3-yl)pyridin-2-yl)benzamide (2)

To a stirred solution of 1 (200 mg, 0.641 mmol) (from Example 24, Step 1) in DCM (20 mL) at rt under an inert atmosphere, were added PPh$_3$ (220 mg, 0.801 mmol) and hexachloroacetone (0.2 mL, 0.961 mmol) and the mixture stirred at rt for 40 min. Int-A (100 mg, 0.496 mmol) was added and stirring continued at rt for 16 h. The mixture was concentrated under reduced pressure and the residue was purified (silica gel; eluting with 2% MeOH in DCM) to afford compound 2 (79 mg, 25%) as an off-white solid. $^1$H NMR (400 MHz, DMSO-d$_6$): δ 10.98 (s, 1H), 8.86 (s, 1H), 8.21 (m, 1H), 8.03 (m, 1H), 7.91 (m, 1H), 7.83 (m, 1H), 7.55 (m, 1H), 7.45-7.49 (m, 2H), 7.42 (m, 1H), 7.13 (m, 1H), 5.69 (m, 1H), 1.44 (m, 6H); LCMS Mass: 497.1 (M$^+$+1).

Step 2: 5-((6-Bromopyridin-2-yl)oxy)-2-fluoro-N-(6-(4-isopropyl-4H-1,2,4-triazol-3-yl)pyridin-2-yl)benzamide hydrochloride (Compound 1-336)

To a stirred solution of 2 (79 mg, 0.158 mmol) in DCM (5 mL) at 0° C., was added 4M HCl in 1,4-dioxane (0.5 mL) and the mixture stirred for 1 h. The reaction mixture was concentrated under reduced pressure and the residue purified via trituration with a mixture of Et$_2$O and n-pentane to afford compound 1-336 (40 mg, 41%) as an off-white solid. $^1$H NMR (400 MHz, DMSO-d$_6$): δ 11.00 (s, 1H), 8.97 (s, 1H), 8.22 (m, 1H), 8.04 (m, 1H), 7.91 (m, 1H), 7.84 (m, 1H), 7.54 (m, 1H), 7.45-7.49 (m, 2H), 7.42 (m, 1H), 7.13 (m, 1H), 5.71 (m, 1H), 4.77 (br s, 1H), 1.44 (m, 6H); LCMS Mass: 497.0 (M$^+$+1).

Example 29: 5-((5-Bromopyridin-2-yl)oxy)-2-fluoro-N-(6-(4-isopropyl-4H-1,2,4-triazol-3-yl)pyridin-2-yl)benzamide hydrochloride (Compound 1-337)

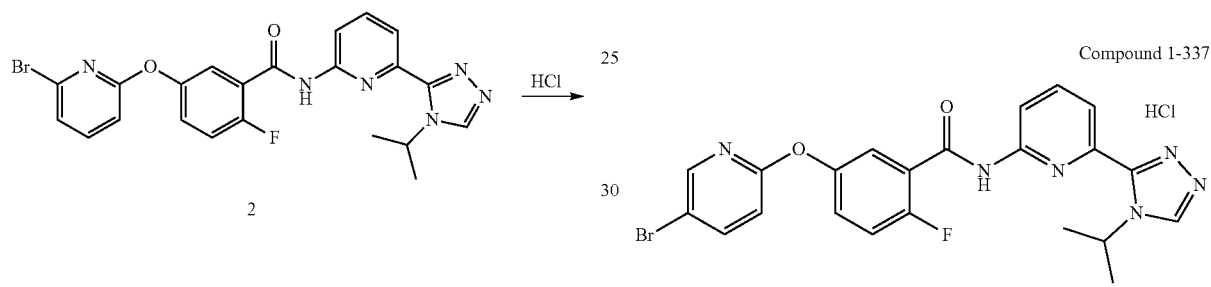

Compound 1-337

The title compound (1-337) was prepared using the procedure described for Example 5, using 5-bromo-2-fluoropyridine in Step 1. $^1$H NMR (400 MHz, DMSO-d$_6$) δ 11.00 (s, 1H), 9.00 (s, 1H), 8.28 (m, 1H), 8.21 (m, 1H), 8.10 (m, 1H), 8.04 (m, 1H), 7.91 (m, 1H), 7.51 (m, 1H), 7.41-7.47 (m, 2H), 7.14 (m, 1H), 5.71 (m, 1H), 3.98 (br s, 1H), 1.44 (m, 6H); LCMS Mass: 497.1 (M$^+$+1).

Example 30: 5-Benzamido-N-(6-(4-cyclopropyl-4H-1,2,4-triazol-3-yl)pyridin-2-yl)-2-fluorobenzamide hydrochloride (Compound 1-338)

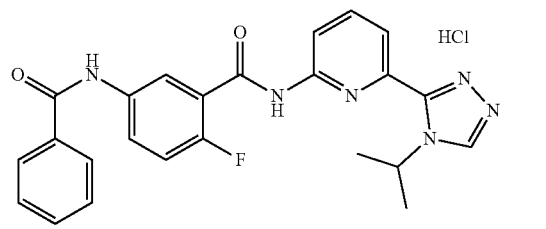

Compound 1-338

The title compound (1-338) was prepared using the procedure described for Example 26, using benzoyl chloride in Step 1, and Int-C in Step 4. $^1$H NMR (400 MHz, DMSO-d$_6$) δ 10.89 (s, 1H), 10.50 (s, 1H), 8.72 (s, 1H), 8.27 (m, 1H), 8.17 (m, 1H), 7.97-8.05 (m, 4H), 7.88 (m, 1H), 7.61 (m, 1H), 7.52-7.56 (m, 2H), 7.40 (m, 1H), 4.21 (m, 1H), 4.00 (br s, 1H), 0.95-1.00 (m, 4H).

Example 31: N-(6-(4-Cyclopropyl-4H-1,2,4-triazol-3-yl)pyridin-2-yl)-5-(3,4-difluorobenzamido)-2-fluorobenzamide hydrochloride (Compound 1-339)

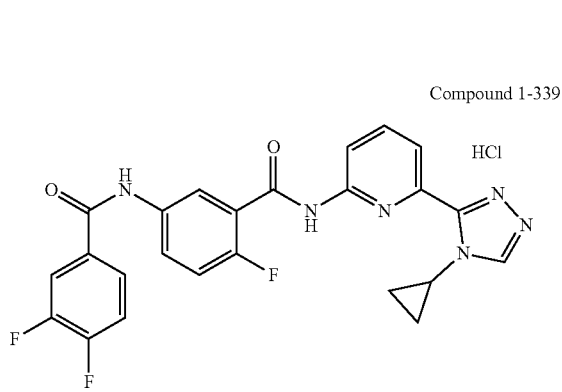 [SMILES: O=C(Nc1ccc(F)c(C(=O)Nc2cccc(-c3nncn3C3CC3)n2)c1)c1ccc(F)c(F)c1 ; Cl]

Compound 1-339

The title compound (1-339) was prepared using the procedure described for Example 26, using Int-C in Step 4. $^1$H NMR (400 MHz, DMSO-d$_6$) δ 10.91 (s, 1H), 10.60 (s, 1H), 8.93 (s, 1H), 8.30 (m, 1H), 7.88-8.14 (m, 6H), 7.66 (m, 1H), 7.38 (m, 1H), 4.94 (br s, 1H), 4.23 (m, 1H), 0.98-1.10 (m, 4H). LCMS Mass: 479.0 (M$^+$+1).

Example 32: 5-Benzamido-N-(6-(4-(1,3-difluoropropan-2-yl)-4H-1,2,4-triazol-3-yl)pyridin-2-yl)-2-fluorobenzamide hydrochloride (Compound 1-340)

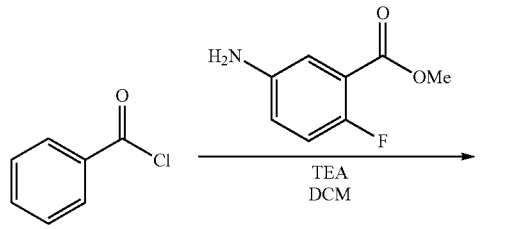

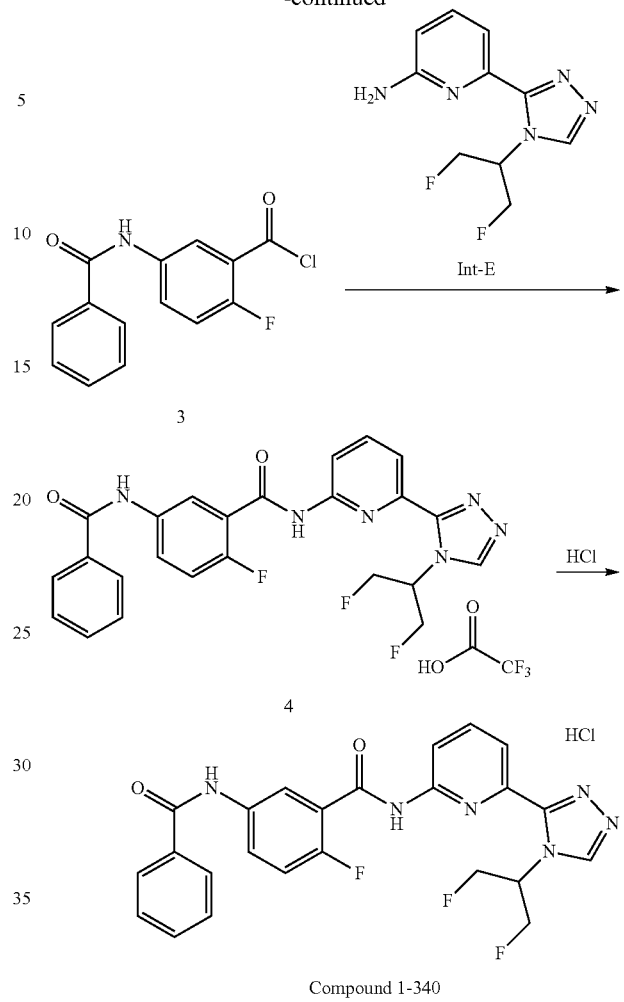

Compound 1-340

Step 1: Methyl 5-benzamido-2-fluorobenzoate (1)

To a stirred solution of methyl 5-amino-2-fluorobenzoate (500 mg, 2.99 mmol) in DCM (18 mL) at rt, was added dropwise benzoyl chloride (457 mg, 3.25 mmol) followed by TEA (1.0 mL, 7.48 mmol). The mixture was allowed to warm to rt and stirred for 16 h. The mixture was diluted with water and the organic layer separated and concentrated under reduced pressure. The residue was was purified (silica gel; eluting with 0-100% EtOAc in hexanes) to afford compound 1 (755 mg, 94%) as a white solid. LCMS Mass: 274.0 (M$^+$+1).

Step 2: 5-Benzamido-2-fluorobenzoic acid (2)

To a stirred solution of 1 (750 mg, 2.74 mmol) in THF (20 mL) and water (5 mL), was added aq. 4M NaOH (4.8 mL). The mixture was stirred at rt for 64 h. The THF was removed via concentration under reduced pressure, and the remaining aq. solution was acidified to pH 2 with aq. 3M HCl. The obtained solid was collected via filtration and dried under high vacuum to afford compound 2 (650 mg, 91%) as a white solid. LCMS Mass: 260.0 (M$^+$+1).

Step 3: 5-Benzamido-2-fluorobenzoyl chloride (3)

To a stirred mixture of 2 (200 mg, 0.771 mmol) in DCM (3.7 mL) at 0° C., was added oxalyl chloride (92 μL, 1.08 mmol) followed by 4 drops DMF. The mixture was allowed to stir at 0° C. for 15 min, then warmed to rt and stirred for 45 min. The mixture was concentrated under reduced pressure and the residue dried under high vacuum for 1 h, to afford compound 3 (200 mg) as an off-white solid which was not purified further.

Step 4: 5-Benzamido-N-(6-(4-(1,3-difluoropropan-2-yl)-4H-1,2,4-triazol-3-yl)pyridin-2-yl)-2-fluorobenzamide trifluoroacetate (4)

To a stirred solution of 3 (80 mg, 0.29 mmol) in DCM (2 mL) at rt under an inert atmosphere, were added DMAP (35 mg, 0.288 mmol) and Int-E (76 mg, 0.32 mmol). The mixture was stirred at rt for 2 h. To the mixture was added sat. NaHCO$_3$ solution, and the organic layer separated. The organic layer was concentrated under reduced pressure and the obtained residue was purified via reverse-phase preparative HPLC (Waters XTerra® Prep MS C-18 OBD 5 μm 50×100 mm column; eluting with 10-90% MeCN/H$_2$O containing 0.1% TFA, over 20 min) to afford compound 4 (14 mg, 8%) as an off-white solid. LCMS Mass: 481.0 (M$^+$+1).

Step 5: 5-Benzamido-N-(6-(4-(1,3-difluoropropan-2-yl)-4H-1,2,4-triazol-3-yl)pyridin-2-yl)-2-fluorobenzamide (Compound 1-340)

To a stirred solution of 4 (14 mg, 0.023 mmol) in DCM (1.5 mL) at rt, was added 2M HCl in diethyl ether (0.5 mL) and the mixture stirred at rt for 15 min. The reaction mixture was concentrated under reduced pressure and the residue purified via trituration with a mixture of Et$_2$O and n-pentane to afford compound 1-340 (10 mg, 85%) as a white solid. $^1$H NMR (400 MHz, DMSO-d$_6$): δ 10.96 (s, 1H), 10.51 (s, 1H), 8.97 (s, 1H), 8.15-8.21 (m, 2H), 7.90-8.10 (m, 5H), 7.60 (m, 1H), 7.50-7.58 (m, 2H), 7.40 (m, 1H), 6.35 (br m, 1H), 5.06 (m, 1H), 4.90-5.00 (m, 2H), 4.85 (m, 1H); LCMS Mass: 481.0 (M$^+$+1).

Example 33: (R)-5-Benzamido-2-fluoro-N-(6-(4-(1-hydroxypropan-2-yl)-4H-1,2,4-triazol-3-yl)pyridin-2-yl)benzamide (Compound 1-341)

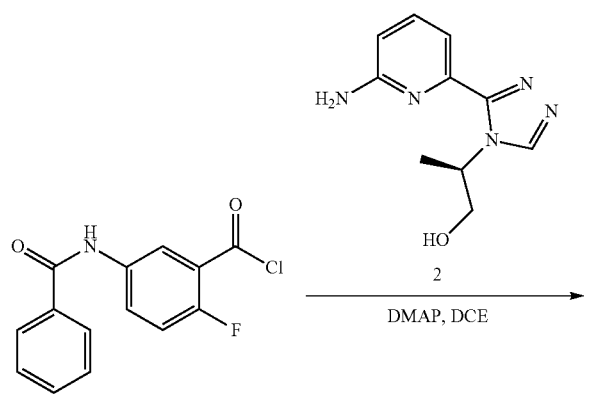

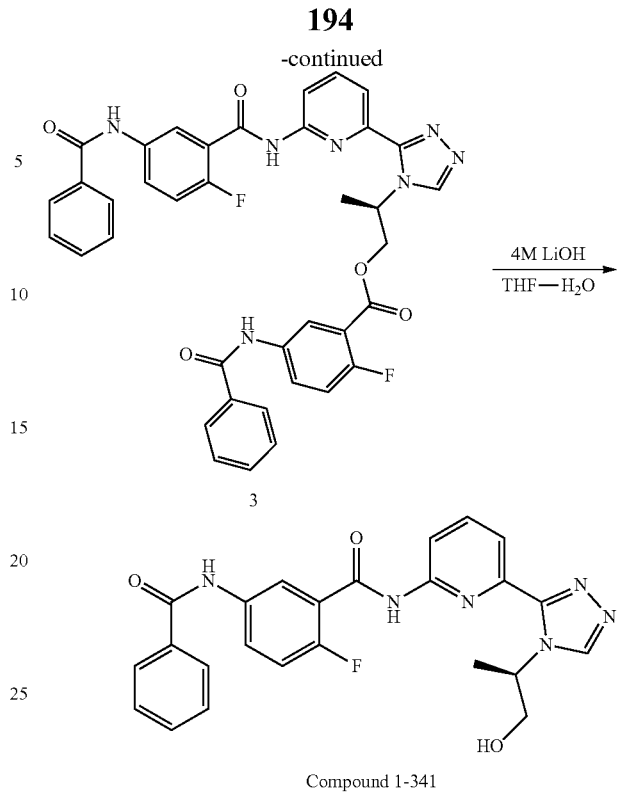

Compound 1-341

Step 1: (R)-2-(3-(6-(5-Benzamido-2-fluorobenzamido)pyridin-2-yl)-4H-1,2,4-triazol-4-yl)propyl 5-benzamido-2-fluorobenzoate (3)

To a stirred solution of 5-benzamido-2-fluorobenzoyl chloride 1 (149 mg, 0.536 mmol) (from Example 32, Step 3) in DCE (3 mL) at rt, was added (R)-2-(3-(6-aminopyridin-2-yl)-4H-1,2,4-triazol-4-yl)propan-1-ol 2 (56 mg, 0.255 mmol) (from Int-F, Step 1) and DMAP (131 mg, 1.07 mmol), and the mixture stirred at rt for 16 h. The mixture was concentrated under reduced pressure and the residue partitioned between water and DCM. The organic layer was separated and the aq. layer re-extracted with additional DCM. The combined organic layers were dried (Na$_2$SO$_4$), filtered, and concentrated under reduced pressure. The residue was purified via reverse-phase preparative HPLC (Waters XTerra® Prep MS C-18 OBD 5 μm 50×100 mm column; eluting with 10-90% MeCN/H$_2$O containing 0.1% TFA, over 20 min) to afford compound 3 (57 mg, 32%) as a white solid. $^1$H NMR (400 MHz, DMSO-d$_6$): δ 10.86 (s, 1H), 10.50 (s, 1H), 10.46 (s, 1H), 8.90 (s, 1H), 8.10-8.20 (m, 3H), 7.80-8.00 (m, 8H), 7.50-7.60 (m, 6H), 7.25-7.40 (m, 2H), 6.13 (m, 1H), 4.62 (m, 2H), 1.64 (m, 3H); LCMS Mass: 702.0 (M$^+$+1).

Step 2: (R)-5-Benzamido-2-fluoro-N-(6-(4-(1-hydroxypropan-2-yl)-4H-1,2,4-triazol-3-yl)pyridin-2-yl)benzamide (Compound 1-341)

To a stirred solution of 3 (52 mg, 0.074 mmol) in THF (0.75 mL) and water (0.25 mL) at rt, was added aq. 4M LiOH (129 μL, 0.519 mmol). The mixture was stirred at rt for 4 h. The THF was removed via concentration under reduced pressure and the remaining aq. layer diluted with water. The mixture was neutralized to pH 7 with dilute aq. HCl, and then extracted several times with EtOAc. The combined organic layers were washed with sat. aq. NaHCO$_3$, then water, then dried (Na$_2$SO$_4$), filtered, and concentrated under reduced pressure to afford compound 1-341 (16 mg, 47%) as a white solid. $^1$H NMR (400 MHz, DMSO-d$_6$): δ 10.88 (s, 1H), 10.47 (s, 1H), 8.79 (s, 1H), 8.15-8.22 (m, 2H), 7.95-8.05 (m, 4H), 7.90 (m, 1H), 7.50-7.60 (m, 3H), 7.38 (m, 1H), 5.59 (m, 1H), 4.92 (m, 2H), 3.62 (m, 1H), 1.42 (m, 3H); LCMS Mass: 461.0 (M$^+$+1).

Example 34: (R)-2-Fluoro-5-((4-fluorophenyl)amino)-N-(6-(4-(1-hydroxypropan-2-yl)-4H-1,2,4-triazol-3-yl)pyridin-2-yl)benzamide (Compound 1-342)

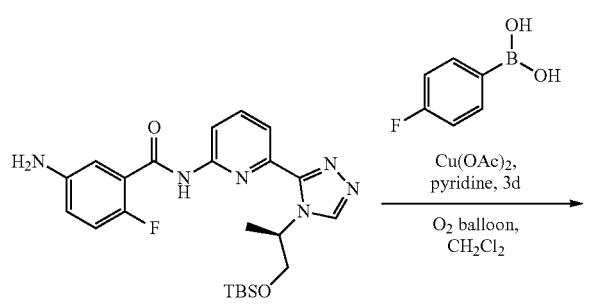

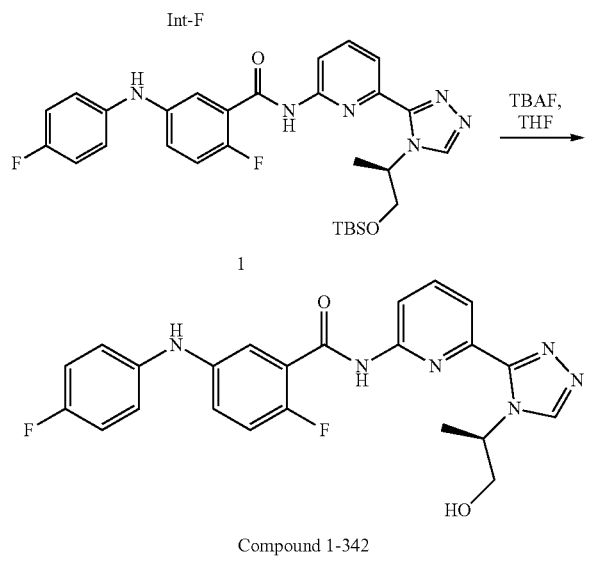

Compound 1-342

Step 1: (R)—N-(6-(4-(1-((tert-Butyldimethylsilyl)oxy)propan-2-yl)-4H-1,2,4-triazol-3-yl)pyridin-2-yl)-2-fluoro-5-((4-fluorophenyl)amino)benzamide (1)

To a solution of Int-F (100 mg, 0.21 mmol) in DCM (40 mL) was added 4-fluorophenylboronic acid (88 mg, 0.63 mmol), Cu(OAc)$_2$ (84 mg, 0.42 mmol) and pyridine (17 mg, 0.21 mmol). The reaction was stirred at rt under atmospheric oxygen for 3 days. Water was added, and the aqueous layer extracted with EtOAc. The combined organic layers were dried, filtered, and evaporated under reduced pressure. The residue was purified (silica gel; 66% EtOAc in petroleum ether) to afford compound 1 (54 mg, 50%) as a yellow solid. $^1$H NMR (400 MHz, DMSO-d$_6$): δ 10.71 (s, 1H), 8.48 (s, 1H), 8.27 (s, 1H), 8.15 (m, 1H), 8.01 (m, 1H), 7.91 (m, 1H), 7.28 (s, 1H), 7.23 (m, 1H), 7.18 (s, 1H), 7.10 (m, 4H), 4.96 (m, 1H), 4.30 (m, 1H), 3.93 (s, 1H), 1.11 (m, 3H), 0.70 (s, 9H), −0.21 (s, 3H), −0.46 (m, 3H).

Step 2: (R)-2-Fluoro-5-((4-fluorophenyl)amino)-N-(6-(4-(1-hydroxypropan-2-yl)-4H-1,2,4-triazol-3-yl)pyridin-2-yl)benzamide (Compound 1-342)

To a solution of 1 (54 mg, 0.1 mmol) in THF (10 mL) was added TBAF (0.1 mL, 0.2 mmol). The reaction was stirred at rt for 2 h. Water was added and the aqueous layer extracted several times with EtOAc. The combined organic layers were dried, filtered, and evaporated under reduced pressure. The residue was purified (silica gel; eluting with 50% EtOAc in petroleum ether) to afford compound 1-342 (25 mg, 56%) as a yellow solid. $^1$H NMR (400 MHz, DMSO-d$_6$): δ 10.74 (s, 1H), 8.53 (s, 1H), 8.37 (s, 1H), 8.17 (m, 1H), 8.01 (m, 1H), 7.92 (m, 1H), 7.17-7.34 (m, 3H), 7.11 (m, 4H), 4.90 (m, 1H), 4.77 (m, 1H), 4.38 (m, 1H), 3.81 (s, 1H), 1.03 (m, 3H). LCMS Mass: 451.1 (M$^+$+1).

Example 35: (R)-2-Fluoro-5-((4-fluorobenzyl)amino)-N-(6-(4-(1-hydroxypropan-2-yl)-4H-1,2,4-triazol-3-yl)pyridin-2-yl)benzamide hydrochloride (Compound 1-343)

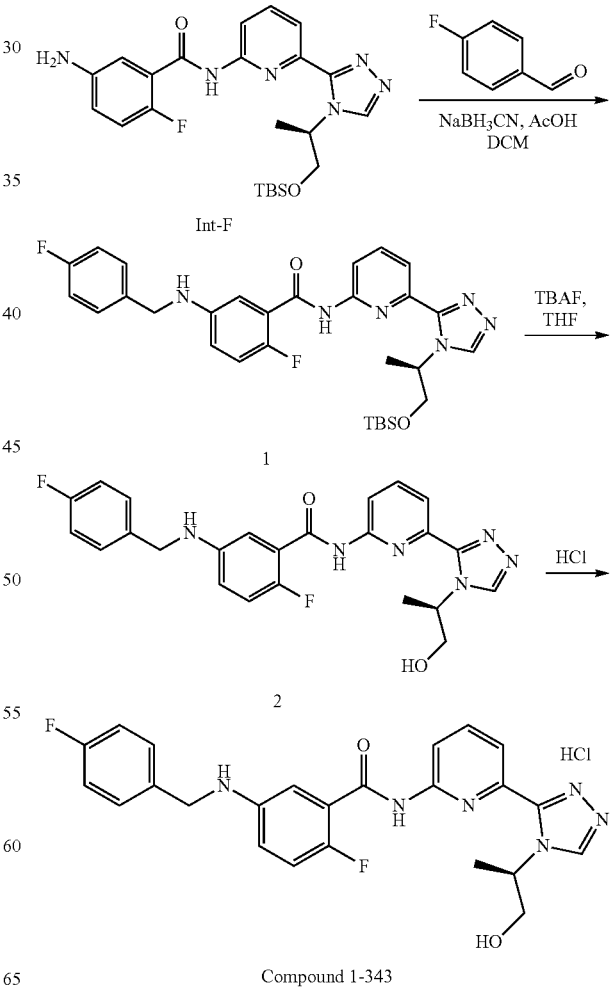

Compound 1-343

Step 1: (R)—N-(6-(4-(1-((tert-Butyldimethylsilyl)oxy)propan-2-yl)-4H-1,2,4-triazol-3-yl)pyridin-2-yl)-2-fluoro-5-((4-fluorobenzyl)amino)benzamide (1)

To a solution of Int-F (100 mg, 0.21 mmol) in MeOH (15 mL) was added 4-fluorobenzaldehyde (53 mg, 0.42 mmol), NaH$_3$BCN (40 mg, 0.63 mmol) and HOAc (0.05 mL). The reaction was stirred at rt overnight. Water was added and the aqueous layer extracted several times with EtOAc. The combined organic layers were dried, filtered, and evaporated under reduced pressure to afford compound 1 (44 mg, 36%) as a yellow solid which was used for next step without further purification.

Step 2: (R)-2-Fluoro-5-((4-fluorobenzyl)amino)-N-(6-(4-(1-hydroxypropan-2-yl)-4H-1,2,4-triazol-3-yl)pyridin-2-yl)benzamide (2)

To a solution of 1 (44 mg, 0.08 mmol) in THF (10 mL) was added TBAF (0.08 mL, 0.16 mmol). The reaction was stirred at rt for 2 h. Water was added, and the organic layer extracted several times with EtOAc. The combined organic layers were dried and evaporated under reduced pressure. The residue was purified (silica gel; eluting with 50% EtOAc in petroleum ether) to afford compound 2 (25 mg, 68%) as a yellow solid.

Step 3: (R)-2-Fluoro-5-((4-fluorobenzyl)amino)-N-(6-(4-(1-hydroxypropan-2-yl)-4H-1,2,4-triazol-3-yl)pyridin-2-yl)benzamide hydrochloride (Compound 1-343)

A solution of 2 (25 mg, 0.05 mmol) in EtOAc/HCl (5 mL) was stirred at rt for 2 h. The reaction mixture was concentrated under reduced pressure to afford compound 1-343 (25 mg, 93%) as a yellow solid. $^1$H NMR (400 MHz, DMSO-d$_6$): δ 10.74 (s, 1H), 8.53 (s, 1H), 8.37 (s, 1H), 8.17 (m, 1H), 8.01 (m, 1H), 7.92 (m, 1H), 7.17-7.34 (m, 3H), 7.11 (m, 4H), 4.90 (m, 1H), 4.77 (m, 1H), 4.38 (m, 1H), 3.81 (s, 1H), 3.50 (m, 1H), 1.03 (m, 3H). LCMS Mass: 465.2 (M$^+$+1).

Example A-1: Parenteral Pharmaceutical Composition

To prepare a parenteral pharmaceutical composition suitable for administration by injection (subcutaneous, intravenous), 1-1000 mg of a compound described herein, or a pharmaceutically acceptable salt or solvate thereof, is dissolved in sterile water and then mixed with 10 mL of 0.9% sterile saline. A suitable buffer is optionally added as well as optional acid or base to adjust the pH. The mixture is incorporated into a dosage unit form suitable for administration by injection Example A-2: Oral Solution To prepare a pharmaceutical composition for oral delivery, a sufficient amount of a compound described herein, or a pharmaceutically acceptable salt thereof, is added to water (with optional solubilizer(s), optional buffer(s) and taste masking excipients) to provide a 20 mg/mL solution.

Example A-3: Oral Tablet

A tablet is prepared by mixing 20-50% by weight of a compound described herein, or a pharmaceutically acceptable salt thereof, 20-50% by weight of microcrystalline cellulose, 1-10% by weight of low-substituted hydroxypropyl cellulose, and 1-10% by weight of magnesium stearate or other appropriate excipients. Tablets are prepared by direct compression. The total weight of the compressed tablets is maintained at 100-500 mg.

Example A-4: Oral Capsule

To prepare a pharmaceutical composition for oral delivery, 10-500 mg of a compound described herein, or a pharmaceutically acceptable salt thereof, is mixed with starch or other suitable powder blend. The mixture is incorporated into an oral dosage unit such as a hard gelatin capsule, which is suitable for oral administration.

In another embodiment, 10-500 mg of a compound described herein, or a pharmaceutically acceptable salt thereof, is placed into Size 4 capsule, or size 1 capsule (hypromellose or hard gelatin) and the capsule is closed.

Example A-5: Topical Gel Composition

To prepare a pharmaceutical topical gel composition, a compound described herein, or a pharmaceutically acceptable salt thereof, is mixed with hydroxypropyl celluose, propylene glycol, isopropyl myristate and purified alcohol USP. The resulting gel mixture is then incorporated into containers, such as tubes, which are suitable for topical administration.

Biological Assays

Example B-1: Human ASK1 ADP-Glo Assay

The ability of test compounds to inhibit ASK1 kinase activity was determined using the luminescent ADP-Glo™ Kinase Assay and Myelin Basic Protein (MBP) as a substrate (Promega Corporation, Madison, Wis.). During the kinase reaction, ASK1 utilizes ATP and generates ADP. The remaining ATP is then depleted by addition of the ADP-Glo™ reagent which also terminates the reaction. Subsequent addition of the Kinase Detection Reagent converts the ADP that was produced during the kinase reaction to ATP, and this newly synthesized ATP is converted to light using the luciferase/luciferin reactions. The assay was performed according to the manufacturer's instructions. Briefly, purified, recombinant ASK1 (amino acids 649-946) (10-20 ng/well) was added to a 384-well, F bottom, small volume, HIbase, white plate (Greiner Bio-One, Monroe, N.C. #784075) containing 1-2 µL 5× test compound or vehicle control (diluted 1:20 from a 100% DMSO stock solution into 1× Reaction Buffer A). The enzyme was allowed to pre-incubate with test compound from 15-120 min at 30° C. before the addition of the ATP/substrate mix (final concentrations of 50 µM ATP+250 ng MBP in 1× Reaction Buffer A). The mixture was then incubated at room temperature for 40 min before the addition of of ADP-Glo™ reagent and a second 40 minute room temperature incubation. Following the addition of the Kinase Detection Reagent, the plate was incubated for an additional 40 min at room temperature before reading luminescence on a FlexStation 3 (Molecular Devices, Sunnyvale, Calif.). Maximum activity was determined from wells treated with vehicle and was set to 100% and minimum activity was determined from wells containing no enzyme and this was set to 0%. Percent inhibition was calculated relative to the controls and the data graphed in Collaborative Drug Discovery (CDD) Vault (Burlingame, Calif.).

Illustrative biological activity of exemplary compounds is demonstrated in the following Table:

TABLE 3

| Example | Compound | IC$_{50}$ |
|---|---|---|
| 1 | 1-179 | A |
| 2 | 1-23 | A |
| 3 | 1-24 | B |
| 4 | 1-181 | A |
| 5 | 1-210 | A |
| 6 | 1-211 | A |
| 7 | 1-213 | A |
| 8 | 1-217 | A |
| 9 | 1-305 | A |
| 10 | 1-306 | A |
| 11 | 1-307 | A |
| 12 | 1-308 | A |
| 13 | 1-309 | A |
| 14 | 1-311 | A |
| 15 | 1-313 | A |
| 16 | 1-314 | A |
| 17 | 1-329 | B |
| 18 | 1-330 | A |
| 19 | 1-331 | A |
| 20 | 1-332 | A |
| 21 | 1-333 | A |
| 22 | 2-1 | C |
| 23 | 1-223 | A |
| 24 | 1-225 | B |
| 25 | 1-227 | A |
| 26 | 1-334 | A |
| 27 | 1-335 | A |
| 28 | 1-336 | A |
| 29 | 1-337 | B |
| 30 | 1-338 | A |
| 32 | 1-340 | A |
| 33 | 1-341 | A |
| 34 | 1-342 | B |
| 35 | 1-343 | A |

A is <300 nM;
B is 300 nM to 1000 nM;
C is >1000 nM

Example B-2: Human LOXL2 Amine Oxidase Activity Assay

LOXL2 amine oxidase activity was evaluated by measuring Amplex Red fluorescence using 10-20× concentrated conditioned media from CHO cells stably expressing human LOXL2. To assay for amine oxidase activity, 10 μL of the concentrated conditioned media was incubated with 2 μL of test compound in DMSO and 73 μL Assay Buffer (50 mM Borate Buffer, pH8) for 2 h at 37° C. After the 2 h incubation, 5 μL of 10 mM 1,5-Diaminopentane (DAP) diluted in Assay Buffer and 10 μL of Amplex Red Mix (8.5 μL Assay Buffer+0.5 μL of 10 mM Amplex Red+1 μL of 500 U/ml Horseradish Peroxidase) were added and the plate mixed and immediately placed on the FlexStation for fluorescence measurements. Fluorescence was read in kinetic mode every 2 min for 0.5-1 hour at excitation=544 and emission=590. The amine oxidase activity was calculated from the slope of the linear portion of the curve. Wells containing vehicle (DMSO) represented maximum activity and were set to 0% inhibition and wells containing 100 μM βAPN (3-aminopropionitrile) represented no activity and were set to 100% inhibition.

Illustrative biological activity of exemplary compounds is demonstrated in the following Table:

TABLE 4

| Example | Compound | IC$_{50}$ |
|---|---|---|
| 10 | 1-306 | C |
| 18 | 1-330 | A |
| 19 | 1-331 | A |
| 22 | 2-1 | A |

A is <300 nM;
B is 300 nM to 1000 nM;
C is >1000 nM

Example B-3: LOXL2 Human Blood Assay

The amine oxidase activity of human LOXL2 in the context of human whole blood was measured using an Amplex Red assay. Purified human recombinant LOXL2 (Sino Biologicals, Beijing, China) was resuspended to 0.25 μg/mL using sterile water, then 16 μL LOXL2 added to 182 μL fresh human blood collected in heparin vacutainer tubes. 2 μL test compound in DMSO (or DMSO alone) was added and incubated at 37° C. for 2 h. After the 2 h incubation, the blood was centrifuged at 2000×g for 15 min at room temperature to isolate the plasma. 50 μL of plasma was removed and mixed with 25 μL of 40 mM DAP (diluted in water) and 25 μL Amplex Red Mix (23.5 μL 50 mM Borate Buffer, pH 8+0.5 μL 10 mM Amplex Red+1 μL 500 U/ml Horseradish Peroxidase). Samples were mixed and immediately placed on the FlexStation for fluorescence measurements. Fluorescence was read in kinetic mode every 2 min for 1 hour at excitation=544 and emission=590. The amine oxidase activity was calculated from the slope of the linear portion of the curve. Wells containing vehicle (DMSO) represented maximum activity and were set to 0% inhibition and wells containing blood not spiked with LOXL2 represented no activity and were set to 100% inhibition.

Example B-4: Mouse LPS-induced TNFα Release Pharmacodynamic Assay

The administration of lipopolysaccharide (LPS) induces the release of TNFα through the activation of ASK1. Mice (C56B1/6, Balb/c, C3H) are administered test compound orally, intraperitoneally, intravenously or subcutaneously 1-24 hours prior to LPS. Mice are then injected intraperitoneally with 0.3 mg/kg LPS (*Salmonella typhosa*) and ninety minutes later, animals are anesthetized with 3-4% isoflurane and blood collected via cardiac puncture into serum separator tubes. Blood is allowed to sit at room temperature for ~1 hour then centrifuged at 12,000 rmp for 10 minutes at 4° C. to prepare serum. TNFα concentrations in serum are measured using a commercially available ELISA.

Example B-5: Mouse Oropharyngeal Bleomycin Model of Lung Fibrosis

Lung fibrosis was induced in C57B1/6 male mice by administering bleomycin (0.1-4 U/kg) via oropharyngeal instillation. Mice were either pretreated with vehicle or test compound orally, intraperitoneally, intravenously or subcutaneously either prophylactically (1 day to 1 hour before bleomycin instillation) or therapeutically (7-14 days post bleomycin instillation). The route and frequency of dosing were based on previously determined pharmacokinetic properties for the inhibitors in mouse. After bleomycin instillation, animals were monitored daily for weight loss and clinical signs for 14-28 days prior to sacrifice. Animals were euthanized at study termination and weighed. Blood (for isolation of plasma) and bronchoalveolar lavage fluid were collected and frozen for subsequent analyses. Lungs were removed, weighed, then either inflated and fixed by instillation of 10% formalin and prepared for histological examination or homogenized in 1 mL PBS for collagen determination using a hydroxyproline assay. For histological examination, lung slices were stained with Masson's trichrome or picrosirius red to measure fibrillar collagen as an indicator of fibrosis and an Ashcroft score of lung fibrosis and inflammatory damage determined. For lung hydroxyproline content, 0.5 ml of the lung homogenate is removed and added to 0.5 mL 12 N HCl and the samples heated at 120° C. overnight. After the acid hydrolysis, 25-100 µL of the supernatant is dried down, resuspended in 25 µL water and the hydroxyproline content determined by the addition of 0.5 mL Chloramine T solution (140 mg Chloramine T in 6.5 ml ddH$_2$O+1 ml n-propanol+2.5 mL 1M sodium acetate) and incubation at room temperature for 20 min. After the incubation, 0.5 mL Erlich's solution (1.48 g of 4-(dimethylamino (benzaldehyde) in 7 mL n-propanol+2.88 ml 60% perchloric acid and 0.12 mL ddH$_2$O) is added and incubated at 65° C. for 15 min before reading the absorbance at 550 nm.

Example B-6: Rat/Mouse CCl$_4$ Model of Liver Fibrosis

Liver fibrosis is induced in mice (Balb/c or C57Bl/6) by intraperitoneal administration of CCl$_4$ (0.5-2 ml/kg body weight) diluted in corn oil twice weekly for 4-8 weeks or by oral administration two-three times weekly using an escalating dose protocol (Popov et al. 2011 Gastroenetrology; 140(5): 1642-1652.). Liver fibrosis is induced in rats by either intraperitoneal administration (1-2.5 ml/kg) or by oral administration in oil (mineral, olive or corn) twice weekly for 6-12 weeks. Inhibitors are delivered orally, intraperitoneally, intravenously or subcutaneously 1 day to 1 hour prior to the initial CCl$_4$ dosing (prophylactic dosing) or 1-4 weeks after the initial CCl$_4$ dosing (therapeutic dosing). At the end of the study, mice are sacrificed by opening the chest cavity under isoflurane, blood is drawn via cardiac puncture into EDTA vacutainer tubes and the liver is harvested. Part of the liver is fixed in 10% neutral buffered formalin for subsequent histopathological analysis of inflammation and fibrosis by H&E staining and Picrosirius red staining. The remaining tissue is snap frozen at −80° C. for subseuquent hydroxyproline analysis of total collagen content.

Example B-7: Thioacetamide (TAA) Model of Liver Fibrosis in Mouse

Liver fibrosis is induced in Balb/c or C57Bl/6 mice by intraperitoneal injection of thioacetamide (TAA) at doses ranging from 100-400 mg/kg 3×/week. Doses of TAA are either constant throughout the study period (100-200 mg/kg) or escalate from 100 mg/kg to 400 mg/kg every 2 weeks to increase tolerance to the TAA treatment. Inhibitors are administered orally, intraperitoneally, intravenously or subcutaneously given prophylactically (starting prior to TAA administration) or therapeutically (3-6 weeks after initiation of TAA administration). Liver fibrosis is studied 8-12 weeks after initiation of TAA. At the end of the study, mice are sacrificed by opening the chest cavity under isoflurane, blood is drawn via cardiac puncture into EDTA vacutainer tubes and the liver is harvested. Part of the liver is fixed in 10% neutral buffered formalin for subsequent histopathological analysis of inflammation and fibrosis by H&E staining and picrosirius red staining. Unstained histology sections are also assessed using 2 photon fluorescence and second-harmonic generation imaging. The remaining tissue is snap frozen at −80° C. for subsequent hydroxyproline analysis of total collagen content or mRNA analyses. Serum is collected for analysis of liver biochemistries (ALT, AST, ALP, and bilirubin) as a measure of liver function.

Example B-8: Mouse Model of NASH Induced Through a Choline Deficient, Amino-Acid Defined (CDAA) Diet Supplemented with High Fat Content Liver fibrosis is induced by feeding C57Bl/6 mice a choline-deficient L-amino acid-defined high-fat diet (CDAAHFD) containing 60% kcal % fat and 0.1% methionine (Research Diets C/N A06071302) starting at 6 weeks of age. Once on diet for 4-6 weeks of age, mice are screened for and those with abnormally elevated bilirubin levels are excluded. Remaining mice are assigned to groups and dosing initiated. Inhibitors are administered orally, intraperitoneally, intravenously or subcutaneously at 30-100 mg/kg/day for an additional 8-12 weeks. At the end of the study, mice are sacrificed by opening the chest cavity under isoflurane, blood is drawn via cardiac puncture into EDTA vacutainer tubes and the liver is harvested. Part of the liver is fixed in 10% neutral buffered formalin for subsequent histopathological analysis of inflammation and fibrosis by H&E, trichrome and/or Picrosirius red staining. The remaining tissue is snap frozen at −80° C. for subsequent hydroxyproline analysis of total collagen content, total cholesterol, liver triglyceride and/or mRNA analyses.

The examples and embodiments described herein are for illustrative purposes only and various modifications or changes suggested to persons skilled in the art are to be included within the spirit and purview of this application and scope of the appended claims.

What is claimed is:

1. A compound of Formula (I), or a pharmaceutically acceptable salt, or solvate thereof:

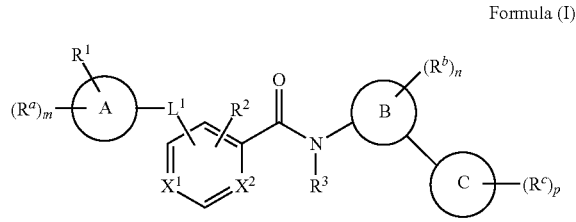

Formula (I)

wherein,
ring A is a phenyl, 6-membered heteroaryl, or a 5-membered heteroaryl;
each $R^a$ is independently H, D, halogen, —CN, —OR$^5$, —SR$^5$, —S(=O)R$^4$, —S(=O)$_2$R$^4$, —S(=O)$_2$N(R$^5$)$_2$, —NR$^5$S(=O)$_2$R$^4$, —C(=O)R$^4$, —OC(=O)R$^4$, —CO$_2$R$^5$, —OCO$_2$R$^4$, —N(R$^5$)$_2$, —OC(=O)N(R$^5$)$_2$, —C(=O)N(R$^5$)$_2$, —NR$^5$C(=O)R$^4$, —NR$^5$C(=O)OR$^4$, —NR$^5$C(=O)N(R$^5$)$_2$, substituted or unsubstituted C$_1$-C$_6$alkyl, substituted or unsubstituted C$_1$-C$_6$fluoroalkyl, substituted or unsubstituted C$_1$-C$_6$deuteroalkyl, substituted or unsubstituted C$_1$-C$_6$heteroalkyl, substituted or unsubstituted C$_3$-C$_6$cycloalkyl;
m is 0, 1, 2, or 3;

R¹ is H, D, halogen, —CN, —OR⁵, —SR⁵, —S(=O)R⁴, —S(=O)₂R⁴, —N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, or substituted or unsubstituted —C₁-C₄alkylene-N(R⁵)₂;

L¹ is linker that is —X²—, L², -L²-X²—, —X²-L³-, or -L²-X²-L³-;

X² is —O—, —S—, —S(=O)—, —S(=O)₂—, —S(=O)₂NR⁶—, —C(=O)—, —C(=O)O—, —C(=O)NR⁶—, —OC(=O)NR⁶—, —NR⁶C(=O)O—, —NR⁶C(=O)NR⁶—, —OC(=O)—, —NR⁶C(=O)—, —NR⁶S(=O)₂—, or —NR⁶—;

R⁶ is H, C₁-C₆alkyl, C₁-C₆fluoroalkyl, or C₁-C₆deuteroalkyl;

L² is substituted or unsubstituted C₁-C₄alkylene, substituted or unsubstituted C₂-C₄alkenylene or substituted or unsubstituted C₂-C₄alkynylene;

L³ is C₁-C₄alkylene;

X¹ is CR² or N;

X² is CR² or N;

each R² is independently H, D, halogen, —CN, —OR⁵, —SR⁵, —S(=O)R⁴, —S(=O)₂R⁴, —N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, substituted or unsubstituted C₃-C₆cycloalkyl;

R³ is H, substituted or unsubstituted C₁-C₆alkyl, substituted or unsubstituted C₁-C₆fluoroalkyl, or substituted or unsubstituted C₁-C₆deuteroalkyl;

ring B is pyridinyl;

each Rᵇ is independently H, D, halogen, —CN, —OR⁵, —SR⁵, —S(=O)R⁴, —S(=O)₂R⁴, —S(=O)₂N(R⁵)₂, —NR⁵S(=O)₂R⁴, —C(=O)R⁴, —OC(=O)R⁴, —CO₂R⁵, —OCO₂R⁴, —N(R⁵)₂, —OC(=O)N(R⁵)₂, —NR⁵C(=O)R⁴, —NR²C(=O)OR⁴, —C(=O)N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, substituted or unsubstituted C₃-C₆cycloalkyl;

n is 0, 1, 2, 3, or 4;

ring C is triazolyl;

each Rᶜ is independently H, D, halogen, —CN, —OR⁵, —SR⁵, —S(=O)R⁴, —S(=O)₂R⁴, —S(=O)₂N(R⁵)₂, —NR⁵S(=O)₂R⁴, —C(=O)R⁴, —OC(=O)R⁴, —CO₂R⁵, —OCO₂R⁴, —N(R⁵)₂, —OC(=O)N(R⁵)₂, —NR⁵C(=O)R⁴, —NR⁵C(=O)OR⁴, —C(=O)N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, or substituted or unsubstituted C₃-C₆cycloalkyl;

p is 0, 1, 2, or 3;

each R⁴ is independently selected from C₁-C₆alkyl, C₁-C₆fluoroalkyl, C₁-C₆deuteroalkyl, C₁-C₆heteroalkyl, substituted or unsubstituted C₃-C₁₀cycloalkyl, substituted or unsubstituted C₂-C₁₀heterocycloalkyl, substituted or unsubstituted aryl, substituted or unsubstituted benzyl and substituted or unsubstituted heteroaryl;

each R⁵ is independently selected from H, C₁-C₆alkyl, C₁-C₆fluoroalkyl, C₁-C₆deuteroalkyl, C₁-C₆heteroalkyl, substituted or unsubstituted C₃-C₁₀cycloalkyl, substituted or unsubstituted C₂-C₁₀heterocycloalkyl, substituted or unsubstituted aryl, substituted or unsubstituted benzyl and substituted or unsubstituted heteroaryl; or two R⁵ on the same N atom are taken together with the N atom to which they are attached to a substituted or unsubstituted N-containing heterocycle.

2. The compound of claim 1, or a pharmaceutically acceptable salt, or solvate thereof, wherein:

ring A is phenyl, pyridinyl, pyrimidinyl, pyrazinyl, pyridazinyl, or triazinyl; or ring A is triazolyl, imidazolyl, pyrazolyl, tetrazolyl, furyl, thienyl, isoxazolyl, thiazolyl, oxazolyl, isothiazolyl, pyrrolyl, oxadiazolyl, thiadiazolyl, or furazanyl.

3. The compound of claim 1, or a pharmaceutically acceptable salt, or solvate thereof, wherein:

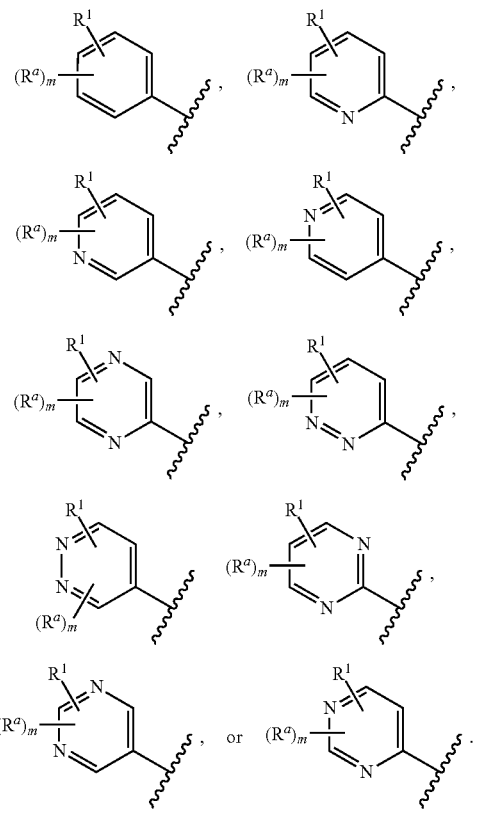

4. The compound of claim 1, or a pharmaceutically acceptable salt, or solvate thereof, wherein:

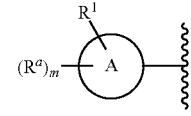

is

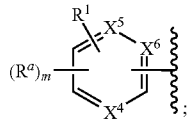

X⁴ is N or CRᵃ;
X⁵ is N or CRᵃ;
X⁶ is N or CRᵃ.

5. The compound of claim 1, or a pharmaceutically acceptable salt, or solvate thereof, wherein:
   each $R^a$ is independently selected from the group consisting of H, D, F, Cl, Br, —CN, —OH, —OCH₃, —OCF₃, —CH₃, —CH₂F, —CHF₂, —CF₃, —CD₃, —OCD₃, cyclopropyl, cyclobutyl, cyclopentyl, and cyclohexyl.

6. The compound of claim 1, or a pharmaceutically acceptable salt, or solvate thereof, wherein:
   $R^1$ is H, D, F, Cl, Br, —CN, —OH, —OCH₃, —OCH₂CH₃, —OCF₃, —OCH₂CF₃, —CH₃, —CH₂CH₃, —CH₂F, —CHF₂, —CF₃, —CH₂CH₂F, —CH₂CHF₂, —CH₂CF₃, —CD₃, —OCD₃, —CH₂NH₂, CD₂NH₂, or CF₂NH₂.

7. The compound of claim 1, or a pharmaceutically acceptable salt, or solvate thereof, wherein:
   $L^2$ is —CH₂—, —CH=CH—, —C≡C—; and
   $L^3$ is —CH₂—.

8. The compound of claim 1, or a pharmaceutically acceptable salt, or solvate thereof, wherein:
   $L^1$ is —X²—, L², -L²-X²—, or —X²-L³-.

9. The compound of claim 8, or a pharmaceutically acceptable salt, or solvate thereof, wherein:
   $X^2$ is —O—, —S—, —S(=O)—, —S(=O)₂—, —C(=O)—, —C(=O)NR⁶—, —NR⁶C(=O)—, or —NR⁶—.

10. The compound of claim 1, or a pharmaceutically acceptable salt, or solvate thereof, wherein:
    $L^1$ is —O—, —O—CH₂—, —CH₂—, —CH=CH—, —C≡C—, —C(=O)—, —C(=O)NHCH₂—, —NHC(=O)—, —C(=O)NH—, or —NHC(=O)CH₂—.

11. The compound of claim 1, or a pharmaceutically acceptable salt, or solvate thereof, wherein:

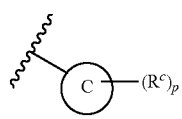

is

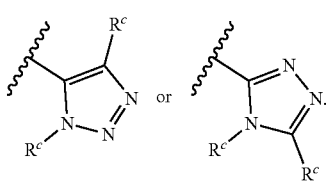

12. The compound of claim 1, or a pharmaceutically acceptable salt, or solvate thereof, wherein:

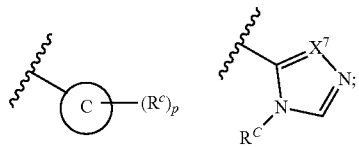

and
$X^7$ is N.

13. The compound of claim 1, wherein the compound of Formula (I) has the following structure of Formula (III), or a pharmaceutically acceptable salt, or solvate thereof:

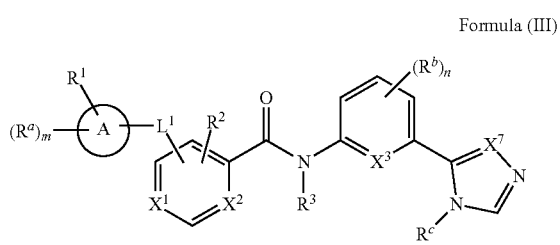

Formula (III)

wherein,
$X^1$ is CR² or N;
$X^2$ is CR² or N;
$X^3$ is N; and
$X^7$ is N.

14. The compound of claim 1, wherein the compound has the structure of Formula (IV), or a pharmaceutically acceptable salt, or solvate thereof:

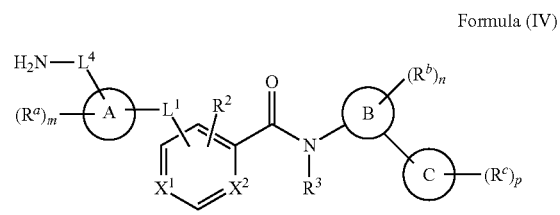

Formula (IV)

wherein,
ring A is a phenyl, 6-membered heteroaryl, or a 5-membered heteroaryl;
   each $R^a$ is independently H, D, halogen, —CN, —OR⁵, —SR⁵, —S(=O)R⁴, —S(=O)₂R⁴, —S(=O)₂N(R⁵)₂, —NR⁵S(=O)₂R⁴, —C(=O)R⁴, —OC(=O)R⁴, —CO₂R⁵, —OCO₂R⁴, —N(R⁵)₂, —OC(=O)N(R⁵)₂, —C(=O)N(R⁵)₂, —NR⁵C(=O)R⁴, —NR⁵C(=O)OR⁴, —NR⁵C(=O)N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, substituted or unsubstituted C₃-C₆cycloalkyl;
m is 0, 1, 2, or 3;
$L^4$ is C₁-C₄alkylene, C₁-C₄fluoroalkylene, or C₁-C₄deuteroalkylene;
$L^1$ is linker that is —X²—, L², -L²-X²—, —X²-L³-, or -L²-X²-L³-;
$X^2$ is —O—, —S—, —S(=O)—, —S(=O)₂—, —S(=O)₂NR⁶—, —C(=O)—, —C(=O)O—, —C(=O)NR⁶—, —OC(=O)NR⁶—, —NR⁶C (=O)O—, —NR⁶C(=O)NR⁶—, —OC(=O)—, —NR⁶C(=O)—, —NR⁶S(=O)₂—, or —NR⁶—;
R⁶ is H, C₁-C₆alkyl, C₁-C₆fluoroalkyl, or C₁-C₆deuteroalkyl;
L² is substituted or unsubstituted C₁-C₄alkylene, substituted or unsubstituted C₂-C₄alkenylene or substituted or unsubstituted C₂-C₄alkynylene;
L³ is C₁-C₄alkylene;
X¹ is CR² or N;
X² is CR² or N;
each R² is independently H, D, halogen, —CN, —OR⁵, —SR⁵, —S(=O)R⁴, —S(=O)₂R⁴, —N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, substituted or unsubstituted C₃-C₆cycloalkyl;
R³ is H, substituted or unsubstituted C₁-C₆alkyl, substituted or unsubstituted C₁-C₆fluoroalkyl, or substituted or unsubstituted C₁-C₆deuteroalkyl;
ring B is pyridinyl;
each Rᵇ is independently H, D, halogen, —CN, —OR⁵, —SR⁵, —S(=O)R⁴, —S(=O)₂R⁴, —S(=O)₂N(R⁵)₂, —NR⁵S(=O)₂R⁴, —C(=O)R⁴, —OC(=O)R⁴, —CO₂R⁵, —OCO₂R⁴, —N(R⁵)₂, —OC(=O)N(R⁵)₂, —NR⁵C(=O)R⁴, —NR²C(=O)OR⁴, —C(=O)N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, substituted or unsubstituted C₃-C₆cycloalkyl;
n is 0, 1, 2, 3, or 4;
ring C is triazolyl;
each Rᶜ is independently H, D, halogen, —CN, —OR⁵, —SR⁵, —S(=O)R⁴, —S(=O)₂R⁴, —S(=O)₂N(R⁵)₂, —NR⁵S(=O)₂R⁴, —C(=O)R⁴, —OC(=O)R⁴, —CO₂R⁵, —OCO₂R⁴, —N(R⁵)₂, —OC(=O)N(R⁵)₂, —NR⁵C(=O)R⁴, —NR⁵C(=O)OR⁴, —C(=O)N(R⁵)₂, substituted or unsubstituted C₁-C₆alkyl, substituted or unsubstituted C₁-C₆fluoroalkyl, substituted or unsubstituted C₁-C₆deuteroalkyl, substituted or unsubstituted C₁-C₆heteroalkyl, or substituted or unsubstituted C₃-C₆cycloalkyl;
p is 0, 1, 2, or 3;
each R⁴ is independently selected from C₁-C₆alkyl, C₁-C₆fluoroalkyl, C₁-C₆deuteroalkyl, C₁-C₆heteroalkyl, substituted or unsubstituted C₃-C₁₀cycloalkyl, substituted or unsubstituted C₂-C₁₀heterocycloalkyl, substituted or unsubstituted aryl, substituted or unsubstituted benzyl and substituted or unsubstituted heteroaryl;
each R⁵ is independently selected from H, C₁-C₆alkyl, C₁-C₆fluoroalkyl, C₁-C₆deuteroalkyl, C₁-C₆heteroalkyl, substituted or unsubstituted C₃-C₁₀cycloalkyl, substituted or unsubstituted C₂-C₁₀heterocycloalkyl, substituted or unsubstituted aryl, substituted or unsubstituted benzyl and substituted or unsubstituted heteroaryl; or two R⁵ on the same N atom are taken together with the N atom to which they are attached to a substituted or unsubstituted N-containing heterocycle.

15. The compound of claim 1, wherein the compound is:
N-(6-(4-Isopropyl-4H-1,2,4-triazol-3-yl)pyridin-2-yl)-3-phenoxybenzamide (Compound 1-1);
N-(6-(4-Isopropyl-4H-1,2,4-triazol-3-yl)pyridin-2-yl)-3-(pyridin-2-yloxy)benzamide (Compound 1-2);
N-(6-(4-Isopropyl-4H-1,2,4-triazol-3-yl)pyridin-2-yl)-3-(pyridin-3-yloxy)benzamide (Compound 1-3);
N-(6-(4-Isopropyl-4H-1,2,4-triazol-3-yl)pyridin-2-yl)-3-(pyridin-4-yloxy)benzamide (Compound 1-4);
N-(6-(4-isopropyl-4H-1,2,4-triazol-3-yl)pyridin-2-yl)-3-(pyrimidin-4-yloxy)benzamide (Compound 1-5);
N-(6-(4-Isopropyl-4H-1,2,4-triazol-3-yl)pyridin-2-yl)-3-(pyrimidin-5-yloxy)benzamide (Compound 1-6);
N-(6-(4-Isopropyl-4H-1,2,4-triazol-3-yl)pyridin-2-yl)-3-(pyrimidin-2-yloxy)benzamide (Compound 1-7);
N-(6-(4-Isopropyl-4H-1,2,4-triazol-3-yl)pyridin-2-yl)-3-(pyrazin-2-yloxy)benzamide (Compound 1-8);
N-(6-(4-Isopropyl-4H-1,2,4-triazol-3-yl)pyridin-2-yl)-3-(pyridazin-3-yloxy)benzamide (Compound 1-9);
N-(6-(4-Isopropyl-4H-1,2,4-triazol-3-yl)pyridin-2-yl)-3-(pyridazin-4-yloxy)benzamide (Compound 1-10);
3-((6-Cyclopropylpyridin-2-yl)oxy)-N-(6-(4-isopropyl-4H-1,2,4-triazol-3-yl)pyridin-2-yl)benzamide (Compound 1-11);
N-(6-(4-Isopropyl-4H-1,2,4-triazol-3-yl)pyridin-2-yl)-3-((6-(trifluoromethyl)pyridin-2-yl)oxy)benzamide (Compound 1-12);
N-(6-(4-Isopropyl-4H-1,2,4-triazol-3-yl)pyridin-2-yl)-3-((6-methoxypyridin-2-yl)oxy)benzamide (Compound 1-13);
N-(6-(4-Isopropyl-4H-1,2,4-triazol-3-yl)pyridin-2-yl)-3-((6-(pyrrolidin-1-yl)pyridin-2-yl)oxy)benzamide (Compound 1-14);
3-((6-(Dimethylamino)pyridin-2-yl)oxy)-N-(6-(4-isopropyl-4H-1,2,4-triazol-3-yl)pyridin-2-yl)benzamide (Compound 1-15);
3-((6-(Dimethylamino)pyridin-3-yl)oxy)-N-(6-(4-isopropyl-4H-1,2,4-triazol-3-yl)pyridin-2-yl)benzamide (Compound 1-16);
N-(6-(4-Isopropyl-4H-1,2,4-triazol-3-yl)pyridin-2-yl)-3-((5,6,7,8-tetrahydro-1,8-naphthyridin-2-yl)oxy)benzamide (Compound 1-17);
6-(3-((6-(4-Isopropyl-4H-1,2,4-triazol-3-yl)pyridin-2-yl)carbamoyl)phenoxy)picolinic acid (Compound 1-18);
3-((5-Cyclopropylpyridin-2-yl)oxy)-N-(6-(4-isopropyl-4H-1,2,4-triazol-3-yl)pyridin-2-yl)benzamide (Compound 1-19);
N-(6-(4-Isopropyl-4H-1,2,4-triazol-3-yl)pyridin-2-yl)-3-((5-(trifluoromethyl)pyridin-2-yl)oxy)benzamide (Compound 1-20);
N-(6-(4-Isopropyl-4H-1,2,4-triazol-3-yl)pyridin-2-yl)-3-((5-methoxypyridin-2-yl)oxy)benzamide (Compound 1-21);
6-(3-((6-(4-Isopropyl-4H-1,2,4-triazol-3-yl)pyridin-2-yl)carbamoyl)phenoxy)nicotinic acid (Compound 1-22);
3-((4-Cyano-6-(trifluoromethyl)pyridin-2-yl)oxy)-N-(6-(4-isopropyl-4H-1,2,4-triazol-3-yl)pyridin-2-yl)benzamide (Compound 1-23);
2-(3-((6-(4-Isopropyl-4H-1,2,4-triazol-3-yl)pyridin-2-yl)carbamoyl)phenoxy)-6-(trifluoromethyl)isonicotinic acid (Compound 1-24);
3-((2-Cyclopropylpyrimidin-4-yl)oxy)-N-(6-(4-isopropyl-4H-1,2,4-triazol-3-yl)pyridin-2-yl)benzamide (Compound 1-25);
N-(6-(4-Isopropyl-4H-1,2,4-triazol-3-yl)pyridin-2-yl)-3-((2-(trifluoromethyl)pyrimidin-4-yl)oxy)benzamide (Compound 1-26);
N-(6-(4-Isopropyl-4H-1,2,4-triazol-3-yl)pyridin-2-yl)-3-((2-methoxypyrimidin-4-yl)oxy)benzamide (Compound 1-27);

N-(6-(4-Isopropyl-4H-1,2,4-triazol-3-yl)pyridin-2-yl)-3-((2-(2-(pyrrolidin-1-yl)ethoxy)pyrimidin-4-yl)oxy) benzamide (Compound 1-28);

N-(6-(4-Isopropyl-4H-1,2,4-triazol-3-yl)pyridin-2-yl)-3-((2-(pyrrolidin-1-yl)pyrimidin-4-yl)oxy)benzamide (Compound 1-29);

4-(3-((6-(4-Isopropyl-4H-1,2,4-triazol-3-yl)pyridin-2-yl) carbamoyl)phenoxy)pyrimidine-2-carboxylic acid (Compound 1-30);

3-((2-Cyclopropylpyrimidin-5-yl)oxy)-N-(6-(4-isopropyl-4H-1,2,4-triazol-3-yl)pyridin-2-yl)benzamide (Compound 1-31);

N-(6-(4-Isopropyl-4H-1,2,4-triazol-3-yl)pyridin-2-yl)-3-((2-(trifluoromethyl)pyrimidin-5-yl)oxy)benzamide (Compound 1-32);

N-(6-(4-Isopropyl-4H-1,2,4-triazol-3-yl)pyridin-2-yl)-3-((2-methoxypyrimidin-5-yl)oxy)benzamide (Compound 1-33);

N-(6-(4-Isopropyl-4H-1,2,4-triazol-3-yl)pyridin-2-yl)-3-((2-(2-(pyrrolidin-1-yl)ethoxy)pyrimidin-5-yl)oxy) benzamide (Compound 1-34);

N-(6-(4-Isopropyl-4H-1,2,4-triazol-3-yl)pyridin-2-yl)-3-((2-(pyrrolidin-1-yl)pyrimidin-5-yl)oxy)benzamide (Compound 1-35);

5-(3-((6-(4-Isopropyl-4H-1,2,4-triazol-3-yl)pyridin-2-yl) carbamoyl)phenoxy)pyrimidine-2-carboxylic acid (Compound 1-36);

N-(6-(4-Isopropyl-4H-1,2,4-triazol-3-yl)pyridin-2-yl)-3-(phenylamino)benzamide (Compound 1-37);

N-(6-(4-Isopropyl-4H-1,2,4-triazol-3-yl)pyridin-2-yl)-3-(pyridin-2-ylamino)benzamide (Compound 1-38);

N-(6-(4-Isopropyl-4H-1,2,4-triazol-3-yl)pyridin-2-yl)-3-(pyridin-3-ylamino)benzamide (Compound 1-39);

N-(6-(4-Isopropyl-4H-1,2,4-triazol-3-yl)pyridin-2-yl)-3-(pyridin-4-ylamino)benzamide (Compound 1-40);

N-(6-(4-Isopropyl-4H-1,2,4-triazol-3-yl)pyridin-2-yl)-3-(pyrimidin-4-ylamino)benzamide (Compound 1-41);

N-(6-(4-Isopropyl-4H-1,2,4-triazol-3-yl)pyridin-2-yl)-3-(pyrimidin-5-ylamino)benzamide (Compound 1-42);

N-(6-(4-Isopropyl-4H-1,2,4-triazol-3-yl)pyridin-2-yl)-3-(pyrimidin-2-ylamino)benzamide (Compound 1-43);

N-(6-(4-Isopropyl-4H-1,2,4-triazol-3-yl)pyridin-2-yl)-3-(pyrazin-2-ylamino)benzamide (Compound 1-44);

N-(6-(4-Isopropyl-4H-1,2,4-triazol-3-yl)pyridin-2-yl)-3-(pyridazin-3-ylamino)benzamide (Compound 1-45);

N-(6-(4-Isopropyl-4H-1,2,4-triazol-3-yl)pyridin-2-yl)-3-(pyridazin-4-ylamino)benzamide (Compound 1-46);

3-((6-Cyclopropylpyridin-2-yl)amino)-N-(6-(4-isopropyl-4H-1,2,4-triazol-3-yl)pyridin-2-yl)benzamide (Compound 1-47);

N-(6-(4-Isopropyl-4H-1,2,4-triazol-3-yl)pyridin-2-yl)-3-((6-(trifluoromethyl)pyridin-2-yl)amino)benzamide (Compound 1-48);

N-(6-(4-Isopropyl-4H-1,2,4-triazol-3-yl)pyridin-2-yl)-3-((6-methoxypyridin-2-yl)amino)benzamide (Compound 1-49);

N-(6-(4-Isopropyl-4H-1,2,4-triazol-3-yl)pyridin-2-yl)-3-((6-(pyrrolidin-1-yl)pyridin-2-yl)amino)benzamide (Compound 1-50);

N-(6-(4-Isopropyl-4H-1,2,4-triazol-3-yl)pyridin-2-yl)-3-((5,6,7,8-tetrahydro-1,8-naphthyridin-2-yl)amino)benzamide (Compound 1-51);

6-((3-((6-(4-Isopropyl-4H-1,2,4-triazol-3-yl)pyridin-2-yl)carbamoyl)phenyl)amino)picolinic acid (Compound 1-52);

3-((5-Cyclopropylpyridin-2-yl)amino)-N-(6-(4-isopropyl-4H-1,2,4-triazol-3-yl)pyridin-2-yl)benzamide (Compound 1-53);

N-(6-(4-Isopropyl-4H-1,2,4-triazol-3-yl)pyridin-2-yl)-3-((5-(trifluoromethyl)pyridin-2-yl)amino)benzamide (Compound 1-54);

N-(6-(4-Isopropyl-4H-1,2,4-triazol-3-yl)pyridin-2-yl)-3-((5-methoxypyridin-2-yl)amino)benzamide (Compound 1-55);

6-((3-((6-(4-Isopropyl-4H-1,2,4-triazol-3-yl)pyridin-2-yl)carbamoyl)phenyl)amino)nicotinic acid (Compound 1-56);

3-((2-Cyclopropylpyrimidin-4-yl)amino)-N-(6-(4-isopropyl-4H-1,2,4-triazol-3-yl)pyridin-2-yl)benzamide (Compound 1-57);

N-(6-(4-Isopropyl-4H-1,2,4-triazol-3-yl)pyridin-2-yl)-3-((2-(trifluoromethyl)pyrimidin-4-yl)amino)benzamide (Compound 1-58);

N-(6-(4-Isopropyl-4H-1,2,4-triazol-3-yl)pyridin-2-yl)-3-((2-methoxypyrimidin-4-yl)amino)benzamide (Compound 1-59);

N-(6-(4-Isopropyl-4H-1,2,4-triazol-3-yl)pyridin-2-yl)-3-((2-(2-(pyrrolidin-1-yl)ethoxy)pyrimidin-4-yl)amino) benzamide (Compound 1-60);

N-(6-(4-Isopropyl-4H-1,2,4-triazol-3-yl)pyridin-2-yl)-3-((2-(pyrrolidin-1-yl)pyrimidin-4-yl)amino)benzamide (Compound 1-61);

4-((3-((6-(4-Isopropyl-4H-1,2,4-triazol-3-yl)pyridin-2-yl)carbamoyl)phenyl)amino)pyrimidine-2-carboxylic acid (Compound 1-62);

3-((2-Cyclopropylpyrimidin-5-yl)amino)-N-(6-(4-isopropyl-4H-1,2,4-triazol-3-yl)pyridin-2-yl)benzamide (Compound 1-63);

N-(6-(4-Isopropyl-4H-1,2,4-triazol-3-yl)pyridin-2-yl)-3-((2-(trifluoromethyl)pyrimidin-5-yl)amino)benzamide (Compound 1-64);

N-(6-(4-Isopropyl-4H-1,2,4-triazol-3-yl)pyridin-2-yl)-3-((2-methoxypyrimidin-5-yl)amino)benzamide (Compound 1-65);

N-(6-(4-Isopropyl-4H-1,2,4-triazol-3-yl)pyridin-2-yl)-3-((2-(2-(pyrrolidin-1-yl)ethoxy)pyrimidin-5-yl)amino) benzamide (Compound 1-66);

N-(6-(4-Isopropyl-4H-1,2,4-triazol-3-yl)pyridin-2-yl)-3-((2-(pyrrolidin-1-yl)pyrimidin-5-yl)amino)benzamide (Compound 1-67);

5-((3-((6-(4-Isopropyl-4H-1,2,4-triazol-3-yl)pyridin-2-yl)carbamoyl)phenyl)amino)pyrimidine-2-carboxylic acid (Compound 1-68);

3-((1H-Pyrrol-2-yl)amino)-N-(6-(4-isopropyl-4H-1,2,4-triazol-3-yl)pyridin-2-yl)benzamide (Compound 1-69);

N-(6-(4-Isopropyl-4H-1,2,4-triazol-3-yl)pyridin-2-yl)-3-((1-methyl-1H-pyrrol-2-yl)amino)benzamide (Compound 1-70);

3-(Furan-2-ylamino)-N-(6-(4-isopropyl-4H-1,2,4-triazol-3-yl)pyridin-2-yl)benzamide (Compound 1-71);

N-(6-(4-Isopropyl-4H-1,2,4-triazol-3-yl)pyridin-2-yl)-3-(thiophen-2-ylamino)benzamide (Compound 1-72);

N-(6-(4-Isopropyl-4H-1,2,4-triazol-3-yl)pyridin-2-yl)-3-((1-methyl-1H-pyrazol-5-yl)amino)benzamide (Compound 1-73);

N-(6-(4-Isopropyl-4H-1,2,4-triazol-3-yl)pyridin-2-yl)-3-((1-methyl-1H-pyrazol-3-yl)amino)benzamide (Compound 1-74);

3-((1H-Imidazol-5-yl)amino)-N-(6-(4-isopropyl-4H-1,2,4-triazol-3-yl)pyridin-2-yl)benzamide (Compound 1-75);

N-(6-(4-Isopropyl-4H-1,2,4-triazol-3-yl)pyridin-2-yl)-3-((1-methyl-1H-imidazol-5-yl)amino)benzamide (Compound 1-76);

N-(6-(4-Isopropyl-4H-1,2,4-triazol-3-yl)pyridin-2-yl)-3-((1-methyl-1H-imidazol-4-yl)amino)benzamide (Compound 1-77);

N-(6-(4-Isopropyl-4H-1,2,4-triazol-3-yl)pyridin-2-yl)-3-(oxazol-4-ylamino)benzamide (Compound 1-78);

N-(6-(4-Isopropyl-4H-1,2,4-triazol-3-yl)pyridin-2-yl)-3-(oxazol-5-ylamino)benzamide (Compound 1-79);

N-(6-(4-Isopropyl-4H-1,2,4-triazol-3-yl)pyridin-2-yl)-3-(isoxazol-5-ylamino)benzamide (Compound 1-80);

N-(6-(4-Isopropyl-4H-1,2,4-triazol-3-yl)pyridin-2-yl)-3-(isoxazol-3-ylamino)benzamide (Compound 1-81);

3-((1,3,4-Oxadiazol-2-yl)amino)-N-(6-(4-isopropyl-4H-1,2,4-triazol-3-yl)pyridin-2-yl)benzamide (Compound 1-82);

N-(6-(4-Isopropyl-4H-1,2,4-triazol-3-yl)pyridin-2-yl)-3-(thiazol-5-ylamino)benzamide (Compound 1-83);

3-((1,3,4-Thiadiazol-2-yl)amino)-N-(6-(4-isopropyl-4H-1,2,4-triazol-3-yl)pyridin-2-yl)benzamide (Compound 1-84);

N-(6-(4-Isopropyl-4H-1,2,4-triazol-3-yl)pyridin-2-yl)-3-(phenylthio)benzamide (Compound 1-85);N-(6-(4-Isopropyl-4H-1,2,4-triazol-3-yl)pyridin-2-yl)-3-(pyridin-2-ylthio)benzamide (Compound 1-86);

N-(6-(4-Isopropyl-4H-1,2,4-triazol-3-yl)pyridin-2-yl)-3-(pyridin-3-ylthio)benzamide (Compound 1-87);

N-(6-(4-Isopropyl-4H-1,2,4-triazol-3-yl)pyridin-2-yl)-3-(pyridin-4-ylthio)benzamide (Compound 1-88);

N-(6-(4-Isopropyl-4H-1,2,4-triazol-3-yl)pyridin-2-yl)-3-(pyrimidin-4-ylthio)benzamide (Compound 1-89);

N-(6-(4-Isopropyl-4H-1,2,4-triazol-3-yl)pyridin-2-yl)-3-(pyrimidin-5-ylthio)benzamide (Compound 1-90);

N-(6-(4-Isopropyl-4H-1,2,4-triazol-3-yl)pyridin-2-yl)-3-(pyrimidin-2-ylthio)benzamide (Compound 1-91);

N-(6-(4-Isopropyl-4H-1,2,4-triazol-3-yl)pyridin-2-yl)-3-(pyrazin-2-ylthio)benzamide (Compound 1-92);

N-(6-(4-Isopropyl-4H-1,2,4-triazol-3-yl)pyridin-2-yl)-3-(pyridazin-3-ylthio)benzamide (Compound 1-93);

N-(6-(4-Isopropyl-4H-1,2,4-triazol-3-yl)pyridin-2-yl)-3-(pyridazin-4-ylthio)benzamide (Compound 1-94);

3-((6-Cyclopropylpyridin-2-yl)thio)-N-(6-(4-isopropyl-4H-1,2,4-triazol-3-yl)pyridin-2-yl)benzamide (Compound 1-95);

N-(6-(4-Isopropyl-4H-1,2,4-triazol-3-yl)pyridin-2-yl)-3-((6-(trifluoromethyl)pyridin-2-yl)thio)benzamide (Compound 1-96);

N-(6-(4-Isopropyl-4H-1,2,4-triazol-3-yl)pyridin-2-yl)-3-((6-methoxypyridin-2-yl)thio)benzamide (Compound 1-97);

N-(6-(4-Isopropyl-4H-1,2,4-triazol-3-yl)pyridin-2-yl)-3-((6-(pyrrolidin-1-yl)pyridin-2-yl)thio)benzamide (Compound 1-98);

N-(6-(4-Isopropyl-4H-1,2,4-triazol-3-yl)pyridin-2-yl)-3-((5,6,7,8-tetrahydro-1,8-naphthyridin-2-yl)thio)benzamide (Compound 1-99);

6-((3-((6-(4-Isopropyl-4H-1,2,4-triazol-3-yl)pyridin-2-yl)carbamoyl)phenyl)thio)picolinic acid (Compound 1-100);

3-((5-Cyclopropylpyridin-2-yl)thio)-N-(6-(4-isopropyl-4H-1,2,4-triazol-3-yl)pyridin-2-yl)benzamide (Compound 1-101);

N-(6-(4-Isopropyl-4H-1,2,4-triazol-3-yl)pyridin-2-yl)-3-((5-(trifluoromethyl)pyridin-2-yl)thio)benzamide (Compound 1-102);

N-(6-(4-Isopropyl-4H-1,2,4-triazol-3-yl)pyridin-2-yl)-3-((5-methoxypyridin-2-yl)thio)benzamide (Compound 1-103);

6-((3-((6-(4-Isopropyl-4H-1,2,4-triazol-3-yl)pyridin-2-yl)carbamoyl)phenyl)thio)nicotinic acid (Compound 1-104);

3-((2-Cyclopropylpyrimidin-4-yl)thio)-N-(6-(4-isopropyl-4H-1,2,4-triazol-3-yl)pyridin-2-yl)benzamide (Compound 1-105);

N-(6-(4-Isopropyl-4H-1,2,4-triazol-3-yl)pyridin-2-yl)-3-((2-(trifluoromethyl)pyrimidin-4-yl)thio)benzamide (Compound 1-106);

N-(6-(4-Isopropyl-4H-1,2,4-triazol-3-yl)pyridin-2-yl)-3-((2-methoxypyrimidin-4-yl)thio)benzamide (Compound 1-107);

N-(6-(4-Isopropyl-4H-1,2,4-triazol-3-yl)pyridin-2-yl)-3-((2-(2-(pyrrolidin-1-yl)ethoxy)pyrimidin-4-yl)thio)benzamide (Compound 1-108);

N-(6-(4-Isopropyl-4H-1,2,4-triazol-3-yl)pyridin-2-yl)-3-((2-(pyrrolidin-1-yl)pyrimidin-4-yl)thio)benzamide (Compound 1-109);

4-((3-((6-(4-Isopropyl-4H-1,2,4-triazol-3-yl)pyridin-2-yl)carbamoyl)phenyl)thio)pyrimidine-2-carboxylic acid (Compound 1-110);

3-((2-Cyclopropylpyrimidin-5-yl)thio)-N-(6-(4-isopropyl-4H-1,2,4-triazol-3-yl)pyridin-2-yl)benzamide (Compound 1-111);

N-(6-(4-Isopropyl-4H-1,2,4-triazol-3-yl)pyridin-2-yl)-3-((2-(trifluoromethyl)pyrimidin-5-yl)thio)benzamide (Compound 1-112);

N-(6-(4-Isopropyl-4H-1,2,4-triazol-3-yl)pyridin-2-yl)-3-((2-methoxypyrimidin-5-yl)thio)benzamide (Compound 1-113);

N-(6-(4-Isopropyl-4H-1,2,4-triazol-3-yl)pyridin-2-yl)-3-((2-(2-(pyrrolidin-1-yl)ethoxy)pyrimidin-5-yl)thio)benzamide (Compound 1-114);

N-(6-(4-Isopropyl-4H-1,2,4-triazol-3-yl)pyridin-2-yl)-3-((2-(pyrrolidin-1-yl)pyrimidin-5-yl)thio)benzamide (Compound 1-115);

5-((3-((6-(4-Isopropyl-4H-1,2,4-triazol-3-yl)pyridin-2-yl)carbamoyl)phenyl)thio)pyrimidine-2-carboxylic acid (Compound 1-116);

N-(6-(4-Isopropyl-4H-1,2,4-triazol-3-yl)pyridin-2-yl)-3-(phenylsulfonyl)benzamide (Compound 1-117);

N-(6-(4-Isopropyl-4H-1,2,4-triazol-3-yl)pyridin-2-yl)-3-(pyridin-2-ylsulfonyl)benzamide (Compound 1-118);

N-(6-(4-Isopropyl-4H-1,2,4-triazol-3-yl)pyridin-2-yl)-3-(pyridin-3-ylsulfonyl)benzamide (Compound 1-119);

N-(6-(4-Isopropyl-4H-1,2,4-triazol-3-yl)pyridin-2-yl)-3-(pyridin-4-ylsulfonyl)benzamide (Compound 1-120);

N-(6-(4-Isopropyl-4H-1,2,4-triazol-3-yl)pyridin-2-yl)-3-(pyrimidin-4-ylsulfonyl)benzamide (Compound 1-121);

N-(6-(4-Isopropyl-4H-1,2,4-triazol-3-yl)pyridin-2-yl)-3-(pyrimidin-5-ylsulfonyl)benzamide (Compound 1-122);

N-(6-(4-Isopropyl-4H-1,2,4-triazol-3-yl)pyridin-2-yl)-3-(pyrimidin-2-ylsulfonyl)benzamide (Compound 1-123);

N-(6-(4-Isopropyl-4H-1,2,4-triazol-3-yl)pyridin-2-yl)-3-(pyrazin-2-ylsulfonyl)benzamide (Compound 1-124);

N-(6-(4-Isopropyl-4H-1,2,4-triazol-3-yl)pyridin-2-yl)-3-(pyridazin-3-ylsulfonyl)benzamide (Compound 1-125);

N-(6-(4-Isopropyl-4H-1,2,4-triazol-3-yl)pyridin-2-yl)-3-(pyridazin-4-ylsulfonyl)benzamide (Compound 1-126);

N¹-(6-(4-Isopropyl-4H-1,2,4-triazol-3-yl)pyridin-2-yl)-N³-phenylisophthalamide (Compound 1-127);

N¹-(6-(4-Isopropyl-4H-1,2,4-triazol-3-yl)pyridin-2-yl)-N³-(pyridin-2-yl)isophthalamide (Compound 1-128);

N¹-(6-(4-Isopropyl-4H-1,2,4-triazol-3-yl)pyridin-2-yl)-N³-(pyridin-3-yl)isophthalamide (Compound 1-129);

N¹-(6-(4-Isopropyl-4H-1,2,4-triazol-3-yl)pyridin-2-yl)-N³-(pyridin-4-yl)isophthalamide (Compound 1-130);

N¹-(6-(4-Isopropyl-4H-1,2,4-triazol-3-yl)pyridin-2-yl)-N³-(pyrimidin-4-yl)isophthalamide (Compound 1-131);

N¹-(6-(4-Isopropyl-4H-1,2,4-triazol-3-yl)pyridin-2-yl)-N³-(pyrimidin-5-yl)isophthalamide (Compound 1-132);

N¹-(6-(4-Isopropyl-4H-1,2,4-triazol-3-yl)pyridin-2-yl)-N³-(pyrimidin-2-yl)isophthalamide (Compound 1-133);

N¹-(6-(4-Isopropyl-4H-1,2,4-triazol-3-yl)pyridin-2-yl)-N³-(pyrazin-2-yl)isophthalamide (Compound 1-134);

N¹-(6-(4-Isopropyl-4H-1,2,4-triazol-3-yl)pyridin-2-yl)-N³-(pyridazin-3-yl)isophthalamide (Compound 1-135);

N¹-(6-(4-Isopropyl-4H-1,2,4-triazol-3-yl)pyridin-2-yl)-N³-(pyridazin-4-yl)isophthalamide (Compound 1-136);

N¹-(6-(4-Isopropyl-4H-1,2,4-triazol-3-yl)pyridin-2-yl)-N³-(1H-pyrrol-2-yl)isophthalamide (Compound 1-137);

N¹-(6-(4-Isopropyl-4H-1,2,4-triazol-3-yl)pyridin-2-yl)-N³-(1-methyl-1H-pyrrol-2-yl)isophthalamide (Compound 1-138);

N¹-(Furan-2-yl)-N³-(6-(4-isopropyl-4H-1,2,4-triazol-3-yl)pyridin-2-yl)isophthalamide (Compound 1-139);

N¹-(6-(4-Isopropyl-4H-1,2,4-triazol-3-yl)pyridin-2-yl)-N³-(thiophen-2-yl)isophthalamide (Compound 1-140);

N¹-(6-(4-Isopropyl-4H-1,2,4-triazol-3-yl)pyridin-2-yl)-N³-(1-methyl-1H-pyrazol-5-yl)isophthalamide (Compound 1-141);

N¹-(6-(4-Isopropyl-4H-1,2,4-triazol-3-yl)pyridin-2-yl)-N³-(1-methyl-1H-pyrazol-3-yl)isophthalamide (Compound 1-142);

N¹-(1H-Imidazol-5-yl)-N³-(6-(4-isopropyl-4H-1,2,4-triazol-3-yl)pyridin-2-yl)isophthalamide (Compound 1-143);

N¹-(6-(4-Isopropyl-4H-1,2,4-triazol-3-yl)pyridin-2-yl)-N³-(1-methyl-1H-imidazol-5-yl)isophthalamide (Compound 1-144);

N¹-(6-(4-Isopropyl-4H-1,2,4-triazol-3-yl)pyridin-2-yl)-N³-(1-methyl-1H-imidazol-4-yl)isophthalamide (Compound 1-145);

N¹-(6-(4-Isopropyl-4H-1,2,4-triazol-3-yl)pyridin-2-yl)-N³-(oxazol-4-yl)isophthalamide (Compound 1-146);

N¹-(6-(4-Isopropyl-4H-1,2,4-triazol-3-yl)pyridin-2-yl)-N³-(oxazol-5-yl)isophthalamide (Compound 1-147);

N¹-(6-(4-Isopropyl-4H-1,2,4-triazol-3-yl)pyridin-2-yl)-N³-(isoxazol-5-yl)isophthalamide (Compound 1-148);

N¹-(6-(4-Isopropyl-4H-1,2,4-triazol-3-yl)pyridin-2-yl)-N³-(isoxazol-3-yl)isophthalamide (Compound 1-149);

N¹-(6-(4-Isopropyl-4H-1,2,4-triazol-3-yl)pyridin-2-yl)-N³-(1,3,4-oxadiazol-2-yl)isophthalamide (Compound 1-150);

N¹-(6-(4-Isopropyl-4H-1,2,4-triazol-3-yl)pyridin-2-yl)-N³-(thiazol-5-yl)isophthalamide (Compound 1-151);

N¹-(6-(4-Isopropyl-4H-1,2,4-triazol-3-yl)pyridin-2-yl)-N³-(1,3,4-thiadiazol-2-yl)isophthalamide (Compound 1-152);

3-Benzamido-N-(6-(4-isopropyl-4H-1,2,4-triazol-3-yl)pyridin-2-yl)benzamide (Compound 1-153);

N-(3-((6-(4-Isopropyl-4H-1,2,4-triazol-3-yl)pyridin-2-yl)carbamoyl)phenyl)picolinamide (Compound 1-154);

N-(3-((6-(4-Isopropyl-4H-1,2,4-triazol-3-yl)pyridin-2-yl)carbamoyl)phenyl)nicotinamide (Compound 1-155);

N-(3-((6-(4-Isopropyl-4H-1,2,4-triazol-3-yl)pyridin-2-yl)carbamoyl)phenyl)isonicotinamide (Compound 1-156);

N-(3-((6-(4-Isopropyl-4H-1,2,4-triazol-3-yl)pyridin-2-yl)carbamoyl)phenyl)pyrimidine-4-carboxamide (Compound 1-157);

N-(3-((6-(4-Isopropyl-4H-1,2,4-triazol-3-yl)pyridin-2-yl)carbamoyl)phenyl)pyrimidine-5-carboxamide (Compound 1-158);

N-(3-((6-(4-Isopropyl-4H-1,2,4-triazol-3-yl)pyridin-2-yl)carbamoyl)phenyl)pyrimidine-2-carboxamide (Compound 1-159);

N-(3-((6-(4-Isopropyl-4H-1,2,4-triazol-3-yl)pyridin-2-yl)carbamoyl)phenyl)pyrazine-2-carboxamide (Compound 1-160);

N-(3-((6-(4-Isopropyl-4H-1,2,4-triazol-3-yl)pyridin-2-yl)carbamoyl)phenyl)pyridazine-3-carboxamide (Compound 1-161);

N-(3-((6-(4-Isopropyl-4H-1,2,4-triazol-3-yl)pyridin-2-yl)carbamoyl)phenyl)pyridazine-4-carboxamide (Compound 1-162);

N-(3-((6-(4-Isopropyl-4H-1,2,4-triazol-3-yl)pyridin-2-yl)carbamoyl)phenyl)-1H-pyrrole-2-carboxamide (Compound 1-163);

N-(3-((6-(4-Isopropyl-4H-1,2,4-triazol-3-yl)pyridin-2-yl)carbamoyl)phenyl)-1-methyl-1H-pyrrole-2-carboxamide (Compound 1-164);

N-(3-((6-(4-Isopropyl-4H-1,2,4-triazol-3-yl)pyridin-2-yl)carbamoyl)phenyl)furan-2-carboxamide (Compound 1-165);

N-(3-((6-(4-Isopropyl-4H-1,2,4-triazol-3-yl)pyridin-2-yl)carbamoyl)phenyl)thiophene-2-carboxamide (Compound 1-166);

N-(3-((6-(4-Isopropyl-4H-1,2,4-triazol-3-yl)pyridin-2-yl)carbamoyl)phenyl)-1-methyl-1H-pyrazole-5-carboxamide (Compound 1-167);

N-(3-((6-(4-Isopropyl-4H-1,2,4-triazol-3-yl)pyridin-2-yl)carbamoyl)phenyl)-1-methyl-1H-pyrazole-3-carboxamide (Compound 1-168);

N-(3-((6-(4-Isopropyl-4H-1,2,4-triazol-3-yl)pyridin-2-yl)carbamoyl)phenyl)-1H-imidazole-5-carboxamide (Compound 1-169);

N-(3-((6-(4-Isopropyl-4H-1,2,4-triazol-3-yl)pyridin-2-yl)carbamoyl)phenyl)-1-methyl-1H-imidazole-5-carboxamide (Compound 1-170);

N-(3-((6-(4-Isopropyl-4H-1,2,4-triazol-3-yl)pyridin-2-yl)carbamoyl)phenyl)-1-methyl-1H-imidazole-4-carboxamide (Compound 1-171);

N-(3-((6-(4-Isopropyl-4H-1,2,4-triazol-3-yl)pyridin-2-yl)carbamoyl)phenyl)oxazole-4-carboxamide (Compound 1-172);

N-(3-((6-(4-Isopropyl-4H-1,2,4-triazol-3-yl)pyridin-2-yl)carbamoyl)phenyl)oxazole-5-carboxamide (Compound 1-173);

N-(3-((6-(4-Isopropyl-4H-1,2,4-triazol-3-yl)pyridin-2-yl)carbamoyl)phenyl)isoxazole-5-carboxamide (Compound 1-174);

N-(3-((6-(4-Isopropyl-4H-1,2,4-triazol-3-yl)pyridin-2-yl)carbamoyl)phenyl)isoxazole-3-carboxamide (Compound 1-175);

N-(3-((6-(4-Isopropyl-4H-1,2,4-triazol-3-yl)pyridin-2-yl)carbamoyl)phenyl)-1,3,4-oxadiazole-2-carboxamide (Compound 1-176);

N-(3-((6-(4-Isopropyl-4H-1,2,4-triazol-3-yl)pyridin-2-yl)carbamoyl)phenyl)thiazole-5-carboxamide (Compound 1-177);

N-(3-((6-(4-Isopropyl-4H-1,2,4-triazol-3-yl)pyridin-2-yl)carbamoyl)phenyl)-1,3,4-thiadiazole-2-carboxamide (Compound 1-178);

3-(Benzyloxy)-N-(6-(4-isopropyl-4H-1,2,4-triazol-3-yl)pyridin-2-yl)benzamide (Compound 1-179);

N-(6-(4-Isopropyl-4H-1,2,4-triazol-3-yl)pyridin-2-yl)-3-(pyridin-2-ylmethoxy)benzamide (Compound 1-180);

N-(6-(4-Isopropyl-4H-1,2,4-triazol-3-yl)pyridin-2-yl)-3-(pyridin-3-ylmethoxy)benzamide (Compound 1-181);

N-(6-(4-Isopropyl-4H-1,2,4-triazol-3-yl)pyridin-2-yl)-3-(pyridin-4-ylmethoxy)benzamide (Compound 1-182);

N-(6-(4-isopropyl-4H-1,2,4-triazol-3-yl)pyridin-2-yl)-3-(pyrimidin-4-ylmethoxy)benzamide (Compound 1-183);

N-(6-(4-Isopropyl-4H-1,2,4-triazol-3-yl)pyridin-2-yl)-3-(pyrimidin-5-ylmethoxy)benzamide (Compound 1-184);

N-(6-(4-Isopropyl-4H-1,2,4-triazol-3-yl)pyridin-2-yl)-3-(pyrimidin-2-ylmethoxy)benzamide (Compound 1-185);

N-(6-(4-Isopropyl-4H-1,2,4-triazol-3-yl)pyridin-2-yl)-3-(pyrazin-2-ylmethoxy)benzamide (Compound 1-186);

N-(6-(4-Isopropyl-4H-1,2,4-triazol-3-yl)pyridin-2-yl)-3-(pyridazin-3-ylmethoxy)benzamide (Compound 1-187);

N-(6-(4-Isopropyl-4H-1,2,4-triazol-3-yl)pyridin-2-yl)-3-(pyridazin-4-ylmethoxy)benzamide (Compound 1-188);

3-(Benzylamino)-N-(6-(4-isopropyl-4H-1,2,4-triazol-3-yl)pyridin-2-yl)benzamide (Compound 1-189);

N-(6-(4-Isopropyl-4H-1,2,4-triazol-3-yl)pyridin-2-yl)-3-((pyridin-2-ylmethyl)amino)benzamide (Compound 1-190);

N-(6-(4-Isopropyl-4H-1,2,4-triazol-3-yl)pyridin-2-yl)-3-((pyridin-3-ylmethyl)amino)benzamide (Compound 1-191);

N-(6-(4-Isopropyl-4H-1,2,4-triazol-3-yl)pyridin-2-yl)-3-((pyridin-4-ylmethyl)amino)benzamide (Compound 1-192);

N-(6-(4-Isopropyl-4H-1,2,4-triazol-3-yl)pyridin-2-yl)-3-((pyrimidin-4-ylmethyl)amino)benzamide (Compound 1-193);

N-(6-(4-Isopropyl-4H-1,2,4-triazol-3-yl)pyridin-2-yl)-3-((pyrimidin-5-ylmethyl)amino)benzamide (Compound 1-194);

N-(6-(4-Isopropyl-4H-1,2,4-triazol-3-yl)pyridin-2-yl)-3-((pyrimidin-2-ylmethyl)amino)benzamide (Compound 1-195);

N-(6-(4-Isopropyl-4H-1,2,4-triazol-3-yl)pyridin-2-yl)-3-((pyrazin-2-ylmethyl)amino)benzamide (Compound 1-196);

N-(6-(4-Isopropyl-4H-1,2,4-triazol-3-yl)pyridin-2-yl)-3-((pyridazin-3-ylmethyl)amino)benzamide (Compound 1-197);

N-(6-(4-Isopropyl-4H-1,2,4-triazol-3-yl)pyridin-2-yl)-3-((pyridazin-4-ylmethyl)amino)benzamide (Compound 1-198);

N-(6-(4-Isopropyl-4H-1,2,4-triazol-3-yl)pyridin-2-yl)-3-(phenylethynyl)benzamide (Compound 1-199);

N-(6-(4-Isopropyl-4H-1,2,4-triazol-3-yl)pyridin-2-yl)-3-(pyridin-2-ylethynyl)benzamide (Compound 1-200);

N-(6-(4-Isopropyl-4H-1,2,4-triazol-3-yl)pyridin-2-yl)-3-(pyridin-3-ylethynyl)benzamide (Compound 1-201);

N-(6-(4-Isopropyl-4H-1,2,4-triazol-3-yl)pyridin-2-yl)-3-(pyridin-4-ylethynyl)benzamide (Compound 1-202);

N-(6-(4-Isopropyl-4H-1,2,4-triazol-3-yl)pyridin-2-yl)-3-(pyrimidin-4-ylethynyl)benzamide (Compound 1-203);

N-(6-(4-Isopropyl-4H-1,2,4-triazol-3-yl)pyridin-2-yl)-3-(pyrimidin-5-ylethynyl)benzamide (Compound 1-204);

N-(6-(4-Isopropyl-4H-1,2,4-triazol-3-yl)pyridin-2-yl)-3-(pyrimidin-2-ylethynyl)benzamide (Compound 1-205);

N-(6-(4-Isopropyl-4H-1,2,4-triazol-3-yl)pyridin-2-yl)-3-(pyrazin-2-ylethynyl)benzamide (Compound 1-206);

N-(6-(4-Isopropyl-4H-1,2,4-triazol-3-yl)pyridin-2-yl)-3-(pyridazin-3-ylethynyl)benzamide (Compound 1-207);

N-(6-(4-Isopropyl-4H-1,2,4-triazol-3-yl)pyridin-2-yl)-3-(pyridazin-4-ylethynyl)benzamide (Compound 1-208);

2-Fluoro-N-(6-(4-isopropyl-4H-1,2,4-triazol-3-yl)pyridin-2-yl)-5-phenoxybenzamide (Compound 1-209);

2-Fluoro-N-(6-(4-isopropyl-4H-1,2,4-triazol-3-yl)pyridin-2-yl)-5-(pyridin-2-yloxy)benzamide (Compound 1-210);

2-Fluoro-N-(6-(4-isopropyl-4H-1,2,4-triazol-3-yl)pyridin-2-yl)-5-(pyridin-3-yloxy)benzamide (Compound 1-211);

2-Fluoro-N-(6-(4-isopropyl-4H-1,2,4-triazol-3-yl)pyridin-2-yl)-5-(pyridin-4-yloxy)benzamide (Compound 1-212);

5-((6-Cyclopropylpyridin-2-yl)oxy)-2-fluoro-N-(6-(4-isopropyl-4H-1,2,4-triazol-3-yl)pyridin-2-yl)benzamide (Compound 1-213);

5-((6-(Dimethylamino)pyridin-2-yl)oxy)-2-fluoro-N-(6-(4-isopropyl-4H-1,2,4-triazol-3-yl)pyridin-2-yl)benzamide (Compound 1-214);

5-((6-(Dimethylamino)pyridin-3-yl)oxy)-2-fluoro-N-(6-(4-isopropyl-4H-1,2,4-triazol-3-yl)pyridin-2-yl)benzamide (Compound 1-215);

6-(4-Fluoro-3-((6-(4-isopropyl-4H-1,2,4-triazol-3-yl)pyridin-2-yl)carbamoyl)phenoxy)picolinic acid (Compound 1-216);

2-Fluoro-N-(6-(4-isopropyl-4H-1,2,4-triazol-3-yl)pyridin-2-yl)-5-(pyrimidin-4-yloxy)benzamide (Compound 1-217);

2-Fluoro-N-(6-(4-isopropyl-4H-1,2,4-triazol-3-yl)pyridin-2-yl)-5-(pyrimidin-5-yloxy)benzamide (Compound 1-218);

2-Fluoro-N-(6-(4-isopropyl-4H-1,2,4-triazol-3-yl)pyridin-2-yl)-5-(pyrimidin-2-yloxy)benzamide (Compound 1-219);

2-Fluoro-N-(6-(4-isopropyl-4H-1,2,4-triazol-3-yl)pyridin-2-yl)-5-(pyrazin-2-yloxy)benzamide (Compound 1-220);

2-Fluoro-N-(6-(4-isopropyl-4H-1,2,4-triazol-3-yl)pyridin-2-yl)-5-(pyridazin-3-yloxy)benzamide (Compound 1-221);

2-Fluoro-N-(6-(4-isopropyl-4H-1,2,4-triazol-3-yl)pyridin-2-yl)-5-(pyridazin-4-yloxy)benzamide (Compound 1-222);

2-Fluoro-N-(6-(4-isopropyl-4H-1,2,4-triazol-3-yl)pyridin-2-yl)-5-((6-(trifluoromethyl)pyridin-2-yl)oxy)benzamide (Compound 1-223);

2-Fluoro-N-(6-(4-isopropyl-4H-1,2,4-triazol-3-yl)pyridin-2-yl)-5-((6-methoxypyridin-2-yl)oxy)benzamide (Compound 1-224);

2-Fluoro-N-(6-(4-isopropyl-4H-1,2,4-triazol-3-yl)pyridin-2-yl)-5-((6-(pyrrolidin-1-yl)pyridin-2-yl)oxy)benzamide (Compound 1-225);

2-Fluoro-N-(6-(4-isopropyl-4H-1,2,4-triazol-3-yl)pyridin-2-yl)-5-((5,6,7,8-tetrahydro-1,8-naphthyridin-2-yl)oxy)benzamide (Compound 1-226);

5-((5-Cyclopropylpyridin-2-yl)oxy)-2-fluoro-N-(6-(4-isopropyl-4H-1,2,4-triazol-3-yl)pyridin-2-yl)benzamide (Compound 1-227);

2-Fluoro-N-(6-(4-isopropyl-4H-1,2,4-triazol-3-yl)pyridin-2-yl)-5-((5-(trifluoromethyl)pyridin-2-yl)oxy)benzamide (Compound 1-228);

2-Fluoro-N-(6-(4-isopropyl-4H-1,2,4-triazol-3-yl)pyridin-2-yl)-5-((5-methoxypyridin-2-yl)oxy)benzamide (Compound 1-229);

6-(4-Fluoro-3-((6-(4-isopropyl-4H-1,2,4-triazol-3-yl)pyridin-2-yl)carbamoyl)phenoxy)nicotinic acid (Compound 1-230);

5-((2-Cyclopropylpyrimidin-4-yl)oxy)-2-fluoro-N-(6-(4-isopropyl-4H-1,2,4-triazol-3-yl)pyridin-2-yl)benzamide (Compound 1-231);

2-Fluoro-N-(6-(4-isopropyl-4H-1,2,4-triazol-3-yl)pyridin-2-yl)-5-((2-(trifluoromethyl)pyrimidin-4-yl)oxy)benzamide (Compound 1-232);

2-Fluoro-N-(6-(4-isopropyl-4H-1,2,4-triazol-3-yl)pyridin-2-yl)-5-((2-methoxypyrimidin-4-yl)oxy)benzamide (Compound 1-233);

2-Fluoro-N-(6-(4-isopropyl-4H-1,2,4-triazol-3-yl)pyridin-2-yl)-5-((2-(2-(pyrrolidin-1-yl)ethoxy)pyrimidin-4-yl)oxy)benzamide (Compound 1-234);

2-Fluoro-N-(6-(4-isopropyl-4H-1,2,4-triazol-3-yl)pyridin-2-yl)-5-((2-(pyrrolidin-1-yl)pyrimidin-4-yl)oxy)benzamide (Compound 1-235);

4-(4-Fluoro-3-((6-(4-isopropyl-4H-1,2,4-triazol-3-yl)pyridin-2-yl)carbamoyl)phenoxy)pyrimidine-2-carboxylic acid (Compound 1-236);

5-((2-Cyclopropylpyrimidin-5-yl)oxy)-2-fluoro-N-(6-(4-isopropyl-4H-1,2,4-triazol-3-yl)pyridin-2-yl)benzamide (Compound 1-237);

2-Fluoro-N-(6-(4-isopropyl-4H-1,2,4-triazol-3-yl)pyridin-2-yl)-5-((2-(trifluoromethyl)pyrimidin-5-yl)oxy)benzamide (Compound 1-238);

2-Fluoro-N-(6-(4-isopropyl-4H-1,2,4-triazol-3-yl)pyridin-2-yl)-5-((2-methoxypyrimidin-5-yl)oxy)benzamide (Compound 1-239);

2-Fluoro-N-(6-(4-isopropyl-4H-1,2,4-triazol-3-yl)pyridin-2-yl)-5-((2-(2-(pyrrolidin-1-yl)ethoxy)pyrimidin-5-yl)oxy)benzamide (Compound 1-240);

2-Fluoro-N-(6-(4-isopropyl-4H-1,2,4-triazol-3-yl)pyridin-2-yl)-5-((2-(pyrrolidin-1-yl)pyrimidin-5-yl)oxy)benzamide (Compound 1-241);

5-(4-Fluoro-3-((6-(4-isopropyl-4H-1,2,4-triazol-3-yl)pyridin-2-yl)carbamoyl)phenoxy)pyrimidine-2-carboxylic acid (Compound 1-242);

N-(6-(4-Isopropyl-4H-1,2,4-triazol-3-yl)pyridin-2-yl)-4-phenoxypicolinamide (Compound 1-243);

N-(6-(4-Isopropyl-4H-1,2,4-triazol-3-yl)pyridin-2-yl)-4-(pyridin-2-yloxy)picolinamide (Compound 1-244);

N-(6-(4-Isopropyl-4H-1,2,4-triazol-3-yl)pyridin-2-yl)-4-(pyridin-3-yloxy)picolinamide (Compound 1-245);

N-(6-(4-Isopropyl-4H-1,2,4-triazol-3-yl)pyridin-2-yl)-4-(pyridin-4-yloxy)picolinamide (Compound 1-246);

N-(6-(4-Isopropyl-4H-1,2,4-triazol-3-yl)pyridin-2-yl)-4-(pyrimidin-4-yloxy)picolinamide (Compound 1-247);

N-(6-(4-Isopropyl-4H-1,2,4-triazol-3-yl)pyridin-2-yl)-4-(pyrimidin-5-yloxy)picolinamide (Compound 1-248);

N-(6-(4-Isopropyl-4H-1,2,4-triazol-3-yl)pyridin-2-yl)-4-(pyrimidin-2-yloxy)picolinamide (Compound 1-249);

N-(6-(4-Isopropyl-4H-1,2,4-triazol-3-yl)pyridin-2-yl)-4-(pyrazin-2-yloxy)picolinamide (Compound 1-250);

N-(6-(4-Isopropyl-4H-1,2,4-triazol-3-yl)pyridin-2-yl)-4-(pyridazin-3-yloxy)picolinamide (Compound 1-251);

N-(6-(4-Isopropyl-4H-1,2,4-triazol-3-yl)pyridin-2-yl)-4-(pyridazin-4-yloxy)picolinamide (Compound 1-252);

4-((6-Cyclopropylpyridin-2-yl)oxy)-N-(6-(4-isopropyl-4H-1,2,4-triazol-3-yl)pyridin-2-yl)picolinamide (Compound 1-253);

N-(6-(4-Isopropyl-4H-1,2,4-triazol-3-yl)pyridin-2-yl)-4-((6-(trifluoromethyl)pyridin-2-yl)oxy)picolinamide (Compound 1-254);

N-(6-(4-Isopropyl-4H-1,2,4-triazol-3-yl)pyridin-2-yl)-4-((6-methoxypyridin-2-yl)oxy)picolinamide (Compound 1-255);

N-(6-(4-Isopropyl-4H-1,2,4-triazol-3-yl)pyridin-2-yl)-4-((6-(pyrrolidin-1-yl)pyridin-2-yl)oxy)picolinamide (Compound 1-256);

N-(6-(4-Isopropyl-4H-1,2,4-triazol-3-yl)pyridin-2-yl)-4-((5,6,7,8-tetrahydro-1,8-naphthyridin-2-yl)oxy)picolinamide (Compound 1-257);

6-((2-((6-(4-Isopropyl-4H-1,2,4-triazol-3-yl)pyridin-2-yl)carbamoyl)pyridin-4-yl)oxy)picolinic acid (Compound 1-258);

4-((5-Cyclopropylpyridin-2-yl)oxy)-N-(6-(4-isopropyl-4H-1,2,4-triazol-3-yl)pyridin-2-yl)picolinamide (Compound 1-259);

N-(6-(4-Isopropyl-4H-1,2,4-triazol-3-yl)pyridin-2-yl)-4-((5-(trifluoromethyl)pyridin-2-yl)oxy)picolinamide (Compound 1-260);

N-(6-(4-Isopropyl-4H-1,2,4-triazol-3-yl)pyridin-2-yl)-4-((5-methoxypyridin-2-yl)oxy)picolinamide (Compound 1-261);

6-((2-((6-(4-Isopropyl-4H-1,2,4-triazol-3-yl)pyridin-2-yl)carbamoyl)pyridin-4-yl)oxy)nicotinic acid (Compound 1-262);

4-((2-Cyclopropylpyrimidin-4-yl)oxy)-N-(6-(4-isopropyl-4H-1,2,4-triazol-3-yl)pyridin-2-yl)picolinamide (Compound 1-263);

N-(6-(4-Isopropyl-4H-1,2,4-triazol-3-yl)pyridin-2-yl)-4-((2-(trifluoromethyl)pyrimidin-4-yl)oxy)picolinamide (Compound 1-264);

N-(6-(4-Isopropyl-4H-1,2,4-triazol-3-yl)pyridin-2-yl)-4-((2-methoxypyrimidin-4-yl)oxy)picolinamide (Compound 1-265);

N-(6-(4-Isopropyl-4H-1,2,4-triazol-3-yl)pyridin-2-yl)-4-((2-(2-(pyrrolidin-1-yl)ethoxy)pyrimidin-4-yl)oxy)picolinamide (Compound 1-266);

N-(6-(4-Isopropyl-4H-1,2,4-triazol-3-yl)pyridin-2-yl)-4-((2-(pyrrolidin-1-yl)pyrimidin-4-yl)oxy)picolinamide (Compound 1-267);

4-((2-((6-(4-Isopropyl-4H-1,2,4-triazol-3-yl)pyridin-2-yl)carbamoyl)pyridin-4-yl)oxy)pyrimidine-2-carboxylic acid (Compound 1-268);

4-((2-Cyclopropylpyrimidin-5-yl)oxy)-N-(6-(4-isopropyl-4H-1,2,4-triazol-3-yl)pyridin-2-yl)picolinamide (Compound 1-269);

N-(6-(4-Isopropyl-4H-1,2,4-triazol-3-yl)pyridin-2-yl)-4-((2-(trifluoromethyl)pyrimidin-5-yl)oxy)picolinamide (Compound 1-270);

N-(6-(4-Isopropyl-4H-1,2,4-triazol-3-yl)pyridin-2-yl)-4-((2-methoxypyrimidin-5-yl)oxy)picolinamide (Compound 1-271);

N-(6-(4-Isopropyl-4H-1,2,4-triazol-3-yl)pyridin-2-yl)-4-((2-(2-(pyrrolidin-1-yl)ethoxy)pyrimidin-5-yl)oxy)picolinamide (Compound 1-272);

N-(6-(4-Isopropyl-4H-1,2,4-triazol-3-yl)pyridin-2-yl)-4-((2-(pyrrolidin-1-yl)pyrimidin-5-yl)oxy)picolinamide (Compound 1-273);

5-((2-((6-(4-Isopropyl-4H-1,2,4-triazol-3-yl)pyridin-2-yl)carbamoyl)pyridin-4-yl)oxy)pyrimidine-2-carboxylic acid (Compound 1-274);

N-(6-(4-Isopropyl-4H-1,2,4-triazol-3-yl)pyridin-2-yl)-4-methyl-3-phenoxybenzamide (Compound 1-275);

N-(6-(4-Isopropyl-4H-1,2,4-triazol-3-yl)pyridin-2-yl)-4-methyl-3-(pyridin-2-yloxy)benzamide (Compound 1-276);

N-(6-(4-Isopropyl-4H-1,2,4-triazol-3-yl)pyridin-2-yl)-4-methyl-3-(pyridin-3-yloxy)benzamide (Compound 1-277);

N-(6-(4-Isopropyl-4H-1,2,4-triazol-3-yl)pyridin-2-yl)-4-methyl-3-(pyridin-4-yloxy)benzamide (Compound 1-278);

N-(6-(4-Isopropyl-4H-1,2,4-triazol-3-yl)pyridin-2-yl)-4-methyl-3-(pyrimidin-4-yloxy)benzamide (Compound 1-279);

N-(6-(4-Isopropyl-4H-1,2,4-triazol-3-yl)pyridin-2-yl)-4-methyl-3-(pyrimidin-5-yloxy)benzamide (Compound 1-280);

N-(6-(4-Isopropyl-4H-1,2,4-triazol-3-yl)pyridin-2-yl)-4-methyl-3-(pyrimidin-2-yloxy)benzamide (Compound 1-281);

N-(6-(4-Isopropyl-4H-1,2,4-triazol-3-yl)pyridin-2-yl)-4-methyl-3-(pyrazin-2-yloxy)benzamide (Compound 1-282);

N-(6-(4-Isopropyl-4H-1,2,4-triazol-3-yl)pyridin-2-yl)-4-methyl-3-(pyridazin-3-yloxy)benzamide (Compound 1-283);

N-(6-(4-Isopropyl-4H-1,2,4-triazol-3-yl)pyridin-2-yl)-4-methyl-3-(pyridazin-4-yloxy)benzamide (Compound 1-284);

2-Fluoro-N-(6-(4-isopropyl-4H-1,2,4-triazol-3-yl)pyridin-2-yl)-4-methyl-5-phenoxybenzamide (Compound 1-285);

2-Fluoro-N-(6-(4-isopropyl-4H-1,2,4-triazol-3-yl)pyridin-2-yl)-4-methyl-5-(pyridin-2-yloxy)benzamide (Compound 1-286);

2-Fluoro-N-(6-(4-isopropyl-4H-1,2,4-triazol-3-yl)pyridin-2-yl)-4-methyl-5-(pyridin-3-yloxy)benzamide (Compound 1-287);

2-Fluoro-N-(6-(4-isopropyl-4H-1,2,4-triazol-3-yl)pyridin-2-yl)-4-methyl-5-(pyridin-4-yloxy)benzamide (Compound 1-288);

2-Fluoro-N-(6-(4-isopropyl-4H-1,2,4-triazol-3-yl)pyridin-2-yl)-4-methyl-5-(pyrimidin-4-yloxy)benzamide (Compound 1-289);

2-Fluoro-N-(6-(4-isopropyl-4H-1,2,4-triazol-3-yl)pyridin-2-yl)-4-methyl-5-(pyrimidin-5-yloxy)benzamide (Compound 1-290);

2-Fluoro-N-(6-(4-isopropyl-4H-1,2,4-triazol-3-yl)pyridin-2-yl)-4-methyl-5-(pyrimidin-2-yloxy)benzamide (Compound 1-291);

2-Fluoro-N-(6-(4-isopropyl-4H-1,2,4-triazol-3-yl)pyridin-2-yl)-4-methyl-5-(pyrazin-2-yloxy)benzamide (Compound 1-292);

2-Fluoro-N-(6-(4-isopropyl-4H-1,2,4-triazol-3-yl)pyridin-2-yl)-4-methyl-5-(pyridazin-3-yloxy)benzamide (Compound 1-293);

2-Fluoro-N-(6-(4-isopropyl-4H-1,2,4-triazol-3-yl)pyridin-2-yl)-4-methyl-5-(pyridazin-4-yloxy)benzamide (Compound 1-294);

4-Fluoro-$N^3$-(6-(4-isopropyl-4H-1,2,4-triazol-3-yl)pyridin-2-yl)-$N^1$-phenylisophthalamide (Compound 1-295);

4-Fluoro-$N^3$-(6-(4-isopropyl-4H-1,2,4-triazol-3-yl)pyridin-2-yl)-$N^1$-(pyridin-2-yl)isophthalamide (Compound 1-296);

4-Fluoro-$N^3$-(6-(4-isopropyl-4H-1,2,4-triazol-3-yl)pyridin-2-yl)-$N^1$-(pyridin-3-yl)isophthalamide (Compound 1-297);

4-Fluoro-$N^3$-(6-(4-isopropyl-4H-1,2,4-triazol-3-yl)pyridin-2-yl)-$N^1$-(pyridin-4-yl)isophthalamide (Compound 1-298);

4-Fluoro-$N^3$-(6-(4-isopropyl-4H-1,2,4-triazol-3-yl)pyridin-2-yl)-$N^1$-(pyrimidin-4-yl)isophthalamide (Compound 1-299);

4-Fluoro-$N^3$-(6-(4-isopropyl-4H-1,2,4-triazol-3-yl)pyridin-2-yl)-$N^1$-(pyrimidin-5-yl)isophthalamide (Compound 1-300);

4-Fluoro-$N^3$-(6-(4-isopropyl-4H-1,2,4-triazol-3-yl)pyridin-2-yl)-$N^1$-(pyrimidin-2-yl)isophthalamide (Compound 1-301);

4-Fluoro-$N^3$-(6-(4-isopropyl-4H-1,2,4-triazol-3-yl)pyridin-2-yl)-$N^1$-(pyrazin-2-yl)isophthalamide (Compound 1-302);

4-Fluoro-$N^3$-(6-(4-isopropyl-4H-1,2,4-triazol-3-yl)pyridin-2-yl)-$N^1$-(pyridazin-3-yl)isophthalamide (Compound 1-303);

4-Fluoro-$N^3$-(6-(4-isopropyl-4H-1,2,4-triazol-3-yl)pyridin-2-yl)-$N^1$-(pyridazin-4-yl)isophthalamide (Compound 1-304);

5-Benzamido-2-fluoro-N-(6-(4-isopropyl-4H-1,2,4-triazol-3-yl)pyridin-2-yl)benzamide (Compound 1-305);

5-(4-(Aminomethyl)benzamido)-2-fluoro-N-(6-(4-isopropyl-4H-1,2,4-triazol-3-yl)pyridin-2-yl)benzamide (Compound 1-306);

N-(4-Fluoro-3-((6-(4-isopropyl-4H-1,2,4-triazol-3-yl)pyridin-2-yl)carbamoyl)phenyl)picolinamide (Compound 1-307);

N-(4-Fluoro-3-((6-(4-isopropyl-4H-1,2,4-triazol-3-yl)pyridin-2-yl)carbamoyl)phenyl)nicotinamide (Compound 1-308);

N-(4-Fluoro-3-((6-(4-isopropyl-4H-1,2,4-triazol-3-yl)pyridin-2-yl)carbamoyl)phenyl)isonicotinamide (Compound 1-309);

6-Cyclopropyl-N-(4-fluoro-3-((6-(4-isopropyl-4H-1,2,4-triazol-3-yl)pyridin-2-yl)carbamoyl)phenyl)picolinamide (Compound 1-310);

5-Bromo-N-(4-fluoro-3-((6-(4-isopropyl-4H-1,2,4-triazol-3-yl)pyridin-2-yl)carbamoyl)phenyl)picolinamide (Compound 1-311);

N-(4-Fluoro-3-((6-(4-isopropyl-4H-1,2,4-triazol-3-yl)pyridin-2-yl)carbamoyl)phenyl)pyrimidine-4-carboxamide (Compound 1-312);

N-(4-Fluoro-3-((6-(4-isopropyl-4H-1,2,4-triazol-3-yl)pyridin-2-yl)carbamoyl)phenyl)pyrimidine-5-carboxamide (Compound 1-313);

N-(4-Fluoro-3-((6-(4-isopropyl-4H-1,2,4-triazol-3-yl)pyridin-2-yl)carbamoyl)phenyl)pyrimidine-2-carboxamide (Compound 1-314);

N-(4-Fluoro-3-((6-(4-isopropyl-4H-1,2,4-triazol-3-yl)pyridin-2-yl)carbamoyl)phenyl)pyrazine-2-carboxamide (Compound 1-315);

N-(4-Fluoro-3-((6-(4-isopropyl-4H-1,2,4-triazol-3-yl)pyridin-2-yl)carbamoyl)phenyl)pyridazine-3-carboxamide (Compound 1-316);

N-(4-Fluoro-3-((6-(4-isopropyl-4H-1,2,4-triazol-3-yl)pyridin-2-yl)carbamoyl)phenyl)pyridazine-4-carboxamide (Compound 1-317);

N-(4-Fluoro-3-((6-(4-isopropyl-4H-1,2,4-triazol-3-yl)pyridin-2-yl)carbamoyl)phenyl)-5-methyl-1,3,4-oxadiazole-2-carboxamide (Compound 1-318);

N-(6-(4-Cyclopropyl-4H-1,2,4-triazol-3-yl)pyridin-2-yl)-3-phenoxybenzamide (Compound 1-319);

N-(6-(4-Cyclopropyl-4H-1,2,4-triazol-3-yl)pyridin-2-yl)-3-(pyridin-2-yloxy) benzamide (Compound 1-320);

N-(6-(4-Cyclopropyl-4H-1,2,4-triazol-3-yl)pyridin-2-yl)-3-(pyridin-3-yloxy)benzamide (Compound 1-321);

N-(6-(4-Cyclopropyl-4H-1,2,4-triazol-3-yl)pyridin-2-yl)-3-(pyridin-4-yloxy)benzamide (Compound 1-322);

N-(6-(4-Cyclopropyl-4H-1,2,4-triazol-3-yl)pyridin-2-yl)-3-(pyrimidin-4-yloxy)benzamide (Compound 1-323);

N-(6-(4-Cyclopropyl-4H-1,2,4-triazol-3-yl)pyridin-2-yl)-3-(pyrimidin-5-yloxy)benzamide (Compound 1-324);

N-(6-(4-Cyclopropyl-4H-1,2,4-triazol-3-yl)pyridin-2-yl)-3-(pyrimidin-2-yloxy)benzamide (Compound 1-325);

N-(6-(4-Cyclopropyl-4H-1,2,4-triazol-3-yl)pyridin-2-yl)-3-(pyrazin-2-yloxy)benzamide (Compound 1-326);

N-(6-(4-Cyclopropyl-4H-1,2,4-triazol-3-yl)pyridin-2-yl)-3-(pyridazin-3-yloxy)benzamide (Compound 1-327);

N-(6-(4-Cyclopropyl-4H-1,2,4-triazol-3-yl)pyridin-2-yl)-3-(pyridazin-4-yloxy)benzamide (Compound 1-328);

tert-Butyl ((2-((2-((6-(4-cyclopropyl-4H-1,2,4-triazol-3-yl)pyridin-2-yl)carbamoyl)pyridin-4-yl)oxy)-6-(trifluoromethyl)pyridin-4-yl)methyl)carbamate (Compound 1-329);

4-((4-(Aminomethyl)-6-(trifluoromethyl)pyridin-2-yl)oxy)-N-(6-(4-cyclopropyl-4H-1,2,4-triazol-3-yl)pyridin-2-yl)picolinamide (Compound 1-330);

3-((4-(Aminomethyl)-6-(trifluoromethyl)pyridin-2-yl)oxy)-N-(6-(4-isopropyl-4H-1,2,4-triazol-3-yl)pyridin-2-yl)benzamide (Compound 1-331);

4-(Aminomethyl)-N-(4-fluoro-3-((6-(4-isopropyl-4H-1,2,4-triazol-3-yl)pyridin-2-yl)carbamoyl)phenyl)picolinamide (Compound 1-332);

2-Fluoro-N-(6-(4-isopropyl-4H-1,2,4-triazol-3-yl)pyridin-2-yl)-5-(2-phenylacetamido)benzamide (Compound 1-333);

5-(3,4-Difluorobenzamido)-2-fluoro-N-(6-(4-isopropyl-4H-1,2,4-triazol-3-yl)pyridin-2-yl)benzamide (Compound 1-334);

4-((4-Fluoro-3-((6-(4-isopropyl-4H-1,2,4-triazol-3-yl)pyridin-2-yl)carbamoyl)phenyl)carbamoyl)benzoic acid (Compound 1-335);

5-((6-Bromopyridin-2-yl)oxy)-2-fluoro-N-(6-(4-isopropyl-4H-1,2,4-triazol-3-yl)pyridin-2-yl)benzamide (Compound 1-336);

5-((5-Bromopyridin-2-yl)oxy)-2-fluoro-N-(6-(4-isopropyl-4H-1,2,4-triazol-3-yl)pyridin-2-yl)benzamide (Compound 1-337);

5-Benzamido-N-(6-(4-cyclopropyl-4H-1,2,4-triazol-3-yl)pyridin-2-yl)-2-fluorobenzamide (Compound 1-338);

N-(6-(4-Cyclopropyl-4H-1,2,4-triazol-3-yl)pyridin-2-yl)-5-(3,4-difluorobenzamido)-2-fluorobenzamide (Compound 1-339);

5-Benzamido-N-(6-(4-(1,3-difluoropropan-2-yl)-4H-1,2,4-triazol-3-yl)pyridin-2-yl)-2-fluorobenzamide (Compound 1-340);

(R)-5-Benzamido-2-fluoro-N-(6-(4-(1-hydroxypropan-2-yl)-4H-1,2,4-triazol-3-yl)pyridin-2-yl)benzamide (Compound 1-341);

(R)-2-Fluoro-5-((4-fluorophenyl)amino)-N-(6-(4-(1-hydroxypropan-2-yl)-4H-1,2,4-triazol-3-yl)pyridin-2-yl)benzamide (Compound 1-342);

(R)-2-Fluoro-5-((4-fluorobenzyl)amino)-N-(6-(4-(1-hydroxypropan-2-yl)-4H-1,2,4-triazol-3-yl)pyridin-2-yl)benzamide (Compound 1-343);

or a pharmaceutically acceptable salt, or solvate thereof.

16. A pharmaceutical composition comprising a compound, or a pharmaceutically acceptable salt, or solvate thereof, of claim 1, and at least one pharmaceutically acceptable excipient.

17. A method of treating a disease or condition in a mammal that would benefit from the inhibition of apoptosis signal-regulating kinase (ASK1) activity or lysyl oxidase like-2 (LOXL2) activity, or combination thereof, comprising administering to the mammal a compound, or pharmaceutically acceptable salt, or solvate thereof, of claim 1, wherein disease or condition is a fibrosis, cancer, an autoimmune disease or condition, an inflammatory disease or condition, a cardiovascular disease or condition, a neurodegenerative disease or condition, or combinations thereof.

* * * * *